(12) United States Patent
Valade et al.

(10) Patent No.: US 10,105,359 B2
(45) Date of Patent: Oct. 23, 2018

(54) TETRAHYDROISOQUINOLINE DERIVATIVES

(71) Applicant: UCB Biopharma SPRL, Brussels (BE)

(72) Inventors: Anne Valade, Brussels (BE); Eric Jnoff, Brussels (BE); Ali Ates, Brussels (BE); Pierre Burssens, Brussels (BE); David Skolc, Brussels (BE); Zara Sands, Brussels (BE); Benoit Mathieu, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/517,795

(22) PCT Filed: Oct. 6, 2015

(86) PCT No.: PCT/EP2015/073053
§ 371 (c)(1),
(2) Date: Apr. 7, 2017

(87) PCT Pub. No.: WO2016/055479
PCT Pub. Date: Apr. 14, 2016

(65) Prior Publication Data
US 2017/0304292 A1 Oct. 26, 2017

(30) Foreign Application Priority Data

Oct. 8, 2014 (EP) .................................. 14188174

(51) Int. Cl.
| | |
|---|---|
| *C07D 217/06* | (2006.01) |
| *A61K 31/4725* | (2006.01) |
| *C07D 401/06* | (2006.01) |
| *C07D 403/06* | (2006.01) |
| *C07D 413/04* | (2006.01) |

(52) U.S. Cl.
CPC ........ *A61K 31/4725* (2013.01); *C07D 217/06* (2013.01); *C07D 401/06* (2013.01); *C07D 403/06* (2013.01); *C07D 413/04* (2013.01)

(58) Field of Classification Search
None
See application file for complete search history.

(56) References Cited

FOREIGN PATENT DOCUMENTS

| WO | 03/051869 | 6/2003 |
| WO | 2008/109336 | 9/2008 |

OTHER PUBLICATIONS

Schmitz, C. et al. Hippocampal Neuron Loss Exceeds Amyloid Plaque Load in a Transgenic Mouse Model of Alzheimer's Disease. American Journal of Pathology. 2004, vol. 164, p. 1495.*
Karran, E. et al. The amyloid cascade hypothesis for Alzheimer's disease: an appraisal for the development of therapeutics. Nature Reviews. 2011, vol. 10, p. 698.*
Khan, SM. et al. The Alzheimer's disease mitochondrial cascade hypothesis: An update. Experimental Neurology. 2009, vol. 218, p. 308.*
Hashimoto, M. et al. Role of Protein Aggregation in Mitochondrial Dysfunction and Neurodegeneration in Alzheimer's and Parkinson's Diseases. NeuroMolecular Medicine. 2003, vol. 4, p. 21.*
Terry, AV. et al. The Cholinergic Hypothesis of Age and Alzheimer's Disease-Related Cognitive Deficits: Recent Challenges and Their Implications for Novel Drug Development. The Journal of Pharmacology and Experimental Therapeutics. 2003, vol. 306, p. 821.*
Koch, G. et al. Is Dopamine involved in Alzheimer's disease. Frontiers in Aging Neuroscience. 2014, vol. 6, p. 1.*
CAS Registry Database. Chemical Abstracts Service, Columbus, OH, US. Entered STN May 21, 2001, Retrieved from STN database Sep. 18, 2017, CAS Registry No. 336825-07-1.*
CAS Registry Database. Chemical Abstracts Service, Columbus, OH, US. Entered STN May 21, 2001, Retrieved from STN database Sep. 18, 2017, CAS Registry No. 336825-09-3.*
CAS Registry Database. Chemical Abstracts Service, Columbus, OH, US. Entered STN May 21, 2001, Retrieved from STN database Sep. 18, 2017, CAS Registry No. 336825-12-8.*
CAS Registry Database. Chemical Abstracts Service, Columbus, OH, US. Entered STN May 21, 2001, Retrieved from STN database Sep. 18, 2017, CAS Registry No. 336825-17-3.*
CAS Registry Database. Chemical Abstracts Service, Columbus, OH, US. Entered STN May 21, 2001, Retrieved from STN database Sep. 18, 2017, CAS Registry No. 336825-18-4.*
CAS Registry Database. Chemical Abstracts Service, Columbus, OH, US. Entered STN May 21, 2001, Retrieved from STN database Sep. 18, 2017, CAS Registry No. 336825-30-0.*
CAS Registry Database. Chemical Abstracts Service, Columbus, OH, US. Entered STN Nov. 4, 2011, Retrieved from STN database Sep. 18, 2017, CAS Registry No. 1340700-29-9.*

(Continued)

*Primary Examiner* — D Margaret M Seaman
(74) *Attorney, Agent, or Firm* — McDonnell Boehnen Hulbert & Berghoff LLP

(57) ABSTRACT

The present invention relates to tetrahydroisoquinoline derivatives according to formula (I), which are Positive Allosteric Modulators of D1 and accordingly of benefit as pharmaceutical agents for the treatment of diseases in which D1 receptors play a role.

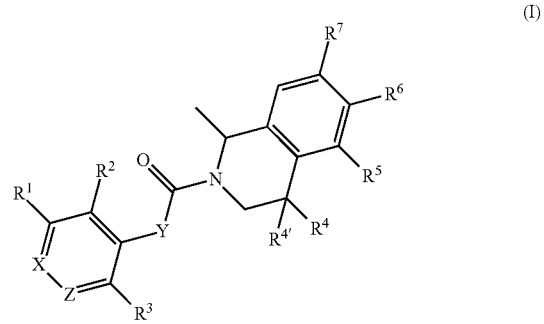

9 Claims, No Drawings

(56) References Cited

OTHER PUBLICATIONS

Database Registry [Online] Chemical Abstracts Service, Coumbus, Ohio, US, Nov. 4, 2011, XP002737207.
Database Registry [Online] Chemical Abstracts Service, Columbus, Ohio, US, May 21, 2001, XP002737209.
International Search Report dated Dec. 4, 2015 for International Application No. PCT/EP2015/073053 filed Oct. 6, 2015, 3 pages.

* cited by examiner

TETRAHYDROISOQUINOLINE DERIVATIVES

This application is the US national phase under 35 U.S.C. § 371 of international application PCT/EP2015/073053, filed Oct. 6, 2015, which claims priority to European application EP 14188174.8, filed Oct. 8, 2014.

FIELD OF THE INVENTION

The invention relates to tetrahydroisoquinoline derivatives and their use in therapy. In particular the present invention relates to pharmacologically active substituted tetrahydroisoquinoline derivatives and analogs thereof. More particularly, the present invention relates to substituted 3,4-dihydroisoquinolin-2(1H)-yl derivatives and analogs thereof.

The compounds according to the present invention are D1 Positive Allosteric Modulators and accordingly of benefit as pharmaceutical agents for the treatment of diseases in which D1 receptors play a role.

BACKGROUND OF THE INVENTION

The monoamine dopamine acts via two families of GPCRs to modulate motor function, reward mechanisms, cognitive processes and other physiological functions. Specifically, dopamine is acting upon neurons via D1-like, comprising dopamine D1 and D5, receptors which couple mainly to the $G_s$ G-protein and thereby stimulate cAMP production, and D2-like, which comprise D2, D3 and D4, receptors which couple to $G_{i/q}$G-proteins and which attenuate cAMP production. These receptors are widely expressed in different brain regions. In particular, D1 receptors are involved in numerous physiological functions and behavioural processes. D1 receptors are, for instance, involved in synaptic plasticity, cognitive function and goal-directed motor functions, but also in reward processes. Due to their role in several physiological/neurological processes, D1 receptors have been implicated in a variety of disorders including cognitive and negative symptoms in schizophrenia, cognitive impairment related to classical antipsychotic therapy, impulsivity, attention disorder with hyperactivity (ADHD), Parkinson's disease and related movement disorders, Huntington's disease dementia with Lewy Body, Alzheimer's disease, age-related cognitive decline, mild cognitive impairment (MCI), drug addiction sleep disorders, apathy It has proven difficult to develop orally-bioavailable small molecules targeting D1 receptors. D1 agonists developed so far are characterized by a catechol moiety and their clinical use has therefore been limited to invasive therapies. Achieving sufficient selectivity has also been challenging due to the high degree of homology in the ligand binding site between dopamine receptors subtypes (e.g. dopamine D1 and D5). Also, D1 agonists are associated with potentially limiting adverse events including dyskinesia and hypotension. In addition, the use of D1 receptor agonists has been associated with the development of tolerance in animal models.

There is therefore a need to design new agents that do not contain a catechol moiety and that could modulate D1 receptors at a novel site to improve selectivity and reduce some side effects.

There has been much interest in the identification of allosteric modulators of GPCRs, both as tools to understand receptor mechanisms and as potential therapeutic agents. GPCRs represent the largest family of cell-surface receptors and a large number of marketed drugs directly activate or block signaling pathways mediated by these receptors. However, for some GPCRs (e.g. peptide receptors), it has proven challenging to develop small molecules or to achieve sufficient selectivity due to the high degree of homology in the ligand binding site between subtypes (e.g. dopamine D1 and D5 or D2 and D3). Accordingly, much drug research has shifted to the identification of small molecules which target sites distinct from the orthosteric natural agonist. Ligands which bind to these sites induce a conformational change in the GPCR thereby allosterically modulating the receptor function. Allosteric ligands have a diverse range of activities including the ability to potentiate (positive allosteric modulator, PAM) or attenuate (negative allosteric modulator, NAM) the effects of the endogenous ligand, by affecting affinity and/or efficacy. As well as subtype selectivity, allosteric modulators can present other potential advantages from a drug discovery perspective such as a lack of direct effect or intrinsic efficacy; only potentiating the effect of the native transmitter where and when it is released; reduced propensity for inducing desensitization arising from constant exposure to an agonist as well as reduced propensity to induce target-related side-effects.

SUMMARY OF THE INVENTION

The compounds according to the present invention potentiate the effect of D1 agonists or the endogenous ligand on D1 receptors through an allosteric mechanism, and are therefore D1 positive allosteric modulators (D1 PAM).

The compounds in accordance with the present invention, being D1 PAM, are therefore beneficial in the treatment and/or prevention of diseases and disorders in which D1 receptors play a role. Such diseases include cognitive and negative symptoms in schizophrenia, cognitive impairment related to classical antipsychotic therapy, impulsivity, attention disorder with hyperactivity (ADHD), Parkinson's disease and related movement disorders, Huntington's disease, dementia with Lewy Body, Alzheimer's disease, age-related cognitive decline, mild cognitive impairment (MCI), drug addiction, sleep disorders and apathy.

The present invention provides in particular tetrahydroisoquinoline derivatives and analogs thereof which are beneficial for the treatment and/or prevention of diseases in which D1 receptors play a role. Chemical names and/or structures of the following tetrahydroisoquinoline derivatives have been entered onto the on-line STN Chemical Abstracts Service registry, under the following Registry Numbers (RN), without description of any means of making and/or use of such compounds:

RN1340700-29-9 (2-(2-fluorophenyl)-1-[(1R)-1-methyl-3,4-dihydro-2(1H)-isoquinolinyl]-1-ethanone;
RN 336825-30-0 (3,4-dihydro-1-methyl-N-(2-methylphenyl)-2(1H)-isoquinolinecarboxamide);
RN 336825-18-4 (N-(2,6-dimethylphenyl)-3,4-dihydro-1-methyl-2(1H)-isoquinolinecarboxamide);
RN 336825-17-3: (N-(2,4-dichlorophenyl)-3,4-dihydro-1-methyl-2(1H)-isoquinolinecarboxamide)
RN 336825-16-2 (N-(2,3-dichlorophenyl)-3,4-dihydro-1-methyl-2(1H)-isoquinolinecarboxamide);
RN 336825-12-8 (N-(2-bromophenyl)-3,4-dihydro-1-methyl-2(1H)-isoquinolinecarboxamide); and
RN 336825-07-1: (N-(2-fluorophenyl)-3,4-dihydro-1-methyl-2(1H)-isoquinolinecarboxamide).

International patent application WO 2013/051869 A1 discloses certain 3,4-dihydro-1H-isoquinolin-2-yl derivatives which are NK2 antagonists.

International patent application WO2008/109336 A1 discloses certain tetrahydroisoquinoline compounds which are modulators of the histamine H3 receptors.

International patent application WO 2014/193781 A1, published Dec. 4, 2014, discloses certain 3,4-dihydroisoquinolin-2(1H)-yl derivatives useful for the treatment of cognitive impairment associated with Parkinson's disease or Schizophrenia.

None of these patent applications, however, disclose or suggest the precise tetrahydroquinoline derivatives as provided by the present invention.

DETAILED DESCRIPTION OF THE INVENTION

The present invention provides a compound of formula (I), or a pharmaceutically acceptable salt thereof,

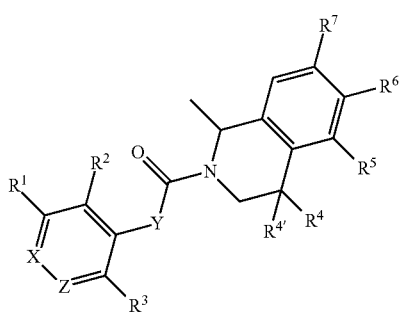

(I)

wherein $R^1$ is hydrogen, halogen, cyano or hydroxy; or $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl or ($C_{1-6}$-alkylsulfonyl)amino, any of which groups may be substituted by one or more substituents;

$R^2$ is hydrogen, cyano, or halogen; or $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl, $C_{1-6}$ alkylsulfonylamino, ($C_{1-6}$ alkylsulfonyl)amino ($C_{1-6}$ alkyl), $C_{1-6}$ alkylamido, ($C_{1-6}$ alkylacyl)amino, ($C_{1-6}$ alkylacyl)amino($C_{1-6}$ alkyl), or heteroaryl, any of which groups may be substituted by one or more substituents; or $R^1$ and $R^2$ are linked together to form with the adjacent aromatic group a heterocycle of formula (i):

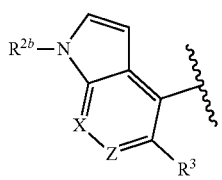

(i)

wherein $R^{2b}$ is hydrogen or $C_{1-6}$ alkylsulfonyl;

$R^3$ is halogen, $C_{1-6}$ alkyl, $C_{1-6}$ alkoxy or cyano;

$R^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ alkylaminocarbonyloxy;

$R^{4'}$ is hydrogen, halogen or $C_{1-6}$ alkyl; or $R^4$ and $R^{4'}$ together form an oxo group;

$R^5$ is hydrogen, cyano or hydroxy; or $C_{1-6}$ alkyl; $C_{1-6}$-alkylsulfonyl, $C_{1-6}$ alkylsulfonylamino; $C_{1-6}$ alkylsulfonylamino($C_{1-6}$ alkyl), heterocycle, $C_{1-6}$ alkylacylamino($C_{1-6}$ alkyl); $C_{1-6}$ alkylureido($C_{1-6}$ alkyl); $C_{1-6}$alkylcarbamate ($C_{1-6}$ alkyl); amido; $C_{1-6}$alkoxycarbonyloxy($C_{1-6}$alkyl); amino group; N-cyano-S—($C_{1-6}$-alkyl)sulfonimidoyl, N,S-(di-$C_{1-6}$-alkyl)sulfonimidoyl, aminosulfinyl; $C_{1-6}$ alkylsulfinyl; aminosulfonyl; (di-$C_{1-6}$-alkyl)(oxido)-$\lambda^6$-sulfanylidene-amino; amino($C_{1-6}$ alkyl); or amido($C_{1-6}$ alkyl); any of which groups may be optionally substituted by one or more substituents;

$R^6$ is hydrogen;

$R^7$ is hydrogen or ($C_{1-6}$ alkylsulfonyl)amino;

X is $CR^9$ or N; wherein $R^9$ is hydrogen, halogen, $C_{1-6}$-alkyl substituted by hydroxy or $C_{1-6}$ alkylsulfinyl;

Z is CH or N; and

Y is $CH_2$ or NH.

The present invention also provides a compound of formula (I) as defined above or a pharmaceutically acceptable salt thereof, for use in therapy.

In another aspect, the present invention also provides a compound of formula (I) as defined above, or a pharmaceutically acceptable salt thereof, for use in the treatment and/or prevention of diseases and/or disorders in which D1 receptors play a role.

In another aspect, the present invention provides a compound of formula (I) as defined above, or a pharmaceutically acceptable salt thereof, for use in the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, Huntington's disease; dementia with Lewy Body, Alzheimer's disease, age-related cognitive decline, mild cognitive impairment (MCI), drug addiction, sleep disorders or apathy.

In a particular aspect, the present invention provides a compound of formula (I) as defined above, or a pharmaceutically acceptable salt thereof, for use in the treatment and/or prevention of Parkinson's disease.

In a further aspect, the present invention provides for the use of a compound of formula (I) as defined above, or a pharmaceutically acceptable salt thereof, for the manufacture of a medicament useful for the treatment and/or prevention of diseases and/or disorders in which D1 receptors play a role.

In another further aspect, the present invention provides for the use of a compound of formula (I) as defined above, or a pharmaceutically acceptable salt thereof, for the manufacture of a medicament useful for the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, Huntington's disease; dementia with Lewy Body, Alzheimer's disease, age-related cognitive decline, mild cognitive impairment (MCI), drug addiction, sleep disorders or apathy.

In a particular aspect, the present invention provides for the use of a compound of formula (I) as defined above, or a pharmaceutically acceptable salt thereof, for the manufacture of a medicament useful for the treatment and/or prevention of Parkinson's disease, The present invention also provides a method for the treatment and/or prevention of disorders for which the administration of D1 positive allosteric modulator is indicated, which comprises administering to a patient in need of such treatment an effective amount of a compound of formula (I) as defined above, or a pharmaceutically acceptable salt thereof.

In another aspect, the present invention provides a method for the treatment and/or prevention of cognitive and negative symptoms in schizophrenia, cognitive impairment related to classical antipsychotic therapy, impulsivity, attention disorder with hyperactivity (ADHD), Parkinson's disease and related movement disorders, Huntington's disease; dementia with Lewy Body, Alzheimer's disease, age-related cognitive decline, mild cognitive impairment (MCI), drug addiction, sleep disorders or apathy which comprises administering to a patient in need of such treatment an effective amount of a compound of formula (I) as defined above, or a pharmaceutically acceptable salt thereof.

In a particular aspect, the present invention provides a method for the treatment and/or prevention of Parkinson's Disease, which comprises administering to a patient in need of such treatment an effective amount of a compound of formula (I) as defined above, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Examples of substituents include "$C_{1-6}$ alkyl", "$C_{3-8}$ cycloalkyl", "amino", "acyl", "acyloxy", "acylamino", "amido", "alkoxycarbonyl", "ureido", "carbamate", "aryl", "heterocycle", "heteroaryl", "heterocycloalkyl", "sulfanyl", "sulfinyl", "sulfonyl", "alkoxy", "sulfanyl", "halogen", "trihalomethyl", "cyano", "hydroxy" and the like. Suitable substituents for each particular groups of compounds formula (I) are further described herein after in the present specification.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in Handbook of Pharmaceutical Salts: Properties, Selection and Use, ed. P. H. Stahl & C. G. Wermuth, Wiley-VCH, 2002. Selected examples of salts according to the present invention include trifluoroacetate salts and hydrochloride salts.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see Pharmaceutical Salts and Co-crystals, ed. J. Wouters & L. Quere, RSC Publishing, 2012).

The term "hydrogen", as used herein encompasses all isotopic forms of hydrogen atom. Therefore each individual hydrogen atom present in formula (I), or in the formulae depicted hereinafter, may be present as a $^1H$, $^2H$ (deuterium) or $^3H$ (tritium) atom, preferably $^1H$.

The term "hydroxy", as used herein, represents a group of formula —OH.

"Halogen" refers to fluoro, chloro, bromo and iodo atoms.

"Cyano" refers to —CN.

"Nitro" refers to —NO$_2$.

"$C_{1-6}$ alkyl" or "$C_{1-4}$ alkyl" refers to an alkyl group which represents saturated, monovalent hydrocarbon radicals having straight (unbranched) or branched moieties or combinations thereof, and containing 1 to 6 carbon atoms, or 1 to 4 carbon atoms. Examples of $C_{1-4}$ alkyl groups are methyl, ethyl, n-propyl, isopropyl, n-butyl, isobutyl, tert-butyl. "$C_{1-4}$" or "$C_{1-6}$ alkyl" groups may be substituted by one or more substituents selected from halogen, hydroxy, cyano, amido, alkoxy, sulfonylamino. Particular alkyl groups according to the present invention are methyl, ethyl, 2,2,2-trifluoroethyl, propyl. Additional alkyl groups include, difluoromethyl, trifluoromethyl, isopropyl, and 2,2-difluoroethyl.

The term "$C_{1-6}$-alkyl hydroxy" or "(hydroxy)$C_{1-6}$-alkyl", as used herein, refers to an alkyl as defined above substituted by one or more "hydroxy". Example of $C_{1-6}$-alkyl hydroxy group according to the present invention is hydroxymethyl.

"$C_{1-6}$ alkoxy" refers to a group of formula —O—R where R is a substituted or unsubstituted "$C_{1-6}$ alkyl". Example of alkoxy groups according to the present invention is methoxy, 2-(methylamino)-2-oxoethoxy or 2-(dimethylamino)-2-oxoethoxy.

"$C_{3-8}$ cycloalkyl" refers to a saturated carbocyclic group of from 3 to 8 carbon atoms having a single ring (e.g., cyclohexyl) or multiple condensed rings (e.g., norbornyl). Cycloalkyl include cyclopropyl, cyclobutyl, cyclopentyl, cyclohexyl, and the like.

"Aryl" refers to an unsaturated aromatic carbocyclic group of from 6 to 14 carbon atoms having a single ring (e.g., phenyl) or multiple condensed rings (e.g., naphthyl). The "aryl" groups may be unsubstituted or substituted by 1 to 3 substituents independently selected from $C_{1-4}$ alkyl, $C_{1-4}$ alkoxy, halogen, cyano, amido, hydroxy or heterocycle. Aryl include phenyl and the like.

"Heterocycle" refers to a saturated or unsaturated ring system containing, in addition to carbon atoms, at least one hetero atom, such as nitrogen, oxygen and/or sulfur. "Heterocycle" includes both "heteroaryl" and "heterocycloalkyl". Unsaturated heterocycles include dihydroimidazolyl, in particular 1-(methylsulfonyl)-4,5-dihydro-1H-imidazol-2-yl.

"Heteroaryl" refers to a monocyclic heteroaromatic, or a bicyclic or a tricyclic fused-ring heteroaromatic group. Particular examples of heteroaromatic groups include optionally substituted pyridyl, oxazolyl, pyrazolyl, or triazolyl. Examples of heteroaryl groups according to the present invention include 1-methyl-1H-pyrazol-3-yl, 1-methyl-1H-pyrazol-5-yl, 1H-1,2,4-triazol-3-yl, pyridine-3-yl, 6-amino-pyridin-3-yl, 2-amino-pyridin-4-yl, 2-amino-pyridin-3-yl, 1H-pyrazol-4-yl, 3-cyano-1H-pyrazol-4-yl, 3-trifluoromethyl-1H-pyrazol-4-yl, 1-methyl-1H-pyrazol-4-yl, 3,5-dimethyl-1H-pyrazol-4-yl, 3,5-dimethyl-1,2-oxazol-4-yl, and 2H-1,2,3-triazol-4-yl.

"Heterocycloalkyl" refers to a $C_{3-8}$ cycloalkyl group according to the definition above, in which 1 to 3 carbon atoms are replaced by hetero atoms chosen from the group consisting of O, S, NR, R being defined as hydrogen, acyl or $C_{1-6}$ alkyl. Preferred heterocycloalkyl include pyrrolidinyl, piperidinyl, morpholinyl, tetrahydropyranyl, and the like. Examples of heterocycloalkyl groups according to the present invention are pyrrolidin-1-yl, piperidin-1-yl, azetidin-1-yl, and tetrahydro-2H-pyran-4-yl.

"Amino group" refers to the group —NRR' where each R, R' is independently hydrogen, "$C_{1-6}$ alkyl", "$C_{3-8}$ cycloalkyl", "heterocycle", "aryl" and where R and R', together with the nitrogen atom to which they are attached, can optionally form a 3-8-membered heterocycloalkyl ring.

"C$_{1-6}$ alkylamino" refers to the group —NRR' wherein R is H or C$_{1-6}$ alkyl and R' is C$_{1-6}$ alkyl. Examples of amino groups according to the present invention are amino, methylamino and dimethylamino.

"Amido" refers to the group —C(=O)NRR' where each R, R' is independently hydrogen, "C$_{1-6}$ alkyl", "C$_{3-8}$ cycloalkyl", "heterocycle", "aryl", and where R and R', together with the nitrogen atom to which they are attached, can optionally form a 3-8-membered heterocycloalkyl ring. "C$_{1-6}$ alkylamido" refers to the group —C(=O)NRR' wherein R is H or "C$_{1-6}$ alkyl" and R' is "C$_{1-6}$ alkyl". "Heterocyclylamido" refers to the group —C(=O)NRR' wherein one of R or R' is an "heterocycle". "C$_{3-8}$ heterocycloalkylamido" refers to the group —C(=O)NRR' wherein R and R', together with the nitrogen atom to which they are attached, can optionally form a 3-8-membered heterocycloalkyl ring. Examples of amido groups according to the present invention include carbamoyl, methylcarbamoyl (also referred to as methylaminocarbonyl), dimethylcarbamoyl (also referred to as dimethylaminocarbonyl), ethylcarbamoyl (also referred to as ethylaminocarbonyl) and isopropylcarbamoyl (also referred to as isopropylaminocarbonyl).

"Acyl" refers to the group —C(=O)R where R is "C$_{1-6}$ alkyl", "C$_{3-8}$ cycloalkyl", "heterocycle" or "aryl". "C$_{1-6}$ alkylacyl" refers to the group —C(=O)R where R is "C$_{1-6}$ alkyl". Example of acyl group according to the present invention is acetyl.

"Acylamino" refers to the group —NHC(=O)R where R is "C$_{1-6}$ alkyl", "C$_{3-8}$ cycloalkyl", "heterocycle" or "aryl". "(C$_{1-6}$-alkylacyl)amino" refers to the group —NHC(=O)R where R is "C$_{1-6}$ alkyl". Example of acylamino group according to the present invention is acetamido.

The term "alkoxycarbonyl" refers to the group —C(O)OR wherein R includes "C$_{1-6}$ alkyl", "C$_{3-8}$ cycloalkyl", "heterocycle" or "aryl". "C$_{1-6}$ alkoxycarbonyl" refers to the group —C(O)OR wherein R is "C$_{1-6}$ alkyl". Example of alkoxycarbonyl according to the present invention is methoxycarbonyl.

"Alkoxycarbonyloxy" refers to the group —OC(O)OR wherein R includes "C$_{1-6}$ alkyl", "C$_{3-8}$ cycloalkyl", "heterocycle" or "aryl". "C$_{1-6}$ alkoxycarbonyloxy" refers to the group —OC(O)OR wherein R is "C$_{1-6}$ alkyl". An example of alkoxycarbonyloxy is methoxycarbonyloxy.

"Aminocarbonyloxy" refers to the group —OC(O)NRR' wherein R and R' are defined as above for amino groups. "C$_{1-6}$ aminocarbonyloxy" refers to the group —OC(O)NRR' wherein R is H or "C$_{1-6}$ alkyl" and R' is "C$_{1-6}$ alkyl".

"Sulfonyl" as used herein refers to a group of formula "—SO$_2$—R" wherein R is "C$_{1-6}$ alkyl", "C$_{3-8}$ cycloalkyl", "heterocycle" or "aryl". "C$_{1-6}$ alkylsulfonyl" refers to a sulfonyl group wherein R is a "C$_{1-6}$ alkyl". Examples of sulfonyl group according to the present invention are methylsulfonyl and (tetrahydro-2H-pyran-4-ylmethyl)sulfonyl.

"Sulfinyl" refers to group of formula "—S(O)—R" wherein R is "C$_{1-6}$ alkyl", "C$_{3-8}$ cycloalkyl", "heterocycle" or "aryl". "C$_{1-6}$ alkylsulfinyl" refers to a sulfinyl group wherein R is "C$_{1-6}$ alkyl".

"Sulfanyl" refers to group of formula "—S—R" wherein R is "C$_{1-6}$ alkyl", "C$_{3-8}$ cycloalkyl", "heterocycle" or "aryl". "C$_{1-6}$ alkylsulfanyl" refers to a sulfanyl group wherein R is "C$_{1-6}$ alkyl".

"Sulfonylamino" as used herein refers to a group of formula —NRSO$_2$—R' wherein R and R' are as defined here above for the amino group. "(C$_{1-6}$alkylsulfonyl)amino" refers to a group of formula —NHSO$_2$—R' wherein R' is "C$_{1-6}$ alkyl". Example of sulfonylamino group according to the present invention is (methylsulfonyl)amino.

"Aminosulfonyl" as used herein refers to a group of formula —SO$_2$—NRR' wherein R and R' are as defined here above for the amino group. "C$_{1-6}$ alkylaminosulfonyl" refers to an aminosulfonyl group wherein R is H or "C$_{1-6}$ alkyl" and R' is "C$_{1-6}$ alkyl". "Heterocyclylaminosulfonyl" refers to the group —SO$_2$—NRR' wherein one of R or R' is an "heterocycle". "C$_{3-8}$-heterocycloalkylaminosulfonyl" refers to the group —SO$_2$—NRR' wherein R and R', together with the nitrogen atom to which they are attached, can optionally form a 3-8-membered heterocycloalkyl ring. Example of aminosulfonyl groups according to the present invention are sulfamoyl, methylsulfamoyl (also referred to as methylaminosulfonyl), ethylsulfamoyl (also referred to as ethylaminosulfonyl), (2,2,2-trifluoroethyl)sulfamoyl, propan-2-ylsulfamoyl, pyrrolidin-1-ylsulfonyl, piperidin-1-ylsulfonyl, azetidin-1-ylsulfonyl, (1-methyl-1H-pyrazol-3-yl)sulfamoyl, (1-methyl-1H-pyrazol-5-yl)sulfamoyl, 1H-1,2,4-triazol-3-ylsulfamoyl.

"Aminosulfinyl" as used herein refers to a group of formula —SO—NRR' wherein R and R' are as defined here above for the amino group. "C$_{1-6}$ alkylaminosulfinyl" refers to an aminosulfinyl group wherein R is hydrogen or "C$_{1-6}$ alkyl" and R' is "C$_{1-6}$ alkyl".

"Oxo" as used herein refers to =O.

"Ureido" as used herein refers to a group of formula —NHC(O)NRR' wherein R and R' are as defined here above for the amino group. Example of ureido is (methoxycarbonyl)amino. "C$_{1-6}$ alkylureido" refers to a group of formula —NHC(O)NRR' wherein R is hydrogen or "C$_{1-6}$ alkyl" and R' is "C$_{1-6}$ alkyl".

"Carbamate", as used herein, refers to a group of formula —NRC(O)OR' wherein R and R' are as defined here above for the amino group. "C$_{1-6}$ alkylcarbamate" refers to a group of formula —NRC(O)OR' wherein R is hydrogen or "C$_{1-6}$ alkyl" and R' is "C$_{1-6}$ alkyl".

"C$_{1-6}$-alkyl carbamate" as used herein refers to a "C$_{1-6}$ alkyl" substituted by a carbamate as defined here above.

"N-cyano-S—(C$_{1-6}$-alkyl)sulfonimidoyl" refers to a group of formula —SR(O)(N—CN) wherein R is "C$_{1-6}$ alkyl".

"N,S-(di-C$_{1-6}$-alkyl)sulfonimidoyl" refers to a group of formula —SR(O)(N—R') wherein R and R' are "C$_{1-6}$ alkyl".

"(Di-C$_{1-6}$-alkyl)(oxido)-λ$^6$-sulfanylidene-amino" refers to a group of formula —N=S(O)RR' wherein R and R' are "C$_{1-6}$ alkyl" or R and R' together with the S atom form a "C$_{3-8}$ heterocycloalkyl"

In one aspect, the present invention relates to a compound of formula (I), or a pharmaceutically acceptable salt thereof,

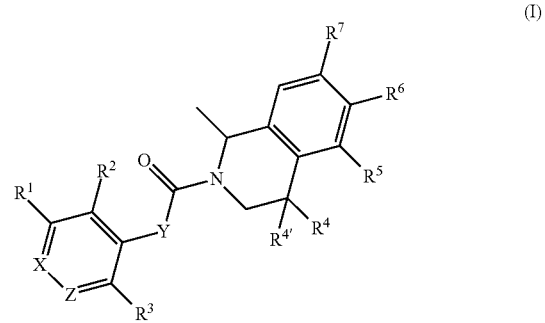

(I)

wherein

R$^1$, R$^2$, R$^3$, R$^4$, R$^{4'}$, R$^5$, R$^6$, R$^7$, X, Z and Y are defined as above, with the exception of the following compounds:

2-(2-fluorophenyl)-1-[(1R)-1-methyl-3,4-dihydro-2(1H)-isoquinolinyl]-1-ethanone;

3,4-dihydro-1-methyl-N-(2-methylphenyl)-2(1H)-isoquinolinecarboxamide;

N-(2,6-dimethylphenyl)-3,4-dihydro-1-methyl-2(1H)-isoquinolinecarboxamide;

N-(2,4-dichlorophenyl)-3,4-dihydro-1-methyl-2(1H)-isoquinolinecarboxamide;

N-(2,3-dichlorophenyl)-3,4-dihydro-1-methyl-2(1H)-isoquinolinecarboxamide;

N-(2-bromophenyl)-3,4-dihydro-1-methyl-2(1H)-isoquinolinecarboxamide; and

N-(2-fluorophenyl)-3,4-dihydro-1-methyl-2(1H)-isoquinolinecarboxamide.

In another aspect, the present invention relates to tetrahydroisoquinoline derivatives according to formula I,

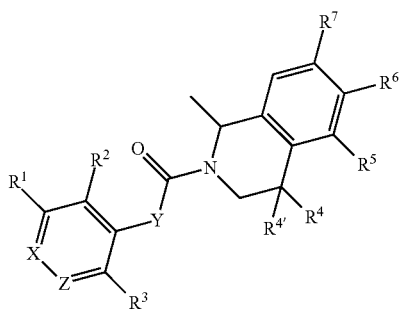

(I)

wherein,

R$^1$ is hydrogen, halogen, hydroxy, C$_{1-6}$-alkyl hydroxy, C$_{1-6}$ alkoxy, C$_{1-6}$ alkylsulfanyl, C$_{1-6}$ alkylsulfinyl, C$_{1-6}$alkylsulfonyl or (C$_{1-6}$-alkylsulfonyl)amino;

R$^2$ is hydrogen, halogen, C$_{1-6}$ alkyl unsubstituted or substituted by one or more halogens, C$_{1-6}$-alkyl hydroxy, C$_{1-6}$ alkoxy, C$_{1-6}$ alkylsulfanyl, C$_{1-6}$ alkylsulfinyl, C$_{1-6}$ alkylsulfonyl, cyano, C$_{1-6}$ alkylamido, pyrazolyl, or a group of formula —CH$_2$R$^{2a}$, —NHR$^{2a}$ or —CH$_2$NHR$^{2a}$ wherein R$^{2a}$ is selected from C$_{1-6}$ alkylacyl or C$_{1-6}$ alkylsulfonyl;

Alternatively R$^1$ and R$^2$ are linked together to form with the adjacent aromatic group a bicycle of formula (i):

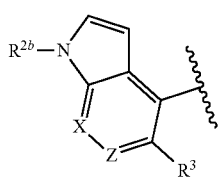

(i)

wherein R$^{2b}$ is hydrogen or C$_{1-6}$ alkylsulfonyl;

R$^3$ is halogen, C$_{1-6}$ alkyl or C$_{1-6}$ alkoxy;

R$^4$ is hydrogen, halogen, C$_{1-6}$ alkyl, hydroxy, C$_{1-6}$ alkoxy, C$_{1-6}$ alkylsulfonyl, C$_{1-6}$ alkoxycarbonyloxy or C$_{1-6}$ aminocarbonyloxy;

R$^{4'}$ is hydrogen, halogen, C$_{1-6}$ alkyl; or R$^4$ and R$^{4'}$ together form an oxo group;

R$^5$ is hydrogen, cyano, hydroxy, amino, carbamoyl, sulfamoyl, C$_{1-6}$ alkylsulfinyl, C$_{1-6}$ alkylaminosulfinyl, C$_{1-6}$ alkylsulfonyl optionally substituted by C$_{1-6}$ alkoxy or heterocycle, N-cyano-S—(C$_{1-6}$-alkyl)sulfonimidoyl, N,S-(di-C$_{1-6}$-alkyl)sulfonimidoyl, (di-C$_{1-6}$-alkyl)(oxido)-λ$^6$-sulfanylidene-amino, (C$_{1-6}$ alkylsulfonyl)amino; or R$^5$ is C$_{1-6}$ alkyl mono- or polysubstituted by hydroxy, halogen, C$_{1-6}$ alkylsulfanyl, C$_{1-6}$ alkylsulfonyl, (C$_{1-6}$ alkylsulfonyl)amino, (C$_{1-6}$-alkylacyl)amino, C$_{1-6}$ alkylureido, C$_{1-6}$ alkylcarbamate, C$_{1-6}$ alkoxycarbonyloxy; or R$^5$ is an heterocycle optionally mono- or polysubstituted by C$_{1-6}$ alkyl or C$_{1-6}$ alkylsulfonyl; or R$^5$ is an amido group selected from C$_{1-6}$ alkylamido optionally mono- or polysubstituted by halogen, substituted or unsubstituted heterocyclylamido, C$_{3-8}$ heterocycloalkylamido optionally mono- or polysubstituted by C$_{1-6}$ alkyl, halogens or hydroxy; or R$^5$ is an aminosulfonyl group selected from C$_{1-6}$ alkylaminosulfonyl optionally substituted by one or more halogens or cyano, heterocyclylaminosulfonyl or C$_{3-8}$ heterocycloalkylaminosulfonyl optionally substituted by one or more halogens;

R$^6$ is hydrogen

R$^7$ is either hydrogen or (C$_{1-6}$-alkylsulfonyl)amino;

X is either CR$^9$ or N, wherein R$^9$ is hydrogen, halogen or C$_{1-6}$-alkyl hydroxy.

Z is CH; and

Y is either CH$_2$ or NH.

In a further aspect, the present invention relates to tetrahydroisoquinoline derivatives of formula (I), or pharmaceutically acceptable salts thereof,

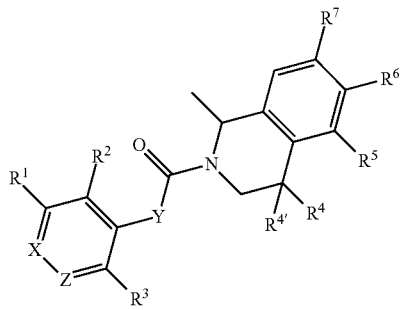

(I)

wherein,

R$^1$ is hydrogen, halogen, hydroxy, C$_{1-6}$-alkylhydroxy, C$_{1-6}$ alkoxy, C$_{1-6}$ alkylsulfanyl, C$_{1-6}$ alkylsulfinyl, C$_{1-6}$ alkylsulfonyl or (C$_{1-6}$-alkylsulfonyl)amino;

R$^2$ is hydrogen, halogen, C$_{1-6}$ alkyl unsubstituted or substituted by one or more halogens, C$_{1-6}$-alkyl hydroxy, C$_{1-6}$ alkoxy, C$_{1-6}$ alkylsulfanyl, C$_{1-6}$ alkylsulfinyl, C$_{1-6}$ alkylsulfonyl, cyano, C$_{1-6}$ alkylamido, pyrazolyl, or a group of formula —CH$_2$R$^{2a}$, —NHR$^{2a}$ or —CH$_2$NHR$^{2a}$ wherein R$^{2a}$ is selected from C$_{1-6}$ alkylacyl or C$_{1-6}$ alkylsulfonyl; or R$^1$ and R$^2$ are linked together to form with the adjacent aromatic group a bicycle of formula (i);

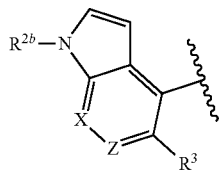

(i)

wherein R$^{2b}$ is hydrogen or C$_{1-6}$ alkylsulfonyl; and

R$^3$ is halogen, C$_{1-6}$ alkyl or C$_{1-6}$ alkoxy;

$R^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ aminocarbonyloxy;

$R^{4'}$ is hydrogen, halogen, $C_{1-6}$ alkyl; or $R^4$ and $R^{4'}$ together form an oxo group;

$R^5$ is hydrogen, cyano, hydroxy, amino, carbamoyl, sulfamoyl, $C_{1-6}$ alkylsulfinyl, $C_{1-6}$ alkylaminosulfinyl, $C_{1-6}$ alkylsulfonyl optionally substituted by $C_{1-6}$ alkoxy or heterocycle, N-cyano-S—($C_{1-6}$-alkyl)sulfonimidoyl, N,S-(di-$C_{1-6}$-alkyl)sulfonimidoyl, (di-$C_{1-6}$-alkyl)(oxido)-$\lambda^6$-sulfanylidene-amino, ($C_{1-6}$alkylsulfonyl)amino; or $R^5$ is $C_{1-6}$ alkyl mono- or polysubstituted by hydroxy, halogen, $C_{1-6}$ alkylsulfanyl, $C_{1-6}$ alkylsulfonyl, ($C_{1-6}$alkylsulfonyl)amino, ($C_{1-6}$-alkylacyl)amino, $C_{1-6}$ alkylureido, $C_{1-6}$ alkylcarbamate, $C_{1-6}$ alkoxycarbonyloxy; or $R^5$ is an heterocycle optionally mono- or polysubstituted by $C_{1-6}$ alkyl or $C_{1-6}$ alkylsulfonyl; or $R^5$ is an amido group selected from $C_{1-6}$ alkylamido optionally mono- or polysubstituted by halogen, substituted or unsubstituted heterocyclylamido, $C_{3-8}$ heterocycloalkylamido optionally mono- or polysubstituted by $C_{1-6}$ alkyl, halogens or hydroxy; or $R^5$ is an aminosulfonyl group selected from $C_{1-6}$ alkylaminosulfonyl optionally substituted by one or more halogens or cyano, heterocyclylaminosulfonyl or $C_{3-8}$ heterocycloalkylaminosulfonyl optionally substituted by one or more halogens;

$R^6$ is hydrogen $R^7$ is either hydrogen or ($C_{1-6}$-alkylsulfonyl)amino;

X is either $CR^9$ or N, wherein $R^9$ is hydrogen, halogen or $C_{1-6}$-alkyl hydroxy.

Z is CH; and

Y is either $CH_2$ or NH;

with the exception of the following compounds:

2-(2-fluorophenyl)-1-[(1R)-1-methyl-3,4-dihydro-2(1H)-isoquinolinyl]-1-ethanone;

3,4-dihydro-1-methyl-N-(2-methylphenyl)-2(1H)-isoquinolinecarboxamide;

N-(2,6-dimethylphenyl)-3,4-dihydro-1-methyl-2(1H)-isoquinolinecarboxamide;

N-(2,4-dichlorophenyl)-3,4-dihydro-1-methyl-2(1H)-isoquinolinecarboxamide;

N-(2,3-dichlorophenyl)-3,4-dihydro-1-methyl-2(1H)-isoquinolinecarboxamide;

N-(2-bromophenyl)-3,4-dihydro-1-methyl-2(1H)-isoquinolinecarboxamide; and

N-(2-fluorophenyl)-3,4-dihydro-1-methyl-2(1H)-isoquinolinecarboxamide.

In a first embodiment, $R^1$ is hydrogen. In a second embodiment, $R^1$ is halogen. In a particular aspect of this embodiment $R^1$ is bromo. In a third embodiment, $R^1$ is cyano. In a fourth embodiment, $R^1$ is hydroxy. In a fifth embodiment, $R^1$ is optionally substituted $C_{1-6}$ alkyl. In one aspect of that embodiment, $R^1$ is $C_{1-6}$ alkyl. In another aspect of this embodiment, $R^1$ is $C_{1-6}$ alkyl substituted by hydroxy. In a particular aspect of this embodiment, $R^1$ is hydroxymethyl. In a sixth embodiment, $R^1$ is optionally substituted $C_{1-6}$ alkoxy. In one aspect of this embodiment, $R^1$ is $C_{1-6}$ alkoxy. In a particular aspect of said embodiment, $R^1$ is methoxy. In a seventh embodiment, $R^1$ is optionally substituted $C_{1-6}$ alkylsulfanyl. In one aspect of this embodiment, $R^1$ is $C_{1-6}$ alkylsulfanyl. In a particular aspect of this embodiment, $R^1$ is methylsulfanyl. In an eighth embodiment, $R^1$ is optionally substituted $C_{1-6}$ alkylsulfinyl. In one aspect of this embodiment, $R^1$ is $C_{1-6}$ alkylsulfinyl. In a particular aspect of this embodiment, $R^1$ is methylsulfinyl. In a ninth embodiment, $R^1$ is optionally substituted $C_{1-6}$ alkylsulfonyl. In one aspect of this embodiment, $R^1$ is $C_{1-6}$ alkylsulfonyl. In a particular aspect of this embodiment, $R^1$ is methylsulfonyl. In a tenth embodiment, $R^1$ is optionally substituted ($C_{1-6}$alkylsulfonyl)amino. In one aspect of this embodiment, $R^1$ is ($C_{1-6}$alkylsulfonyl)amino. In a particular aspect of this embodiment, $R^1$ is (methylsulfonyl)amino.

Examples of optional substituents on $R^1$ include halogen or hydroxy. Particular examples of optional substituents on $R^1$ include hydroxy.

In one embodiment, the present invention provides for compounds of formula (I) wherein, $R^1$ is hydrogen, halogen, cyano or hydroxy; $C_{1-6}$ alkyl substituted by hydroxy, $C_{1-6}$ alkoxy, $C_{1-6}$ alkylsulfanyl, $C_{1-6}$ alkylsulfinyl, $C_{1-6}$ alkylsulfonyl or ($C_{1-6}$alkylsulfonyl)amino.

In a particular embodiment, $R^1$ is hydrogen, halogen, hydroxy, $C_{1-6}$-alkyl substituted by hydroxy, $C_{1-6}$ alkoxy, $C_{1-6}$ alkylsulfanyl, $C_{1-6}$ alkylsulfinyl, $C_{1-6}$ alkylsulfonyl or ($C_{1-6}$-alkylsulfonyl)amino.

Suitably, $R^1$ is hydrogen, bromo, cyano, hydroxy, hydroxymethyl, methoxy, methylsulfanyl, methylsulfinyl, methylsulfonyl, or (methylsulfonyl)amino. Illustratively, $R^1$ is hydrogen, halogen, hydroxy, hydroxymethyl, methoxy, methylsulfanyl, methylsulfinyl, methylsulfonyl, or (methylsulfonyl)amino.

Particularly, $R^1$ is hydrogen, bromo, methoxy, methylsulfanyl, or (methylsulfonyl)amino.

In a particular embodiment, $R^1$ is hydrogen or (methylsulfonyl)amino. In a preferred embodiment, $R^1$ is hydrogen.

In a first embodiment, $R^2$ is hydrogen. In a second embodiment, $R^2$ is cyano. In a third embodiment, $R^2$ is halogen. In one aspect of this embodiment, $R^2$ is chloro. In another aspect of this embodiment, $R^2$ is fluoro. In a fourth embodiment, $R^2$ is optionally substituted $C_{1-6}$ alkyl. In one aspect of this embodiment, $R^2$ is $C_{1-6}$ alkyl. In a particular aspect of this embodiment, $R^2$ is methyl. In another aspect of this embodiment, $R^2$ is $C_{1-6}$ alkyl substituted by hydroxy. In a particular aspect of this embodiment, $R^2$ is hydroxymethyl. In a further aspect of this embodiment $R^2$ is $C_{1-6}$ alkyl substituted by one or more halogens. In a particular aspect of this embodiment, $R^2$ is trifluoromethyl. In a fifth embodiment, $R^2$ is optionally substituted $C_{1-6}$ alkoxy. In one aspect of this embodiment, $R^2$ is $C_{1-6}$ alkoxy. In a particular aspect of said embodiment, $R^2$ is methoxy. In a sixth embodiment, $R^2$ is optionally substituted $C_{1-6}$ alkylsulfanyl. In one aspect of this embodiment, $R^2$ is $C_{1-6}$ alkylsulfanyl. In a particular aspect of this embodiment, $R^2$ is methylsulfanyl. In a seventh embodiment, $R^2$ is optionally substituted $C_{1-6}$ alkylsulfinyl. In one aspect of this embodiment, $R^2$ is $C_{1-6}$ alkylsulfinyl. In a particular aspect of this embodiment, $R^2$ is methylsulfinyl. In an eighth embodiment, $R^2$ is optionally substituted $C_{1-6}$ alkylsulfonyl. In one aspect of this embodiment, $R^2$ is $C_{1-6}$ alkylsulfonyl. In a particular aspect of this embodiment, $R^2$ is methylsulfonyl. In a ninth embodiment, $R^2$ is optionally substituted ($C_{1-6}$alkylsulfonyl)amino. In one aspect of this embodiment, $R^2$ is ($C_{1-6}$alkylsulfonyl)amino. In a particular aspect of this embodiment, $R^2$ is (methylsulfonyl)amino. In a tenth embodiment, $R^2$ is optionally substituted ($C_{1-6}$ alkylsulfonyl)amino($C_{1-6}$ alkyl). In one aspect of this embodiment, $R^2$ is ($C_{1-6}$ alkylsulfonyl)amino($C_{1-6}$ alkyl). In a particular aspect of this embodiment, $R^2$ is methylsulfonylaminomethyl. In an eleventh embodiment, $R^2$ is optionally substituted $C_{1-6}$ alkylamido. In one aspect of this embodiment, $R^2$ is $C_{1-6}$ alkylamido. In a particular aspect of this embodiment, $R^2$ is methylcarbamoyl. In a twelfth embodiment, $R^2$ is optionally substituted ($C_{1-6}$ alkylacyl)amino. In one aspect of this embodiment, $R^2$ is ($C_{1-6}$ alkylacy)lamino. In a particular aspect of this embodiment, $R^2$ is acetamido. In a thirteenth embodiment, $R^2$ is optionally substituted ($C_{1-6}$ alkylacyl)amino($C_{1-6}$ alkyl). In one aspect of this embodiment, $R^2$ is ($C_{1-6}$ alkylacyl)amino($C_{1-6}$ alkyl). In a particular aspect of this embodiment, $R^2$ is acetylaminomethyl. In a fourteenth embodiment, $R^2$ is optionally substituted heteroaryl. In one aspect of this embodiment, $R^2$ is heteroaryl. In a particular aspect of this embodiment $R^2$ is pyrazolyl.

Examples of optional substituents on $R^2$ include halogen, hydroxy, $C_{1-6}$alkylsulfonyl and $C_{1-6}$alkylacyl. Suitable substitutents on $R^2$ include halogen and hydroxy. Particular examples of optional substituents on $R^2$ include fluoro and hydroxy.

In one embodiment the present invention provides for compounds of formula (I) wherein $R^2$ is hydrogen, cyano, halogen, $C_{1-6}$ alkyl, $C_{1-6}$ alkyl substituted by hydroxy, $C_{1-6}$ alkyl substituted by one or more halogens, $C_{1-6}$ alkoxy, $C_{1-6}$ alkylsulfanyl, $C_{1-6}$ alkylsulfinyl, $C_{1-6}$ alkylsulfonyl, ($C_{1-6}$-alkylsulfonyl)amino, ($C_{1-6}$ alkylsulfonyl)amino($C_{1-6}$ alkyl), $C_{1-6}$ alkylamido, ($C_{1-6}$ alkylacyl)amino, ($C_{1-6}$ alkylacyl)amino($C_{1-6}$ alkyl), or heteroaryl.

In another embodiment, the present invention provides for compounds of formula (I) wherein $R^2$ is hydrogen, halogen, $C_{1-6}$ alkyl unsubstituted or substituted by one or more halogens, $C_{1-6}$-alkyl hydroxy, $C_{1-6}$ alkoxy, $C_{1-6}$ alkylsulfanyl, $C_{1-6}$ alkylsulfinyl, $C_{1-6}$ alkylsulfonyl, cyano, $C_{1-6}$ alkylamido, pyrazolyl, or a group of formula —$CH_2R^{2a}$, —$NHR^2$ or —$CH_2NHR^{2a}$ wherein $R^{2a}$ is selected from $C_{1-6}$ alkylacyl or $C_{1-6}$ alkylsulfonyl.

Illustratively, $R^2$ is hydrogen, halogen, methyl, trifluoromethyl, hydroxymethyl, methoxy, methylsulfanyl, methylsulfinyl, methylsulfonyl, cyano, methylcarbamoyl, 1H-pyrazol-4-yl or a group of formula —$CH_2R^{2a}$, —$NHR^2$ or —$CH_2NHR^{2a}$ wherein $R^{2a}$ is selected from acetyl or methylsulfonyl.

Apositely, $R^2$ is chloro, methyl, trifluoromethyl, methoxy, methylsulfanyl, or cyano.

Appropriately, $R^2$ is halogen or cyano.

Particularly, $R^2$ is chloro or cyano.

Preferably, $R^2$ is chloro.

In an alternative embodiment $R^1$ and $R^2$ are linked together to form with the adjacent aromatic group a bicycle of formula (i):

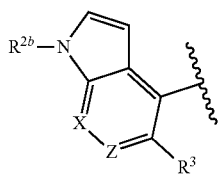

(i)

wherein $R^{2b}$ is hydrogen or methylsulfonyl.

In first alternative embodiment, $R^1$ and $R^2$ are linked together to form with the adjacent aromatic group an optionally substituted 1H-pyrrolo[2,3-b]pyridin-4-yl group.

In a second alternative embodiment, $R^1$ and $R^2$ are linked together to form with the adjacent aromatic group an optionally substituted 1H-indol-4-yl group.

In a particular alternative embodiment, $R^1$ and $R^2$ are linked together to form with the adjacent aromatic group 5-methylsulfonyl-1H-pyrrolo[2,3-b]pyridin-4-yl or 5-chloro-1H-indol-4-yl.

In a first embodiment, $R^3$ is halogen. In one aspect of this embodiment, $R^3$ is chloro. In another aspect of this embodiment, $R^3$ is bromo. In a second embodiment, $R^3$ is $C_{1-6}$ alkyl. In a particular aspect of this embodiment, $R^3$ is methyl. In a third embodiment, $R^3$ is $C_{1-6}$ alkoxy. In a particular aspect of this embodiment, $R^3$ is methoxy. In a fourth embodiment, $R^3$ is cyano.

In one embodiment, the present invention provides for compounds of formula (I) wherein $R^3$ is halogen, $C_{1-6}$ alkyl, $C_{1-6}$ alkoxy or cyano.

In one aspect of that embodiment, $R^3$ is halogen, methyl, methoxy or cyano.

In a particular aspect of that embodiment, $R^3$ is halogen or cyano.

In a further particular aspect of that embodiment, $R^3$ is chloro or cyano.

In another embodiment, $R^3$ is halogen, $C_{1-6}$ alkyl or $C_{1-6}$ alkoxy.

In one aspect of that embodiment, $R^3$ is halogen, methyl or methoxy.

In a particular aspect of that embodiment, $R^3$ is bromo or chloro. In a preferred aspect of that embodiment, $R^3$ is chloro. Generally, $R^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ alkylaminocarbonyloxy.

In a first embodiment, $R^4$ is hydrogen. In a second embodiment, $R^4$ is halogen. In one aspect of this embodiment, $R^4$ is fluoro. In a third embodiment, $R^4$ is $C_{1-6}$ alkyl. In a particular aspect of this embodiment, $R^4$ is methyl. In a fourth embodiment, $R^4$ is $C_{1-6}$ alkoxy. In a particular aspect of said embodiment, $R^4$ is methoxy. In a fifth embodiment, $R^4$ is hydroxy. In a sixth embodiment, $R^4$ is $C_{1-6}$ alkylsulfonyl. In a particular aspect of this embodiment, $R^4$ is methylsulfonyl. In a seventh embodiment, $R^4$ is $C_{1-6}$ alkoxycarbonyloxy. In a particular aspect of this embodiment, $R^4$ is (methoxycarbonyl)oxy. In an eighth embodiment, $R^4$ is $C_{1-6}$ alkylaminocarbonyloxy. In a particular aspect of this embodiment, $R^4$ is (methylcarbamoyl)oxy.

Suitably, $R^4$ is hydrogen, halogen, methyl, hydroxy, methoxy, methylsulfonyl, (methoxycarbonyl)oxy or (methylcarbamoyl)oxy.

Particularly, $R^4$ is hydrogen, hydroxy, (methoxycarbonyl)oxy or (methylcarbamoyl)oxy.

Illustratively, $R^4$ is hydrogen, hydroxy or (methylcarbamoyl)oxy.

Particularly, $R^4$ is hydrogen.

Generally, $R^{4'}$ is hydrogen, halogen or $C_{1-6}$ alkyl.

In a first embodiment, $R^{4'}$ is hydrogen. In a second embodiment, $R^{4'}$ is halogen. In a particular aspect of this embodiment, $R^{4'}$ is fluoro. In a third embodiment, $R^{4'}$ is $C_{1-6}$ alkyl. In a particular aspect of this embodiment, $R^{4'}$ is methyl.

Suitably, $R^{4'}$ is hydrogen, halogen, methyl.

Particularly, $R^{4'}$ is hydrogen.

In an alternative embodiment, $R^4$ and $R^{4'}$ together form a oxo group.

In a first embodiment, $R^5$ is hydrogen. In a second embodiment, $R^5$ is cyano. In a third embodiment, $R^5$ is hydroxy.

In a fourth embodiment, $R^5$ is optionally substituted $C_{1-6}$ alkyl. In a first aspect of that embodiment, $R^5$ is optionally substituted methyl. In a second aspect of this embodiment, $R^5$ is optionally substituted ethyl. In a third aspect of this embodiment, $R^5$ is optionally substituted isopropyl. In a fourth aspect of this embodiment, $R^5$ is optionally substituted propyl.

In a fifth embodiment, $R^5$ is optionally substituted $C_{1-6}$-alkylsulfonyl. In first aspect of this embodiment, $R^5$ is optionally substituted methylsulfonyl. In a second aspect of this embodiment, $R^5$ is optionally substituted ethylsulfonyl. In a third aspect of this embodiment, $R^5$ is optionally substituted isopropylsulfonyl.

In a sixth embodiment, $R^5$ is optionally substituted $C_{1-6}$-alkylsulfonylamino. In one aspect of this embodiment, $R^5$ is optionally substituted methylsulfonylamino.

In a seventh embodiment, $R^5$ is $C_{1-6}$ alkylsulfonylamino ($C_{1-6}$ alkyl). In first aspect of this embodiment, $R^5$ is optionally substituted methylsulfonylaminomethyl. In a second aspect of this embodiment, $R^5$ is optionally substituted methylsulfonylaminoethyl.

In an eighth embodiment, $R^5$ is an optionally substituted heterocycle. In a first aspect of this embodiment $R^5$ is optionally substituted oxazolyl. In a second aspect, $R^5$ is optionally substituted pyridinyl. In a third aspect, $R^5$ is optionally substituted pyrazolyl. In a fourth aspect, $R^5$ is optionally substituted triazolyl. In a fifth aspect, $R^5$ is optionally substituted morpholinyl. In a sixth aspect, $R^5$ is optionally substituted 4,5-dihydroimidazolyl.

In a ninth embodiment, $R^5$ is optionally substituted $C_{1-6}$ alkylacylamino($C_{1-6}$ alkyl). In a first aspect of this embodiment, $R^5$ is optionally substituted (methylcarbonylamino)methyl. In a second aspect, $R^5$ is optionally substituted (methylcarbonylamino)ethyl.

In a tenth embodiment, $R^5$ is optionally substituted $C_{1-6}$ alkylureido($C_{1-6}$ alkyl). In one aspect of this embodiment, $R^5$ is optionally substituted (methylureido)methyl.

In an eleventh embodiment, $R^5$ is optionally substituted $C_{1-6}$alkylcarbamate($C_{1-6}$ alkyl). In one aspect of this embodiment, $R^5$ is optionally substituted (methylcarbamate)methyl.

In a twelfth embodiment, $R^5$ is optionally substituted amido. In a first aspect of this embodiment, $R^5$ is carbamoyl. In a second aspect of this embodiment, $R^5$ is optionally substituted $C_{1-6}$alkylamido. In a third aspect of this embodiment, $R^5$ is optionally substituted $C_{3-8}$heterocycloalkylamido. In a fourth aspect of this embodiment, $R^5$ is optionally substituted heterocyclylamido.

In a thirteenth embodiment, $R^5$ is optionally substituted $C_{1-6}$alkoxycarbonyloxy($C_{1-6}$alkyl). In one aspect, $R^5$ is optionally substituted (methoxycarbonyloxy)methyl.

In a fourteenth embodiment, $R^5$ is optionally substituted amino group. In one aspect of this embodiment, $R^5$ is amino.

In a fifteenth embodiment, $R^5$ is optionally substituted N-cyano-S—($C_{1-6}$-alkyl)sulfonimidoyl. In one aspect of this embodiment, $R^5$ is optionally substituted N-cyano-S-(methyl)sulfonimidoyl.

In a sixteenth embodiment, $R^5$ is optionally substituted N,S-(di-$C_{1-6}$-alkyl)sulfonimidoyl. In a first aspect, $R^5$ is optionally substituted N-methyl-S-methyl-sulfonimidoyl. In a second aspect, $R^5$ is optionally substituted N-ethyl-S-methyl-sulfonimidoyl.

In a seventeenth embodiment, $R^5$ is optionally substituted aminosulfinyl. In one aspect of this embodiment, $R^5$ is optionally substituted $C_{1-6}$-alkylaminosulfinyl.

In an eighteenth embodiment, $R^5$ is optionally substituted $C_{1-6}$-alkylsulfinyl. In one aspect of this embodiment, $R^5$ is optionally substituted methylsulfinyl.

In a nineteenth embodiment, $R^5$ is optionally substituted aminosulfonyl. In a first aspect of this embodiment, $R^5$ is sulfamoyl. In a second aspect of this embodiment, $R^5$ is optionally substituted $C_{1-6}$ alkylaminosulfonyl. In a third aspect of this embodiment, $R^5$ is optionally substituted heterocyclylaminosulfonyl. In a fourth aspect of this embodiment, $R^5$ is optionally substituted $C_{3-8}$heterocycloalkylaminosulfonyl In a twentieth embodiment, $R^5$ is optionally substituted (di-$C_{1-6}$-alkyl)(oxido)-$\lambda^6$-sulfanylidene-amino. In a first aspect of this embodiment, $R^5$ is optionally substituted (1-oxidotetrahydro-1H-1$\lambda^4$-thiophen-1-ylidene)amino. In a second aspect of this embodiment, $R^5$ is optionally substituted (di-methyl)(oxido)-$\lambda^6$-sulfanylidene-amino. In a third aspect of this embodiment, $R^5$ is optionally substituted (4-oxido-1,4-$\lambda^4$-oxathian-4-ylidene)amino.

In a twenty-first embodiment, $R^5$ is optionally substituted amino($C_{1-6}$ alkyl). In a first aspect of this embodiment, $R^5$ is optionally substituted $C_{3-8}$heterocycloalkylamino($C_{1-6}$ alkyl). In a second aspect of this embodiment, $R^5$ is optionally substituted $C_{1-6}$ alkylamino ($C_{1-6}$ alkyl).

In a twenty-second embodiment, $R^5$ is optionally substituted amido($C_{1-6}$ alkyl). In a first aspect of this embodiment, $R^5$ is optionally substituted carbamoyl($C_{1-6}$ alkyl). In a second aspect of this embodiment, $R^5$ is optionally substituted $C_{3-8}$cycloalkylamido($C_{1-6}$ alkyl). In a third aspect, $R^5$ is optionally substituted $C_{3-8}$heterocycloalkylamido($C_{1-6}$ alkyl).

In one embodiment according to the present invention, $R^5$ is hydrogen, cyano, hydroxy, amino, carbamoyl, sulfamoyl, $C_{1-6}$ alkylsulfinyl, $C_{1-6}$ alkylaminosulfinyl, $C_{1-6}$ alkylsulfonyl optionally substituted by $C_{1-6}$ alkoxy or heterocycle, N-cyano-S—($C_{1-6}$-alkyl)sulfonimidoyl, N,S-(di-$C_{1-6}$-alkyl) sulfonimidoyl, (di-$C_{1-6}$-alkyl)(oxido)-$\lambda^6$-sulfanylidene-amino, ($C_{1-6}$ alkylsulfonyl)amino; or $R^5$ is $C_{1-6}$ alkyl mono- or polysubstituted by hydroxy, halogen, $C_{1-6}$ alkylsulfanyl, $C_{1-6}$ alkylsulfonyl, ($C_{1-6}$ alkylsulfonyl)amino, ($C_{1-6}$-alkylacyl)amino, $C_{1-6}$ alkylureido, $C_{1-6}$ alkylcarbamate, $C_{1-6}$ alkoxycarbonyloxy; or $R^5$ is an heterocycle optionally mono- or polysubstituted by $C_{1-6}$ alkyl or $C_{1-6}$ alkylsulfonyl; or $R^5$ is an amido group selected from $C_{1-6}$ alkylamido optionally mono- or polysubstituted by halogen, substituted or unsubstituted heterocyclylamido, $C_{3-8}$ heterocycloalkylamido optionally mono- or polysubstituted by $C_{1-6}$ alkyl, halogens or hydroxy; or $R^5$ is an aminosulfonyl group selected from $C_{1-6}$ alkylaminosulfonyl optionally substituted by one or more halogens or cyano, heterocyclylaminosulfonyl or $C_{3-8}$ heterocycloalkylaminosulfonyl optionally substituted by one or more halogens.

Typically, $R^5$ is hydrogen, cyano or hydroxy; or methyl, ethyl, isopropryl, propyl, methylsulfonyl, ethylsulfonyl, isopropylsulfonyl, methylsufonylamino, methylsulfonylaminomethyl, methylsulfonylaminoethyl, pyridinyl, pyrazolyl, triazolyl, morpholinyl, oxazolyl, 4,5-dihydroimidazolyl, (methylcarbonylamino)methyl, (methylcarbonylamino) ethyl, (methylureido)methyl, (methylcarbamate)methyl, carbamoyl, methylcarbamoyl, (dimethyl)carbamoyl, (isopropyl)carbamoyl, (ethyl)carbamoyl, (diisopropyl)carbamoyl, pyrrolidin-1-yl-carbonyl, morpholin-1-ylcarbonyl, piperidin-1-ylcarbonyl, pyrridinylamido, (triazolyl)amido, (methoxycarbonyloxy)methyl, (methylsulfanyl)methyl, amino, N-cyano-S-(methyl)sulfonimidoyl, N-methyl-S-methyl-sulfonimidoyl, N-ethyl-S-methyl-sulfonimidoyl, (dimethylamino)sulfinyl, methylsulfinyl, sulfamoyl, (methylamino)sulfonyl, (ethylamino)sulfonyl, (isopropylamino) sulfonyl, triazolylaminosulfonyl, (pyrrolidinyl-1-yl)sulfonyl, (1-oxidotetrahydro-1H-1$\lambda^4$-thiophen-1-ylidene)amino, (di-methyl)(oxido)-$\lambda^6$-sulfanylidene-amino, (4-oxido-1,4-$\lambda^4$-oxathian-4-ylidene)amino, (morpholin-yl)ethyl, (methylamino)ethyl, carbamoylmethyl, cyclopropylamidomethyl or oxetanylamidomethyl, any of which groups may be optionally substituted by one or more substituents.

Typical examples of optional substituents on $R^5$ include one, two or three substituents independently selected from halogen, hydroxy, cyano, oxo, $C_{1-6}$ alkyl, $C_{1-6}$ alkoxy, $C_{1-6}$ alkylsulfonyl, $C_{1-6}$alkylsulfanyl, (methyl)oxazolyl, morpholinyl, tetrahydropyranyl, amino, trifluoromethyl and (di-methyl)(oxido)-$\lambda^6$-sulfanylidene-amino.

Illustrative examples of optional substituents on $R^5$ include one, two or three substituents independently selected from chloro, fluoro, hydroxy, cyano, oxo, methyl, methoxy, methylsulfanyl, methylsulfonyl, [(5-methyl)-1,2-oxazol-3-yl], tetrahydro-pyran-4-yl, morpholin-4-yl, amino, trifluoromethyl and (di-methyl)(oxido)-$\lambda^6$-sulfanylidene-amino.

In a particular aspect according to the present invention, $R^5$ is hydrogen, cyano, hydroxy, amino, methylsulfinyl, (dimethylamino)sulfinyl, N-cyano-S-methylsulfonimidoyl, N,S-dimethylsulfonimidoyl or (1-oxidotetrahydro-1H-1$\lambda^4$-thiophen-1-ylidene)amino; or $R^5$ is a $C_{1-4}$ alkyl group mono- or polysubstituted by halogen, hydroxy, (methoxycarbonyl)oxy, methylsulfanyl or methylsulfonyl; or $R^5$ is an heterocycle selected from 1,2-oxazol-4-yl or 4,5-dihydro-1H-imidazol-2-yl and optionally substituted by methyl or methylsulfonyl; or $R^5$ is a group selected from —(CH$_2$)$_n$NHR$^{5a}$, —CONR$^{5b}$R$^{5c}$ or —SO$_2$R$^{5d}$ wherein R$^{5a}$ is acetyl, methylcarbamoyl, methylsulfonyl, methoxycarbonyl, or substituted or unsubstituted pyridinyl; n is 0, 1 or 2; R$^{5b}$ is hydrogen or a $C_{1-4}$ alkyl optionally substituted by one or more fluoro, a substituted or unsubstituted triazolyl or a substituted or unsubstituted pyridinyl.

$R^{5c}$ is hydrogen or $C_{1-4}$ alkyl.

Alternatively, R$^{5b}$ and R$^{5c}$ form together with the nitrogen a ring selected from a substituted or unsubstituted pyrrolidinyl, a substituted or unsubstituted morpholinyl, or a substituted or unsubstituted piperidinyl.

R$^{5d}$ is amino, a substituted or unsubstituted pyrrolidinyl; or R$^{5d}$ is a $C_{1-4}$ alkyl optionally substituted by methoxy, a substituted or unsubstituted pyridinyl, a substituted or unsubstituted 1,2-oxazolyl or a substituted or unsubstituted tetrahydro-2H-pyranyl; or R$^{5d}$ is an amino group mono- or disubstituted by a $C_{1-4}$ alkyl optionally substituted by a fluoro, cyano or a substituted or unsubstituted triazolyl.

Typical values of $R^5$ include hydrogen, cyano, hydroxy, (hydroxy)methyl, (methylsulfanyl)methyl, (methylsulfonyl)methyl, (trifluoromethyl)(hydroxy)methyl, [(di-methyl)(oxido)-$\lambda^6$-sulfanylidene-amino]methyl, (hydroxy)(difluoro)ethyl, (amino)(difluoro)ethyl, (morpholinyl)(difluoro)ethyl, (hydroxy)isopropyl, (hydroxy)propyl, methylsulfonyl, [(5-methyl)-1,2-oxazol-3-yl]methylsulfonyl, (tetrahydro-2H-pyran-4-yl)methylsulfonyl, (methoxy)methylsulfonyl, ethylsulfonyl, isopropylsulfonyl, methylsulfonylamino, methylsulfonylaminomethyl, methylsulfonylaminoethyl, oxazolyl, pyridinyl, (amino)pyridinyl, pyrazolyl, (cyano)pyrazolyl, (trifluoromethyl)pyrazolyl, (methyl)pyrazolyl, (dimethyl)pyrazolyl, triazolyl, (oxo)morpholinyl, (dimethyl)oxazolyl, (methylsulfonyl)4,5-dihydroimidazolyl, (methylcarbonylamino)methyl, (methylcarbonylamino)(difluoro)ethyl, (methylureido)methyl, (methylcarbamate)methyl, carbamoyl, (trifluoromethyl)methylamido, (dimethyl)amido, (isopropyl)amido, (ethyl)amido, (diisopropyl)amido, (methyl)pyrrolidin-1-yl-carbonyl, (dimethyl)pyrrolidin-1-yl-carbonyl, (hydroxy)pyrrolidin-1-yl-carbonyl, (difluoro)pyrrolidin-1-yl-carbonyl, pyrrolidin-1-yl-carbonyl, morpholin-1-ylcarbonyl, (trifluoromethyl)piperidin-1-ylcarbonyl, pyridinylamido, (triazolyl)amido, (methoxycarbonyloxy)methyl, amino, N-cyano-S-(methyl)sulfonimidoyl, N-methyl-S-methyl-sulfonimidoyl, N-ethyl-S-methyl-sulfonimidoyl, (dimethylamino)sulfonyl, (trifluoromethyl)methylsulfinyl, sulfamoyl, (methylamino)sulfonyl, (trifluoromethyl)methylaminosulfonyl, (cyano)methylaminosulfonyl, (ethylamino)sulfonyl, (isopropylamino)sulfonyl, triazolylaminosulfonyl, (difluoro)pyrrolidinyl-1-yl-sulfonyl, (1-oxidotetrahydro-1H-1$\lambda^4$-thiophen-1-ylidene)amino, (di-methyl)(oxido)-$\lambda^6$-sulfanylidene-amino, (4-oxido-1,4-$\lambda^4$-oxathian-4-ylidene)amino, (morphoIilin-yl)ethyl, (methylamino)(difluoro)ethyl, (carbamoyl)(difluoro)methyl, ((methyl)cyclopropyl))amido(difluoro)methyl and ((methyl)oxetanyl)amido(difluoro)methyl.

In a first particular embodiment according to the present invention, R$^5$ is hydrogen, hydroxy, amino, N,S-dimethyl-sulfonimidoyl or (1-oxidotetrahydro-1H-1$\lambda^4$-thiophen-1-ylidene)amino; or R$^5$ is a $C_{1-4}$ alkyl group substituted by hydroxy, halogen, methylsulfanyl, methylsulfonyl or (methoxycarbonyl)-oxy; or R$^5$ is a 1,2-oxazol-4-yl substituted by methyl. Additional R$^5$ groups according to this particular embodiment include $C_{1-4}$ alkyl group substituted by amino, methylcarbonyl, morpholinyl, carbamoyl, (N-(1-methyl)cyclopropyl)aminocarbonyl or 1-(methyl)oxetanyl)aminocarbonyl; pyridine-2-yl, pyridine-3yl substituted by amino, pyridine-4-yl substituted by amino, 1H-pyrazol-4-yl optionally substituted by cyano, trifluoromethyl or methyl, 2H-1,2,3-triazol-4yl or morpholinyl substituted by an oxo group; di-methyl)(oxido)-$\lambda^6$-sulfanylidene-amino, (4-oxido-1,4-$\lambda^4$-oxathian-4-ylidene)amino, N-ethyl-S-methyl-sulfonimidoyl and [(di-methyl)(oxido)-$\lambda^6$-sulfanylidene-amino]methyl.

In a first aspect of embodiment, R$^5$ is hydrogen, hydroxy, amino, N,S-dimethyl-sulfonimidoyl, (1-oxidotetrahydro-1H-1$\lambda^4$-thiophen-1-ylidene)amino, hydroxymethyl, (methylsulfanyl)methyl, (methylsulfonyl)methyl, [(methoxycarbonyl)oxy]methyl, 1-hydroxyethyl, 2,2,2-trifluoro-1-hydroxyethyl, or 3,5-dimethyl-1,2-oxazol-4-yl. Additional R$^5$ groups according to this particular aspect, include 1,1-difluoro-2-hydroxyethyl, 2-amino-1,1-difluoroethyl, 1-acetamido-2,2-difluoroethyl, 1,1-difluoro-2(morpholin-4-yl)ethyl, 1,1-difluoro-2-(methylamino)ethyl, (carbamoyl)(difluoro)methyl, (N-(1-methyl)cyclopropyl))aminocarbonyl)(difluoro)methyl, N-(1-methyl)oxetan-3-yl))aminocarbonyl)(difluoro)methyl, 1-hydroxy-propyl, pyridine-2-yl, 6-amino-pyridin-3-yl, 2-amino-pyridin-4-yl, 2-amino-pyridin-3-yl, 1H-pyrazol-4-yl, 3-cyano-1H-pyrazol-4-yl, 3-trifluoromethyl-1H-pyrazol-4-yl, 1-methyl-1H-pyrazol-4-yl, 3,5-dimethyl-1H-pyrazol-4-yl, 2H-1,2,3-triazol-4-yl, morpholin-3-one, (di-methyl)(oxido)-$\lambda^6$-sulfanylidene-amino, (4-oxido-1,4-$\lambda^4$-oxathian-4-ylidene)amino, N-ethyl-S-methyl-sulfonimidoyl and [(di-methyl)(oxido)-$\lambda^6$-sulfanylidene-amino]methyl.

In a second aspect of this embodiment, R$^5$ is hydrogen, hydroxy, hydroxymethyl, (methyl-sulfanyl)methyl, 1-hydroxyethyl, 2,2,2-trifluoro-1-hydroxyethyl or 3,5-dimethyl-1,2-oxazol-4-yl.

In a second particular embodiment according to the present invention, R$^5$ is a group of formula —(CH$_2$)$_n$NHR$^{5a}$ wherein R$^{5a}$ is acetyl, methylsulfonyl or methoxycarbonyl, and n is 0, 1 or 2.

In a particular aspect of this embodiment, R$^5$ is a group of formula —(CH$_2$)$_n$NHR$^{5a}$ wherein R$^{5a}$ is methylsulfonyl and n is 0 or 1.

In a third particular embodiment according to the present invention, R$^5$ is —CONR$^{5b}$R$^{5c}$ wherein R$^{5b}$ is $C_{1-4}$ alkyl optionally substituted by one or more fluoro, or triazolyl; R$^5$ is hydrogen or $C_{1-4}$ alkyl; or R$^{5b}$ and R$^{5c}$ form together with the nitrogen a ring selected from pyrrolidinyl optionally mono- or di-substituted by methyl or fluoro, morpholinyl, or piperidinyl substituted by trifluoromethyl.

In a particular aspect of this embodiment, R$^5$ is —CONR$^{5b}$R$^{5c}$ wherein R$^{5b}$ is ethyl, 2-propanyl, 2,2,2-trifluoroethyl, 4H-1,2,4-triazol-3-yl; R$^{5c}$ is hydrogen or 2-propanyl; or $R^{5b}$ and $R^{5c}$ form together with the nitrogen a ring selected from pyrrolidin-1-yl, 2-methylpyrrolidin-1-yl, 2,5-dimethylpyrrolidin-1-yl, 3,3-difluoropyrrolidin-1-yl, morpholinyl, or 4-(trifluoromethyl)-piperidin-1-yl.

In another particular aspect of this embodiment, $R^5$ is —CONR$^{5b}$R$^{5c}$ wherein $R^{5b}$ is 2-propanyl, 2,2,2-trifluoroethyl, 4H-1,2,4-triazol-3-yl; $R^{5c}$ is hydrogen or 2-propanyl; or $R^{5b}$ and $R^{5c}$ form together with the nitrogen 2,5-dimethylpyrrolidin-1-yl.

In a fourth particular embodiment according to the present invention, $R^5$ is —SO$_2$R$^{5d}$ wherein $R^{5d}$ is amino, pyrrolidinyl substituted by one or more fluoro; or $R^{5d}$ is a $C_{1-4}$ alkyl optionally substituted by methoxy, pyridinyl, methyl-1,2-oxazolyl or tetrahydro-2H-pyranyl; or $R^{5d}$ is an amino group substituted by a $C_{1-4}$ alkyl optionally substituted by a one or more fluoro, cyano or triazolyl.

In a particular aspect of this embodiment, $R^5$ is —SO$_2$R$^{5d}$ wherein $R^{5d}$ is amino, 3,3-difluoropyrrolidin-1-yl, methyl, methoxymethyl, ethyl, 2-propanyl, pyridin-3-ylmethyl, (5-methyl-1,2-oxazol-3-yl)methyl, tetrahydro-2H-pyran-4-ylmethyl, methylamino, (cyanomethyl)amino, ethylamino, (2,2,2-trifluoroethyl)amino, propan-2-ylamino or (4H-1,2,4-triazol-3-yl)amino.

In another particular aspect of this embodiment, $R^5$ is —SO$_2$R$^{5d}$ wherein $R^{5d}$ is methyl, methoxymethyl, ethyl, 2-propanyl, tetrahydro-2H-pyran-4-ylmethyl, methylamino, (cyanomethyl)amino, ethylamino, (2,2,2-trifluoroethyl)amino, propan-2-ylamino or (4H-1,2,4-triazol-3-yl)amino.

Selected examples of $R^5$ groups are hydrogen, hydroxy, amino, cyano, methylsulfinyl, (dimethylamino)sulfinyl, N,S-dimethylsulfonimidoyl, (1-oxidotetrahydro-1H-1λ$^4$-thiophen-1-ylidene)amino, N-cyano-S-methylsulfonimidoyl, hydroxymethyl, (methylsulfanyl)methyl, (methylsulfonyl)methyl, [(methoxycarbonyl)oxy]methyl, 1-hydroxyethyl, 2,2,2-trifluoro-1-hydroxyethyl, 3,5-dimethyl-1,2-oxazol-4-yl, 1-(methylsulfonyl)-4,5-dihydro-1H-imidazol-2-yl, (acetylamino)methyl, (methyl-sulfonyl)amino, [(methylsulfonyl)amino]methyl, 2-[(methylsulfonyl)amino]ethyl, [(methyl-carbamoyl)amino]methyl, [(methoxycarbonyl)amino]methyl, carbamoyl, methyl-carbamoyl, dimethylcarbamoyl, ethylcarbamoyl, (2,2,2-trifluoroethyl)carbamoyl, propan-2-ylcarbamoyl, dipropan-2-ylcarbamoyl, 4H-1,2,4-triazol-3-ylcarbamoyl, pyridin-2-ylcar-bamoyl, pyrrolidin-1-ylcarbonyl, (2-methylpyrrolidin-1-yl)carbonyl, (2,5-dimethylpyrrolidin-1-yl)carbonyl, (3-hydroxypyrrolidin-1-yl)carbonyl, (3,3-difluoropyrrolidin-1-yl)carbonyl, morpholin-4-ylcarbonyl, [4-(trifluoromethyl)piperidin-1-yl]carbonyl, sulfamoyl, pyrrolidin-1-ylsulfonyl, (3,3-difluoropyrrolidin-1-yl)sulfonyl, methylsulfonyl, (methoxymethyl)sulfonyl, ethylsulfonyl, propan-2-ylsulfonyl, (pyridin-3-ylmethyl)sulfonyl, [(5-methyl-1,2-oxazol-3-yl)methyl]sulfonyl, (tetrahydro-2H-pyran-4-ylmethyl)sulfonyl, methylsulfamoyl, (cyanomethyl)sulfamoyl, ethylsulfamoyl, (2,2,2-trifluoroethyl)sulfamoyl, propan-2-ylsulfamoyl, (4H-1,2,4-triazol-3-yl)sulfamoyl, 1,1-difluoro-2-hydroxyethyl, 2-amino-1,1-difluoroethyl, 1-acetamido-2,2-difluoroethyl, 1,1-difluoro-2(morpholin-4-yl)ethyl, 1,1-difluoro-2-(methylamino)ethyl, (carbamoyl)(difluoro)methyl, (N-(1-methyl)cyclopropyl))aminocarbonyl)(difluoro)methyl, N-(1-methyl)oxetan-3-yl))aminocarbonyl)(difluoro)methyl, 1-hydroxy-propyl, pyridine-2-yl, 6-amino-pyridin-3-yl, 2-amino-pyridin-4-yl, 2-amino-pyridin-3-yl, 1H-pyrazol-4-yl, 3-cyano-1H-pyrazol-4-yl, 3-trifluoromethyl-1H-pyrazol-4-yl, 1-methyl-1H-pyrazol-4-yl, 3,5-dimethyl-1H-pyrazol-4-yl, 2H-1,2,3-triazol-4-yl, morpholin-3-one, (di-methyl)(oxido)-λ$^6$-sulfanylidene-amino, (4-oxido-1,4-λ$^4$-oxathian-4-ylidene) amino, N-ethyl-S-methyl-sulfonimidoyl or [(di-methyl)(oxido)-λ$^6$-sulfanylidene-amino]methyl.

Selected examples of $R^5$ groups are hydrogen, hydroxy, amino, cyano, methylsulfinyl, (dimethylamino)sulfinyl, N,S-dimethylsulfonimidoyl, (1-oxidotetrahydro-1H-1λ$^4$-thiophen-1-ylidene)amino, N-cyano-S-methylsulfonimidoyl, hydroxymethyl, (methylsulfanyl)methyl, (methylsulfonyl)methyl, [(methoxycarbonyl)oxy]methyl, 1-hydroxyethyl, 2,2,2-trifluoro-1-hydroxyethyl, 3,5-dimethyl-1,2-oxazol-4-yl, 1-(methylsulfonyl)-4,5-dihydro-1H-imidazol-2-yl, (acetylamino)methyl, (methyl-sulfonyl)amino, [(methylsulfonyl)amino]methyl, 2-[(methylsulfonyl)amino]ethyl, [(methyl-carbamoyl)amino]methyl, [(methoxycarbonyl)amino]methyl, carbamoyl, methyl-carbamoyl, dimethylcarbamoyl, ethylcarbamoyl, (2,2,2-trifluoroethyl)carbamoyl, propan-2-ylcarbamoyl, dipropan-2-ylcarbamoyl, 4H-1,2,4-triazol-3-ylcarbamoyl, pyridin-2-ylcar-bamoyl, pyrrolidin-1-ylcarbonyl, (2-methylpyrrolidin-1-yl)carbonyl, (2,5-dimethylpyrrolidin-1-yl)carbonyl, (3-hydroxypyrrolidin-1-yl)carbonyl, (3,3-difluoropyrrolidin-1-yl)carbonyl, morpholin-4-ylcarbonyl, [4-(trifluoromethyl)piperidin-1-yl]carbonyl, sulfamoyl, pyrrolidin-1-ylsulfonyl, (3,3-difluoropyrrolidin-1-yl)sulfonyl, methylsulfonyl, (methoxymethyl)sulfonyl, ethylsulfonyl, propan-2-ylsulfonyl, (pyridin-3-ylmethyl)sulfonyl, [(5-methyl-1,2-oxazol-3-yl)methyl]sulfonyl, (tetrahydro-2H-pyran-4-ylmethyl)sulfonyl, methylsulfamoyl, (cyanomethyl)sulfamoyl, ethylsulfamoyl, (2,2,2-trifluoroethyl)sulfamoyl, propan-2-ylsulfamoyl or (4H-1,2,4-triazol-3-yl)sulfamoyl.

In a preferred embodiment, $R^5$ groups may be selected from hydrogen, hydroxy, amino, N,S-dimethylsulfonimidoyl, (1-oxidotetrahydro-1H-1λ$^4$-thiophen-1-ylidene)amino, hydroxymethyl, (methylsulfanyl)methyl, (methylsulfonyl)methyl, [(methoxycarbonyl)oxy]methyl, 1-hydroxyethyl, 2,2,2-trifluoro-1-hydroxyethyl, 3,5-dimethyl-1,2-oxazol-4-yl, (acetylamino)methyl, (methylsulfonyl)amino, [(methylsulfonyl)amino]methyl, 2-[(methylsulfonyl)amino]ethyl, [(methoxycarbonyl)amino]-methyl, ethylcarbamoyl, (2,2,2-trifluoroethyl)carbamoyl, dipropan-2-ylcarbamoyl, 4H-1,2,4-triazol-3-ylcarbamoyl, pyrrolidin-1-ylcarbonyl, (2-methylpyrrolidin-1-yl)carbonyl, (2,5-dimethylpyrrolidin-1-yl)carbonyl, (3,3-difluoropyrrolidin-1-yl) carbonyl, morpholin-4-yl-carbonyl, [4-(trifluoromethyl)piperidin-1-yl]carbonyl, sulfamoyl, (3,3-difluoropyrrolidin-1-yl)sulfonyl, methylsulfonyl, (methoxymethyl)sulfonyl, ethylsulfonyl, propan-2-ylsulfonyl, (pyridin-3-ylmethyl)sulfonyl, [(5-methyl-1,2-oxazol-3-yl)methyl]sulfonyl, (tetrahydro-2H-pyran-4-ylmethyl)sulfonyl, methylsulfamoyl, (cyanomethyl)sulfamoyl, ethylsulfamoyl, (2,2,2-trifluoroethyl)sulfamoyl, propan-2-ylsulfamoyl and (4H-1,2,4-triazol-3-yl)sulfamoyl.

In a particularly preferred embodiment, $R^5$ groups may be selected from hydrogen, hydroxy, hydroxymethyl, (methylsulfanyl)methyl, 1-hydroxyethyl, 2,2,2-trifluoro-1-hydroxyethyl, 3,5-dimethyl-1,2-oxazol-4-yl, (methylsulfonyl)amino, [(methylsulfonyl)amino]methyl, 2-[(methylsulfonyl)amino]ethyl, (2,2,2-trifluoroethyl)carbamoyl, dipropan-2-ylcarbamoyl, 4H-1,2,4-triazol-3-ylcarbamoyl, (2,5-dimethylpyrrolidin-1-yl)carbonyl, [4-(trifluoromethyl)piperidin-1-yl]carbonyl, methyl-sulfonyl, (methoxymethyl)sulfonyl, ethylsulfonyl, propan-2-ylsulfonyl, (tetrahydro-2H-pyran-4-ylmethyl)sulfonyl, methylsulfamoyl, (cyanomethyl)sulfamoyl, ethylsulfamoyl, (2,2,2-trifluoroethyl)sulfamoyl, propan-2-ylsulfamoyl and (4H-1,2,4-triazol-3-yl)sulfamoyl.

Typically, $R^6$ is hydrogen.

In a first embodiment, $R^7$ is hydrogen. In a second embodiment, $R^7$ is ($C_{1-6}$ alklysulfonyl)amino.

Illustratively, $R^7$ is either hydrogen or (methylsulfonyl) amino. In a preferred embodiment, $R^7$ is hydrogen.

In a first embodiment, X is $CR^9$. In a first aspect of this embodiment, $R^9$ is hydrogen. In a second aspect of this embodiment $R^9$ is halogen. In a third aspect of that embodiment, $R^9$ is $C_{1-6}$ alkyl substituted by hydroxy. In a fourth aspect of that embodiment, $R^9$ is $C_{1-6}$ alkylsulfinyl, for example methylsulfinyl.

In a second embodiment, X is N.

In a specific embodiment, X is either $CR^9$ or N, wherein $R^9$ is hydrogen, halogen or hydroxymethyl.

In a further specific embodiment, X is $CR^9$ wherein $R^9$ is hydrogen or fluoro, preferably hydrogen.

In a particular embodiment, X is N. In another particular embodiment, X is CH.

In one embodiment, Z is CH.

In one embodiment, Y is $CH_2$.

In a second embodiment, Y is NH.

In a particular embodiment, the 1-methyl-1,2,3,4-tetrahydroisoquinolin-5-yl has the (S) configuration.

In another particular embodiment, the 1-methyl-1,2,3,4-tetrahydroisoquinolin-5-yl has the (R) configuration.

In a particular embodiment, the present invention relates to tetrahydroisoquinoline derivatives according to formula I,

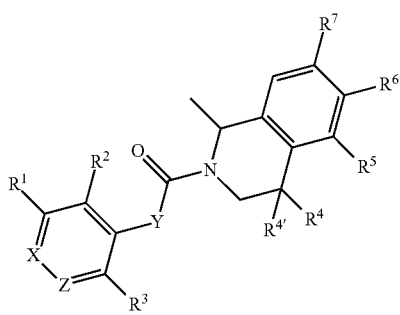

(I)

wherein $R^1$ is hydrogen, halogen, hydroxy, hydroxymethyl, methoxy, methylsulfanyl, methylsulfinyl, methylsulfonyl, hydroxymethyl or (methylsulfonyl)amino;

$R^2$ is hydrogen, halogen, methyl, trifluoromethyl, hydroxymethyl, methoxy, methylsulfanyl, methylsulfinyl, methylsulfonyl, cyano, methylcarbamoyl, 1H-pyrazol-4-yl or a group of formula —$CH_2R^{2a}$, —$NHR^{2a}$ or —$CH_2NHR^{2a}$ wherein $R^{2a}$ is selected from acetyl or methylsulfonyl;

or $R^1$ and $R^2$ are linked together to form with the adjacent aromatic group a bicycle of formula (i):

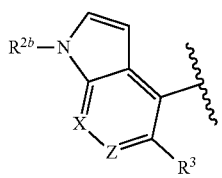

(i)

wherein $R^{2b}$ is hydrogen or methylsulfonyl.

$R^3$ is halogen, methyl or methoxy.

$R^4$ is hydrogen, halogen, methyl, hydroxy, methoxy, methylsulfonyl, (methoxycarbonyl)oxy or (methylcarbamoyl)oxy.

$R^{4'}$ is hydrogen, halogen, methyl; or $R^4$ and $R^{4'}$ together form a oxo group.

$R^5$ is hydrogen, cyano, hydroxy, amino, methylsulfinyl, (dimethylamino)sulfinyl, N-cyano-S-methylsulfonimidoyl, N,S-dimethylsulfonimidoyl or (1-oxidotetrahydro-1H-1$\lambda^4$-thiophen-1-ylidene)amino; or $R^5$ is a $C_{1-4}$ alkyl group mono- or polysubstituted by halogen, hydroxy, (methoxycarbonyl)oxy, methylsulfanyl or methylsulfonyl; or $R^5$ is an heterocycle selected from 1,2-oxazol-4-yl or 4,5-dihydro-1H-imidazol-2-yl and optionally substituted by methyl or methylsulfonyl; or $R^5$ is a group selected from —$(CH_2)_n$NHR$^{5a}$, —CONR$^{5b}$R$^{5c}$ or —$SO_2R^{5d}$ wherein $R^{5a}$ is acetyl, methylcarbamoyl, methylsulfonyl, methoxycarbonyl, or substituted or unsubstituted pyridinyl.

n is 0, 1 or 2.

$R^{5b}$ is hydrogen or a $C_{1-4}$ alkyl optionally substituted by one or more fluoro, a substituted or unsubstituted triazolyl or a substituted or unsubstituted pyridinyl.

$R^{5c}$ is hydrogen or $C_{1-4}$ alkyl;

or $R^{5b}$ and $R^{5c}$ form together with the nitrogen a ring selected from a substituted or unsubstituted pyrrolidinyl, a substituted or unsubstituted morpholinyl, or a substituted or unsubstituted piperidinyl.

$R^{5d}$ is amino, a substituted or unsubstituted pyrrolidinyl; or $R^{5d}$ is a $C_{1-4}$ alkyl optionally substituted by methoxy, a substituted or unsubstituted pyridinyl, a substituted or unsubstituted 1,2-oxazolyl or a substituted or unsubstituted tetrahydro-2H-pyranyl; or $R^{5d}$ is an amino group mono- or disubstituted by a $C_{1-4}$ alkyl optionally substituted by a fluoro, cyano or a substituted or unsubstituted triazolyl.

$R^6$ is hydrogen.

$R^7$ is either hydrogen or (methylsulfonyl)amino.

X is either $CR^9$ or N, wherein $R^9$ is hydrogen, halogen or hydroxymethyl.

Z is CH or N; and

Y is either $CH_2$ or NH.

A particular sub-class of compound of formula (I) according to the present invention is represented by tetrahydroisoquinoline derivatives of formula I-A,

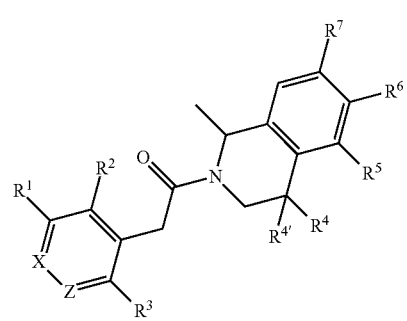

(I-A)

wherein $R^1$, $R^2$, $R^3$, $R^4$, $R^{4'}$, $R^5$, $R^6$, $R^7$, X and Z are defined as above for compounds of formula I.

In a particular aspect, the present invention relates to the sub-class of tetrahydroisoquinolines represented by formula (I-A) as defined above with the exception of 2-(2-fluorophenyl)-1-[(1R)-1-methyl-3,4-dihydro-2(1H)-isoquinolinyl]-1-ethanone.

A particular sub-group of compounds of formula (I-A) is represented by compounds of formula (I-A-A), or a pharmaceutically acceptable salt thereof,

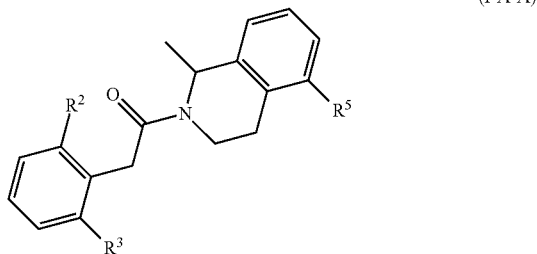

(I-A-A)

wherein $R^2$, $R^3$, and $R^5$ are as defined above.

Suitably, the present invention relates to compounds of formula (I-A-A) wherein $R^2$ and $R^3$ are independently halogen or cyano, and $R^5$ is hydrogen, cyano or hydroxy; or $C_{1-6}$ alkyl, $C_{1-6}$-alkylsulfonyl, $C_{1-6}$ alkylsulfonylamino; $C_{1-6}$ alkylsulfonylamino($C_{1-6}$ alkyl), heterocycle, $C_{1-6}$ alkylacylamino($C_{1-6}$ alkyl); $C_{1-6}$ alkylureido($C_{1-6}$ alkyl), $C_{1-6}$alkylcarbamate ($C_{1-6}$ alkyl), amido, $C_{1-6}$alkoxycarbonyloxy($C_{1-6}$alkyl), amino; N-cyano-S—($C_{1-6}$-alkyl)sulfonimidoyl, N,S-(di-$C_{1-6}$-alkyl)sulfonimidoyl, aminosulfinyl, $C_{1-6}$-alkylsulfinyl; aminosulfonyl, (di-$C_{1-6}$-alkyl)(oxido)-$\lambda^6$-sulfanylidene-amino; amino($C_{1-6}$ alkyl) or amido($C_{1-6}$ alkyl), any of which groups may be optionally substituted by one or more substituents.

In one embodiment, $R^2$ represents halogen. In a particular aspect of this embodiment, $R^2$ represents chloro. In another embodiment, $R^2$ represents cyano.

In one embodiment, $R^3$ represents halogen. In a particular aspect of this embodiment, $R^3$ represents chloro. In another embodiment, $R^3$ represents cyano.

In a first embodiment, $R^5$ is hydrogen. In a second embodiment, $R^5$ is cyano. In a third embodiment, $R^5$ is hydroxy.

In a fourth embodiment, $R^5$ is optionally substituted $C_{1-6}$ alkyl. In a first aspect of that embodiment, $R^5$ is optionally substituted methyl. In a second aspect of this embodiment, $R^5$ is optionally substituted ethyl. In a third aspect of this embodiment, $R^5$ is optionally substituted isopropyl. In a fourth aspect of this embodiment, $R^5$ is optionally substituted propyl.

In a fifth embodiment, $R^5$ is optionally substituted $C_{1-6}$-alkylsulfonyl. In first aspect of this embodiment, $R^5$ is optionally substituted methylsulfonyl. In a second aspect of this embodiment, $R^5$ is optionally substituted ethylsulfonyl. In a third aspect of this embodiment, $R^5$ is optionally substituted isopropylsulfonyl.

In a sixth embodiment, $R^5$ is optionally substituted $C_{1-6}$-alkylsulfonylamino. In one aspect of this embodiment, $R^5$ is optionally substituted methylsulfonylamino.

In a seventh embodiment, $R^5$ is $C_{1-6}$-alkylsulfonylamino ($C_{1-6}$ alkyl). In first aspect of this embodiment, $R^5$ is optionally substituted methylsulfonylaminomethyl. In a second aspect of this embodiment, $R^5$ is optionally substituted methylsulfonylaminoethyl.

In an eighth embodiment, $R^5$ is an optionally substituted heterocycle. In a first embodiment of this embodiment, $R^5$ is optionally substituted oxazolyl. In a second aspect of this embodiment, $R^5$ is optionally substituted pyridinyl. In a third aspect of this embodiment, $R^5$ is optionally substituted pyrazolyl. In a third aspect of this embodiment, $R^5$ is optionally substituted triazolyl. In a fourth aspect of this embodiment, $R^5$ is optionally substituted morpholinyl. In a fifth aspect of this embodiment, $R^5$ is optionally substituted 4,5-dihydroimidazolyl.

In a ninth embodiment, $R^5$ is optionally substituted $C_{1-6}$ alkylacylamino($C_{1-6}$ alkyl). In a first aspect of this embodiment, $R^5$ is optionally substituted (methylcarbonylamino) methyl. In a second aspect, $R^5$ is optionally substituted (methylcarbonylamino)ethyl.

In a tenth embodiment, $R^5$ is optionally substituted $C_{1-6}$ alkylureido($C_{1-6}$ alkyl). In one aspect of this embodiment, $R^5$ is optionally substituted (methylureido)methyl.

In an eleventh embodiment, $R^5$ is optionally substituted $C_{1-6}$alkylcarbamate($C_{1-6}$ alkyl). In one aspect of this embodiment; $R^5$ is optionally substituted (methylcarbamate) methyl.

In a twelfth embodiment, $R^5$ is optionally substituted amido. In a first aspect of this embodiment, $R^5$ is carbamoyl. In a second aspect of this embodiment, $R^5$ is optionally substituted $C_{1-6}$alkylamido. In a third aspect of this embodiment, $R^5$ is optionally substituted $C_{3-8}$heterocycloalkylamido. In a fourth aspect of this embodiment, $R^5$ is optionally substituted heterocyclylamido.

In a thirteenth embodiment, $R^5$ is optionally substituted $C_{1-6}$alkoxycarbonyloxy($C_{1-6}$alkyl). In one aspect, $R^5$ is optionally substituted (methoxycarbonyloxy)methyl.

In a fourteenth embodiment, $R^5$ is optionally substituted amino group. In one aspect of this embodiment, $R^5$ is amino.

In a fifteenth embodiment, $R^5$ is optionally substituted N-cyano-S—($C_{1-6}$-alkyl)sulfonimidoyl. In one aspect of this embodiment, $R^5$ is optionally substituted N-cyano-S-(methyl)sulfonimidoyl.

In a sixteenth embodiment, $R^5$ is optionally substituted N,S-(di-$C_{1-6}$-alkyl)sulfonimidoyl. In a first aspect, $R^5$ is optionally substituted N-methyl-S-methyl-sulfonimidoyl. In a second aspect, $R^5$ is optionally substituted N-ethyl-S-methyl-sulfonimidoyl.

In a seventeenth embodiment, $R^5$ is optionally substituted aminosulfinyl. In one aspect, $R^5$ is optionally substituted $C_{1-6}$-alkylaminosulfinyl.

In an eighteenth embodiment, $R^5$ is optionally substituted $C_{1-6}$-alkylsulfinyl. In one aspect of this embodiment, $R^5$ is optionally substituted methylsulfinyl.

In a nineteenth embodiment; $R^5$ is optionally substituted aminosulfonyl. In a first aspect of this embodiment, $R^5$ is sulfamoyl. In a second aspect of this embodiment, $R^5$ is optionally substituted $C_{1-6}$ alkylaminosulfonyl. In a third aspect of this embodiment, $R^5$ is optionally substituted heterocyclylaminosulfonyl. In a fourth aspect of this embodiment, $R^5$ is optionally substituted $C_{3-8}$heterocycloalkylaminosulfonyl In a twentieth embodiment, $R^5$ is optionally substituted (di-$C_{1-6}$-alkyl)(oxido)-$\lambda^6$-sulfanylidene-amino. In a first aspect of this embodiment, $R^5$ is optionally substituted (1-oxidotetrahydro-1H-1$\lambda^4$-thiophen-1-ylidene)amino. In a second aspect of this embodiment, $R^5$ is optionally substituted (di-methyl)(oxido)-$\lambda^6$-sulfanylidene-amino. In a third aspect of this embodiment, $R^5$ is optionally substituted (4-oxido-1,4-$\lambda^4$-oxathian-4-ylidene)amino.

In a twenty-first embodiment, $R^5$ is optionally substituted amino($C_{1-6}$ alkyl). In a first aspect of this embodiment, $R^5$ is optionally substituted $C_{3-8}$heterocycloalkylamino($C_{1-6}$ alkyl). In a second aspect of this embodiment, $R^5$ is optionally substituted $C_{1-6}$ alkylamino ($C_{1-6}$ alkyl).

In a twenty-second embodiment, $R^5$ is optionally substituted amido($C_{1-6}$ alkyl). In a first aspect of this embodiment, R⁵ is optionally substituted carbamoyl(C$_{1-6}$ alkyl). In a second aspect of this embodiment, R⁵ is optionally substituted C$_{3-8}$cycloalkylamido(C$_{1-6}$ alkyl). In a third aspect, R⁵ is optionally substituted C$_{3-8}$heterocycloalkylamido(C$_{1-6}$ alkyl).

In a particular embodiment, R⁵ is hydrogen, cyano, hydroxy, amino, carbamoyl, sulfamoyl, C$_{1-6}$ alkylsulfinyl, C$_{1-6}$ alkylaminosulfinyl, C$_{1-6}$ alkylsulfonyl optionally substituted by C$_{1-6}$ alkoxy or heterocycle, N-cyano-S—(C$_{1-6}$-alkyl)sulfonimidoyl, N,S-(di-C$_{1-6}$-alkyl)sulfonimidoyl, (di-C$_{1-6}$-alkyl)(oxido)-λ⁶-sulfanylidene-amino, (C$_{1-6}$-alkylsulfonyl)amino; or R⁵ is C$_{1-6}$ alkyl mono- or polysubstituted by hydroxy, halogen, C$_{1-6}$ alkylsulfanyl, C$_{1-6}$ alkylsulfonyl, (C$_{1-6}$-alkylsulfonyl)amino, (C$_{1-6}$-alkylacyl)amino, C$_{1-6}$ alkylureido, C$_{1-6}$ alkylcarbamate, C$_{1-6}$ alkoxycarbonyloxy; or R⁵ is an heterocycle optionally mono- or polysubstituted by C$_{1-6}$ alkyl or C$_{1-6}$ alkylsulfonyl; or R⁵ is an amido group selected from C$_{1-6}$ alkylamido optionally mono- or polysubstituted by halogen, substituted or unsubstituted heterocyclylamido, C$_{3-8}$ heterocycloalkylamido optionally mono- or polysubstituted by C$_{1-6}$ alkyl, halogens or hydroxy; or R⁵ is an aminosulfonyl group selected from C$_{1-6}$ alkylaminosulfonyl optionally substituted by one or more halogens or cyano, heterocyclylaminosulfonyl or C$_{3-8}$ heterocycloalkylaminosulfonyl optionally substituted by one or more halogens.

In a further particular embodiment, R⁵ is hydrogen, cyano, hydroxy, amino, methylsulfinyl, (dimethylamino) sulfinyl, N-cyano-S-methylsulfonimidoyl, N,S-dimethylsulfonimidoyl or (1-oxidotetrahydro-1H-1λ⁴-thiophen-1-ylidene)amino; or R⁵ is a C$_{1-4}$ alkyl group mono- or polysubstituted by halogen, hydroxy, (methoxycarbonyl) oxy, methylsulfanyl or methylsulfonyl; or R⁵ is an heterocycle selected from 1,2-oxazol-4-yl or 4,5-dihydro-1H-imidazol-2-yl and optionally substituted by methyl or methylsulfonyl; or R⁵ is a group selected from —(CH$_2$)$_n$NHR$^{5a}$, —CONR$^{5b}$R$^{5c}$ or —SO$_2$R$^{5d}$ wherein R$^{5a}$ is acetyl, methylcarbamoyl, methylsulfonyl, methoxycarbonyl, or substituted or unsubstituted pyridinyl; n is 0, 1 or 2; R$^{5b}$ is hydrogen or a C$_{1-4}$ alkyl optionally substituted by one or more fluoro, a substituted or unsubstituted triazolyl or a substituted or unsubstituted pyridinyl.

Illustratively, R⁵ is C$_{1-6}$ alkyl aminosulfonyl optionally substituted by trifluoromethyl; C$_{1-6}$ alkyl optionally substituted by hydroxy, halogen, carbamoyl or trifluoromethyl; pyrazolyl optionally substituted by trifluoromethyl or methyl; or (di-C$_{1-6}$-alkyl)(oxido)-λ⁶-sulfanylidene-amino.

In a particular aspect, the present invention relates to the sub-group of tetrahydroisoquinolines represented by formula (I-A-A) as defined above with the exception of 2-(2-fluorophenyl)-1-[(1R)-1-methyl-3,4-dihydro-2(1H)-isoquinolinyl]-1-ethanone.

Another particular sub-class of compound of formula (I) according to the present invention is represented by tetrahydroisoquinoline derivatives of formula (I-B),

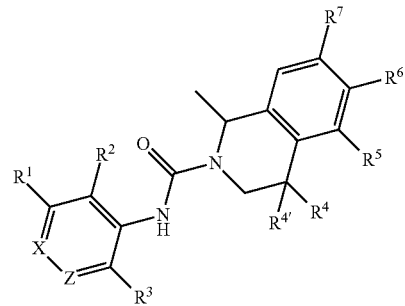

(I-B)

wherein R¹, R², R³, R⁴, R⁴', R⁵, R⁶, R⁷, X and Z are defined as above for compounds of formula I.

In a particular aspect, the present invention relates to the sub-class of tetrahydroisoquinolines represented by formula (I-B) as defined above with the exception of
3,4-dihydro-1-methyl-N-(2-methylphenyl)-2(1H)-isoquinolinecarboxamide;
N-(2,6-dimethylphenyl)-3,4-dihydro-1-methyl-2(1H)-isoquinolinecarboxamide;
N-(2,4-dichlorophenyl)-3,4-dihydro-1-methyl-2(1H)-isoquinolinecarboxamide;
N-(2,3-dichlorophenyl)-3,4-dihydro-1-methyl-2(1H)-isoquinolinecarboxamide;
N-(2-bromophenyl)-3,4-dihydro-1-methyl-2(1H)-isoquinolinecarboxamide; and
N-(2-fluorophenyl)-3,4-dihydro-1-methyl-2(1H)-isoquinolinecarboxamide.

Specific novel compounds in accordance with the present invention include each of the compounds whose preparation is described in the accompanying Examples, and pharmaceutically acceptable salts and solvates thereof, and co-crystals thereof.

Therefore, in a particular aspect, the present invention relates to compounds of formula (I) which are those selected from the group consisting of:
2-(2,6-dichlorophenyl)-1-(1-methyl-3,4-dihydroisoquinolin-2(1H)-yl)ethanone;
2-(2,6-dichlorophenyl)-1-[(1S)-1-methyl-3,4-dihydroisoquinolin-2(1H)-yl]ethanone;
2-(2,6-dichlorophenyl)-1-[(1R)-1-methyl-3,4-dihydroisoquinolin-2(1H)-yl]ethanone;
2-(3,5-dichloropyridin-4-yl)-1-[(1S)-1-methyl-3,4-dihydroisoquinolin-2(1H)-yl]ethanone;
N-{(1R)-2-[(2,6-dichlorophenyl)acetyl]-1-methyl-1,2,3,4-tetrahydroisoquinolin-5-yl}methanesulfonamide;
N-{(1S)-2-[(2,6-dichlorophenyl)acetyl]-1-methyl-1,2,3,4-tetrahydroisoquinolin-5-yl}methanesulfonamide;
2,4-dichloro-3-{2-[(1S)-1-methyl-3,4-dihydroisoquinolin-2(1H)-yl]-2-oxoethyl}benzonitrile;
2-(2,6-dichlorophenyl)-1-(4,4-difluoro-1-methyl-3,4-dihydroisoquinolin-2(1H)-yl)ethanone;
2-(2,6-dichlorophenyl)-1-[4,4-difluoro-1-methyl-3,4-dihydroisoquinolin-2(1H)-yl]ethanone;
2-(2,6-dichlorophenyl)-1-(1,4,4-trimethyl-3,4-dihydroisoquinolin-2(1H)-yl)ethanone;
2-(3-bromo-2,6-dichlorophenyl)-1-[(1S)-1-methyl-3,4-dihydroisoquinolin-2(1H)-yl]ethanone;
2-(3,5-dichloropyridin-4-yl)-1-[(1S)-5-(hydroxymethyl)-1-methyl-3,4-dihydroisoquinolin-2(1H)-yl]ethanone;
2-(5-chloro-1H-pyrrolo[2,3-b]pyridin-4-yl)-1-[(1S)-1-methyl-3,4-dihydroisoquinolin-2(1H)-yl]ethanone;

N-{(1S)-2-[(2-chloro-6-methylphenyl)acetyl]-1-methyl-1,2,
3,4-tetrahydroisoquinolin-5-yl}methanesulfonamide;
N-{(1S)-2-[(2-chloro-6-cyanophenyl)acetyl]-1-methyl-1,2,
3,4-tetrahydroisoquinolin-5-yl}methanesulfonamide;
2-(3,5-dichloro-2-methoxypyridin-4-yl)-1-[(1S)-1-methyl-
3,4-dihydroisoquinolin-2(1H)-yl]ethanone;
2-(2-bromo-6-methoxyphenyl)-1-[(1S)-1-methyl-3,4-dihydroisoquinolin-2(1H)-yl]ethanone;
2-(3-chloro-5-methylpyridin-4-yl)-1-[(1S)-1-methyl-3,4-dihydroisoquinolin-2(1H)-yl]ethanone;
3-chloro-2-{2-[(1S,4R)-4-hydroxy-1-methyl-3,4-dihydroisoquinolin-2(1H)-yl]-2-oxoethyl}benzonitrile;
2-(2,6-dichlorophenyl)-1-[(1S,4R)-4-hydroxy-1-methyl-3,
4-dihydroisoquinolin-2(1H)-yl]ethanone;
3-chloro-2-{2-[(1S,4S)-4-hydroxy-1-methyl-3,4-dihydroisoquinolin-2(1H)-yl]-2-oxoethyl}benzonitrile;
2-(2,6-dichlorophenyl)-1-[(1S,4S)-4-hydroxy-1-methyl-3,
4-dihydroisoquinolin-2(1H)-yl]ethanone;
2-(3,5-dichloropyridin-4-yl)-1-[(1S)-1-methyl-5-(methylsulfonyl)-3,4-dihydroisoquinolin-2(1H)-yl]ethanone;
3-chloro-2-{2-[(1S)-1-methyl-5-(methylsulfonyl)-3,4-dihydroisoquinolin-2(1H)-yl]-2-oxoethyl}benzonitrile;
2-(3,5-dichloropyridin-4-yl)-1-[(1S,4R)-4-hydroxy-1-methyl-3,4-dihydroisoquinolin-2(1H)-yl]ethanone;
2-(2,6-dichloro-4-fluorophenyl)-1-[(1S,4S)-4-hydroxy-1-methyl-3,4-dihydroisoquinolin-2(1H)-yl]ethanone;
2-(2-chloro-6-methoxyphenyl)-1-[(1S)-1-methyl-3,4-dihydroisoquinolin-2(1H)-yl]ethanone;
2-[2-chloro-6-(trifluoromethyl)phenyl]-1-[(1S)-1-methyl-3,
4-dihydroisoquinolin-2(1H)-yl]ethanone;
5-chloro-4-{2-[(1S)-1-methyl-3,4-dihydroisoquinolin-2
(1H)-yl]-2-oxoethyl}pyridine-3-carbonitrile;
N-({2-[(2,6-dichlorophenyl)acetyl]-1-methyl-1,2,3,4-tetrahydroisoquinolin-5-yl}methyl)methanesulfonamide;
2-(2,6-dichlorophenyl)-1-[5-(3,5-dimethyl-1,2-oxazol-4-
yl)-1-methyl-3,4-dihydroisoquinolin-2(1H)-yl]ethanone;
(1S)-2-[(2,6-dichlorophenyl)acetyl]-1-methyl-1,2,3,4-tetrahydroisoquinoline-5-carbonitrile;
N-{2-[(2,6-dichlorophenyl)acetyl]-1-methyl-1,2,3,4-tetrahydroisoquinolin-7-yl}methanesulfonamide;
N-({(1S)-2-[(2,6-dichlorophenyl)acetyl]-1-methyl-1,2,3,4-
tetrahydroisoquinolin-5-yl}methyl)methanesulfonamide;
N-({(1S)-2-[(2,6-dichlorophenyl)acetyl]-1-methyl-1,2,3,4-
tetrahydroisoquinolin-5-yl}methyl)acetamide;
1-({(1S)-2-[(2,6-dichlorophenyl)acetyl]-1-methyl-1,2,3,4-
tetrahydroisoquinolin-5-yl}methyl)-3-methylurea;
methyl ({(1S)-2-[(2,6-dichlorophenyl)acetyl]-1-methyl-1,2,
3,4-tetrahydroisoquinolin-5-yl}methyl)carbamate;
2-(2,6-dichlorophenyl)-1-[(1S)-5-(hydroxymethyl)-1-
methyl-3,4-dihydroisoquinolin-2(1H)-yl]ethanone;
(1S)-2-[(2,6-dichlorophenyl)acetyl]-1-methyl-1,2,3,4-tetrahydroisoquinoline-5-carboxamide;
(1S)-2-[(2,6-dichlorophenyl)acetyl]-N,1-dimethyl-1,2,3,4-
tetrahydroisoquinoline-5-carboxamide;
(1S)-2-[(2,6-dichlorophenyl)acetyl]-N,N,1-trimethyl-1,2,3,
4-tetrahydroisoquinoline-5-carboxamide;
(1S)-2-[(2,6-dichlorophenyl)acetyl]-1-methyl-N-(propan-2-
yl)-1,2,3,4-tetrahydroisoquinoline-5-carboxamide;
2-(2,6-dichlorophenyl)-1-[(1S)-1-methyl-5-(pyrrolidin-1-
ylcarbonyl)-3,4-dihydroisoquinolin-2(1H)-yl]ethanone;
2-(2,6-dichlorophenyl)-1-[(1S)-1-methyl-5-[(2-methylpyrrolidin-1-yl)carbonyl]-3,4-dihydroisoquinolin-2(1H)-yl]
ethanone;
(1S)-2-[(2,6-dichlorophenyl)acetyl]-1-methyl-N-(2,2,2-trifluoroethyl)-1,2,3,4-tetrahydroisoquinoline-5-carboxamide;
(1S)-2-[(2,6-dichlorophenyl)acetyl]-N-ethyl-1-methyl-1,2,
3,4-tetrahydroisoquinoline-5-carboxamide;
2-(2,6-dichlorophenyl)-1-[(1S)-1-methyl-5-(morpholin-4-
ylcarbonyl)-3,4-dihydroisoquinolin-2(1H)-yl]ethanone;
2-(2,6-dichlorophenyl)-1-[(1S)-1-methyl-5-{[4-(trifluoromethyl)piperidin-1-yl]carbonyl}-3,4-dihydroisoquinolin-2
(1H)-yl]ethanone;
2-(2,6-dichlorophenyl)-1-[(1S)-5-[(2,5-dimethylpyrrolidin-
1-yl)carbonyl]-1-methyl-3,4-dihydroisoquinolin-2(1H)-
yl]ethanone;
(1S)-2-[(2,6-dichlorophenyl)acetyl]-1-methyl-N-(4H-1,2,4-
triazol-3-yl)-1,2,3,4-tetrahydroisoquinoline-5-carboxamide;
2-(2,6-dichlorophenyl)-1-[(1S)-5-{[(3S)-3-hydroxypyrrolidin-1-yl]carbonyl}-1-methyl-3,4-dihydroisoquinolin-2
(1H)-yl]ethanone;
2-(2,6-dichlorophenyl)-1-[(1S)-5-[(3,3-difluoropyrrolidin-
1-yl)carbonyl]-1-methyl-3,4-dihydroisoquinolin-2(1H)-
yl]ethanone;
(1S)-2-[(2,6-dichlorophenyl)acetyl]-1-methyl-N,N-di(propan-2-yl)-1,2,3,4-tetrahydroisoquinoline-5-carboxamide;
(1S)-2-[(2,6-dichlorophenyl)acetyl]-1-methyl-N-(pyridin-2-
yl)-1,2,3,4-tetrahydroisoquinoline-5-carboxamide;
2-[2-chloro-6-(hydroxymethyl)phenyl]-1-[(1S)-1-methyl-3,
4-dihydroisoquinolin-2(1H)-yl]ethanone;
3-chloro-N-methyl-2-{2-[(1S)-1-methyl-3,4-dihydroisoquinolin-2(1H)-yl]-2-oxoethyl}benzamide;
2-[2,6-dichloro-4-(hydroxymethyl)phenyl]-1-(1-methyl-3,
4-dihydroisoquinolin-2(1H)-yl]ethanone;
{(1S)-2-[(2,6-dichlorophenyl)acetyl]-1-methyl-1,2,3,4-tetrahydroisoquinolin-5-yl}methyl methyl carbonate;
3-chloro-2-{2-[(1S)-1-methyl-3,4-dihydroisoquinolin-2
(1H)-yl]-2-oxoethyl}benzonitrile;
N-(2,4-dichloro-3-{2-[(1S)-1-methyl-3,4-dihydroisoquinolin-2(1H)-yl]-2-oxoethyl}phenyl)methanesulfonamide;
2-[2,6-dichloro-3-(methylsulfanyl)phenyl]-1-[(1S)-1-
methyl-3,4-dihydroisoquinolin-2(1H)-yl]ethanone;
N-(3-chloro-2-{2-[(1S)-1-methyl-3,4-dihydroisoquinolin-2
(1H)-yl]-2-oxoethyl}benzyl)methanesulfonamide;
N-(3-chloro-2-{2-[(1S)-1-methyl-3,4-dihydroisoquinolin-2
(1H)-yl]-2-oxoethyl}benzyl)acetamide;
2-[2,6-dichloro-3-(methylsulfonyl)phenyl]-1-[(1S)-1-
methyl-3,4-dihydroisoquinolin-2(1H)-yl]ethanone;
2-[2,6-dichloro-3-(methylsulfinyl)phenyl]-1-[(1S)-1-
methyl-3,4-dihydroisoquinolin-2(1H)-yl]ethanone;
2-(2,6-dichlorophenyl)-1-[(1S)-1-methyl-5-[(methylsulfanyl)methyl]-3,4-dihydroisoquinolin-2(1H)-yl]ethanone;
2-(2,6-dichlorophenyl)-1-[(1S)-1-methyl-5-(methylsulfonyl)-3,4-dihydroisoquinolin-2(1H)-yl]ethanone;
N-(3-chloro-2-{2-[(1S)-1-methyl-3,4-dihydroisoquinolin-2
(1H)-yl]-2-oxoethyl}phenyl)methanesulfonamide;
N-(3-chloro-2-{2-[(1S)-1-methyl-3,4-dihydroisoquinolin-2
(1H)-yl]-2-oxoethyl}phenyl)acetamide;
1-[(1S)-5-amino-1-methyl-3,4-dihydroisoquinolin-2(1H)-
yl]-2-(2,6-dichlorophenyl)ethanone;
2-(2,6-dichlorophenyl)-1-[(1S)-5-[1-hydroxyethyl]-1-
methyl-3,4-dihydroisoquinolin-2(1H)-yl]ethanone;
N-(2-{(1S)-2-[(2,6-dichlorophenyl)acetyl]-1-methyl-1,2,3,
4-tetrahydroisoquinolin-5-yl}ethyl)methanesulfonamide;
2-(2,6-dichlorophenyl)-1-[(1S)-1-methyl-5-[1-(methylsulfonyl)-4,5-dihydro-1H-imidazol-2-yl]-3,4-dihydroisoquinolin-2(1H)-yl]ethanone;
2-[2-chloro-6-(1H-pyrazol-4-yl)phenyl]-1-[(1S)-1-methyl-
3,4-dihydroisoquinolin-2(1H)-yl]ethanone trifluoroacetate;
(1S)-2-[(2,6-dichlorophenyl)acetyl]-1-methyl-2,3-dihydroisoquinolin-4(1H)-one;

2-{2,6-dichloro-4-[methylsulfinyl]phenyl}-1-[(1S)-1-methyl-3,4-dihydroisoquinolin-2(1H)-yl]ethanone;
[2-(2,6-dichlorophenyl)-1-[(1S)-5-(N-cyano-S-methylsulfonimidoyl)-1-methyl-3,4-dihydroisoquinolin-2(1H)-yl]ethanone;
2-(2,6-dichlorophenyl)-1-[(1S)-5-(N,S-dimethylsulfonimidoyl)-1-methyl-3,4-dihydroisoquinolin-2(1H)-yl]ethanone;
(1S)-2-[(2,6-dichlorophenyl)acetyl]-N,N,1-trimethyl-1,2,3,4-tetrahydroisoquinoline-5-sulfinamide;
2-(2,6-dichlorophenyl)-1-[(1S)-1-methyl-5-[(S)-methylsulfinyl]-3,4-dihydroisoquinolin-2(1H)-yl]ethanone;
2-(2,6-dichlorophenyl)-1-[(1S)-1-methyl-5-[methylsulfinyl]-3,4-dihydroisoquinolin-2(1H)-yl]ethanone;
(1S)-2-[(2,6-dichlorophenyl)acetyl]-N,1-dimethyl-1,2,3,4-tetrahydroisoquinoline-5-sulfonamide;
2-(2,6-dichlorophenyl)-1-[(1S)-5-hydroxy-1-methyl-3,4-dihydroisoquinolin-2(1H)-yl]ethanone;
2-[2-chloro-6-(methylsulfanyl)phenyl]-1-[(1S)-1-methyl-3,4-dihydroisoquinolin-2(1H)-yl]ethanone;
2-[2-chloro-6-(methylsulfinyl)phenyl]-1-[(1S)-1-methyl-3,4-dihydroisoquinolin-2(1H)-yl]ethanone;
2-[2-chloro-6-(methylsulfonyl)phenyl]-1-[(1S)-1-methyl-3,4-dihydroisoquinolin-2(1H)-yl]ethanone;
2-[5-chloro-1-(methylsulfonyl)-1H-pyrrolo[2,3-b]pyridin-4-yl]-1-[(1S)-1-methyl-3,4-dihydroisoquinolin-2(1H)-yl]ethanone trifluoroacetate;
3,5-dichloro-4-{2-[(1S)-1-methyl-3,4-dihydroisoquinolin-2(1H)-yl]-2-oxoethyl}pyridin-2(1H)-one;
2-(2,6-dichlorophenyl)-1-[(1S)-1-methyl-5-(propan-2-ylsulfonyl)-3,4-dihydroisoquinolin-2(1H)-yl]ethanone;
2-(2,6-dichlorophenyl)-1-[(1S)-5-(ethylsulfonyl)-1-methyl-3,4-dihydroisoquinolin-2(1H)-yl]ethanone;
3-methoxy-2-{2-[(1S)-1-methyl-3,4-dihydroisoquinolin-2(1H)-yl]-2-oxoethyl}benzonitrile;
2-{2-chloro-6-[(methylsulfonyl)methyl]phenyl}-1-[(1S)-1-methyl-3,4-dihydroisoquinolin-2(1H)-yl]ethanone;
2-(2,6-dichlorophenyl)-1-[(1S)-1-methyl-5-[(methylsulfonyl)methyl]-3,4-dihydroisoquinolin-2(1H)-yl]ethanone;
2-(2,6-dichlorophenyl)-1-[(1S,4S)-4-methoxy-1-methyl-3,4-dihydroisoquinolin-2(1H)-yl]ethanone;
2-(2,6-dichlorophenyl)-1-[(1S,4R)-4-methoxy-1-methyl-3,4-dihydroisoquinolin-2(1H)-yl]ethanone;
(1S,4S)-2-[(2,6-dichlorophenyl)acetyl]-1-methyl-1,2,3,4-tetrahydroisoquinolin-4-yl methylcarbamate;
(1S,4S)-2-[(2,6-dichlorophenyl)acetyl]-1-methyl-1,2,3,4-tetrahydroisoquinolin-4-yl methyl carbonate;
(1S,4R)-2-[(2,6-dichlorophenyl)acetyl]-1-methyl-1,2,3,4-tetrahydroisoquinolin-4-yl methyl carbonate;
2-[2,6-dichloro-3-(hydroxymethyl)phenyl]-1-[(1S)-1-methyl-5-(methylsulfonyl)-3,4-dihydroisoquinolin-2(1H)-yl]ethanone;
2-(2,6-dichlorophenyl)-1-[(1S)-1-methyl-4-(methylsulfonyl)-3,4-dihydroisoquinolin-2(1H)-yl]ethanone;
2-(2,6-dichlorophenyl)-1-[(1S)-1-methyl-5-(pyrrolidin-1-ylsulfonyl)-3,4-dihydroisoquinolin-2(1H)-yl]ethanone;
(1S)-2-[(2,6-dichlorophenyl)acetyl]-N-ethyl-1-methyl-1,2,3,4-tetrahydroisoquinoline-5-sulfonamide;
(1S)-2-[(2,6-dichlorophenyl)acetyl]-1-methyl-N-(propan-2-yl)-1,2,3,4-tetrahydroisoquinoline-5-sulfonamide;
(1S)-2-[(2,6-dichlorophenyl)acetyl]-1-methyl-N-(2,2,2-trifluoroethyl)-1,2,3,4-tetrahydroisoquinoline-5-sulfonamide;
(1S)-2-[(2,6-dichlorophenyl)acetyl]-1-methyl-N-(4H-1,2,4-triazol-3-yl)-1,2,3,4-tetrahydroisoquinoline-5-sulfonamide;
2-(2,6-dichlorophenyl)-1-[(1S)-5-[(3,3-difluoropyrrolidin-1-yl)sulfonyl]-1-methyl-3,4-dihydroisoquinolin-2(1H)-yl]ethanone;
(1S)—N-(cyanomethyl)-2-[(2,6-dichlorophenyl)acetyl]-1-methyl-1,2,3,4-tetrahydroisoquinoline-5-sulfonamide;
(1S)-2-[(2,6-dichlorophenyl)acetyl]-1-methyl-1,2,3,4-tetrahydroisoquinoline-5-sulfonamide;
2-(2,6-dichlorophenyl)-1-[(1S)-1-methyl-5-{[(5-methyl-1,2-oxazol-3-yl)methyl]sulfonyl}-3,4-dihydroisoquinolin-2(1H)-yl]ethanone;
2-(2,6-dichlorophenyl)-1-[(1S)-1-methyl-5-[(pyridin-3-ylmethyl)sulfonyl]-3,4-dihydroisoquinolin-2(1H)-yl]ethanone;
2-(2,6-dichlorophenyl)-1-[(1S)-1-methyl-5-[(tetrahydro-2H-pyran-4-ylmethyl)sulfonyl]-3,4-dihydroisoquinolin-2(1H)-yl]ethanone;
2-(2,6-dichlorophenyl)-1-[(1S)-5-[(methoxymethyl)sulfonyl]-1-methyl-3,4-dihydroisoquinolin-2(1H)-yl]ethanone;
2-(2,6-dichlorophenyl)-1-[(1S)-1-methyl-5-[(1-oxidotetrahydro-1H-1λ4-thiophen-1-ylidene)amino]-3,4-dihydroisoquinolin-2(1H)-yl]ethanone;
2-(2,6-dichlorophenyl)-1-[(1S)-1-methyl-5-((1S)-2,2,2-trifluoro-1-hydroxyethyl)-3,4-dihydroisoquinolin-2(1H)-yl]ethanone;
2-(3,5-dichloropyridin-4-yl)-1-[(1S)-1-methyl-5-((1S)-2,2,2-trifluoro-1-hydroxyethyl)-3,4-dihydroisoquinolin-2(1H)-yl]ethanone;
3-chloro-2-{2-[(1S)-1-methyl-5-((1R)-2,2,2-trifluoro-1-hydroxyethyl)-3,4-dihydroisoquinolin-2(1H)-yl]-2-oxoethyl}benzonitrile;
3-chloro-2-{2-[(1S)-1-methyl-5-((1S)-2,2,2-trifluoro-1-hydroxyethyl)-3,4-dihydroisoquinolin-2(1H)-yl]-2-oxoethyl}benzonitrile;
N-(2,6-dichlorophenyl)-1-methyl-3,4-dihydroisoquinoline-2(1H)-carboxamide;
(1S)—N-(2,6-dichlorophenyl)-1-methyl-3,4-dihydroisoquinoline-2(1H)-carboxamide;
(1R)—N-(2,6-dichlorophenyl)-1-methyl-3,4-dihydroisoquinoline-2(1H)-carboxamide;
(1S)—N-(2,6-dichlorophenyl)-1-methyl-5-[(methylsulfonyl)amino]-3,4-dihydroisoquinoline-2(1H)-carboxamide;
(1S,4S)—N-(2,6-dichlorophenyl)-4-hydroxy-1-methyl-3,4-dihydroisoquinoline-2(1H)-carboxamide;
(1S,4R)—N-(2,6-dichlorophenyl)-4-hydroxy-1-methyl-3,4-dihydroisoquinoline-2(1H)-carboxamide;
(1S)—N-(2,6-dichlorophenyl)-5-(hydroxymethyl)-1-methyl-3,4-dihydroisoquinoline-2(1H)-carboxamide;
(1S)—N-(2,6-dichlorophenyl)-1-methyl-5-(methylsulfonyl)-3,4-dihydroisoquinoline-2(1H)-carboxamide;
(1S)—N-(2-bromo-6-fluorophenyl)-1-methyl-3,4-dihydroisoquinoline-2(1H)-carboxamide;
(1S)—N-(2-bromophenyl)-1-methyl-3,4-dihydroisoquinoline-2(1H)-carboxamide;
(1S)—N-(2,6-dimethylphenyl)-1-methyl-3,4-dihydroisoquinoline-2(1H)-carboxamide;
(1S)—N-(5-bromo-2-chlorophenyl)-1-methyl-3,4-dihydroisoquinoline-2(1H)-carboxamide;
(1S)—N-(2-chloro-6-methylphenyl)-1-methyl-3,4-dihydroisoquinoline-2(1H)-carboxamide;
(1S)—N-(2-bromo-6-methoxyphenyl)-1-methyl-3,4-dihydroisoquinoline-2(1H)-carboxamide;
2-(2-chloro-6-fluorophenyl)-1-[(1S)-1-methyl-5-[2,2,2-trifluoro-1-hydroxyethyl]-3,4-dihydroisoquinolin-2(1H)-yl]ethanone;

2-(5-chloro-1H-indol-4-yl)-1-[(1S)-1-methyl-5-[(1S)-2,2,2-trifluoro-1-hydroxyethyl]-3,4-dihydroisoquinolin-2(1H)-yl]ethanone;
3-chloro-2-{2-[(1S)-1-methyl-5-(pyridin-3-yl)-3,4-dihydroisoquinolin-2(1H)-yl]-2-oxoethyl}benzonitrile;
3-chloro-2-{2-[(1S)-1-methyl-5-(pyridin-4-yl)-3,4-dihydroisoquinolin-2(1H)-yl]-2-oxoethyl}benzonitrile;
2-{2-[(1S)-5-(6-aminopyridin-3-yl)-1-methyl-3,4-dihydroisoquinolin-2(1H)-yl]-2-oxoethyl}-3-chlorobenzonitrile trifluoroacetate;
3-chloro-2-{2-[(1S)-5-(3,5-dimethyl-1,2-oxazol-4-yl)-1-methyl-3,4-dihydroisoquinolin-2(1H)-yl]-2-oxoethyl}benzonitrile;
3-chloro-2-{2-[(1S)-1-methyl-5-(1-methyl-1H-pyrazol-4-yl)-3,4-dihydroisoquinolin-2(1H)-yl]-2-oxoethyl}benzonitrile;
3-chloro-2-{2-[(1S)-1-methyl-5-(1H-pyrazol-4-yl)-3,4-dihydroisoquinolin-2(1H)-yl]-2-oxoethyl}benzonitrile;
3-chloro-2-{2-[(1S)-5-(3,5-dimethyl-1H-pyrazol-4-yl)-1-methyl-3,4-dihydroisoquinolin-2(1H)-yl]-2-oxoethyl}benzonitrile;
1-[(1S)-5-(6-aminopyridin-3-yl)-1-methyl-3,4-dihydroisoquinolin-2(1H)-yl]-2-(2,6-dichlorophenyl)ethanone;
2-(2,6-dichlorophenyl)-1-[(1S)-1-methyl-5-(2-methylpyridin-3-yl)-3,4-dihydroisoquinolin-2(1H)-yl]ethanone;
1-[(1S)-5-(6-aminopyridin-3-yl)-1-methyl-3,4-dihydroisoquinolin-2(1H)-yl]-2-(2,6-dichlorophenyl)ethanone;
2-(2,6-dichlorophenyl)-1-[(1S)-5-(3,5-dimethyl-1H-pyrazol-4-yl)-1-methyl-3,4-dihydroisoquinolin-2(1H)-yl]ethanone;
2-(2,6-dichlorophenyl)-1-[(1S)-5-{[dimethyl(oxido)-$\lambda^6$-sulfanylidene]amino}-1-methyl-3,4-dihydroisoquinolin-2(1H)-yl]ethanone;
2-(2,6-dichlorophenyl)-1-[(1S)-1-methyl-5-[(4-oxido-1,4-$\lambda^4$-oxathian-4-ylidene)amino]-3,4-dihydroisoquinolin-2(1H)-yl]ethanone;
3-chloro-2-{2-[(1S)-5-{[dimethyl(oxido)-$\lambda^6$-sulfanylidene]amino}-1-methyl-3,4-dihydroisoquinolin-2(1H)-yl]-2-oxoethyl}benzonitrile;
2-(2,6-dichlorophenyl)-1-[(1S)-5-(N-ethyl-S-methylsulfonimidoyl)-1-methyl-3,4-dihydroisoquinolin-2(1H)-yl]ethanone;
2-(2,6-dichlorophenyl)-1-[(1S)-5-({[dimethyl(oxido)-$\lambda^6$-sulfanylidene]amino}methyl)-1-methyl-3,4-dihydroisoquinolin-2(1H)-yl]ethanone;
2-(2,6-dichlorophenyl)-1-[(1S)-5-(1,1-difluoro-2-hydroxyethyl)-1-methyl-3,4-dihydroisoquinolin-2(1H)-yl]ethanone;
1-[(1S)-5-(2-amino-1,1-difluoroethyl)-1-methyl-3,4-dihydroisoquinolin-2(1H)-yl]-2-(2,6-dichlorophenyl)ethanone;
N-(2-{(1S)-2-[(2,6-dichlorophenyl)acetyl]-1-methyl-1,2,3,4-tetrahydroisoquinolin-5-yl}-2,2-difluoroethyl)acetamide;
2-(2,6-dichlorophenyl)-1-[(1S)-5-[1,1-difluoro-2-(morpholin-4-yl)ethyl]-1-methyl-3,4-dihydroisoquinolin-2(1H)-yl]ethanone;
2-(2,6-dichlorophenyl)-1-[(1S)-5-[1,1-difluoro-2-(methylamino)ethyl]-1-methyl-3,4-dihydroisoquinolin-2(1H)-yl]ethanone;
2-{(1S)-2-[(2,6-dichlorophenyl)acetyl]-1-methyl-1,2,3,4-tetrahydroisoquinolin-5-yl}-2,2-difluoroacetamide;
2-{(1S)-2-[(2,6-dichlorophenyl)acetyl]-1-methyl-1,2,3,4-tetrahydroisoquinolin-5-yl}-2,2-difluoro-N-(1-methylcyclopropyl)acetamide;
2-{(1S)-2-[(2,6-dichlorophenyl)acetyl]-1-methyl-1,2,3,4-tetrahydroisoquinolin-5-yl}-2,2-difluoro-N-(3-methyloxetan-3-yl)acetamide;
2-(2,6-dichlorophenyl)-1-[(1S)-1-methyl-5-(2H-1,2,3-triazol-4-yl)-3,4-dihydroisoquinolin-2(1H)-yl]ethanone;
2-(2,6-dichlorophenyl)-1-[(1S)-5-(3-hydroxypropyl)-1-methyl-3,4-dihydroisoquinolin-2(1H)-yl]ethanone;
6-[(1S)-2-[2-(2,6-dichlorophenyl)acetyl]-1-methyl-3,4-dihydro-1H-isoquinolin-5-yl]morpholin-3-one;
4-{(1S)-2-[(2-chloro-6-cyanophenyl)acetyl]-1-methyl-1,2,3,4-tetrahydroisoquinolin-5-yl}-1H-pyrazole-3-carbonitrile;
3-chloro-2-{2-[(1S)-1-methyl-5-[3-(trifluoromethyl)-1H-pyrazol-4-yl]-3,4-dihydroisoquinolin-2(1H)-yl]-2-oxoethyl}benzonitrile;
2-{2-[(1S)-5-(2-aminopyridin-4-yl)-1-methyl-3,4-dihydroisoquinolin-2(1H)-yl]-2-oxoethyl}-3-chlorobenzonitrile trifluoroacetate; and
3-chloro-2-{2-[(1S)-1-methyl-5-(pyridin-2-yl)-3,4-dihydroisoquinolin-2(1H)-yl]-2-oxoethyl}benzonitrile.

Compounds according to the present invention may be used in monotherapy or combination therapy.

As used herein, the term <<combination therapy>> refers to the administration of the compound of Formula I together with at least one additional pharmaceutical or medicinal agent (e.g. antiparkinsonian or antischizophrenia agent), either in a sequential or simultaneous way.

The present invention includes the use of a combination of a compound of Formula I and one or more additional pharmaceutically active agent(s). If a combination of active agents is administered, then they may be administered sequentially or simultaneously, in separate dosage forms or combined in a single dosage form.

Various pharmaceutically active agents may be selected for use in conjunction with the compound of Formula I, depending on the disease, disorder or condition to be treated.

Pharmaceutically active agents that may be used in combination with the compositions of the present invention include, without limitation:

Levodopa (or its methyl or ethyl ester), alone or in combination with a DOPA decarboxylase inhibitor (e.g. carbidopa (SINEMET®, CARBILEV®, PARCOPA®));

N-methyl-D-aspartate (NMDA) receptor antagonists such as memantine (NAMENDA®, AXURA®, EBIXA®) or amantadine (SYMMETREL®);

Monoamine oxidase (MAO) inhibitors such as selegiline (EMSAM®, ZELAPAR®) or rasagiline (AZILATECT®);

Catechol-O-methyl transferase (COMT) inhibitors like entacapone (COMTAN®, STALEVO®) or tolcapone (TASMAR®);

Dopamine receptor agonists such as ropinirole (REQUIP®, REPREVE®, RONIROL®, ADARTEL®), pramipexole (MIRAPEX®, MIRAPEXIN®, SIFROL®), rotigotine (NEUPRO®), piribedil (TRASTAL®, TRIVASTAN®, PRONORAN®), apomorphine (APOKYN®);

Adenosine 2A antagonist such as istradefylline (NOURIAST®);

Anticholinergics like benztropine (COGENTIN®); and

Acetylcholinesterase inhibitors such as donepezil hydrochloride (ARICEPT®, MEMAC®), rivastigmine (EXELON®, NIMVASTID®).

Examples of additional therapeutic agents or classes include, without limitation: antipsychotics (anti-schizophrenia) like paliperidone, bifeprunox, ziprasidone, risperidone, aripiprazole, olanzapine and quietapine; anti-depressant-like norepinephrine reuptake inhibitors, selective serotonin reuptake inhibitors (SSRIs), serotonin and noradrenaline reuptake inhibitors (SNRIs), tertiary or secondary amine tricyclics (amitriptyline, clomipramine, desipramine, imipramine); anti-anxiety like benzodiazepines (alprazolam, clonazepam, diazepam, lorazepam);

Stimulants like methylphenidate, dextroamphetamine, modafinil, atomoxetine, clonidine; and sedative-hypnotic agents like zolpidem, eszopiclone, ramelteon.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, oxalic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The invention also relates to all stereoisomeric forms such as enantiomeric and diastereoisomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically. Also, comprised are any deuterated variants of compounds of formula I, whereby deuteration could mean at any position.

Compounds according to the present invention may exist in different polymorphic forms. Although not explicitly indicated in the above formula, such forms are intended to be included within the scope of the present invention.

Some of the compounds of formula I may also exist in tautomeric forms. Such forms although not explicitly indicated in the above formula are intended to be included within the scope of the present invention. Examples of tautomers include keto ($CH_2C=O$)⇌enol ($CH=CHOH$) tautomers or amide ($NHC=O$)⇌hydroxyimine ($N=COH$) tautomers. Formula (I) and the formulae depicted hereinafter are intended to represent all individual tautomers and all possible mixtures thereof, unless stated or shown otherwise.

The invention also includes within its scope pro-drug forms of the compounds of formula I and its various sub-scopes and sub-groups.

The compounds in accordance with the present invention are beneficial in the treatment and/or prevention of various human ailments. These include cognitive and negative symptoms in schizophrenia, cognitive impairment related to classical antipsychotic therapy, impulsivity, attention disorder with hyperactivity (ADHD), Parkinson's disease and related movement disorders, Huntington's disease; dementia with Lewy Body, Alzheimer's disease, age-related cognitive decline, mild cognitive impairment (MCI), drug addiction, sleep disorders and apathy.

Activity in any of the above-mentioned therapeutic indications or disorders can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients.

Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenytoin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

In compositions for parenteral administration, the quantity of compound of formula I present is at least 0.5% by weight and can be up to 33% by weight with respect to the total weight of the composition. For the preferred parenteral compositions, the dosage unit is in the range 0.5 mg to 3000 mg of compounds of formula I.

The daily dose can fall within a wide range of dosage units of compound of formula I and is generally in the range 0.5 to 3000 mg. However, it should be understood that the specific doses can be adapted to particular cases depending on the individual requirements, at the physician's discretion.

The compounds of formula I according to the invention can be prepared analogously to conventional methods as understood by the person skilled in the art of synthetic organic chemistry.

According to one embodiment, some compounds of general formula I-A (compounds of formula I wherein Y is CH$_2$) may be prepared by reaction of an acid of formula II with an amine of formula III (or a corresponding salt) according to the equation:

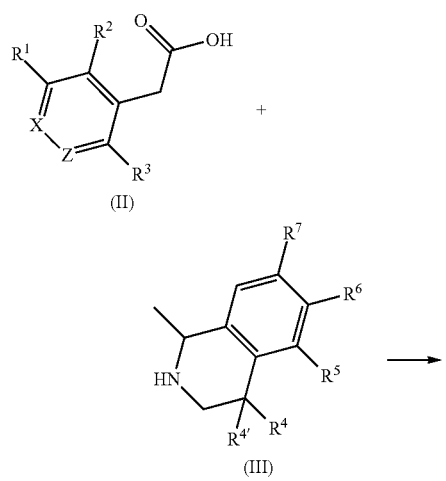

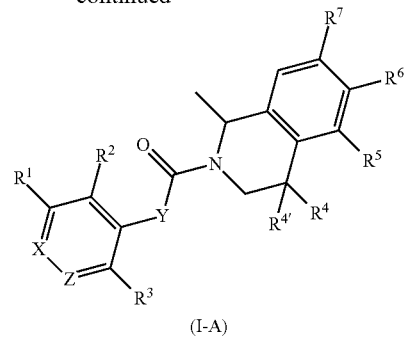

This reaction may be performed in the presence of classical coupling agents such as benzotriazolyl derivatives (BOP and the like) or uronium derivatives (COMU® and the like) or other reagents known by the person skilled in the art, in the presence of a base such as triethylamine or diisopropylethylamine in a solvent such as N,N-dimethylformamide or dichloromethane at a temperature ranging from 20 to 60° C.

Alternatively, some compounds of formula I-A (compounds of formula I wherein Y is CH$_2$ and wherein X is nitrogen) may be prepared starting from the corresponding alkyl ester II', in which R$^8$ is an alkyl group, with an amine of formula III (or a corresponding salt) in the presence of a trialkylaluminium derivative according to the equation:

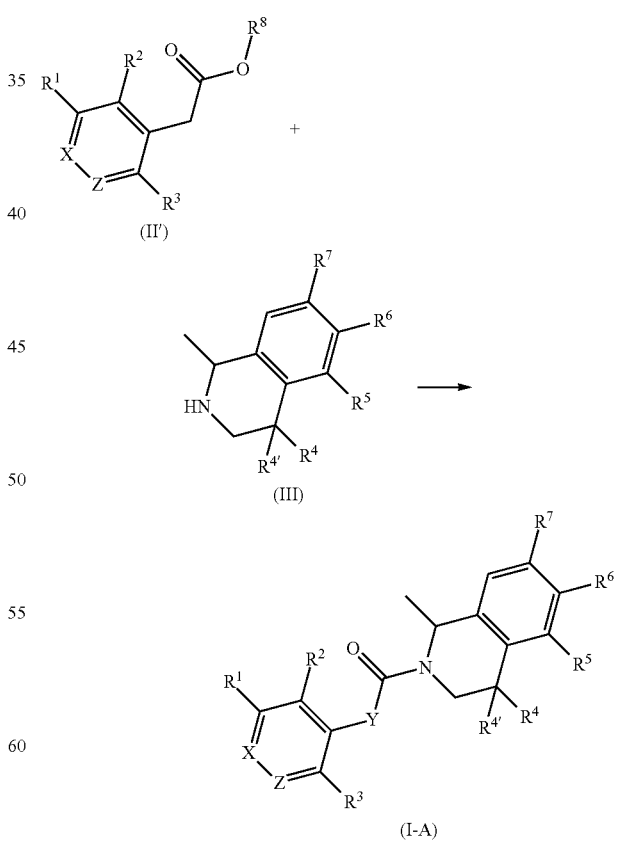

This reaction may be performed in a solvent such as dichloromethane at room temperature.

Compounds II' can be prepared analogously to conventional methods as understood by the person skilled in the art of synthetic organic chemistry.

According to another embodiment, some compounds of general formula I-B (compounds of formula I wherein Y is NH) may be prepared by reaction of an isocyanate of formula IV with an amine of formula III (or a corresponding salt) according to the equation:

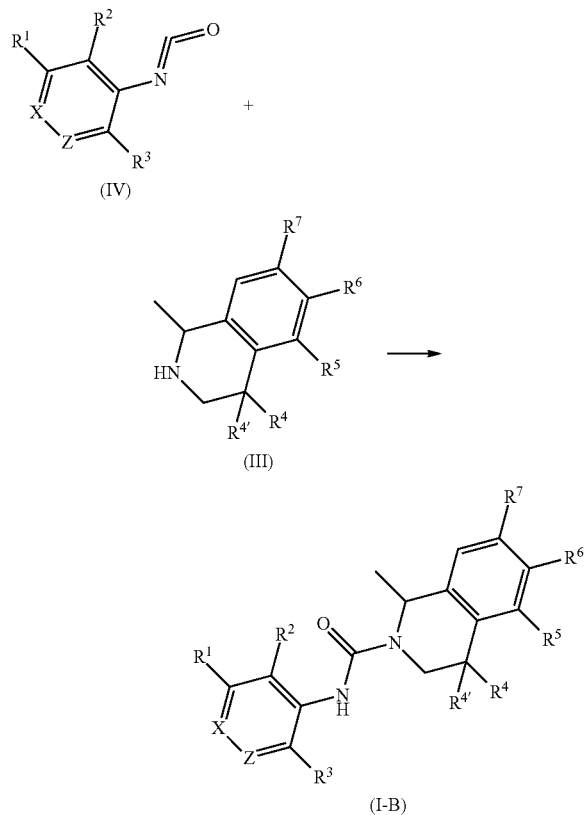

This reaction may be performed in the presence of a base such as triethylamine or diisopropylethylamine in a solvent such as dichloromethane and tetrahydrofuran from 20° C. to 60° C.

Alternatively, some compounds of formula I-B may be prepared by reaction of an aniline of formula V with an amine of formula III (or a corresponding salt) according to the equation:

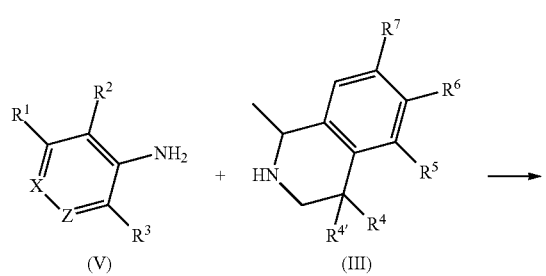

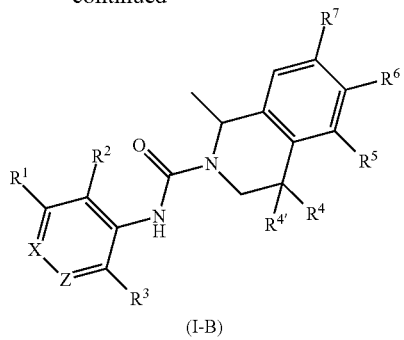

This reaction may be performed using of triphosgene in the presence of a base such as triethylamine in a polar solvent such as tetrahydrofuran at 60° C.

Anilines of formula V are commercially available or may be prepared according to any method known to the person skilled in the art.

Alternatively, some compounds having the general formula I may be prepared by functional group conversion on already assembled analogs of compounds having the general formula I (I-A, I-B), using procedures described in the literature or known to the person skilled in the art.

In particular, compounds I wherein $R^5$ is —$(CH_2)_n$—$NHR^{5a}$, n=1 and $R^{5a}$ is methylsulfonyl, acetyl, methylcarbamoyl or methoxycarbonyl may be prepared starting from compounds VI wherein $R^5$ is —$(CH_2)$—$NH_2$ according to any procedure known by the person skilled in the art. Compound VI wherein $R^5$ is —$(CH_2)$—$NH_2$ may be prepared according to any method known to the person skilled in the art starting from an intermediate VII wherein $R^5$ is a halogen atom, preferentially bromine or iodine.

Alternatively, compounds of formula I wherein $R^5$ is a $C_{1-4}$ alkyl group substituted by hydroxyl or (methoxycarbonyl)oxy may be prepared starting from an intermediate VIII wherein $R^5$ is alkoxycarbonyl according to methods known to the person skilled in the art. Intermediate VIII may be prepared starting from an intermediate VII wherein $R^5$ is a halogen atom, preferentially bromine or iodine.

Alternatively, compounds of formula I wherein $R^5$ is —$CONR^{5b}R^{5c}$ may be prepared by coupling starting from an intermediate IX wherein $R^5$ is a carboxylic acid. Intermediate IX may be prepared starting from an intermediate VIII wherein $R^5$ is alkoxycarbonyl according to methods known to the person skilled in the art.

Alternatively, compounds of formula I wherein $R^5$ is a $C_{1-4}$ alkyl group substituted by methylsulfanyl or methylsulfonyl may be prepared starting from a compound of formula I wherein $R^5$ is a $C_{1-4}$ alkyl group substituted by hydroxyl according to methods known to the person skilled in the art.

Alternatively, compounds of formula I wherein $R^5$ is —$S(O)_nR^{5d}$, n=1 or 2 and $R^{5d}$ is a $C_{1-4}$ alkyl may be prepared by oxidation of an intermediate X wherein $R^5$ is $SR^{5d}$, $R^{5d}$ having the same definition as above according to any method known to the person skilled in the art. Intermediate X wherein $R^5$ is $SR^{5d}$ may be prepared starting from an intermediate VII wherein $R^5$ is a halogen atom, preferentially bromine or iodine.

Alternatively, compounds of formula I wherein $R^5$ is —$SO_2R^{5d}$ and $R^{5d}$ is a amino, a substituted or unsubstituted pyrrolidinyl; or $R^{5d}$ is a $C_{1-4}$ alkyl substituted by a substituted or unsubstituted pyridinyl, a substituted or unsubstituted 1,2-oxazolyl or a substituted or unsubstituted tetrahydro-2H-pyranyl; or $R^{5d}$ is an amino group mono- or disubstituted by a $C_{1-4}$ alkyl optionally substituted by a fluoro, cyano or a substituted or unsubstituted triazolyl may be prepared by reaction of an intermediate XI wherein $R^5$ is a sodium sulfinate salt with a primary or secondary amine in the presence of N-bromosuccinimide; or with an alkyl bromide in a polar solvent such as dimethylsulfoxide. Intermediate XI wherein $R^5$ is a sodium sulfinate salt may be prepared by coupling from intermediate VII wherein $R^5$ is a halogen atom, preferentially bromine or iodine, in the presence of sodium metabisulfite, tetrabutylammonium bromide, a palladium salt, preferably palladium (II) acetate, 1,10-phenantroline and triphenylphosphine in a polar solvent such as tetrahydrofuran.

Alternatively, compounds of formula I wherein $R^5$ is a substituted or unsubstituted heterocycle such as 1,2-oxazol-4-yl may be prepared by Suzuki-type coupling from intermediate VII wherein $R^5$ is a halogen atom, preferentially bromine or iodine, in the presence of the corresponding boronic acid or ester, a palladium salt such as tetrakis(triphenylphosphine)palladium(0) and a base such as potassium carbonate according to methods known to the person skilled in the art.

Alternatively, compounds of formula I wherein $R^5$ is an amino group may be prepared by coupling of intermediate VII wherein $R^5$ is a halogen atom, preferentially bromine, with sodium azide in the presence of a copper salt such as copper iodide in the presence of a base such as potassium phosphate in a polar solvent such as N,N-dimethylformamide; or by any method known to the person skilled in the art.

Alternatively, compounds I wherein $R^5$ or $R^7$ is —$(CH_2)_n$—$NHR^{5a}$, n=0 and $R^{5a}$ is methylsulfonyl may be prepared starting from compounds I wherein $R^5$ or $R^7$ is an amino group according to any procedure known by the person skilled in the art. Alternatively such compounds could be prepared starting from intermediate VII wherein $R^5$ is a halogen atom, preferentially iodine or bromine. Alternatively, compounds I wherein $R^5$ is —$(CH_2)_n$—$NHR^{5a}$, n=2 and $R^{5a}$ is methylsulfonyl may be prepared from intermediate XII wherein $R^5$ is $CH_2$—X wherein X is an halogen, preferably bromine, according to any methods known to the person skilled in the art. Intermediate XII may be prepared starting from a compound of formula I wherein $R^5$ is a $C_{1-4}$ alkyl group substituted by hydroxyl.

Alternatively, compounds of formula I wherein $R^5$ is a substituted or unsubstituted heterocycle such as 4,5-dihydro-1H-imidazol-2-yl may be prepared by conversion of an intermediate XIII wherein $R^5$ is an aldehyde by any method known to the person skilled in the art. Intermediate XIII may be prepared by oxidation of compound of formula I wherein $R^5$ is a methyl group substituted by hydroxyl.

Alternatively, compounds of formula I and intermediates III (section B.12) wherein $R^5$ is a $C_{1-4}$ alkyl group substituted by 1-hydroxyethyl or 2,2,2-trifluoro-1-hydroxyethyl may be prepared starting from an intermediate XIII wherein $R^5$ is an aldehyde using alkyl metal reagents or (trifluoromethyl)trimethylsilane in the presence of cesium fluoride in the presence of a base such as potassium carbonate in a polar solvent such as N,N-dimethylformamide at a high temperature such as 75° C.; or by any method known to the person skilled in the art.

Alternatively, compounds of formula I wherein $R^5$ is a (dimethylamino)sulfinyl may be prepared by reaction of intermediate XIV with a methylating agent such as iodomethane in a solvent such as acetonitrile at room temperature. Compounds of formula I wherein $R^5$ is a N,S-dimethylsulfonimidoyl may be prepared by reaction of the same intermediate XIV with formaldehyde and formic acid at a high temperature such as 70° C. according to the equation:

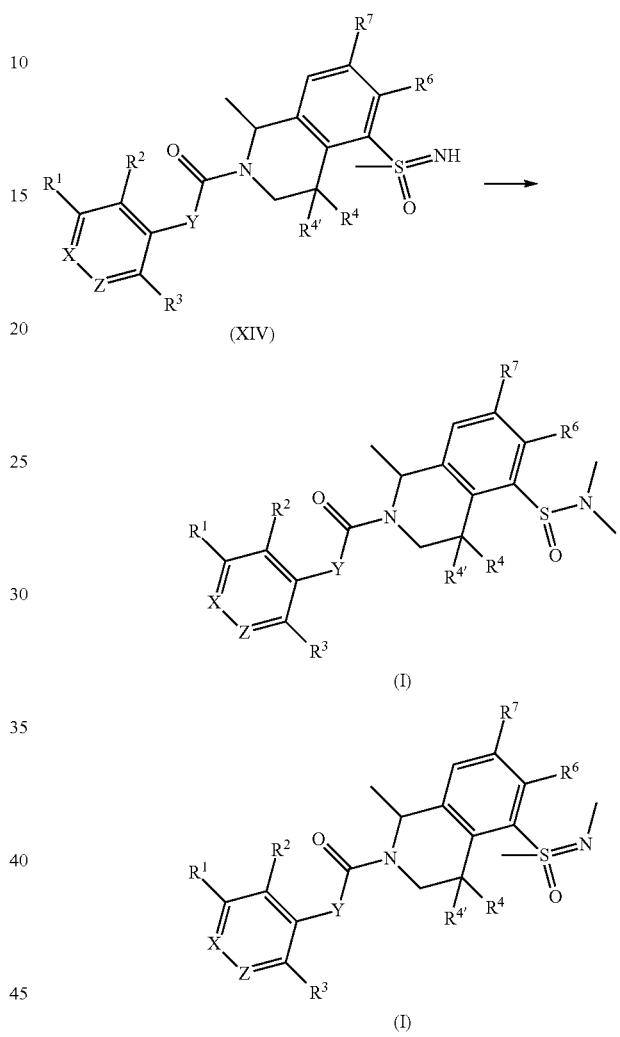

Intermediate XIV may be prepared by decyanation of a compound of formula I in which $R^5$ is (methyl)oxido-$\lambda^6$-sulfanylidene cyanamide according to the equation:

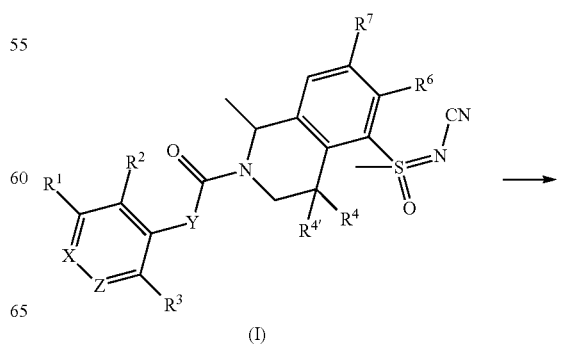

-continued

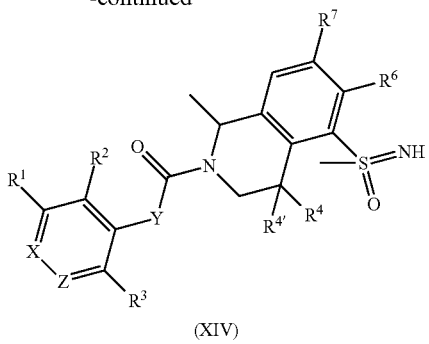

(XIV)

This reaction may be performed in the presence of an aqueous solution of sulfuric acid at 100° C.

Alternatively, compound of formula I in which $R^5$ is (methyl)oxido-$\lambda^6$-sulfanylidene cyanamide may be prepared by oxidation of an intermediate XV in which $R^5$ is methyl sulfanilydene cyanamide according to the equation:

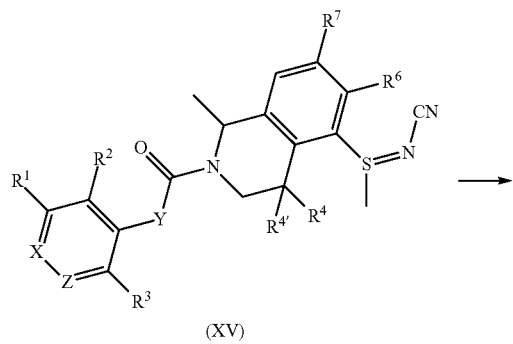

(XV)

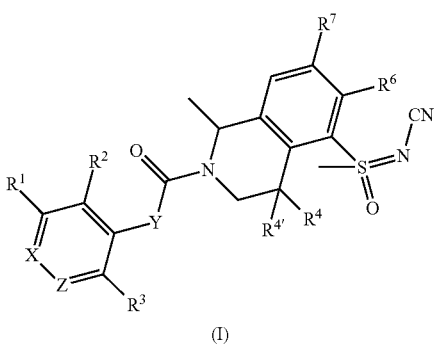

(I)

This reaction may be performed in the presence of an oxidizing agent such as m-CPBA in the presence of a base such as potassium carbonate in a polar solvent such as ethanol at room temperature.

Intermediate XV may be prepared by reaction of an intermediate X wherein $R^5$ is $SR^{5d}$, $R^{5d}$ being a methyl group, according to the equation:

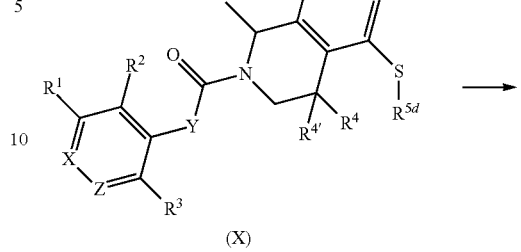

(X)

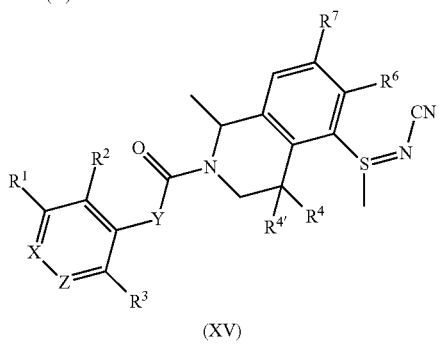

(XV)

This reaction may be carried out using cyanamide in the presence of N-bromosuccinimide and a base such as potassium tert-butoxide in a polar solvent such as methanol at room temperature.

Alternatively, compounds of formula I wherein $R^5$ is an heterocycle such as (1-oxidotetrahydro-1H-1$\lambda^4$-thiophen-1-ylidene)amino may be prepared by coupling of intermediate VII wherein $R^5$ is an halogen, preferably bromine or iodine, with sulfoximine in the presence of a palladium salt, such as palladium(II) acetate, a phosphine such as bis(diphenylphosphino)-1,1'-binaphthyl and a base such as cesium carbonate.

Alternatively, compounds of formula I wherein $R^5$ is —$(CH_2)_n$—$R^{5e}$, n=1, $R^{5e}$ is (dialkyloxidosulfanylidene)amine may be prepared from intermediate XII wherein $R^5$ is $CH_2$—X wherein X is an halogen, preferably bromine or iodine, according to any methods known to the person skilled in the art.

Alternatively, compounds of formula I wherein $R^5$ is 1,1-difluoro-2-hydroxyethyl may be prepared by reduction of an intermediate XXVIII wherein $R^5$ is alkyl-2,2-difluoroacetate according to methods known to the person skilled in the art. Intermediate XXVIII may be prepared by coupling of intermediate VII wherein $R^5$ is an halogen, preferably iodine, with alkyl bromodifluoroacetate in the presence of copper. Alternatively, compounds of formula I wherein $R^5$ is 1,2,3-triazol-4-yl may be prepared by condensation of an intermediate XXIX wherein $R^5$ is alkyne with sodium azide according to methods known to the person skilled in the art. Intermediate XXIX may be prepared by coupling of intermediate VII wherein $R^5$ is an halogen, preferably bromine or iodine, with an alkyne in the presence of copper salt such as cuprous iodide, a palladium salt such as tetrakis(triphenylphosphine)palladium(0) and a base such as triethylamine.

Alternatively, compounds of formula I wherein $R^2$ or $R^9$ is hydroxymethyl may be prepared by reduction of an intermediate XVI wherein $R^2$ or $R^9$ is alkoxycarbonyl according to any method known to the person skilled in the art.

Intermediate XVI may be prepared starting from an intermediate XVII wherein $R^2$ or $R^9$ is an halogen, preferably iodine, according to any method known to the person skilled in the art.

Alternatively, compounds of formula I wherein $R^2$ is alkylcarbamoyl may be prepared by coupling of an intermediate XVIII wherein $R^2$ is a carboxylic acid with an amine according to any method known to the person skilled in the art. Intermediate XVIII may be prepared by hydrolysis of an intermediate XVI.

Alternatively, compounds of formula I wherein $R^2$ or $R^9$ is a group of formula —CH$_2$NHR$^{2a}$ or —CH$_2$NHR$^{9'}$ wherein $R^{2a}$ is selected from acetyl or methylsulfonyl and $R^{9'}$ is selected from acetyl, methoxycarbonyl or methylsulfonyl may be prepared starting from a compound of formula I wherein $R^2$ or $R^9$ is cyano according to any method known to the person skilled in the art.

Compounds of formula I wherein $R^2$ or $R^9$ is cyano may be prepared by palladium coupling of an intermediate XVII with zinc cyanide or according to any method known to the person skilled in the art.

Alternatively, compounds of formula I wherein $R^2$ is —NHR$^{2a}$ wherein $R^{2a}$ has the same definition as above, may be prepared starting from an intermediate XIX wherein $R^2$ is amino according to any method known to the person skilled in the art. Intermediate XIX may be prepared by reduction of an intermediate XX wherein $R^2$ is nitro according to any method known to the person skilled in the art.

Alternatively, compounds of formula I wherein $R^1$, $R^2$, or $R^9$ is a methylsulfonyl or a methylsulfinyl may be prepared by oxidation of a compound of formula I wherein $R^1$, $R^2$ or $R^9$ is a methylsulfanyl according to any method known to the person skilled in the art. Compounds of formula I wherein $R^1$, $R^2$ or $R^9$ is a methylsulfanyl may be prepared by palladium coupling of an intermediate XVII with sodium thiomethoxide or according to any method known to the person skilled in the art. Alternatively, compounds of formula I wherein $R^1$, $R^2$ or $R^9$ is a methylsulfanyl may be prepared by metal-halogen exchange and subsequent substitution with dimethyldisulfide starting from an intermediate XVII.

Alternatively, compounds of formula I wherein $R^1$ is (methylsulfonyl)amino group may be prepared by coupling of an intermediate XVII wherein $R^1$ is an halogen, preferably bromine or iodine, with methanesulfonamide in the presence of a copper salt such as cuprous iodide in the presence of a base such as potassium phosphate in a polar solvent such as N,N-dimethylformamide.

Alternatively, compounds of formula I wherein $R^2$ is an heterocycle such as 1H-pyrazol-4-yl may be prepared by a Suzuki-type coupling from intermediate XVII wherein $R^2$ is a halogen atom, preferably bromine or iodine, in the presence of the corresponding boronic acid and a palladium salt such as tetrakis(triphenylphosphine)palladium(0) according to methods known to the person skilled in the art.

Alternatively, compounds of formula I wherein $R^2$ is a group of formula —CH$_2$R$^{2a}$ and $R^{2a}$ is selected from acetyl or methylsulfonyl, may be prepared according to any method known to the person skilled in the art starting from compounds of formula I wherein $R^2$ is hydroxymethyl.

Alternatively, compounds of formula I in which $R^1$ and $R^2$ are linked together to form with the adjacent aromatic group a bicycle and wherein $R^{2b}$ is alkylsulfonyl may be prepared by reaction of a compound of formula I wherein $R^{2b}$ is hydrogen with alkylsulfonyl chloride according to methods known to the person skilled in the art.

Alternatively, compounds of formula I wherein $R^4$ and $R^{4'}$ form together a carbonyl group may be prepared by oxidation of compounds of formula I wherein $R^4$ is hydroxy using an oxidating agent such as Dess-Martin periodinane or according to any other method known to the person skilled in the art.

Alternatively, compounds of formula I wherein $R^4$ is methoxy may be prepared by methylation of compounds of formula I wherein $R^4$ is hydroxyl with a base such as sodium hydride and an alkylating agent such as methyl iodide or according to any other method known to the person skilled in the art.

Alternatively, compounds of formula I wherein $R^4$ is (methoxycarbonyl)oxy or (methylcarbamoyl)oxy may be prepared by alkylation of compounds of formula I wherein $R^4$ is hydroxyl with a base such as diidopropylamine and an alkylating agent according to any method known to the person skilled in the art.

Alternatively, compounds of formula I wherein $R^4$ is methylsulfonyl may be prepared by oxidation of an intermediate XXI wherein $R^4$ is methylsulfanyl according to any method known to the person skilled in the art. Intermediate XXI may be prepared by substitution of compounds of formula I wherein $R^4$ is hydroxyl according to any method known to the person skilled in the art.

Acids of formula II may be prepared by functional group conversion using procedures described in the literature or known to the person skilled in the art. In particular, they may be prepared by hydrolysis of the corresponding cyanides of formula XXII or alkyl esters of formula XXIII. Cyanides or alkyl esters may be prepared according to classical procedures described in the literature or known to the person skilled in the art.

Amines of formula III are either commercially available or may be prepared by classical functional groups transformations according to methods known to the person skilled in the art.

Some amines of formula III wherein $R^4$ or $R^{4'}$ is hydroxyl may be prepared by deprotection of N-protected intermediates of formula XXIV or XXV, wherein P is a protecting group such as p-toluenesulfonyl according to the equation:

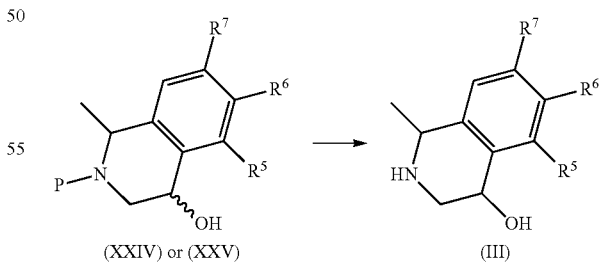

(XXIV) or (XXV)     (III)

This reaction may be performed using classical deprotecting agents such as sodium in liquid ammonia in a polar solvent such as tetrahydrofuran. Intermediates of formula XXIV or XXV may be prepared by enantioselective reduction of an intermediate of formula XXVI wherein $R^4$ and $R^{4'}$ form together a keto group according to the equation:

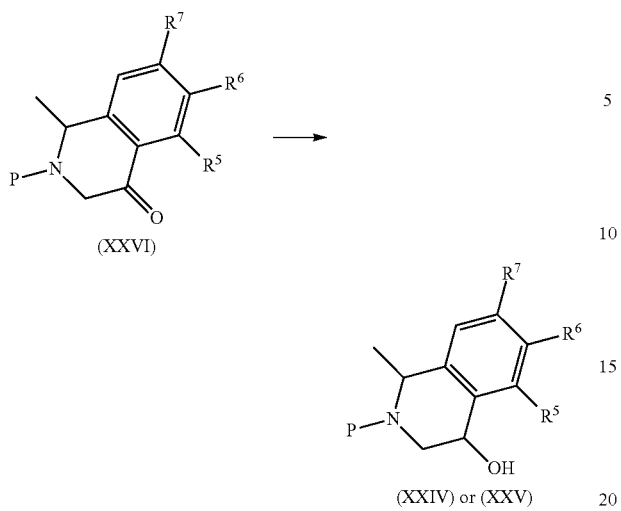

This reaction may be performed using using a chiral reducing agent such as an oxazaborolidine borane derivative in a polar solvent such as tetrahydrofuran. Intermediate of formula XXVI may be prepared by cyclization of an intermediate XXVII, for example using a Friedel-Crafts type reaction or by any method known to the person skilled in the art. Intermediate XXVII may be prepared by functional groups transformations according to any procedure known to the person skilled in the art.

EXAMPLES

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

All reactions involving air or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4.6 mm column. The gradient runs from 100% solvent A (water/ACN/ammonium formate solution 85/5/10 (v/v/v)) to 100% solvent B (water/ACN/ammonium formate solution 5/85/10 (v/v/v) in 6 min. with a hold at 100% B of 5 minutes. The flow rate is set at 8 mL/min during 6 min. then increased at 3 mL/min during 2 min. with a hold at 3 mL/min during 3 minutes. A split of 1/25 is used just before API source. The chromatography is carried out at 45° C. The ammonium formate solution (pH~8.5) is prepared by dissolution of ammonium formate (630 mg) in water (1 L) and addition of ammonium hydroxide 30% (500 µL).

Mass spectrometric measurements in LC-MS mode are performed as follows:
for acidic elution, analyses are performed using:
1. Method A=A QDA Waters simple quadrupole mass spectrometer is used for LC-MS analysis. This spectrometer is equipped with an ESI source and an UPLC Acquity Hclass with diode array detector (210 to 400 nm). Data are acquired in a full MS scan from m/z 50 to 1000 in positive mode with an acidic elution. The reverse phase separation is carried out at 45° C. on a Waters Acquity UPLC HSS T3 1.8 µm (2.1×50 mm) column for acidic elution. Gradient elution is done with Water (solvent A), ACN (solvent B), Water/ACN/Formic Acid 0.5% (solvent C). HPLC flow rate: 0.6 ml/min to 0.7 mL/min, injection volume: 1 µL. Full flow in MS.
2. Method B=A SQD Waters single quadrupole mass spectrometer is used for LC-MS analysis. This spectrometer is equipped with an ESI source and an UPLC Waters with diode array detector (210 to 400 nm)

MS Parameters:
ESI capillary voltage 3.0 kV. Cone and Extractor voltage 25 and 2 V, respectively. Source block temperature 130° C. Desolvation temperature 370° C. Cone gaz flow 120 L/h (Nitrogen), Desolvation Gas flow 800 L/h. Multiplier voltage 470 V. Data are acquired in a full MS scan from m/z 50 to 750 in positive and negative mode.

LC Parameters:
The reverse phase separation is carried out at 45° C. on an Acquity UPLC HSS T3 C18 column (1.7 µm, 2.1×100 mm). Gradient elution is done with Formic Acid 0.5 mL/L in ACN/water 5/95 (pH~3) (solvent A1), Formic Acid 0.375 mL/L ACN (solvent B1). HPLC flow rate: 0.4 mL/min to 0.5 mL/min, injection volume: 0.4 µL. Full flow in MS.

for basic elution, analyses are performed using:
3. Method C=A QM Waters triple quadrupole mass spectrometer is used for LC-MS analysis. This spectrometer is equipped with an ESI source and an HPLC Waters 2795 quaternary pump with diode array detector (210 to 400 nm).

Ms Parameters:
ESI capillary voltage 2.8 kV, Cone and Extractor voltage 30 and 2 V, respectively, Source block temperature 120° C., Desolvation temperature 320° C., Cone gaz flow 120 L/h (Nitrogen), Desolvation Gas flow 550 L/h. Multiplier voltage 600 V. Data are acquired in a full MS scan from m/z 50 to 750 in positive mode with an acidic elution and both in positive and negative modes with a basic elution.

Lc Parameters:
The reverse phase separation is carried out at 45° C. on a Waters XBridge MS C18 column (3.5 µm, 100×4.6 mm) for basic elution. Gradient elution is done with Water (solvent A), ACN (solvent B), Ammonium Formate in water 630 mg/L+500 µL/L NH$_4$OH 30% (solvent D) (pH~8.5). HPLC flow rate: 8 ml/min to 3 mL/min, injection volume: 5 µL. The splitting ratio is set at +/−150 µL to MS.

Some reaction mixtures could be treated using Isolute® separator phase cartridges (from Biotage), acidic columns or catch and release SPE (Solid Phase Extraction) cartridges. Crude materials could be purified by normal phase chromatography, (acidic or basic) reverse phase chromatography, chiral separation or recrystallization.

Normal reverse phase chromatography are performed using silica gel columns (100:200 mesh silica gel or Puriflase®-50SIHC-JP columns from Interchim).

Preparative reverse phase chromatography are performed as follows:

LC-MS purification (Basic mode, LC-MS prep) using a SQD or QM Waters triple quadrupole mass spectrometer is used for LC-MS purification. This spectrometer is equipped with an ESI source and a Prep LC controller Waters quaternary pump with diode array detector (210 to 400 nm).

MS Parameters:

ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC Parameters:

The reverse phase separation is carried out at rt on a Sunfire prep OBD C18 column (5 µm, 30×50 mm) for acidic elution a XBridge prep OBD C18 column (5 µm, 30×50 mm) for basic elution. Gradient elution is done with Water (solvent A), ACN (solvent B), Water/ACN/TFA: 49.5/49.5/1, v/v/v (solvent C) (pH~1), Ammonium bicarbonate in water 8 g/L+500 µL/L NH$_4$OH 30% (solvent D) (pH~8.5). HPLC flow rate: 35 mL/min to 60 mL/min, injection volume: 1 mL. The splitting ratio is set at +/−1/6000 to MS.

Standard acidic or basic reverse phase chromatography (Acidic or Basic mode, standard LC) is carried out at rt on a Kromasil C18 column (10 µm, 8×19 cm) for acidic or neutral elution and a Kromasil Eternity or Eternity XT column (10 µm, 8×14 cm) for basic elution. Gradient elution is done with Water (solvent A), ACN (solvent B), Water/TFA: 98/2 v/v (pH~1) OR: water/NH$_4$OH 99.5/0.5 v/v (pH~10) (solvent C).

Acidic "40-70" Gradient Program

| Time (min) | A (%) | B (%) | C (%) | Flow (mL/min) |
|---|---|---|---|---|
| 0 | 55 | 40 | 5 | 180 |
| 4 | 55 | 40 | 5 | 180 |
| 14 | 25 | 70 | 5 | 180 |
| 14.2 | 0 | 95 | 5 | 180 |
| 20 | 0 | 95 | 5 | 180 |
| 20.1 | 55 | 40 | 5 | 180 |
| 25 | 55 | 40 | 5 | 180 |

Basic "20-50" Gradient Program

| Time (min) | A (%) | B (%) | C (%) | Flow (mL/min) |
|---|---|---|---|---|
| 0 | 75 | 20 | 5 | 180 |
| 4 | 75 | 20 | 5 | 180 |
| 14 | 45 | 50 | 5 | 180 |
| 14.2 | 0 | 95 | 5 | 180 |
| 20 | 0 | 95 | 5 | 180 |
| 20.1 | 75 | 20 | 5 | 180 |
| 25 | 75 | 20 | 5 | 180 |

It will be apparent to the one skilled in the art that different retention times (RT) may be obtained for LCMS data may be obtained if different analytical conditions are used.

Preparative Chiral Chromatographic separations are performed on using liquid phase chromatography or supercritical fluid chromatography (SFC) instruments with various mixtures of lower alcohols and C5 to C8 linear, branched or cyclic alkanes at 360 mL/min. Solvent mixtures as well as columns are described in individual procedures.

Products were generally dried under vacuum before final analyses and submission to biological testing.

NMR spectra are recorded on a BRUKER AVANCE 400 MHz NMR Spectrometer fitted with a Linux workstation running XWIN NMR 3.5 software and a 5 mm inverse $^1$H/BB probehead, or BRUKER DRX 400 NMR fitted with a SG Fuel running XWIN NMR 2.6 software and a 5 mm inverse geometry $^1$H/$^{13}$C/$^{19}$F triple probehead. The compound is studied in d$_6$-dimethylsulfoxide (or d$_3$-chloroform) solution at a probe temperature of 300 K and at a concentration of 10 mg/mL. The instrument is locked on the deuterium signal of d$_6$-dimethylsulfoxide (or d$_3$-chloroform). Chemical shifts are given in ppm downfield from TMS (tetramethylsilane) taken as internal standard.

Abbreviations/Recurrent Reagents

ACN: Acetonitrile
AcOH: Acetic acid
BINAP: (2,2'-bis(diphenylphosphino)-1,1'-binaphthyl
BOP: (Benzotriazol-1-yloxy)tris(dimethylamino)phosphonium hexafluorophosphate
Brine: Saturated aqueous sodium chloride solution
tBuONO: tert-butyl nitrite
CBS: Corey-Bakshi-Shibata catalyst
COMU: (1-Cyano-2-ethoxy-2-oxoethylidenaminooxy)dimethylamino-morpholino-carbenium hexafluorophosphate.
dba: dibenzylideneacetonate
DCM: Dichloromethane
DIPEA: Diisopropylethylamine
DMAP: 4-(Dimethylamino)pyridine
DMF: N,N-Dimethylformamide
DMSO: Dimethylsulfoxide
dppf: 1,1'-Bis(diphenylphosphino)ferrocene
ES$^+$: Electrospray Positive Ionisation
EtOH: Ethanol
Et$_2$O: Diethyl ether
EtOAc: Ethyl acetate
h: Hour
HCl: Hydrochloric acid
K$_2$CO$_3$: Potassium carbonate
LC: Liquid Chromatography
LCMS: Liquid Chromatography Mass Spectrometry
MeOH: Methanol
MgSO$_4$: Magnesium sulfate
MIDA: N-methyliminodiacetic acid
min.: minutes
NaOH: Sodium hydroxide
Na$_2$SO$_4$: Sodium sulfate
NMR: Nuclear magnetic resonance
PdCl$_2$(dppf): [1,1'-Bis(diphenylphosphino)ferrocene]dichloropalladium(II)
Pd$_2$(dba)$_3$: Tris(dibenzylideneacetone)dipalladium(0)
PrOH: isopropanol
PTSA: ptoluenesulfonic acid
rt: room temperature
TEA: Triethyl amine
THF: Tetrahydrofuran
TLC: Thin Layer Chromatography
cAMP: cyclic adenosinemonophosphate
EC$_{20/50}$: concentration which produces 20%/50% of the maximum response
Erel: relative efficacy
HEPES: 4-(2-hydroxyethyl)-1-piperazineethanesulfonic acid
HTRF: homogenous time-resolved fluoresence
IBMX: 3-Isobutyl-1-methylxanthine Intermediates A. Synthesis of Acids of Formula II or Corresponding Methyl Ester A.1. Synthesis of (3-bromo-2,6-dichlorophenyl)acetic acid a2

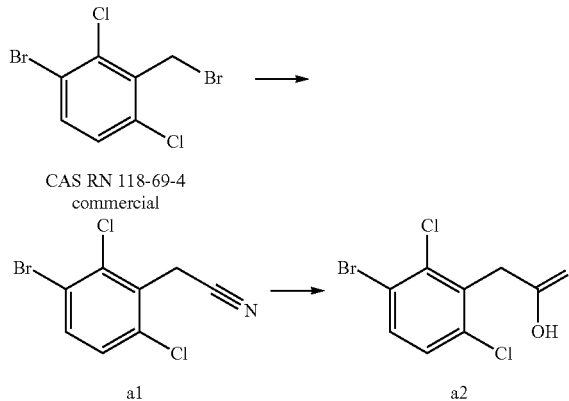

CAS RN 118-69-4 commercial

A.1.1. Synthesis of (3-bromo-2,6-dichlorophenyl)acetonitrile a1

To a solution of 1-bromo-3-(bromomethyl)-2,4-dichlorobenzene (commercial, 15 g, 44.66 mmol) in ACN (250 mL) were added trimethylsilylcyanide (7 g, 71.2 mmol) and tetrabutylammonium fluoride (18.5 g, 71.2 mmol). The reaction mixture was stirred at rt for 15 min., concentrated under vacuum and the residue was purified by column chromatography using 5% EtOAc in hexanes as eluent to afford 10 g of (3-bromo-2,6-dichlorophenyl)acetonitrile a1.
Yield: 80%.
$^1$H NMR (400 MHz, DMSO-$d_6$) δ 7.87 (d, J=8.7 Hz, 1H), 7.56 (d, J=8.7 Hz, 1H), 4.27 (s, 2H).

A.1.2. Synthesis of (3-bromo-2,6-dichlorophenyl)acetic acid a2

A solution of (3-bromo-2,6-dichlorophenyl)acetonitrile a1 (10 g, 38 mmol) in concentrated sulphuric acid/water (120 mL, 1:1) was refluxed for 3 h. The reaction mixture was cooled to rt and poured into ice water. The precipitated solid was filtered, washed with water and dried to afford 10 g of (3-bromo-2,6-dichlorophenyl)acetic acid a2.
Yield: 92%.
$^1$H NMR (400 MHz, DMSO-$d_6$) δ 7.75 (d, J=8.7 Hz, 1H), 7.45 (d, J=8.6 Hz, 1H), 3.97 (s, 2H).

A.2. Synthesis of [2,6-dichloro-3-(methoxycarbonyl)phenyl]acetic acid a3

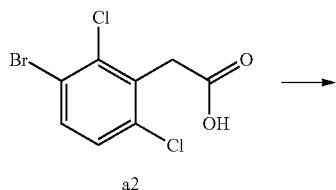

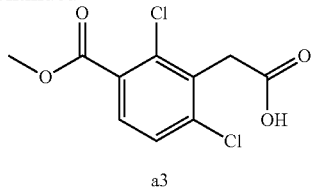

To a solution of (3-bromo-2,6-dichlorophenyl)acetic acid a2 (2.3 g, 8.1 mmol) in MeOH (100 mL) were added TEA (1.6 g, 16.24 mmol) and PdCl$_2$(dppf) (0.59 g, 0.81 mmol). The reaction mixture was heated at 120° C. under carbon monoxide atmosphere for 8 h, then concentrated under reduced pressure, and the residue was purified by column chromatography using 40% EtOAc in hexanes as eluent to afford 1.5 g of [2,6-dichloro-3-(methoxycarbonyl)phenyl]acetic acid a3.
Yield: 70%.
$^1$H NMR (400 MHz, DMSO-$d_6$) δ 12.81 (s, 1H), 7.78-7.59 (m, 2H), 3.97 (s, 2H), 3.87 (s, 3H).

[2,6-dichloro-4-(methoxycarbonyl)phenyl]acetic acid a3b may be synthesized according to a method analogous to the method described above using (4-bromo-2,6-dichlorophenyl)acetic acid.

A.3. Synthesis of (2,6-dichloro-3-cyanophenyl)acetic acid a6

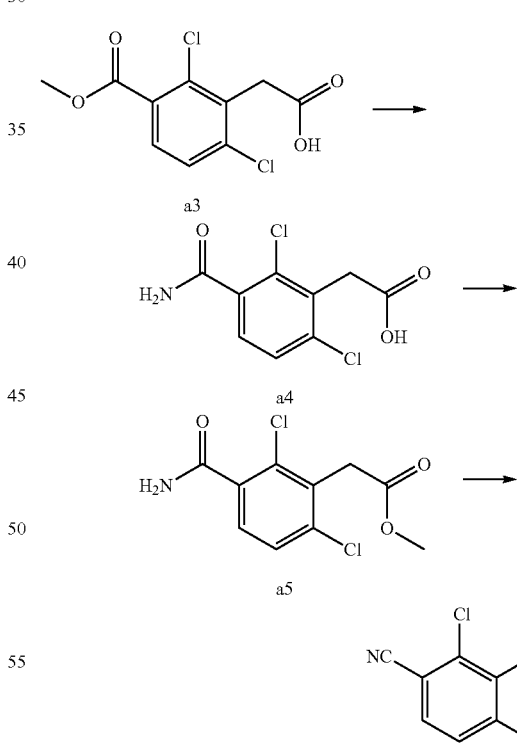

A.3.1. Synthesis of (3-carbamoyl-2,6-dichlorophenyl)acetic acid a4

A solution of [2,6-dichloro-3-(methoxycarbonyl)phenyl]acetic acid a3 (1.5 g, 5.7 mmol) in methanolic ammonia (40 mL) was heated in a steel bomb at 120° C. for 8 h. The reaction mixture was cooled to rt and concentrated under vacuum to afford 1 g of (3-carbamoyl-2,6-dichlorophenyl) acetic acid a4.

Yield: 71% (crude).

$^1$H NMR (400 MHz, DMSO-d$_6$) δ 7.90 (s, 1H), 7.58 (s, 1H), 7.43 (d, J=8.2 Hz, 1H), 7.25 (d, J=8.2 Hz, 1H), 3.73 (d, J=4.9 Hz, 2H).

A.3.2. Synthesis of methyl(3-carbamoyl-2,6-dichlorophenyl)acetate a5

TEA (0.81 g, 8 mmol) was added to a solution of (3-carbamoyl-2,6-dichlorophenyl)acetic acid a4 (1 g, 4 mmol) in DCM (50 mL) at 0° C., and the reaction mixture was stirred for 10 min. Methyl chloroformate (0.8 g, 8.8 mmol) was added and the reaction mixture was allowed to warm to rt and stirred for 12 h. The reaction mixture was concentrated under vacuum, then EtOAc was added. The precipitated solid was filtered and the filtrate was concentrated under vacuum to afford 0.7 g of methyl (3-carbamoyl-2,6-dichlorophenyl)acetate a5.

Yield: 66%.

$^1$H NMR (400 MHz, DMSO-d$_6$) δ 7.98 (s, 1H), 7.73-7.61 (m, 1H), 7.54 (d, J=8.2 Hz, 1H), 7.39 (d, J=8.2 Hz, 1H), 4.04 (s, 2H), 3.66 (s, 3H).

A.3.3. Synthesis of (2,6-dichloro-3-cyanophenyl)acetic acid a6

To a solution of methyl (3-carbamoyl-2,6-dichlorophenyl)acetate a5 (0.7 g, 2.83 mmol) in DCM (50 mL) at 0° C. were added TEA (2.8 g, 28.34 mmol) and trifluoroacetic anhydride (2.9 g, 14.17 mmol). The reaction mixture was stirred at rt for 1 h, concentrated under vacuum and extracted with EtOAc. The organic layer was dried over Na$_2$SO$_4$, filtered and concentrated under vacuum. The residue was dissolved in MeOH (10 mL), then an 5N aqueous solution of NaOH (5 mL) was added and the reaction mixture was stirred at rt for 2 h and concentrated under vacuum. The aqueous layer was acidified with a dilute aqueous solution of HCl. The compound was extracted with EtOAc. The organic layer was dried over Na$_2$SO$_4$, filtered and concentrated under vacuum to afford 0.5 g of (2,6-dichloro-3-cyanophenyl)acetic acid a6.

Yield: 77% (crude).

$^1$H NMR (400 MHz, DMSO-d$_6$) δ 12.95 (s, 1H), 7.97 (d, J=8.4 Hz, 1H), 7.75 (d, J=8.5 Hz, 1H), 3.97 (s, 2H).

A.4. Synthesis of (4-bromo-2,6-dichlorophenyl)acetic acid a8

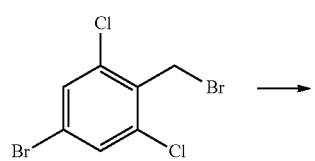

274671-76-0
commercial

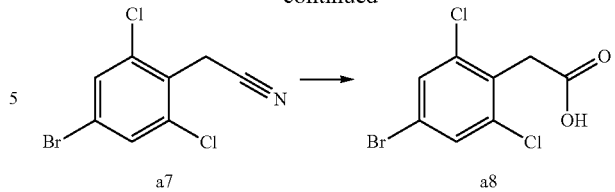

A.4.1. Synthesis of (4-bromo-2,6-dichlorophenyl)acetonitrile a7

To a solution of 5-bromo-2-(bromomethyl)-1,3-dichlorobenzene (commercial, 15 g, 47.6 mmol) in ACN (150 mL) at 0° C. were added trimethylsilylcyanide (9 mL, 71.4 mmol) and tetrabutylammonium fluoride (18.63 g, 71.4 mmol). The reaction mixture was stirred at rt for 1 h, then concentrated under vacuum. The residue was purified by column chromatography using 15% EtOAc in hexanes as eluent to afford 11.7 g of (4-bromo-2,6-dichlorophenyl)acetonitrile a7.

Yield: 93%.

$^1$H NMR (400 MHz, DMSO-d$_6$) δ 7.93 (s, 2H), 4.16 (s, 2H).

A.4.2. Synthesis of (4-bromo-2,6-dichlorophenyl)acetic acid a8

Concentrated sulphuric acid (50 mL) was added dropwise to a solution of (4-bromo-2,6-dichlorophenyl)acetonitrile a7 (10 g, 38 mmol) in water (50 mL) at 0° C. The reaction mixture was stirred for 10 min., then heated at 120° C. for 3 h. The reaction mixture was poured into ice water and the compound was extracted with EtOAc. The organic layer was dried over Na$_2$SO$_4$, filtered and concentrated under vacuum. The residue was triturated thrice with Et$_2$O to afford 7.29 g of (4-bromo-2,6-dichlorophenyl)acetic acid a8.

Yield: 66%.

$^1$H NMR (400 MHz, DMSO-d$_6$) δ 12.77 (s, 1H), 7.79 (s, 2H), 3.85 (s, 2H).

A.5. Synthesis of (2,6-dichloro-4-cyanophenyl)acetic acid a11

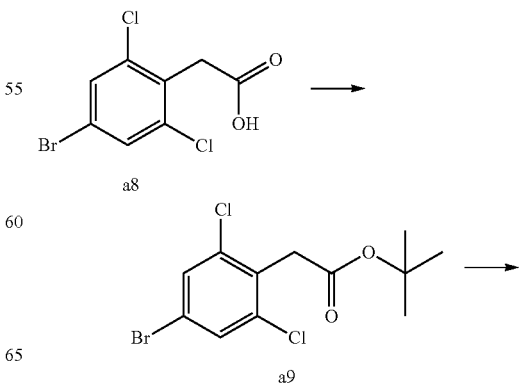

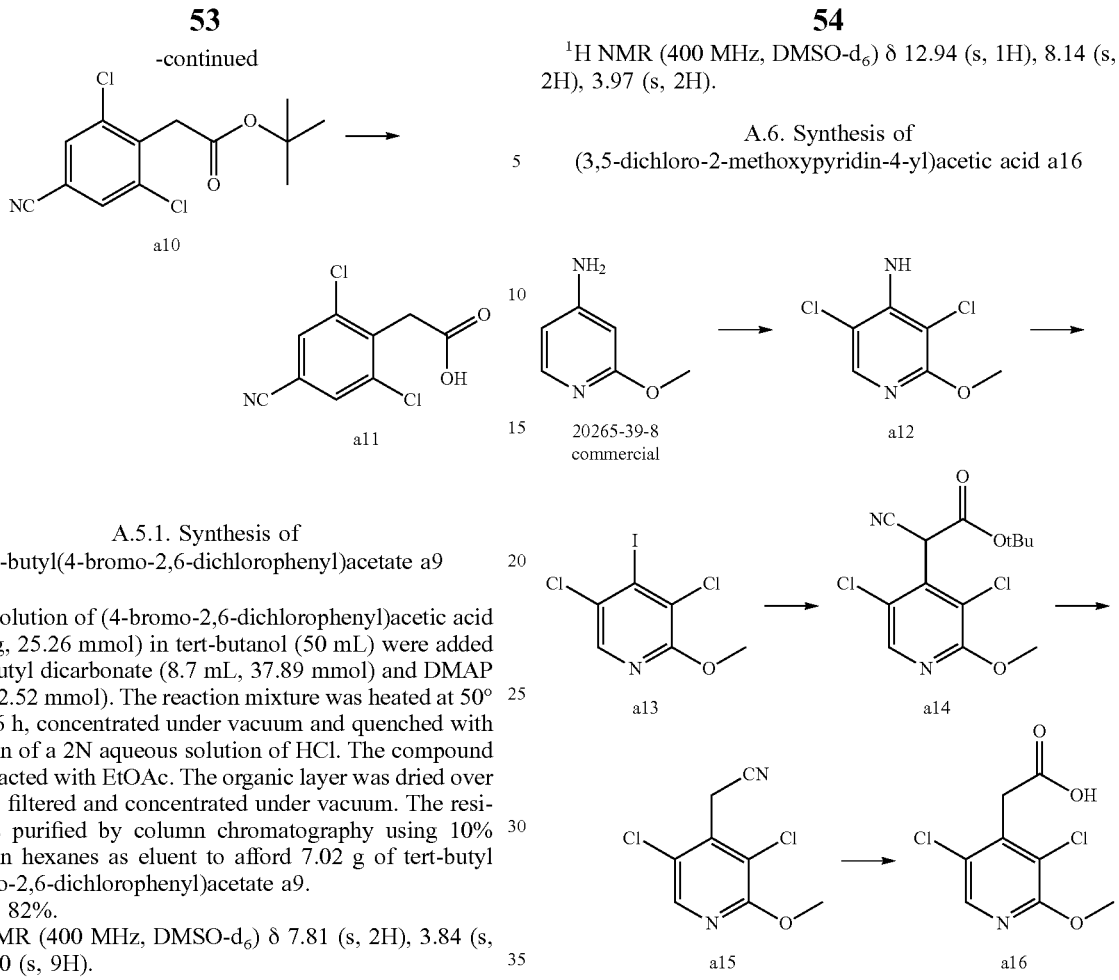

¹H NMR (400 MHz, DMSO-d₆) δ 12.94 (s, 1H), 8.14 (s, 2H), 3.97 (s, 2H).

A.6. Synthesis of (3,5-dichloro-2-methoxypyridin-4-yl)acetic acid a16

A.5.1. Synthesis of tert-butyl(4-bromo-2,6-dichlorophenyl)acetate a9

To a solution of (4-bromo-2,6-dichlorophenyl)acetic acid a8 (7.2 g, 25.26 mmol) in tert-butanol (50 mL) were added di-tert-butyl dicarbonate (8.7 mL, 37.89 mmol) and DMAP (0.31 g, 2.52 mmol). The reaction mixture was heated at 50° C. for 16 h, concentrated under vacuum and quenched with a solution of a 2N aqueous solution of HCl. The compound was extracted with EtOAc. The organic layer was dried over Na₂SO₄, filtered and concentrated under vacuum. The residue was purified by column chromatography using 10% EtOAc in hexanes as eluent to afford 7.02 g of tert-butyl (4-bromo-2,6-dichlorophenyl)acetate a9.

Yield: 82%.

¹H NMR (400 MHz, DMSO-d₆) δ 7.81 (s, 2H), 3.84 (s, 2H), 1.40 (s, 9H).

A.5.2. Synthesis of tert-butyl(2,6-dichloro-4-cyanophenyl)acetate a10

A solution of tert-butyl (4-bromo-2,6-dichlorophenyl)acetate a9 (2 g, 5.88 mmol) in DMF (20 mL) was degassed with argon for 10 min. Pd₂(dba)₃ (0.54 g, 0.59 mmol), PdCl₂(dppf) (0.43 g, 0.59 mmol) and zinc cyanide (0.55 g, 4.7 mmol) were added and the reaction mixture was further degassed with argon for 15 min. The reaction mixture was heated at 100° C. for 12 h, filtered through Celite® and the filtrate was extracted with EtOAc. The organic layer was washed with water, dried over Na₂SO₄, filtered and concentrated under vacuum. The residue was purified by column chromatography using 10% EtOAc in hexanes as eluent to afford 0.8 g tert-butyl (2,6-dichloro-4-cyanophenyl)acetate a10.

Yield: 47%.

¹H NMR (400 MHz, DMSO-d₆) δ 8.14 (d, J=1.3 Hz, 2H), 3.96 (d, J=1.1 Hz, 2H), 1.39 (d, J=1.3 Hz, 9H).

A.5.3. Synthesis of (2,6-dichloro-4-cyanophenyl)acetic acid a11

To a solution of tert-butyl (2,6-dichloro-4-cyanophenyl) acetate a10 (1.8 g, 6.29 mmol) in dry DCM (15 mL) was added trifluoroacetic acid (5 mL) at 0° C. The reaction mixture was stirred at rt for 16 h, concentrated under vacuum and the residue was washed thrice with hexanes to afford 1.38 g of (2,6-dichloro-4-cyanophenyl)acetic acid a11 as grey solid.

Yield: 96%.

A.6.1. Synthesis of 3,5-dichloro-2-methoxypyridin-4-amine a12

To a solution of 2-methoxypyridin-4-amine (commercial, 30 g, 241.6 mmol) in ACN (1 L) at rt, N-chlorosuccinimide (129 g, 966.6 mmol) was added portion wise and the reaction mixture was stirred at rt for 16 h. The reaction mixture was concentrated under vacuum, the residue was diluted with a 20% aqueous solution of K₂CO₃ (500 mL) and the mixture was extracted with EtOAc. The organic layer was washed with brine, dried over Na₂SO₄, filtered and concentrated under vacuum. The residue was purified by column chromatography using 50% EtOAc in hexanes as eluent to afford 35.1 g of 3,5-dichloro-2-methoxypyridin-4-amine a12.

Yield: 75%.

LCMS: 194 (M+H)⁺.

¹H NMR (400 MHz, DMSO-d₆) δ 7.70-7.91 (m, 1H), 6.50 (s, 2H), 3.80-3.97 (m, 3H).

A.6.2. Synthesis of 3,5-dichloro-4-iodo-2-methoxypyridine a13

To a solution of CuI (59 g, 311 mmol) in ACN (1000 mL) was added dropwise at 50° C. t-BuONO (93 mL, 777 mmol). The reaction mixture was heated at 80° C. for 30 min. A solution of 3,5-dichloro-2-methoxypyridin-4-amine a12 (30 g, 155 mmol) in ACN (500 mL) was added by fractions (evolution of nitrogen gas was observed) and the mixture was stirred at 80° C. for 2 h. The reaction mixture was concentrated under vacuum and the residue was taken up with EtOAc (100 mL) and hexanes (2 L). The resulting suspension was passed through a short silica bed and the filtrate was concentrated under vacuum to afford 34.9 g of 3,5-dichloro-4-iodo-2-methoxypyridine a13 as a pale yellow solid.

Yield: 74%.

$^1$H NMR (400 MHz, DMSO-$d_6$) δ 8.19-8.34 (m, 1H), 3.87-4.00 (m, 3H).

A.6.3. Synthesis of tert-butyl cyano(3,5-dichloro-2-methoxypyridin-4-yl)acetate a14

To a solution of 3,5-dichloro-4-iodo-2-methoxypyridine a13 (10 g, 32.9 mmol), tert-butyl 2-cyanoacetate (9.4 ml, 65.8 mmol), cesium carbonate (42.9 g, 131.6 mmol) in DMF (160 mL) was added CuI (0.63 g, 3.29 mmol) and the reaction mixture was stirred at 100° C. for 3 h. The reaction mixture was poured into ice cold water and neutralized with a 6N aqueous solution of HCl. The mixture was extracted with EtOAc. The organic layer was washed with brine, dried over $Na_2SO_4$, filtered and concentrated under vacuum. The residue was purified by column chromatography using 20% EtOAc in hexanes as eluent to afford 6.7 g of tert-butyl cyano(3,5-dichloro-2-methoxypyridin-4-yl)acetate a14.

Yield: 64%.

$^1$H NMR (400 MHz, DMSO-$d_6$) δ 8.39-8.53 (m, 1H), 6.32 (s, 1H), 3.92-4.07 (m, 3H), 1.42 (s, 9H).

A.6.4. Synthesis of (3,5-dichloro-2-methoxypyridin-4-yl)acetonitrile a15

To a solution of tert-butyl cyano(3,5-dichloro-2-methoxypyridin-4-yl)acetate a14 (20 g, 63.05 mmol) in DCM (500 mL) was added TFA (80 mL) at rt. The reaction mixture was refluxed for 2 h, concentrated under vacuum and the residue was neutralized with an aqueous saturated solution of sodium bicarbonate. The mixture was extracted with EtOAc. The organic layer was dried over $Na_2SO_4$, filtered and concentrated under vacuum to afford 13.5 g of (3,5-dichloro-2-methoxypyridin-4-yl)acetonitrile a15 as yellow solid which was used in next step without any further purification.

Yield: 98% (crude).

$^1$H NMR (400 MHz, DMSO-$d_6$) δ 8.31-8.47 (m, 1H), 4.19-4.30 (m, 2H), 3.86-4.06 (m, 3H).

A.6.5. Synthesis of (3,5-dichloro-2-methoxypyridin-4-yl)acetic acid a16

An aqueous saturated solution of NaOH (93.5 mL, 933 mmol) was added to a solution of (3,5-dichloro-2-methoxypyridin-4-yl)acetonitrile a15 (13.5 g, 62 mmol) in EtOH (300 mL) and the mixture was refluxed for 12 h, then water and ammonium chloride (60 g) were added. The solvent was concentrated under vacuum and the aqueous layer was acidified to pH 5 with a 6N aqueous solution HCl. The compound was extracted with a solution of 5% MeOH in DCM. The organic layer was dried over $Na_2SO_4$, filtered and concentrated under vacuum. The residue was purified by column chromatography using 5% MeOH in DCM as eluent. The reaction product was further washed with 50% DCM in hexanes, filtered and dried to afford 5 g of (3,5-dichloro-2-methoxypyridin-4-yl)acetic acid a16 as an off-white solid.

Yield: 34%.

LCMS: 237 (M+H)$^+$.

$^1$H NMR (400 MHz, MeOH-$d_4$) δ 8.03-8.18 (m, 1H), 3.99 (d, J=3.02 Hz, 3H), 3.26-3.42 (m, 2H).

A.7. Synthesis of (2-bromo-6-methoxyphenyl)acetic acid a18

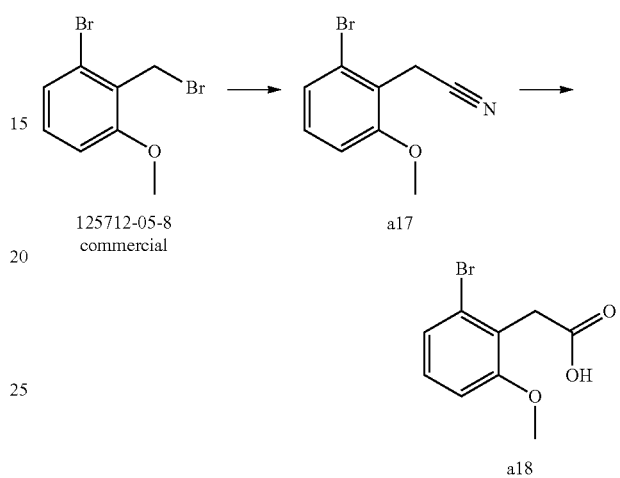

A.7.1. Synthesis of (2-bromo-6-methoxyphenyl)acetonitrile a17

Trimethylsilyl cyanide (7.4 mL, 59.35 mmol) and tetrabutylammonium fluoride (1M solution in THF, 59.4 mL, 59.35 mmol) were added dropwise to a solution of 1-bromo-2-(bromomethyl)-3-methoxybenzene (commercial, 11 g, 39.56 mmol) in ACN (100 mL) at 0° C. The reaction mixture was stirred at rt for 1.5 h, concentrated under vacuum and the mixture was extracted with EtOAc. The organic layer was washed with brine, dried over $Na_2SO_4$, filtered and concentrated under vacuum. The residue was purified by column chromatography using 5% EtOAc in hexanes as eluent to afford 6.8 g of (2-bromo-6-methoxyphenyl)acetonitrile a17.

Yield: 76%.

$^1$H NMR (400 MHz, DMSO-$d_6$) δ 7.24-7.35 (m, 2H), 7.12-7.18 (m, 1H), 3.93 (s, 2H), 3.88 (s, 3H).

A.7.2. Synthesis of (2-bromo-6-methoxyphenyl)acetic acid a18

To a solution of (2-bromo-6-methoxyphenyl)acetonitrile a17 (13 g, 58.6 mmol) in EtOH (100 mL) were added an aqueous 10N solution of NaOH (34.82 g, 870.5 mmol) and water (87 mL). The reaction mixture was stirred at 105° C. for 12 h, then concentrated under vacuum and the aqueous layer was acidified to pH 2 with a 1N aqueous solution of HCl. The mixture was extracted with EtOAc. The organic layer was dried dried over $Na_2SO_4$, filtered and concentrated under vacuum. The residue was purified by column chromatography using 5% MeOH in DCM as eluent to afford 8.53 g of (2-bromo-6-methoxyphenyl)acetic acid a18.

Yield: 60%.

LCMS: 245 (M+H)$^+$.

$^1$H NMR (400 MHz, DMSO-d$_6$) δ 12.34 (s, 1H), 7.17-7.27 (m, 2H), 7.03 (dd, J=6.36, 2.85 Hz, 1H), 3.79 (s, 3H), 3.66-3.74 (m, 2H).

A.8. Synthesis of (3-chloro-5-methylpyridin-4-yl)acetic acid a22

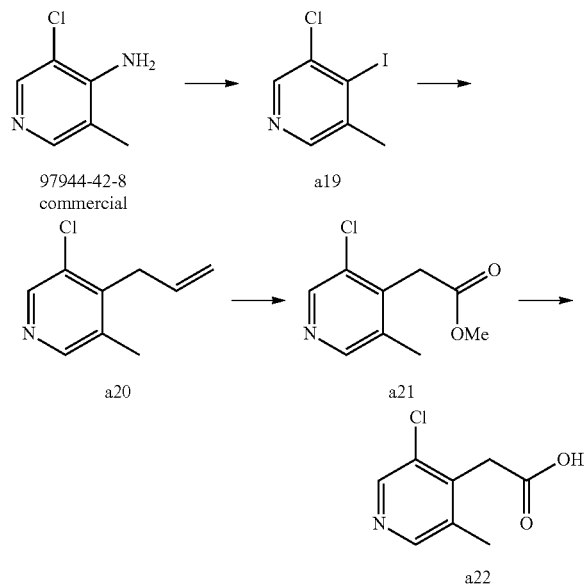

A.8.1. Synthesis of 3-chloro-4-iodo-5-methylpyridine a19

To a solution of 3-chloro-5-methylpyridin-4-amine (commercial, 6 g, 42.25 mmol) in aqueous tetrafluoroboric acid (60 mL) at 0° C. was added dropwise a solution of sodium nitrite (29.15 g, 422.5 mmol) in water (20 mL). The mixture was stirred at 0° C. for 30 min., then added dropwise to a solution of potassium iodide (11.22 g, 67.6 mmol) in acetone/water (1:1, 50 mL). The reaction mixture was stirred for 10 min., neutralized with an aqueous saturated solution of sodium bicarbonate and the mixture was extracted with EtOAc. The organic layer was washed with brine, over Na$_2$SO$_4$, filtered and concentrated under vacuum. The residue was purified by column chromatography using 4% EtOAc in hexanes as eluent to afford 5.1 g of 3-chloro-4-iodo-5-methylpyridine a19.

Yield: 48%.
LCMS: 254 (M+H)$^+$.
$^1$H NMR (400 MHz, CDCl$_3$) δ 8.33 (s, 1H), 8.18 (s, 1H), 2.48 (s, 3H).

A.8.2. Synthesis of 3-chloro-5-methyl-4-(prop-2-en-1-yl)pyridine a20

2-Allyl-4,4,5,5-tetramethyl-1,3,2-dioxaborolane (2.49 g, 14.82 mmol) and CsF (3 g, 19.76 mmol) were added to a solution of 3-chloro-4-iodo-5-methylpyridine a19 (2.5 g, 9.88 mmol) in DMF/THF (1:1, 60 mL), and the reaction mixture was degassed with argon for 20 min. Pd(PPh$_3$)$_4$ (1.13 g, 0.98 mmol) was added and the reaction mixture was further degassed for 10 min., then allowed to heat at 120° C. for 5 h. The reaction mixture was concentrated under vacuum and the mixture was extracted with EtOAc. The organic layer was washed with water, dried over Na$_2$SO$_4$, filtered and concentrated under vacuum. The residue was purified by column chromatography using 5% EtOAc in hexanes as eluent to afford 805 mg of 3-chloro-5-methyl-4-(prop-2-en-1-yl)pyridine a20.

Yield: 48%.
$^1$H NMR (400 MHz, CDCl$_3$) δ 8.42 (s, 1H), 8.26 (s, 1H), 5.77-5.95 (m, 1H), 5.09 (d, J=9.93 Hz, 1H), 4.91-5.00 (m, 1H), 3.54 (d, J=5.87 Hz, 2H), 2.31 (s, 3H).

A.8.3. Synthesis of methyl(3-chloro-5-methylpyridin-4-yl)acetate a21

To a solution of 3-chloro-5-methyl-4-(prop-2-en-1-yl)pyridine a20 (0.4 g, 2.39 mmol) in dry DCM (15 mL) at −78° C. was added a 2.5M methanolic solution of NaOH (12 mL) and the reaction mixture was stirred for 2 h under ozone atmosphere. The reaction mixture was quenched with water and concentrated under vacuum. The compound was extracted with EtOAc, the organic layer was washed with water, over Na$_2$SO$_4$, filtered and concentrated under vacuum. The residue was purified by column chromatography using 15% EtOAc in hexanes as eluent to afford 225 mg of methyl (3-chloro-5-methylpyridin-4-yl)acetate a21.

Yield: 47%.
LCMS: 200 (M+H)$^+$.
$^1$H NMR (400 MHz, CDCl$_3$-d) δ 8.41-8.49 (m, 1H), 8.31 (s, 1H), 3.85 (s, 2H), 3.73 (s, 3H), 2.32 (s, 3H).

A.8.4. Synthesis of (3-chloro-5-methylpyridin-4-yl)acetic acid a22

A solution of NaOH (715 mg, 17.88 mmol) in water (11 mL) was added to a solution of methyl (3-chloro-5-methylpyridin-4-yl)acetate a21 (0.89 g, 4.47 mmol) in MeOH (54 mL) at 0° C., and the reaction mixture was stirred at rt for 3 h. The reaction mixture was quenched with ammonium chloride (1.4 g) and water. The mixture was concentrated under vacuum, then extracted with 5% MeOH in DCM. The organic layer was washed with water, dried over Na$_2$SO$_4$, filtered and concentrated under vacuum. The residue was triturated with Et$_2$O to afford 0.45 g of (3-chloro-5-methylpyridin-4-yl)acetic acid a22.

Yield: 54%.
LCMS: 186 (M+H)$^+$.
$^1$H NMR (400 MHz, MeOH-d$_4$) δ 8.40 (s, 1H), 8.30 (s, 1H), 3.87-3.96 (m, 2H), 2.33-2.41 (m, 3H).

A.9. Synthesis of (2,6-dichloro-4-fluorophenyl)acetic acid a24

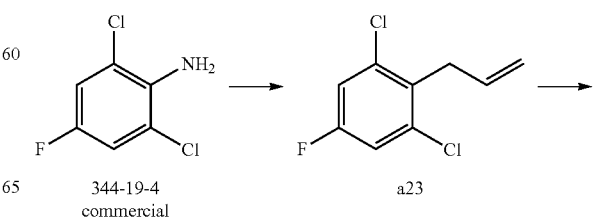

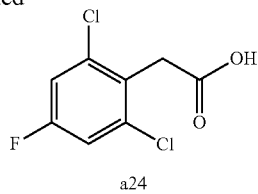

a24

A.9.1. Synthesis of 1,3-dichloro-5-fluoro-2-(prop-2-en-1-yl)benzene a23

To a solution of allyl bromide (21.6 mL, 249.9 mmol) in degassed ACN (80 mL) was added tert-butyl nitrite (3.99 mL, 33.22 mmol). A solution of 2,6-dichloro-4-fluoroaniline (3 g, 16.66 mmol) in ACN (5 mL) was added dropwise within 20 min. The reaction mixture was stirred at rt for 90 min. and concentrated under vacuum. The residue was taken up EtOAc and washed with water. The organic layer was dried over $Na_2SO_4$, filtered and concentrated under vacuum. The residue was purified by column chromatography using 1% EtOAc in hexanes as eluent to afford 1.4 g of 1,3-dichloro-5-fluoro-2-(prop-2-en-1-yl)benzene a23.

Yield: 41%

LCMS: 205 (M+H)$^+$.

$^1$H NMR (400 MHz, DMSO-d$_6$) δ 7.54 (d, J=8.4 Hz, 2H), 5.91-5.82 (m, 1H), 5.07 (d, J=9.9 Hz, 1H), 4.91 (m, 1H), 3.59 (d, J=5.2 Hz, 2H).

A.9.2. Synthesis of (2,6-dichloro-4-fluorophenyl)acetic acid a24

To a solution of 1,3-dichloro-5-fluoro-2-(prop-2-en-1-yl)benzene a23 (2 g, 9.803 mmol) in a mixture of ACN/CCl$_4$/water (1:1:1.5, 70 mL) was added RuCl$_3$ (80 mg, 0.38 mmol) then NaIO$_4$ (20.88 g, 98.03 mmol). The reaction mixture was stirred at rt for 2 h, then extracted with DCM. The organic layer was dried over Na$_2$SO$_4$, filtered and concentrated under vacuum. The residue was purified by column chromatography using 15% EtOAc in hexanes as eluent to afford 1.15 g of (2,6-dichloro-4-fluorophenyl)acetic acid a24.

Yield: 53%

LCMS: 223 (M+H)$^+$.

$^1$H NMR (400 MHz, DMSO-d$_6$) δ 12.73 (s, 1H), 7.56 (d, J=8.5 Hz, 2H), 3.85 (s, 2H).

A.10. Synthesis of (5-chloro-1H-indazol-4-yl)acetic acid a28

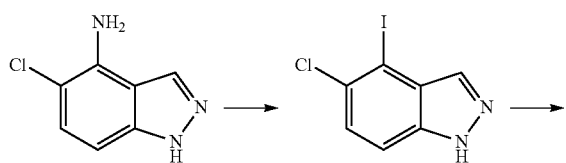

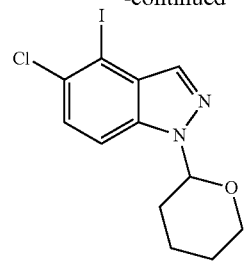

a26

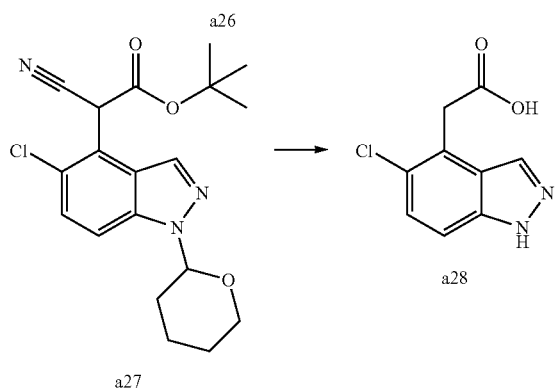

A.10.1. Synthesis of 5-chloro-4-iodo-1H-indazole a25

To a solution of 5-chloro-1H-indazol-4-amine (commercial, 2 g, 11.97 mmol) in a 6 N aqueous solution of HCl (150 mL) at 0° C. was added a solution of NaNO$_2$ (1.23 g, 17.96 mmol) in water (25 mL). The mixture was stirred at 0° C. for 30 min, then a solution of KI (3.97 g, 23.94 mmol) in water (25 mL) was added dropwise at 0° C. The reaction mixture was stirred at rt for 1 h, diluted with EtOAc and washed with an aqueous saturated solution of sodium bicarbonate. The organic layer was dried over Na$_2$SO$_4$, filtered and concentrated under vacuum. The residue was purified by column chromatography using 20% EtOAc in hexanes as eluent to afford 2.8 g of 5-chloro-4-iodo-1H-indazole a25.

Yield: 84%.

LCMS: 279 (M+H)$^+$.

$^1$H NMR (400 MHz, DMSO-d$_6$) δ 13.56 (s, 1H), 7.88 (s, 1H), 7.59 (d, J=8.7 Hz, 1H), 7.47 (d, J=8.7 Hz, 1H).

A.10.2. Synthesis of 5-chloro-4-iodo-1-(tetrahydro-2H-pyran-2-yl)-1H-indazole a26

To a solution of 5-chloro-4-iodo-1H-indazole a25 (5 g, 17.9 mmol) in chloroform (250 mL) were added PTSA (0.68 g, 3.5 mmol), then dihydropyrane (4.5 g, 53.9 mmol) at 0° C. The reaction mixture was stirred at rt for 1 h and concentrated under vacuum. The residue was taken up with EtOAc, then successively washed with water, an aqueous saturated solution of sodium bicarbonate and water. The organic layer was dried over Na$_2$SO$_4$, filtered and concentrated under vacuum. The residue was purified by column chromatography using 7% EtOAc in hexanes as eluent to afford 4 g of 5-chloro-4-iodo-1-(tetrahydro-2H-pyran-2-yl)-1H-indazole a26.

Yield: 61%.

$^1$H NMR (400 MHz, DMSO-d$_6$) δ 7.93 (s, 1H), 7.81 (d, J=8.8 Hz, 1H), 7.55 (d, J=8.8 Hz, 1H), 5.87 (dd, J=9.5, 2.4 Hz, 1H), 3.82-3.57 (m, 2H), 2.08-1.92 (m, 2H), 1.83-1.66 (m, 4H).

A.10.3. Synthesis of tert-butyl [5-chloro-1-(tetrahydro-2H-pyran-2-yl)-1H-indazol-4-yl](cyano)acetate a27

To a solution of 5-chloro-4-iodo-1-(tetrahydro-2H-pyran-2-yl)-1H-indazole a26 (2 g, 5.52 mmol) in DMF (15 mL) were added CuI (0.2 g, 1.1 mmol), cesium carbonate (4.5 g, 13.8 mmol) and tert-butyl 2-cyanoacetate (1.55 g, 11.04 mmol). The reaction was stirred at 100° C. for 16 h, then diluted with water and extracted with EtOAc. The organic layer was washed with brine, dried over Na$_2$SO$_4$, filtered and concentrated under vacuum. The residue was purified by column chromatography using 6% EtOAc in hexanes as eluent to afford 1.55 g of tert-butyl [5-chloro-1-(tetrahydro-2H-pyran-2-yl)-1H-indazol-4-yl](cyano)acetate a27.
Yield: 75%.
LCMS: 376 (M+H)$^+$.
$^1$H NMR (400 MHz, DMSO-d$_6$) δ 8.35 (s, 1H), 7.88 (d, J=8.9 Hz, 1H), 7.58 (d, J=8.9 Hz, 1H), 6.33 (s, 1H), 5.92 (d, J=9.4 Hz, 1H), 3.88 (d, J=11.6 Hz, 1H), 3.76 (m, 1H), 2.44-2.34 (m, 2H), 2.07-1.95 (m, 2H), 1.80-1.70 (m, 2H), 1.42 (m, 9H).

A.10.4. Synthesis of (5-chloro-1H-indazol-4-yl)acetic acid a28

A stirred solution of tert-butyl [5-chloro-1-(tetrahydro-2H-pyran-2-yl)-1H-indazol-4-yl](cyano)acetate a27 (3 g, 8.0 mmol) in a 6 N aqueous solution of HCl (30 mL) was heated at 95° C. for 16 h. The reaction mixture was basified with an aqueous saturated solution of sodium bicarbonate and washed with EtOAc. The aqueous layer was acidified to pH 5 with a 6 N aqueous solution of HCl and extracted with EtOAc. The organic layer was dried over Na$_2$SO$_4$, filtered and concentrated under vacuum. The residue was triturated with Et$_2$O to afford 1.2 g of (5-chloro-1H-indazol-4-yl)acetic acid a28.
Yield: 71%.
LCMS: 211 (M+H)$^+$.
$^1$H NMR (400 MHz, DMSO-d$_6$) δ 13.21 (s, 1H), 12.52 (s, 1H), 8.20 (s, 1H), 7.48 (d, J=8.8, 1H), 7.36 (d, J=8.8 Hz, 1H), 4.02 (s, 2H).

A.11. Synthesis of (5-chloro-1H-pyrrolo[2,3-b]pyridin-4-yl)acetic acid a32

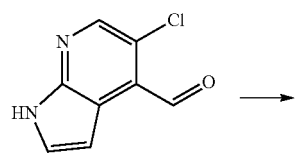

CAS RN 1015610-39-5
commerical

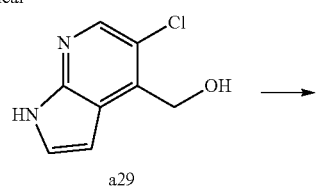

a29

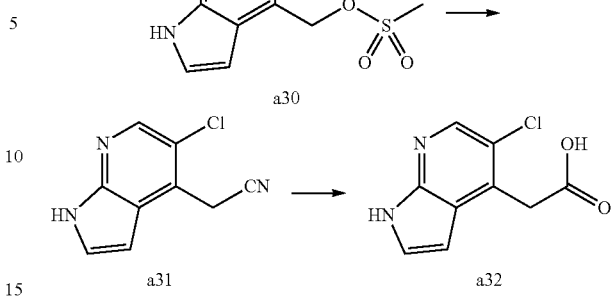

A.11.1. Synthesis of (5-chloro-1H-pyrrolo[2,3-b]pyridin-4-yl)methanol a29

5-chloro-1H-pyrrolo[2,3-b]pyridine-4-carbaldehyde (commercial, 450 mg, 2.49 mmol) was dissolved in MeOH/THF (1:1, 30 mL) at 0° C. Sodium borohydride (189 mg, 4.98 mmol) was added. The mixture was stirred for few min. at 0° C. then warmed up to rt. The reaction mixture was poured on a catch and release acidic column (5 g). The product was released by a 1M solution of ammonia in MeOH (20 mL) and concentrated under vacuum to afford 474 mg of crude (5-chloro-1H-pyrrolo[2,3-b]pyridin-4-yl)methanol a29 which was used in the next step without any further purification.
Yield: 104% (crude).
LCMS (ES$^+$): 183/185 (M+H)$^+$.

A.11.2. Synthesis of (5-chloro-1H-pyrrolo[2,3-b]pyridin-4-yl)methyl methanesulfonate a30

To a solution of (5-chloro-1H-pyrrolo[2,3-b]pyridin-4-yl)methanol a29 (475 mg, 2.60 mmol) in DCM (27 mL) at 0° C. were added DIPEA (686 mg, 5.20 mmol) and methanesulfonyl chloride (448.3 mg, 3.90 mmol). The mixture was stirred for few min. at 0° C. then warmed up to rt. The reaction mixture was concentrated under vacuum to afford crude (5-chloro-1H-pyrrolo[2,3-b]pyridin-4-yl)methyl methanesulfonate a30 as a yellow oil which was used in the next step without any further purification.

A.11.3. Synthesis of (5-chloro-1H-pyrrolo[2,3-b]pyridin-4-yl)acetonitrile a31

Crude (5-chloro-1H-pyrrolo[2,3-b]pyridin-4-yl)methyl methanesulfonate a30 (678 mg, 2.60 mmol) was dissolved in DMSO (9 mL) at rt. Sodium cyanide (255 mg, 5.20 mmol) was added. The mixture was stirred at rt for 3 h. The reaction mixture was quenched with an aqueous saturated solution of NaHCO$_3$, then extracted thrice with EtOAc. The organic layer was washed with brine, dried over Na$_2$SO$_4$, filtered and concentrated under vacuum. The residue was purified by basic reverse phase chromatography to yield 112 mg (5-chloro-1H-pyrrolo[2,3-b]pyridin-4-yl)acetonitrile a31.
Yield: 22.5%.
LCMS (ES$^+$): 192/194 (M+H)$^+$, 100% purity.

A.11.4. Synthesis of (5-chloro-1H-pyrrolo[2,3-b]pyridin-4-yl)acetic acid a32

(5-chloro-1H-pyrrolo[2,3-b]pyridin-4-yl)acetonitrile a31 (112.4 mg, 0.59 mmol) was dissolved in a mixture of water (2 mL) and concentrated H$_2$SO$_4$ (2 mL). The mixture was stirred at 110° C. for 1 h. The reaction mixture was cooled to rt, neutralized with an aqueous saturated solution of NaOH, then filtered. EtOH was added to the filtrate, and the mixture was filtered a second time. The filtrate was evaporated under vacuum to afford 121 mg of (5-chloro-1H-pyrrolo[2,3-b]pyridin-4-yl)acetic acid a32 as a off-white solid.

Yield: 98%.
LCMS (ES$^+$): 210/212 (M+H)$^+$.

A.12. Synthesis of methyl(3-chloro-5-cyanopyridin-4-yl)acetate a38

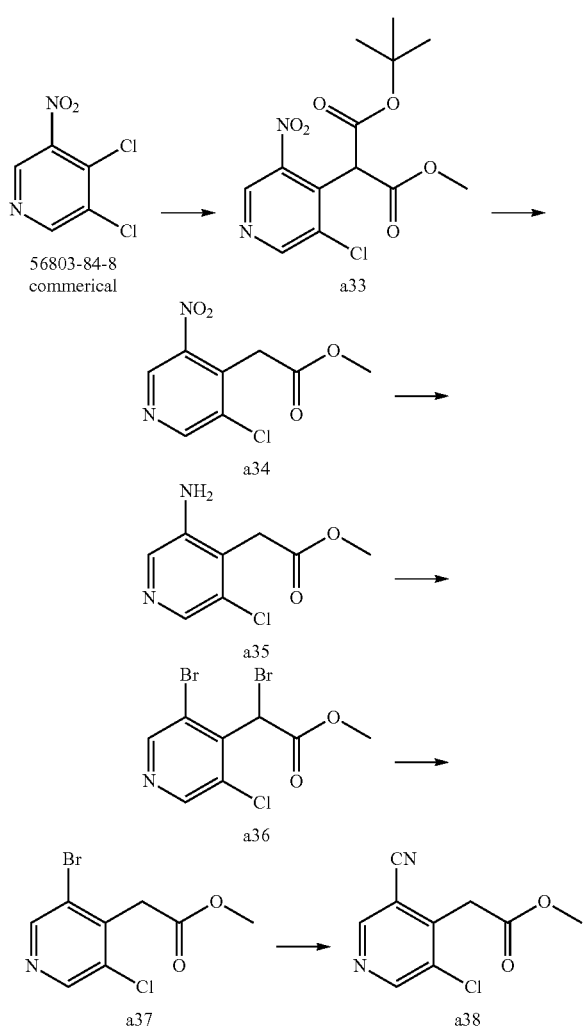

A.12.1. Synthesis of tert-butyl methyl (3-chloro-5-nitropyridin-4-yl)propanedioate a33

To a solution of sodium hydride (1.33 g, 33.42 mmol) in DMF (40 mL) at 0° C. was added dropwise tert-butyl methyl malonate (5.65 mL, 33.42 mmol) in DMF (10 mL). The reaction mixture was stirred at rt for 30 min, then 3,4-dichloro-5-nitropyridine (4.3 g, 22.28 mmol) in DMF (10 mL) was added dropwise at 0° C. The reaction mixture was stirred at rt for 6 h, then acidified to pH 3 with a 2N aqueous solution of HCl. The reaction mixture was poured into ice water and extracted with Et$_2$O. The organic layer was dried over Na$_2$SO$_4$, filtered and concentrated under vacuum. The residue was purified by column chromatography using 20% EtOAc in hexanes to afford 3.83 g of tert-butyl methyl (3-chloro-5-nitropyridin-4-yl)propanedioate a33 as pale yellow solid.

Yield: 52%.
$^1$H NMR (400 MHz, CDCl$_3$) δ 9.15 (s, 1H), 8.88 (s, 1H), 5.37-5.51 (m, 1H), 3.79 (s, 3H), 1.46 (s, 9H).

A.12.2. Synthesis of methyl(3-chloro-5-nitropyridin-4-yl)acetate a34

TFA (27 mL) was added at rt to a solution of tert-butyl methyl (3-chloro-5-nitropyridin-4-yl)propanedioate a33 (11.5 g, 34.84 mmol) in DCM (200 mL). The reaction mixture was refluxed for 2 h and concentrated under vacuum. The residue was taken up with DCM and washed with an aqueous saturated solution of sodium bicarbonate. The organic layer was dried over Na$_2$SO$_4$, filtered and concentrated under vacuum to afford 7.9 g of crude methyl (3-chloro-5-nitropyridin-4-yl)acetate a34 which was used in next step without any further purification.

Yield (crude): 98%.
$^1$H NMR (400 MHz, CDCl$_3$) δ 9.09-9.21 (m, 1H) 8.74-8.98 (m, 1H), 4.25 (s, 2H), 3.64-3.83 (m, 3H).

A.12.3. Synthesis of methyl(3-amino-5-chloropyridin-4-yl)acetate a35

To a solution of methyl (3-chloro-5-nitropyridin-4-yl)acetate a34 (1 g, 4.33 mmol) in MeOH (125 mL) were added iron powder (3.63 g, 65 mmol) and ammonium chloride (3.47 g, 65 mmol). The reaction mixture was refluxed for 16 h, filtered through Celite® and the filtrate was concentrated under reduced pressure. The residue was taken up with EtOAc and the mixture was washed with water. The organic layer was dried over Na$_2$SO$_4$, filtered and concentrated under vacuum. The residue was purified by column chromatography using 5% MeOH in DCM as eluent to afford 0.53 g of methyl (3-amino-5-chloropyridin-4-yl)acetate a35 as a white solid.

Yield: 61%.
LCMS: 201 (M+H)$^+$.
$^1$H NMR (400 MHz, DMSO-d$_6$) δ 7.91 (s, 1H), 7.76 (s, 1H), 3.75 (s, 2H), 3.62 (s, 3H).

A.12.4. Synthesis of methyl bromo(3-bromo-5-chloropyridin-4-yl)acetate a36

To a solution of CuBr$_2$ (1.11 g, 4.98 mmol) in ACN (15 mL) at 50° C. was added tBuONO (1.5 mL, 12.45 mmol) and the reaction mixture was stirred at 80° C. for 30 min. Methyl (3-amino-5-chloropyridin-4-yl)acetate a35 (0.5 g, 2.49 mmol) as a solid compound was added and the reaction mixture was further refluxed for 1 h. The reaction mixture was cooled to rt, diluted with EtOAc and filtered through Celite®. The filtrate was concentrated under vacuum, the residue was taken up with EtOAc and washed with an aqueous saturated solution of sodium bicarbonate. The organic layer was dried over Na$_2$SO$_4$, filtered and concentrated under vacuum. The residue was purified by column chromatography to afford 0.57 g of methyl bromo(3-bromo-5-chloropyridin-4-yl)acetate a36 as a sticky solid.

Yield: 68%.
LCMS: 344 (M+H)$^+$.

A.12.5. Synthesis of methyl(3-bromo-5-chloropyridin-4-yl)acetate a37

To a solution of methyl bromo(3-bromo-5-chloropyridin-4-yl)acetate a36 (2.1 g, 6.11 mmol) in MeOH (50 mL) were added dropwise at rt indium metal (1.75 g, 15.28 mmol) and AcOH (3.5 mL, 61.11 mmol). The reaction mixture was stirred at rt for 12 h and concentrated under vacuum. The residue was taken up with EtOAc and washed with an aqueous saturated solution of sodium bicarbonate. The organic layer was dried over $Na_2SO_4$, filtered and concentrated under vacuum to afford 1.6 g of crude methyl (3-bromo-5-chloropyridin-4-yl)acetate a37 as pale yellow oil which was used in next step without any further purification.

Yield: 99% (crude).
LCMS (ES$^+$): 265 (M+H)$^+$.
$^1$H NMR (400 MHz, DMSO-$d_6$) δ 8.75 (s, 1H), 8.67 (s, 1H), 4.06 (s, 2H), 3.62-3.72 (m, 3H).

A.12.6. Synthesis of methyl(3-chloro-5-cyanopyridin-4-yl)acetate a38

A solution of methyl (3-bromo-5-chloropyridin-4-yl)acetate a37 (0.2 g, 0.76 mmol) and zinc cyanide (60 g, 0.53 mmol) in DMF (8 mL) was degassed with argon for 30 min. $PdCl_2$(dppf) (55 mg, 0.76 mmol) and $Pd_2$(dba)$_3$ (70 mg, 0.76 mmol) were added and the mixture was further degassed for 10 min. The reaction mixture was heated at 100° C. for 16 h, then diluted with EtOAc and filtered through Celite®. The filtrate was washed with water and the organic layer was dried over $Na_2SO_4$, filtered and concentrated under vacuum. The residue was purified by column chromatography using 10% EtOAc in hexanes as eluent to afford 0.12 g of methyl (3-chloro-5-cyanopyridin-4-yl)acetate a38 as a pale yellow oil.

Yield: 75%.
LCMS (ES$^+$): 211 (M+H)$^+$.
$^1$H NMR (400 MHz, DMSO-$d_6$) δ 9.04 (s, 1H) 8.98 (s, 1H) 4.10 (s, 2H) 3.69 (s, 3H).

A.13. Synthesis of 2-(5-chloro-1H-indol-4-yl)acetic acid a111

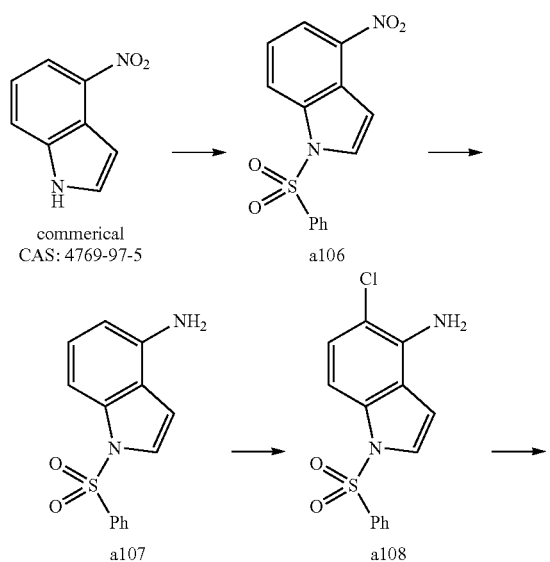

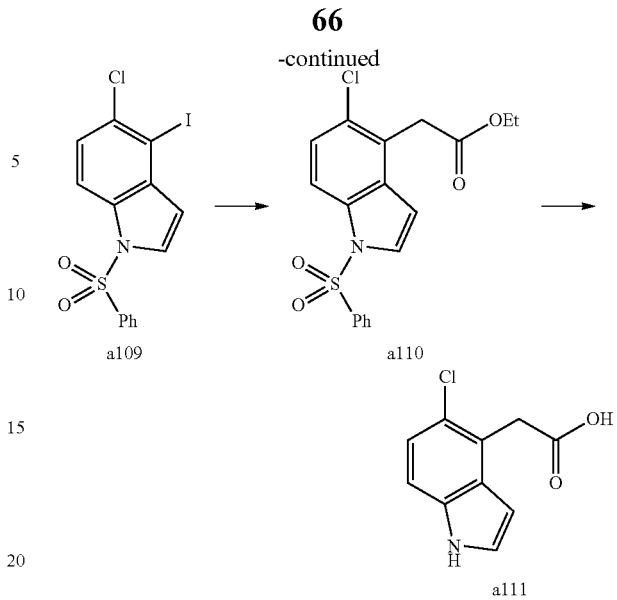

A.13.1. Synthesis of 1-(benzenesulfonyl)-4-nitro-indole a106

To a solution of 4-nitro-1H-indole (25 g, 154.32 mmol) in ACN (250 mL), DIPEA (29.5 mL, 169.75 mmol) was added at rt. The reaction was cooled to 0° C. and benzensulfonyl chloride (23 mL, 185.18 mmol) was added. The reaction was heated at 80° C. for 3 h. After completion, the reaction was quenched with an aqueous saturated solution of sodium bicarbonate and extracted with EtOAc. The organic layer was separated, washed with water, dried over $Na_2SO_4$, filtered and concentrated under vacuum to afford 34.95 g of 1-(benzenesulfonyl)-4-nitro-indole a106.

Yield: 97% (crude).
$^1$H NMR (400 MHz, DMSO-$d_6$) δ 8.47-8.39 (m, 1H), 8.26-8.17 (m, 2H), 8.12-8.04 (m, 2H), 7.78-7.68 (m, 1H), 7.67-7.54 (m, 3H), 7.38-7.26 (m, 1H).

A.13.2. Synthesis of 1-(benzenesulfonyl)indol-4-amine a107

To a stirred solution of 1-(benzenesulfonyl)-4-nitro-indole a106 (25 g, 82.78 mmol) in MeOH (250 mL), Fe (69.53 g, 1241.72 mmol) and $NH_4Cl$ (67.05 g, 1241.72 mmol) were added and the reaction mixture was heated to reflux for 15 h. After completion, the reaction was filtered through Celite® and the filtrate was concentrated under reduced pressure. The crude product was purified by column chromatography using 10% EtOAc in hexanes as eluent to afford 7 g of 1-(benzenesulfonyl)indol-4-amine a107.

Yield: 31%
LCMS (ES$^+$): 273 (M+H)$^+$.
$^1$H NMR (400 MHz, DMSO-$d_6$) δ 7.95-7.85 (m, 2H), 7.72-7.49 (m, 4H), 7.14-6.91 (m, 3H), 6.35 (d, J=7.7 Hz, 1H), 5.55 (s, 2H).

A.13.3. Synthesis of 1-(benzenesulfonyl)-5-chloro-indol-4-amine a108

To a stirred solution of 1-(benzenesulfonyl)indol-4-amine a107 (35.36 g, 130 mmol) in DCM (300 mL) at 0° C., a solution of N-chlorosuccinimide (17.29 g, 130 mmol) solution in DCM (100 mL) was added. The mixture was stirred at the same temperature for 1 h, then at rt for 1 h. After completion, the reaction mixture was quenched with an aqueous saturated solution of sodium bicarbonate and extracted with DCM. The organic layer was separated, washed with water, dried over Na$_2$SO$_4$, filtered and concentrated under vacuum. The crude product was purified by column chromatography using 10% EtOAc in n-hexanes as eluent to afford 14.8 g of 1-(benzenesulfonyl)-5-chloro-indol-4-amine a108, Yield: 37%

$^1$H NMR (400 MHz, DMSO-d$_6$) δ 7.95-7.87 (m, 2H), 7.76-7.54 (m, 4H), 7.09 (dd, J=17.3, 3.3 Hz, 3H), 5.82 (s, 2H).

A.13.4. Synthesis of 1-(benzenesulfonyl)-5-chloro-4-iodo-indole a109

To a solution of 1-(benzenesulfonyl)-5-chloro-indol-4-amine a108 (13.8 g, 45.09 mmol) in a 12N aqueous solution of HCl (414 mL) at 0° C., a solution of NaNO$_2$ (7.77 g, 112.74 mmol) in water (70 mL) was added dropwise. The mixture was stirred for 30 min at the same temperature. A solution of KI (74.84 g, 450.9 mmol) in water (137 mL) was then added dropwise at 0° C. and the mixture was stirred at the same temperature for 3 h. After completion, the reaction was extracted with EtOAc. The organic layer was separated, washed with water, dried over Na$_2$SO$_4$, filtered and concentrated under vacuum. The crude product was purified by column chromatography using 10% EtOAc in hexanes as eluent to afford 17.2 g of 1-(benzenesulfonyl)-5-chloro-4-iodo-indole a109.

Yield: 92%

$^1$H NMR (400 MHz, DMSO-d$_6$) δ 8.05-7.85 (m, 4H), 7.77-7.67 (m, 1H), 7.62 (t, J=7.8 Hz, 2H), 7.51 (d, J=8.8 Hz, 1H), 6.70 (d, J=3.7 Hz, 1H).

A.13.5. Synthesis of ethyl 2-[1-(benzenesulfonyl)-5-chloro-indol-4-yl]acetate a110

To a stirred solution of activated zinc (12.23 g, 188.2 mmol) in dry THF (75 mL), chlorotrimethylsilane (2.39 mL, 18.82 mmol) was added. The mixture was stirred at rt for 15 min followed by dropwise addition of ethyl bromo acetate (8.3 mL, 75.41 mmol) at rt. The molarity of Reformatsky reagent was measured by titration method (LiCl and iodine method). 1-(Benzenesulfonyl)-5-chloro-4-iodo-indole a109 (5 g, 11.97 mmol) was dissolved in THF (50 mL) and purged with argon for 15 min. Pd(t-Bu$_3$P)$_2$ (0.608 g, 1.19 mmol) was added, followed by addition of Reformatsky reagent. The reaction was heated at 65° C. for 16 h. After completion, the reaction mixture was quenched with an aqueous saturated solution of ammonium chloride and extracted with EtOAc. The organic layer was separated, washed with water, dried over Na$_2$SO$_4$, filtered and concentrated under vacuum. The crude product was purified by column chromatography using 10% EtOAc in hexanes as eluent to afford 3.34 g of ethyl 2-[1-(benzenesulfonyl)-5-chloro-indol-4-yl]acetate a110.

Yield: 74% (crude).

LCMS (ES$^+$): 378 (M+H)$^+$.

$^1$H NMR (400 MHz, DMSO-d$_6$) δ 8.00 (dd, J=7.8, 1.6 Hz, 2H), 7.94-7.85 (m, 2H), 7.71 (t, J=7.4 Hz, 1H), 7.60 (t, J=7.8 Hz, 2H), 7.41 (d, J=8.8 Hz, 1H), 7.02 (d, J=3.8 Hz, 1H), 4.12 (q, J=7.1 Hz, 2H), 4.02 (s, 2H), 1.14 (t, J=7.1 Hz, 3H).

A.13.6. Synthesis of 2-(5-chloro-1H-indol-4-yl)acetic acid a111

To a stirred solution of ethyl 2-[1-(benzenesulfonyl)-5-chloro-indol-4-yl]acetate a110 (4.547 g, 12.06 mmol) in EtOH (40 mL), a 3N aqueous solution of NaOH (20 mL) was added. The mixture was heated to reflux for 8 h. After completion, the reaction was evaporated under reduced pressure. The residue was diluted with water, acidified to pH 2 using a 1N aqueous solution of HCl and extracted with EtOAc. The organic layer was separated, washed with water, dried over Na$_2$SO$_4$, filtered and concentrated under vacuum to afford 2.5 g of 2-(5-chloro-1H-indol-4-yl)acetic acid a111.

Yield: 99%

$^1$H NMR (400 MHz, DMSO-d$_6$) δ 12.31 (s, 1H), 11.27 (s, 1H), 7.38-7.40 (m, 1H), 7.32 (dd, J=8.6, 0.9 Hz, 1H), 7.10 (d, J=8.6 Hz, 1H), 6.50-6.52 (m, 1H), 3.91 (s, 2H).

B. Synthesis of Amines of Formula III

B.1. Synthesis of 5-bromo-1-methyl-1,2,3,4-tetrahydroisoquinoline a41

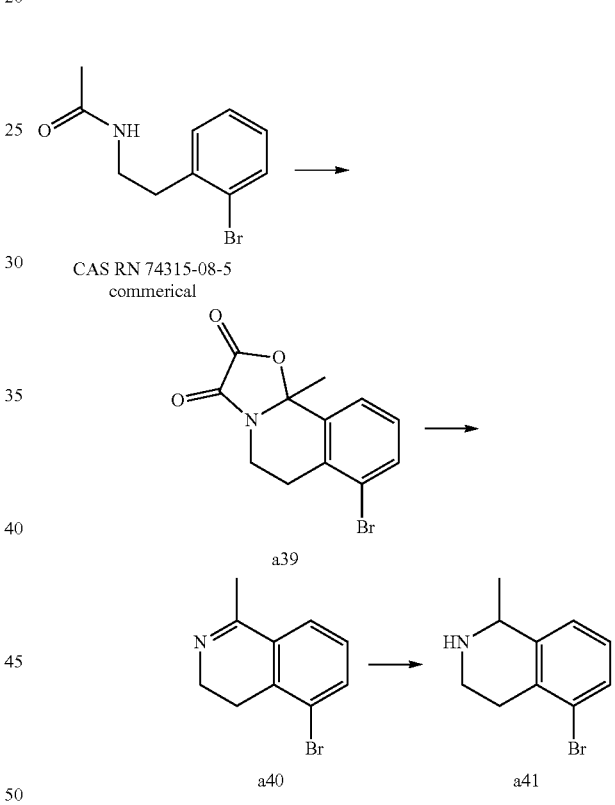

B.1.1. Synthesis of 7-bromo-10b-methyl-6,10b-dihydro-5H-[1,3]oxazolo[2,3-a]isoquinoline-2,3-dione a39

To a solution of N-[2-(2-bromophenyl)ethyl]acetamide (106.5 g, 439.8 mmol) in DCM (1.5 L) was added dropwise at 0° C. oxalyl chloride (72 mL, 792.3 mmol). The mixture was stirred at 0° C. for 2 h, then allowed to warm to rt and stirred for 3 h. The reaction mixture was then cooled to 0° C. and ferric chloride (86 g, 530.2 mmol) was added in 2 portions. The reaction mixture was allowed to warm to rt, stirred overnight at rt, diluted with DCM (2.5 L) and then quenched at 0° C. with a 12M concentrated solution of ammonia (200 mL). The organic layer was dried over Na$_2$SO$_4$, filtered and concentrated under vacuum to yield 108 g of 7-bromo-10b-methyl-6,10b-dihydro-5H-[1,3]ox-azolo[2,3-a]isoquinoline-2,3-dione a39 as a brown solid which was used in next step without any further purification.

Yield: 83%.

LCMS (ES⁺): 296/298 (M+H)⁺.

B.1.2. Synthesis of 5-bromo-1-methyl-3,4-dihydroisoquinoline a40

To a suspension of 7-bromo-10b-methyl-6,10b-dihydro-5H-[1,3]oxazolo[2,3-a]isoquinoline-2,3-dione a39 (108 g, 364.72 mmol) in MeOH (1.5 L) was added dropwise at rt sulfuric acid (75 mL). The reaction mixture was stirred overnight at 65° C., then quenched at 0° C. with a 15M concentrated solution of ammonia (300 mL). The mixture was concentrated under vacuum and water (300 mL) was added. The aqueous layer was extracted 6 times with DCM (1 L). The organic layer was dried over MgSO₄, filtered and concentrated under vacuum to afford 86.44 g of 5-bromo-1-methyl-3,4-dihydroisoquinoline a40 as a brown solid which was used in next step without any further purification.

Yield: 95%.

HPLC (Basic Mode) RT 4.75 min, 87% purity.

B.1.3. Synthesis of 5-bromo-1-methyl-1,2,3,4-tetrahydroisoquinoline a41

To a solution of 5-bromo-1-methyl-3,4-dihydroisoquinoline a40 (86.44 g, 347.1 mmol) in EtOH (2 L) was added at 0° C. sodium borohydride (13.2 g, 349 mmol) portionwise (13*1 g). The mixture was stirred at 0° C. for 2 h, then a 5N aqueous solution of HCl solution (250 mL) was added at 0° C. The reaction mixture was stirred overnight at rt, then EtOH was concentrated under vacuum. DCM (1 L) was added and the mixture was quenched at 0° C. with a 6M concentrated solution of ammonia (400 mL). The organic layer was extracted twice with DCM (500 mL), dried over MgSO₄, filtered and concentrated under vacuum to afford 83 g of 5-bromo-1-methyl-1,2,3,4-tetrahydroisoquinoline a41 as a brown solid which was used in next step without any further purification.

Yield: 85%.

HPLC (Basic Mode) RT 4.53 min, 80% purity.

B.2. Synthesis of tert-butyl 5-bromo-1-methyl-3,4-dihydroisoquinoline-2(1H)-carboxylate a42 and enantiomers, and (1S)-5-bromo-1-methyl-1,2,3,4-tetrahydroisoquinoline hydrochloride a41-(S)

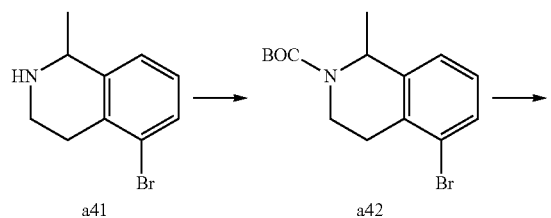

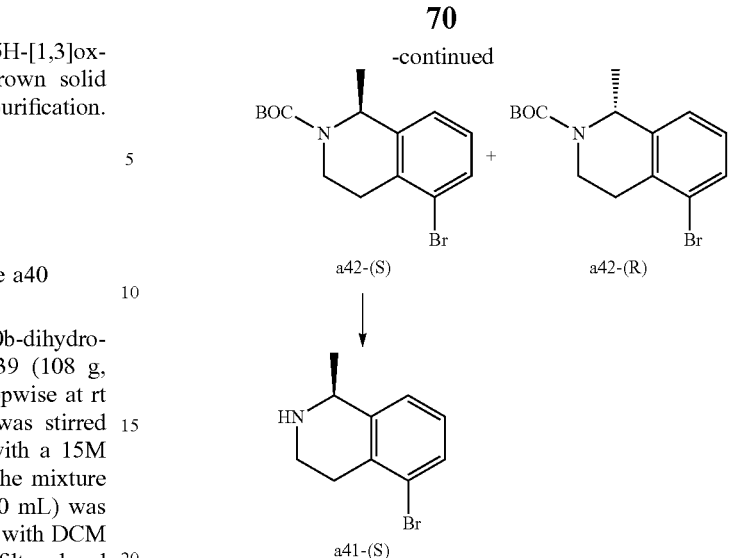

B.2.1. Synthesis of tert-butyl 5-bromo-1-methyl-3,4-dihydroisoquinoline-2(1H)-carboxylate a42

To a solution of 5-bromo-1-methyl-1,2,3,4-tetrahydroisoquinoline a41 (78 g, 276 mmol) in DCM (1 L) was added TEA (160 mL, 1136 mmol) at 0° C. A solution of di-tert-butyl dicarbonate (65 g, 294.8 mmol) in DCM (250 mL) was then added dropwise at 0° C. The reaction mixture was stirred overnight at rt and quenched with water (100 mL). The organic layer was dried over MgSO₄, filtered and concentrated under vacuum. The residue was triturated twice in a mixture of MeOH/hexanes (1:2, 450 mL) to yield 63 g of tert-butyl 5-bromo-1-methyl-3,4-dihydroisoquinoline-2(1H)-carboxylate a42 as a white solid.

Yield: 70%.

HPLC (Basic Mode) RT 6.59 min, 98% purity.

B.2.2. Synthesis of tert-butyl(1S)-5-bromo-1-methyl-3,4-dihydroisoquinoline-2(1H)-carboxylate a42-(S) and tert-butyl (1R)-5-bromo-1-methyl-3,4-dihydroisoquinoline-2(1H)-carboxylate a42-(R)

Chiral separation (SFC, Whelko 01(R,R), 50*227 mm, 360 mL/min, 220 nm, 25° C., eluent: from 20% iPrOH) of racemate tert-butyl 5-bromo-1-methyl-3,4-dihydroisoquinoline-2(1H)-carboxylate a42 afforded:

25.1 g of tert-butyl (1S)-5-bromo-1-methyl-3,4-dihydroisoquinoline-2(1H)-carboxylate a42-(S) as a solid.
Yield: 40%.
HPLC (Basic Mode) RT 6.59 min, 91% purity.
Chiral analysis (LC, Whelko-01 (R,R), 250*4.6 mm, 1 mL/min, 220 nm, 30° C., eluent: iPrOH/n-heptane/DEA 50/50/0.1) RT 4.86 min, 97.7% ee.

29.3 g of tert-butyl (1R)-5-bromo-1-methyl-3,4-dihydroisoquinoline-2(1H)-carboxylate a42-(R) as a solid.
Yield: 46%.
HPLC (Basic Mode) RT 6.59 min, 98% purity.
Chiral analysis (LC, Whelko-01 (R,R), 250*4.6 mm, 1 mL/min, 220 nm, 30° C., eluent: iPrOH/n-heptane/DEA 50/50/0.1) RT 5.62 min, 92.4% ee.

B.2.3. Synthesis of (1S)-5-bromo-1-methyl-1,2,3,4-tetrahydroisoquinoline hydrochloride a41-(S)

To a solution of tert-butyl (1S)-5-bromo-1-methyl-3,4-dihydroisoquinoline-2(1H)-carboxylate a42-(S) (10 g, 30.7 mmol) in EtOH (250 mL) was added a 4N solution of HCl in dioxane (32 mL, 128 mmol). The reaction mixture was stirred overnight at rt, then concentrated under vacuum. The resulting solid was dried under vacuum to afford 8 g of (1S)-5-bromo-1-methyl-1,2,3,4-tetrahydroisoquinoline hydrochloride a41-(S) which was used in next steps without any further purification.

Yield: 99% (crude).

HPLC (Basic Mode) RT 4.41 min, 99.2% purity.

B.3. Synthesis of N-(8-methyl-1,2,3,4-tetrahydroisoquinolin-5-yl)methanesulfonamide hydrochloride a44

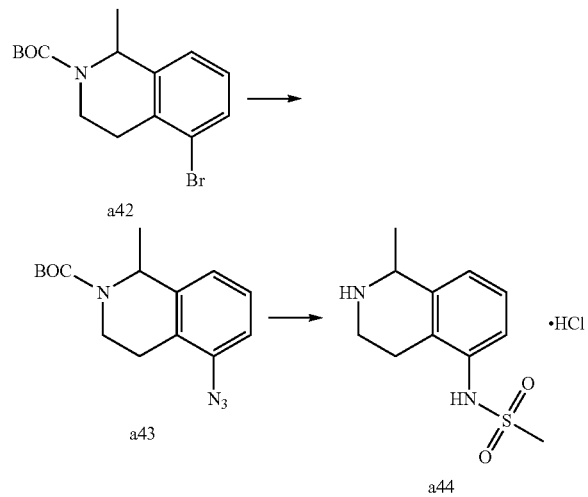

B.3.1. Synthesis of tert-butyl 5-azido-1-methyl-3,4-dihydroisoquinoline-2(1H)-carboxylate a43

To a solution of tert-butyl 5-bromo-1-methyl-3,4-dihydroisoquinoline-2(1H)-carboxylate a42 (295 mg, 0.9 mmol) in 1,4-dioxane (5 mL) in a Schlenk tube were added sequentially at rt sodium azide (145 mg, 2.23 mmol), CuI (35 mg, 0.18 mmol), N,N'-dimethyl-1,2-cyclohexanediamine (60 µL, 0.4 mmol) and a solution of potassium phosphate tribasic (590 mg, 2.69 mmol) in water (500 µL). The tube was degased under vacuum and stirred overnight at 120° C. in an oil bath. The reaction mixture was quenched with an aqueous saturated solution of NaHCO$_3$ (100 mL) and extracted twice with DCM (100 mL). The organic layer was dried over MgSO$_4$, filtered and concentrated under vacuum to yield 282 mg of tert-butyl 5-azido-1-methyl-3,4-dihydroisoquinoline-2(1H)-carboxylate a43 which was used in next step without any further purification.

Yield: 85% (crude).

LCMS (ES$^+$): 233 (M+H)$^+$.

B.3.2. Synthesis of N-(8-methyl-1,2,3,4-tetrahydroisoquinolin-5-yl)methanesulfonamide hydrochloride a44

To a solution of tert-butyl 5-azido-1-methyl-3,4-dihydroisoquinoline-2(1H)-carboxylate a43 (282 mg, 0.98 mmol) in THF (10 mL) and water (2 mL) was added triphenylphosphine (266 mg, 1 mmol) at rt. The mixture was stirred at rt for 1 h, then heated at 60° C. overnight. Water (2 mL) was added. The reaction mixture was heated at 75° C. for 2 h, then concentrated under vacuum. The aqueous layer was extracted twice with DCM (50 mL), dried over MgSO$_4$, filtered and concentrated under vacuum to yield crude tert-butyl 5-amino-1-methyl-3,4-dihydroisoquinoline-2(1H)-carboxylate.

To a solution of tert-butyl 5-amino-1-methyl-3,4-dihydroisoquinoline-2(1H)-carboxylate (256 mg, 0.976 mmol) in DCM (5 mL) were added at rt TEA (0.7 mL, 5 mmol) and methanesulfonyl chloride (150 µmL, 1.9 mmol). The reaction mixture was stirred at rt for 30 min, then concentrated to yield crude tert-butyl 5-(methanesulfonamido)-1-methyl-3,4-dihydro isoquinoline-2(1H)-carboxylate.

LCMS (ES$^+$): 339 (M−H).

To a solution of tert-butyl 5-(methanesulfonamido)-1-methyl-3,4-dihydro isoquinoline-2(1H)-carboxylate (332 mg, 0.97 mmol) in EtOH (3 mL) was added at rt an aqueous saturated solution of HCl in EtOH (3 mL). The reaction mixture was stirred overnight and concentrated under vacuum. The residue was triturated in diisopropyl ether to afford 83 mg of N-(8-methyl-1,2,3,4-tetrahydroisoquinolin-5-yl)methanesulfonamide hydrochloride a44.

Yield: 21% (3 steps).

LCMS (ES$^+$): 241 (M+H)$^+$.

B.4. Synthesis of 7-bromo-1-methyl-1,2,3,4-tetrahydroisoquinoline hydrochloride a47

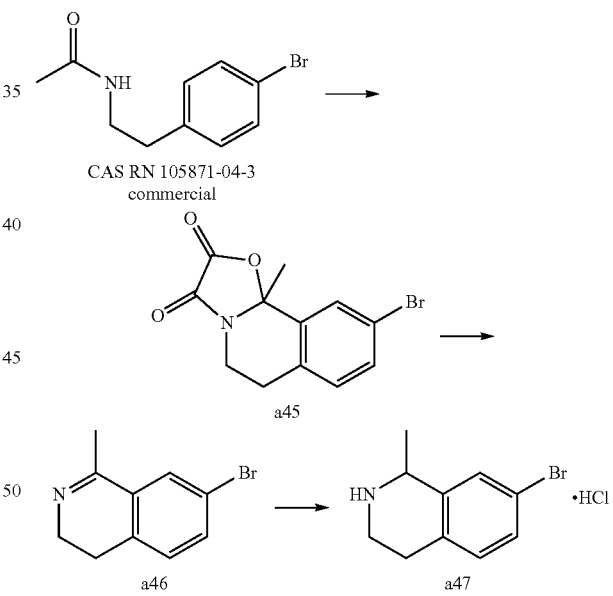

B.4.1. Synthesis of 9-bromo-10b-methyl-6,10b-dihydro-5H-[1,3]oxazolo[2,3-a]isoquinoline-2,3-dione a45

N-[2-(4-bromophenyl)ethyl]acetamide (1.1 g, 4.5 mmol) was dissolved in DCM (20 mL) and the mixture was cooled at 0° C. Oxalyl chloride (0.43 mL, 5.0 mmol) was added dropwise and the mixture was stirred at rt overnight. Ferric chloride (0.88 g, 5.5 mmol) was added and the mixture was stirred at rt for 3 h. The reaction mixture was quenched with water, then extracted twice with DCM. The organic layer was dried over MgSO$_4$, filtered and concentrated under vacuum to yield 1.4 g of 9-bromo-10b-methyl-6,10b-dihydro-5H-[1,3]oxazolo[2,3-a]isoquinoline-2,3-dione a45 as a brown solid which was used in next step without any further purification.

Yield: 100% (crude).
LCMS (ES$^+$): 296/298 (M+H)$^+$.

B.4.2. Synthesis of 7-bromo-1-methyl-3,4-dihydroisoquinoline a46

To 9-bromo-10b-methyl-6,10b-dihydro-5H-[1,3]oxazolo[2,3-a]isoquinoline-2,3-dione a45 (1.4 g, 4.7 mmol) dissolved in EtOH (20 mL) was added sulfuric acid (1 mL). The mixture was stirred at 60° C. overnight, then concentrated under vacuum. The residue was dissolved in MeOH (30 mL) and the mixture was stirred at 60° C. for 2 days. An aqueous solution of ammonia (20-30%) was added until basic pH. The reaction mixture was concentrated under vacuum. The residue was washed twice with EtOAc, filtered and the filtrate was concentrated under vacuum to yield 800 mg of 7-bromo-1-methyl-3,4-dihydroisoquinoline a46 as a red gum which was used in next step without any further purification.

Yield: 76% (crude).
LCMS (ES$^+$): 224/226 (M+H)$^+$.

B.4.3. Synthesis of 7-bromo-1-methyl-1,2,3,4-tetrahydroisoquinoline hydrochloride a47

7-bromo-1-methyl-3,4-dihydroisoquinoline a46 (0.8 g, 3.57 mmol) was dissolved in EtOH (30 mL) and the mixture was cooled at 0° C. Sodium borohydride (0.15 g, 3.92 mmol) was added. The mixture was stirred at 0° C. for 2 h. The mixture was quenched with a 5N aqueous solution of HCl until acidic pH. The mixture was stirred at rt for 30 min. then concentrated under vacuum. The residue was poured in iPrOH sonicated, stirred, filtered, washed twice with iPrOH, then concentrated under vacuum to afford 1.1 g of 7-bromo-1-methyl-1,2,3,4-tetrahydroisoquinoline hydrochloride a47 as an orange oil which was used in next step without any further purification.

Yield: 120% (crude).
LCMS (ES$^+$): 226/228 (M+H)$^+$.

B.5. Synthesis of methyl(1S)-1-methyl-1,2,3,4-tetrahydroisoquinoline-5-carboxylate a49

B.5.1. Synthesis of 2-tert-butyl 5-methyl (1S)-1-methyl-3,4-dihydroisoquinoline-2,5(1H)-dicarboxylate a48

To a suspension of tert-butyl (1S)-5-bromo-1-methyl-3,4-dihydroisoquinoline-2(1H)-carboxylate a42-(S) (4 g, 12.26 mmol) in MeOH (100 mL) in an autoclave were added DIPEA (7 mL, 39.38 mmol) and dibromo[(S)-(+2,2'-bis(diphenylphosphino)-1,1'-binaphthyl]palladium(II) (480 mg, 0.52 mmol). The autoclave was then pressurized with carbon monoxide at 8 bars, and the mixture was stirred overnight at 80° C. The solvent was removed under vacuum and the residue was poured in DCM (300 mL). The organic layer was washed with a 1N aqueous solution of HCl (100 mL), dried over MgSO$_4$, filtered and concentrated under vacuum to yield 3.6 g of 2-tert-butyl 5-methyl (1S)-1-methyl-3,4-dihydroisoquinoline-2,5(1H)-dicarboxylate a48 as a solid which was used in next step without any further purification.

Yield: 87% (crude).
LCMS (ES$^+$): 250 (M+H)$^+$.

B.5.2. Synthesis of methyl(1S)-1-methyl-1,2,3,4-tetrahydroisoquinoline-5-carboxylate a49

To a solution of 2-tert-butyl 5-methyl (1S)-1-methyl-3,4-dihydroisoquinoline-2,5(1H)-dicarboxylate a48 (1.8 g, 4.7 mmol) in EtOH (50 mL) was added a 4N solution of HCl in dioxane (30 mL, 120 mmol). The reaction mixture was stirred overnight at rt, then concentrated under vacuum. The residue was taken up with DCM (200 mL). The organic layer was washed with an aqueous saturated solution of NaHCO$_3$ (100 mL), dried over MgSO$_4$, filtered and concentrated under vacuum to afford 1.8 g of methyl (1S)-1-methyl-1,2,3,4-tetrahydroisoquinoline-5-carboxylate a49 as a yellow oil which was used in next step without any further purification.

Yield: 93% (crude).
HPLC (Basic Mode) RT 3.66 min.

B.6. Synthesis of N-[(1S)-1-methyl-1,2,3,4-tetrahydroisoquinolin-5-yl]methanesulfonamide hydrochloride a51

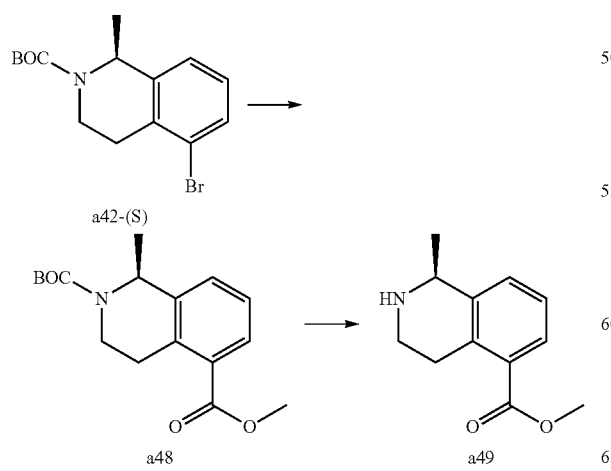

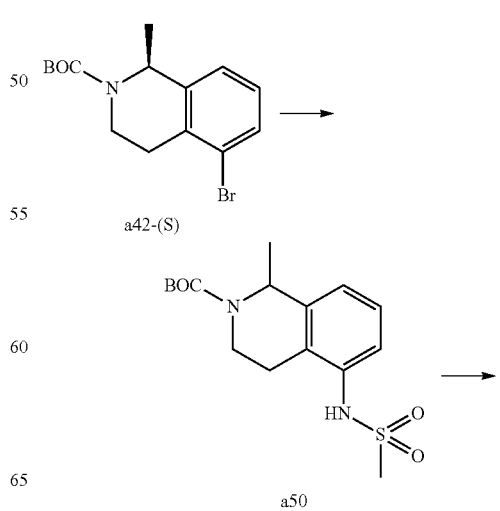

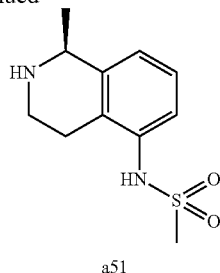

a51

B.6.1. Synthesis of tert-butyl(1S)-1-methyl-5-[(methylsulfonyl)amino]-3,4-dihydroisoquinoline-2(1H)-carboxylate a50

To a solution of tert-butyl (1S)-5-bromo-1-methyl-3,4-dihydroisoquinoline-2(1H)-carboxylate a42-(S) (2 g, 6.1 mmol) and methanesulfonamide (1.17 g, 12.1 mmol) in DMF (20 mL) in a Schlenk tube were added potassium phosphate tribasic (4.02 g, 18.4 mmol), CuI (584 mg, 3.07 mmol) and (1R,2R)-(−)-1,2-diaminocyclohexane (0.74 mL, 6.2 mmol). The tube was degased and stirred in an oil bath at 150° C. overnight. The reaction mixture was poured in EtOAc (250 mL) and successively washed with brine (250 mL), a 1N aqueous solution of HCl (100 mL), and water (250 mL). The organic layer was dried over MgSO₄, filtered and concentrated under vacuum to yield 1.5 g of tert-butyl (1S)-1-methyl-5-[(methylsulfonyl)amino]-3,4-dihydroisoquinoline-2(1H)-carboxylate a50 which was used in next step without any further purification.

Yield: 72% (crude).
LCMS: 285 (M+H)⁺.

B.6.2. Synthesis of N-[(1S)-1-methyl-1,2,3,4-tetrahydroisoquinolin-5-yl]methanesulfonamide hydrochloride a51

To a solution of tert-butyl (1S)-1-methyl-5-[(methylsulfonyl)amino]-3,4-dihydroisoquinoline-2(1H)-carboxylate a50 (1.5 g, 4.4 mmol) in EtOH (20 mL) was added at rt a 4N solution of HCl in dioxane (20 mL). The reaction mixture was stirred at rt overnight, then concentrated under vacuum to yield 1 g of N-[(1S)-1-methyl-1,2,3,4-tetrahydroisoquinolin-5-yl]methanesulfonamide hydrochloride a51 as a yellow-green solid which was used in next step without any further purification.

Yield: 82% (crude).
LCMS: 240 (M+H)⁺.

B.7. Synthesis of 4,4-difluoro-1-methyl-1,2,3,4-tetrahydroisoquinoline a55

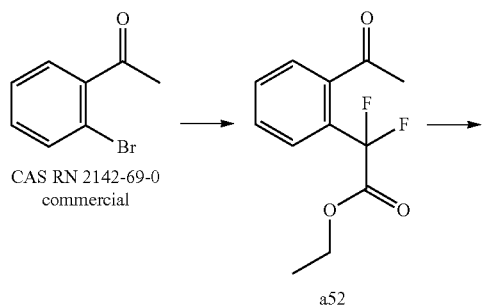

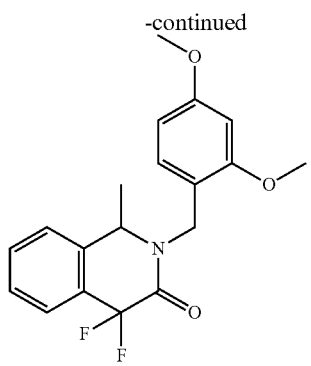

a53

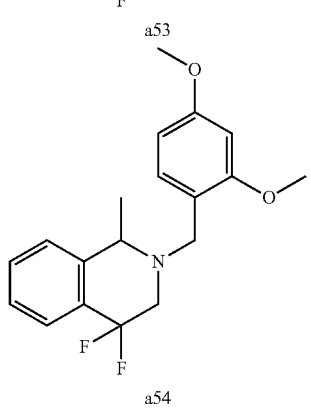

a54

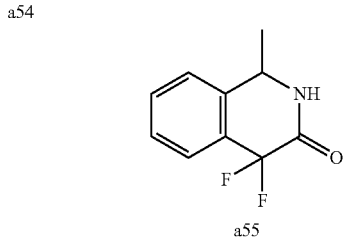

a55

B.7.1. Synthesis of ethyl(2-acetylphenyl)(difluoro)acetate a52

1-(2-Bromophenyl)ethanone (commercial, 1 g, 5.02 mmol), ethyl bromodifluoroacetate (1.04 g, 5.02 mmol) and copper (639 mg, 10 mmol) were dissolved in DMSO (12 mL). The mixture was degased under argon, then stirred at rt for 4 days. The reaction mixture was filtered. EtOAc (50 mL), water (20 mL) were added. The mixture was extracted twice with brine. The organic layer was dried over Na₂SO₄, filtered and concentrated under vacuum. The residue was purified by column chromatography using DCM as eluent to yield 950 mg of ethyl (2-acetylphenyl)(difluoro)acetate a52 as a colour oil.

Yield: 78%.
LCMS (ES⁺): 243 (M+H)⁺, 96.3% purity.

B.7.2. Synthesis of 2-(2,4-dimethoxybenzyl)-4,4-difluoro-1-methyl-1,4-dihydroisoquinolin-3(2H)-one a53

2,4-Dimethoxybenzylamine (517 mg, 3.09 mmol), ethyl (2-acetylphenyl)(difluoro)acetate a52 (500 mg, 2.06 mmol), Titanium(IV) isopropoxide (1.79 g, 6.19 mmol) were dissolved in MeOH (7.5 mL) at rt. After 5 min. stirring at rt, sodium borohydride (118 mg, 3.09 mmol) was added. The reaction mixture was stirred at rt for 88 h, then quenched with a 1N aqueous solution of NaOH and stirred 30 min. at rt. The formed solid was filtered and rinsed with EtOAc. The organic layer was dried over Na$_2$SO$_4$, filtered and concentrated under vacuum. The residue was dissolved in a 1/1 mixture of water and EtOAc. This mixture was extracted thrice by EtOAc. The organic layer was dried over Na$_2$SO$_4$, filtered and concentrated under vacuum. The residue was purified by reverse phase chromatography (basic mode, standard LC) to yield 215 mg of 2-(2,4-dimethoxybenzyl)-4,4-difluoro-1-methyl-1,4-dihydroisoquinolin-3(2H)-one a53.

Yield: 30%.

LCMS (ES): 348 (M+H)$^+$.

B.7.3. Synthesis of 2-(2,4-dimethoxybenzyl)-4,4-difluoro-1-methyl-1,2,3,4-tetrahydroisoquinoline a54

2-(2,4-dimethoxybenzyl)-4,4-difluoro-1-methyl-1,4-dihydroisoquinolin-3(2H)-one a53 (215 mg, 0.62 mmol) was dissolved in DCM (10 mL) at rt. Borane dimethyl sulfide complex solution (2M solution in THF, 1.5 mL, 3 mmol) was added. The reaction mixture was stirred at 55° C. for 4 h, cooled to rt and quenched with a 1/1 solution of MeOH/water. The mixture was poured on a catch and release acidic column (2*5 g). The product was released by elution with a 1M solution of methanolic ammonia (20 mL) and concentrated under vacuum to afford 222 mg of crude 2-(2,4-dimethoxybenzyl)-4,4-difluoro-1-methyl-1,2,3,4-tetrahydroisoquinoline a54 as a colorless oil.

Yield: 107% (crude).

LCMS (ES): 334 (M+H)$^+$, 95% purity.

B.7.4. Synthesis of 4,4-difluoro-1-methyl-1,2,3,4-tetrahydroisoquinoline a55

2-(2,4-Dimethoxybenzyl)-4,4-difluoro-1-methyl-1,2,3,4-tetrahydroisoquinoline a54 (223 mg, 0.67 mmol) was dissolved in a 4N solution of HCl in 1,4-dioxane (2 mL) at rt. The mixture was stirred at 80° C. for 16 h, then concentrated under vacuum. The residue was taken up with water and filtered. The filtrate was concentrated under vacuum to afford 108 mg of 4,4-difluoro-1-methyl-1,2,3,4-tetrahydroisoquinoline a55 as a colour oil which was used in next step without any further purification.

Yield: 74% (crude).

LCMS (ES): 184 (M+H)$^+$.

B.8. Synthesis of [(1S)-1-methyl-1,2,3,4-tetrahydroisoquinolin-5-yl]methanol hydrochloride a57

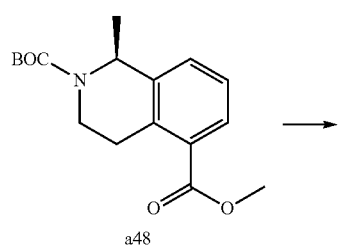

B.8.1. Synthesis of tert-butyl(1S)-5-(hydroxymethyl)-1-methyl-3,4-dihydroisoquinoline-2(1H)-carboxylate a56

To a solution of 2-tert-butyl 5-methyl (1S)-1-methyl-3,4-dihydroisoquinoline-2,5(1H)-dicarboxylate a48 (2.24 g, 5.87 mmol) in THF (50 mL) was added lithium borohydride (850 mg, 37.07 mmol) and the mixture was stirred overnight at rt. The reaction mixture was diluted with DCM (300 mL) and quenched with a 1N aqueous solution of HCl (100 mL). The reaction mixture was stirred for 1 h. The aqueous phase was extracted again with DCM (200 mL). The organic layer was dried over MgSO$_4$, filtered and concentrated under vacuum to yield 2 g of tert-butyl (1S)-5-(hydroxymethyl)-1-methyl-3,4-dihydroisoquinoline-2(1H)-carboxylate a56 which was used in next step without any further purification.

Yield: 98% (crude).

HPLC (Basic Mode) RT 4.98 min, 80% purity.

B.8.2. Synthesis of [(1S)-1-methyl-1,2,3,4-tetrahydroisoquinolin-5-yl]methanol hydrochloride a57

To a solution of tert-butyl (1S)-5-(hydroxymethyl)-1-methyl-3,4-dihydroisoquinoline-2(1H)-carboxylate a56 (2 g, 5.77 mmol) in EtOH (50 mL) was added a 4N solution of HCl in 1,4-dioxane (15 mL) at rt. The mixture was stirred overnight at rt, then concentrated under vacuum. The residue was triturated in Et$_2$O to afford 1.28 g of [(1S)-1-methyl-1,2,3,4-tetrahydroisoquinolin-5-yl]methanol hydrochloride a57 as a solid.

Yield: 94%.

LCMS (ES$^+$): 178 (M+H)$^+$.

B.9. Synthesis of (1S,4S)-1-methyl-1,2,3,4-tetrahydroisoquinolin-4-ol a63-(S,S)

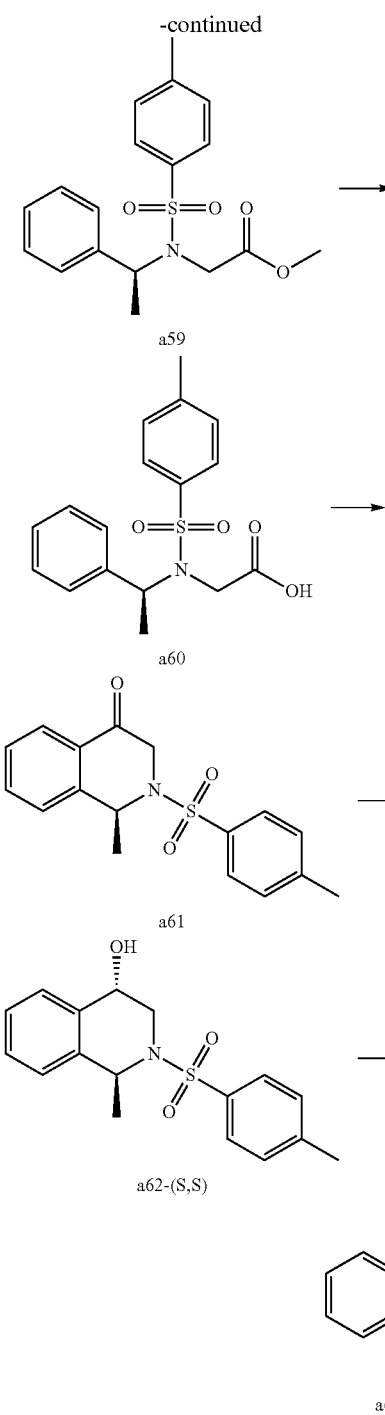

washed with an aqueous saturated solution of sodium bicarbonate and brine. The organic layer was dried over Na$_2$SO$_4$, filtered and concentrated under vacuum. The residue was purified by column chromatography using 20% EtOAc in hexanes as eluent to afford 19.6 g of methyl {[(1S)-1-phenylethyl]amino}acetate a58.

Yield: 61%.
LCMS (ES$^+$): 194 (M+H)$^+$.
$^1$H NMR (400 MHz, DMSO-d$_6$) δ 7.27-7.34 (m, 4H), 7.22 (dd, J=8.75, 4.26 Hz, 1H), 3.74 (q, J=6.43 Hz, 1H), 3.59 (s, 3H), 3.16-3.22 (m, 1H),3.10 (s, 1H) 2.39 (brs, 1H), 1.25 (d, J=6.73 Hz, 3H).

B.9.2. Synthesis of methyl{[(4-methylphenyl)sulfonyl][(1S)-1-phenylethyl]amino}acetate a59

To a solution of methyl {[(1S)-1-phenylethyl]amino}acetate a58 (30 g, 155.4 mmol) in DCM (300 mL) was added TEA (65.5 mL, 470.9 mmol). The mixture was stirred at rt for 15 min., then cooled to 0° C. and 4-toluenesulfonyl chloride (32.6 g, 170.9 mmol) was added over a period of 15 min. The reaction mixture was stirred at rt for 12 h, then successively washed with water (350 mL), an aqueous saturated solution of sodium bicarbonate (350 mL) and a 1N aqueous solution of HCl (300 mL). The organic layer was dried over Na$_2$SO$_4$, filtered and concentrated under vacuum. The residue was purified by column chromatography using 30% EtOAc in hexanes as eluent to afford 32 g of methyl {[(4-methylphenyl)sulfonyl][(1S)-1-phenylethyl]amino}acetate a59.

Yield: 59%.
LCMS (ES$^+$): 348 (M+H)$^+$.
$^1$H NMR (400 MHz, DMSO-d$_6$) δ 7.80 (d, J=7.68 Hz, 2H), 7.41 (d, J=7.68 Hz, 2H), 7.24-7.31 (m, 3H), 7.13-7.23 (m, 2H), 4.99 (q, J=6.77 Hz, 1H), 3.92-4.02 (m, 1H), 3.77-3.85 (m, 1H), 3.47 (s, 3H), 3.32 (s, 3H), 2.41 (s, 3H).

B.9.3. Synthesis of {[(4-methylphenyl)sulfonyl][(1S)-1-phenylethyl]amino}acetic acid a60

To a solution of methyl {[(4-methylphenyl)sulfonyl][(1S)-1-phenylethyl]amino}acetate a59 (52 g, 149.8 mmol) in MeOH (500 mL) at 0° C. was added a 50% aqueous solution of NaOH (17 mL, 644.2 mmol) and the mixture was stirred at rt for 3 h. MeOH was removed under vacuum and the aqueous layer was acidified with a 1N aqueous solution of HCl. The product was extracted with a 5% solution of MeOH in DCM. The organic layer was washed with water, dried over Na$_2$SO$_4$, filtered and concentrated under vacuum to afford 42 g of {[(4-methylphenyl)sulfonyl][(1S)-1-phenylethyl]amino}acetic acid a60.

Yield: 84% (crude).
LCMS (ES$^+$): 334 (M+H)$^+$.
$^1$H NMR (400 MHz, DMSO-d$_6$) δ 7.81 (d, J=8.37 Hz, 2H), 7.38 (d, J=7.91 Hz, 2H), 7.21-7.26 (m, 3H), 7.15-7.20 (m, 2H), 4.93 (q, J=6.98 Hz, 1H), 3.86 (d, J=18.14 Hz, 1H), 3.58 (d, J=18.14 Hz, 1H), 2.40 (s, 3H), 1.33 (d, J=6.98 Hz, 3H).

B.9.4. Synthesis of (1S)-1-methyl-2-[(4-methylphenyl)sulfonyl]-2,3-dihydroisoquinolin-4(1H)-one a61

To a solution of {[(4-methylphenyl)sulfonyl][(1S)-1-phenylethyl]amino}acetic acid a60 (42 g, 126 mmol) in dry DCM (480 mL) at 0° C., thionyl chloride (50 g, 420 mmol) was added and the reaction mixture was stirred at rt for 12 h. The reaction mixture was concentrated under vacuum.

B.9.1. Synthesis of methyl{[(1S)-1-phenylethyl]amino}acetate a58

To a solution of methyl 2-bromoacetate (25.25 g, 164.9 mmol) in THF (125 mL) was added TEA (49 mL, 352.2 mmol) and the mixture was stirred at rt or 15 min. The reaction mixture was cooled to 0° C. and (1S)-1-phenylethanamine (commercial, 20 g, 165 mmol) was added slowly over a period of 10 min. The reaction mixture was stirred at rt for 12 h, filtered and the filtrate was concentrated under vacuum. The residue was dissolved in DCM (180 mL), The residue was taken up with DCM (450 mL) and cooled to 0° C. AlCl₃ (56 g, 420 mmol) was added and the reaction mixture was stirred at rt for 12 h. The reaction mixture was quenched with an aqueous saturated solution of sodium bicarbonate. The organic layer was dried over Na₂SO₄, filtered and concentrated under vacuum. The residue was purified by column chromatography using 20% EtOAc in hexanes as eluent to afford 16.3 g of (1S)-1-methyl-2-[(4-methylphenyl)sulfonyl]-2,3-dihydroisoquinolin-4(1H)-one a61.

Yield: 42%.

¹H NMR (400 MHz, DMSO-d₆) δ 7.49-7.59 (m, 2H), 7.46 (d, J=8.19 Hz, 2H), 7.42 (d, J=7.76 Hz, 1H), 7.28 (t, J=7.11 Hz, 1H), 7.12 (d, J=8.19 Hz, 2H), 5.33 (q, J=6.90 Hz, 1H), 4.41-4.49 (m, 1H), 4.24-4.34 (m, 1H), 2.23 (s, 3H), 1.47 (d, J=7.33 Hz, 3H).

B.9.5. Synthesis of (1S,4S)-1-methyl-2-[(4-methylphenyl)sulfonyl]-1,2,3,4-tetrahydroisoquinolin-4-ol a62-(S,S)

To a solution of (1S)-1-methyl-2-[(4-methylphenyl)sulfonyl]-2,3-dihydroisoquinolin-4(1H)-one a61 (8 g, 25.4 mmol) in THF (240 mL) at −25° C. was added (S)-2-methyl-CBS-oxazaborolidine (1.4 g, 5.07 mmol). Then borane dimethyl sulfide complex solution (2M solution in THF, 12.7 mL, 25.4 mmol) was added and the reaction mixture was maintained between −15° C. and −20° C. for 2 h. The TLC showing the presence of starting material, borane dimethyl sulfide complex solution (2M solution in THF, 6.3 mL, 12.7 mmol) was further added and the mixture was stirred at rt for 2 h. The reaction mixture was quenched with MeOH and concentrated under vacuum. The residue was purified by column chromatography using 50% Et₂O in hexanes as eluent to afford 4 g of (1S,4S)-1-methyl-2-[(4-methylphenyl)sulfonyl]-1,2,3,4-tetrahydroisoquinolin-4-ol a62-(S,S).

Yield: 50%.

¹H NMR (400 MHz, DMSO-d₆) δ 7.75 (d, J=8.19 Hz, 2H), 7.28-7.38 (m, 3H), 7.11-7.26 (m, 3H), 5.38-5.48 (m, 1H), 4.89 (q, J=6.90 Hz, 1H), 4.64 (q, J=3.88 Hz, 1H), 3.49-3.57 (m, 2H), 2.28-2.38 (m, 3H), 1.17-1.29 (m, 3H).

(1S,4R)-1-methyl-2-[(4-methylphenyl)sulfonyl]-1,2,3,4-tetrahydroisoquinolin-4-ol a62-(S,R) may be synthesized according to the same procedure using (R)-2-methyl-CBS-oxazaborolidine as reagent.

¹H NMR (400 MHz, DMSO-d₆) δ 7.68 (d, J=8.19 Hz, 2H), 7.38-7.42 (m, 1H), 7.34 (d, J=7.76 Hz, 2H), 7.14-7.24 (m, 3H), 5.66 (d, J=6.47 Hz, 1H), 5.03 (q, J=6.47 Hz, 1H), 4.30-4.39 (m, 1H), 3.89 (dd, J=13.36, 6.47 Hz, 1H), 3.07 (dd, J=13.36, 10.35 Hz, 1H), 2.34 (s, 3H), 1.33 (d, J=6.90 Hz, 3H).

B.9.6. Synthesis of (1S,4S)-1-methyl-1,2,3,4-tetrahydroisoquinolin-4-ol a63-(S,S)

Liquid ammonia was generated in a two neck round bottom flask by condensing ammonia gas at −78° C. Sodium metal (2.9 g, 126.2 mmol) was added to the liquid ammonia solution during which the color of the liquid ammonia changed from colorless to dark blue. A solution of (1S,4S)-1-methyl-2-[(4-methylphenyl)sulfonyl]-1,2,3,4-tetrahydroisoquinolin-4-ol a62-(S,S) (4 g, 12.61 mmol) in THF (20 mL) was added dropwise at −78° C. and the mixture was stirred for 5 min. The reaction mixture was quenched with ammonium chloride (5 g) at the same temperature and a reaction mass led to a thick white solid. The residue was diluted with water and the solution was then extracted with EtOAc. The organic layer was washed with water, dried over Na₂SO₄, filtered and concentrated under vacuum. The residue was purified by column chromatography using 10% MeOH in DCM as eluent to afford 1.03 g of (1S,4S)-1-methyl-1,2,3,4-tetrahydroisoquinolin-4-ol a63-(S,S).

Yield: 50%.

LCMS ((ES⁺): 164 (M+H)⁺.

¹H NMR (400 MHz, DMSO-d₆) δ 7.39-7.48 (m, 1H), 7.07-7.23 (m, 3H), 4.48 (t, J=5.95 Hz, 1H), 3.96 (q, J=6.62 Hz, 1H), 3.29 (brs, 2H), 3.17 (dd, J=11.91, 4.85 Hz, 1H), 2.62 (dd, J=12.13, 8.16 Hz, 1H), 1.30 (d, J=6.62 Hz, 3H).

(1S,4R)-1-methyl-1,2,3,4-tetrahydroisoquinolin-4-ol a63-(S,R) may be synthesized according to the same procedure from (1S,4R)-1-methyl-2-[(4-methylphenyl)sulfonyl]-1,2,3,4-tetrahydroisoquinolin-4-ol a62-(S,R).

LCMS ((ES⁺): 164(M+H)⁺.

¹H NMR (400 MHz, DMSO-d₆) δ 7.31-7.39 (m, 1H), 7.08-7.25 (m, 3H), 4.37 (t, J=4.19 Hz, 1H), 3.84-3.96 (m, 1H), 3.15-3.47 (m, 1H), 2.88-2.96 (m, 2H), 1.29-1.41 (m, 3H).

B.10. Synthesis of 1-methyl-1,2,3,4-tetrahydroisoquinolin-4-ol a65

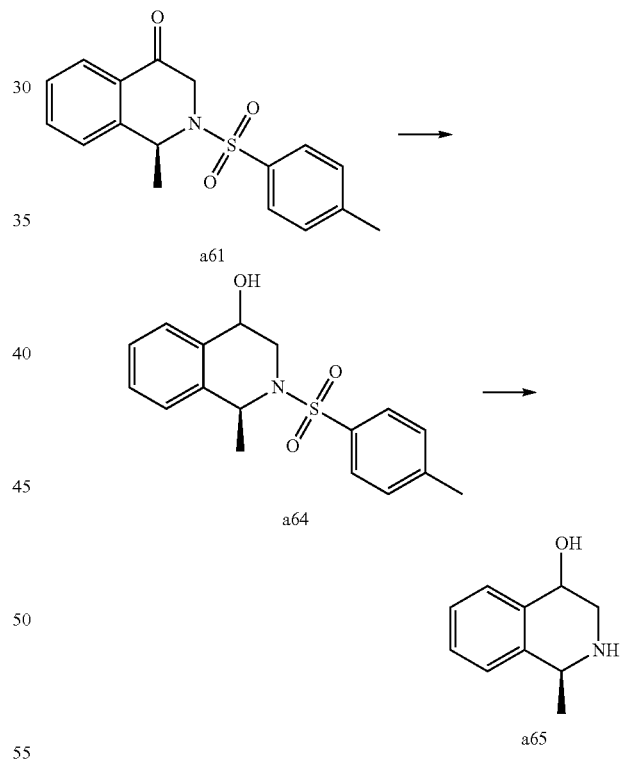

B.10.1. Synthesis of (1S)-1-methyl-2-[(4-methylphenyl)sulfonyl]-1,2,3,4-tetrahydro-isoquinolin-4-ol a64

(1S)-1-methyl-2-[(4-methylphenyl)sulfonyl]-2,3-dihydroisoquinolin-4(1H)-one a61 (700 mg, 2.22 mmol) was dissolved in MeOH (20 mL) at rt. Sodium borohydride (117 mg, 3.11 mmol) was added. The mixture was stirred at rt for 30 min, then quenched with water and extracted twice with EtOAc. The organic layer was washed with brine, dried over Na$_2$SO$_4$, filtered and concentrated under vacuum to yield 691 mg of (1S)-1-methyl-2-[(4-methylphenyl)sulfonyl]-1,2,3,4-tetrahydroisoquinolin-4-ol a64.

Yield: 98% (crude).
LCMS (ES$^+$): 318 (M+H)$^+$.

B.10.2. Synthesis of (1S)-1-methyl-1,2,3,4-tetrahydroisoquinolin-4-ol a65

In a sealed tube, (1S)-1-methyl-2-[(4-methylphenyl)sulfonyl]-1,2,3,4-tetrahydroisoquinolin-4-ol a64 (806 mg, 2.5 mmol) was dissolved in THF (24 mL) at rt. Lithium aluminium hydride (290 mg, 7.6 mmol) was added and the mixture was stirred at 60° C. overnight. The reaction mixture was cooled to rt, quenched with water (1 mL), then successively washed with a 5N aqueous solution of NaOH and twice with water. The aqueous layer was extracted twice with EtOAc. The organic layer was dried over Na$_2$SO$_4$, filtered and concentrated under vacuum to afford 364 mg of (1S)-1-methyl-1,2,3,4-tetrahydroisoquinolin-4-ol a65.

Yield: 88% (crude).
LCMS (ES$^+$): 164.1 (M+H)$^+$.

B.11. Synthesis of (1S)-1-methyl-5-(methylsulfonyl)-1,2,3,4-tetrahydroisoquinoline hydrochloride a68

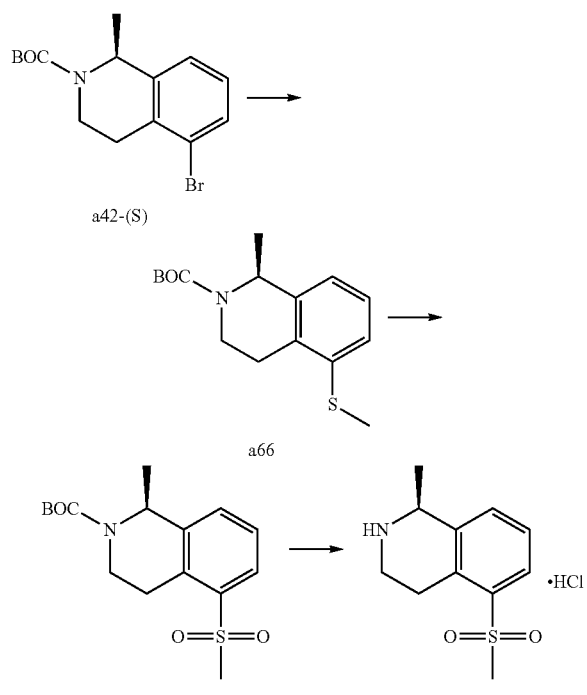

B.11.1. Synthesis of tert-butyl(1S)-1-methyl-5-(methylsulfanyl)-3,4-dihydroisoquinoline-2(1H)-carboxylate a66

Tert-butyl (1S)-5-bromo-1-methyl-3,4-dihydroisoquinoline-2(1H)-carboxylate a42-(S) (1 g, 3.06 mmol), sodium thiomethoxide (1.13 g, 15.33 mmol), 4,5-bis(diphenylphosphino)-9,9-dimethylxanthene (355 mg, 0.61 mmol), tris(dibenzylideneacetone) dipalladium(0) (281 mg, 0.31 mmol), DIPEA (1.1 mL, 6.13 mmol) were dissolved in toluene (20 mL) at rt. The mixture was stirred at 150° C. for 25 min under microwave irradiation. The reaction mixture was cooled to rt, filtered and concentrated under vacuum. The residue was purified by reverse phase chromatography (basic mode, standard LC) to yield 604 mg of tert-butyl (1S)-1-methyl-5-(methylsulfanyl)-3,4-dihydroisoquinoline-2(1H)-carboxylate a66.

Yield: 67%.
LCMS (ES$^+$): 238 (M+H)$^+$, 100% purity.

B.11.2. Synthesis of tert-butyl(1S)-1-methyl-5-(methylsulfonyl)-3,4-dihydroisoquinoline-2(1H)-carboxylate a67

Tert-butyl (1S)-1-methyl-5-(methylsulfanyl)-3,4-dihydroisoquinoline-2(1H)-carboxylate a66 (450 mg, 1.53 mmol) was dissolved in DCM (80 mL) at rt. 3-Chloroperoxybenzoic acid (790 mg, 3.53 mmol) was added. The reaction mixture was stirred at rt for 3 h, then extracted twice with an aqueous saturated solution of NaHCO$_3$. The organic layer was dried over Na$_2$SO$_4$, filtered and concentrated under vacuum. The residue was purified by reverse phase chromatography (basic mode, standard LC) to yield 303 mg of tert-butyl (1S)-1-methyl-5-(methylsulfonyl)-3,4-dihydroisoquinoline-2(1H)-carboxylate a67.

Yield: 61%.
LCMS (ES$^+$): 270 (M+H)$^+$, 100% purity.

B.11.3. Synthesis of (1S)-1-methyl-5-(methylsulfonyl)-1,2,3,4-tetrahydroisoquinoline hydrochloride a68

Tert-butyl (1S)-1-methyl-5-(methylsulfonyl)-3,4-dihydroisoquinoline-2(1H)-carboxylate a67 (303 mg, 0.93 mmol) was dissolved in 4N solution of HCl in 1,4-dioxane (6 mL) at rt. The mixture was stirred at rt overnight, then concentrated under vacuum to afford 210 mg of (1S)-1-methyl-5-(methylsulfonyl)-1,2,3,4-tetrahydroisoquinoline hydrochloride a68 which was used in next step without any further purification.

Yield: 100% (crude).
LCMS (ES$^+$): 226 (M+H)$^+$, 100% purity.

B.12. Synthesis of 2,2,2-trifluoro-1-[(1S)-1-methyl-1,2,3,4-tetrahydroisoquinolin-5-yl]ethanol a114 and isomers a114-A and a114-B

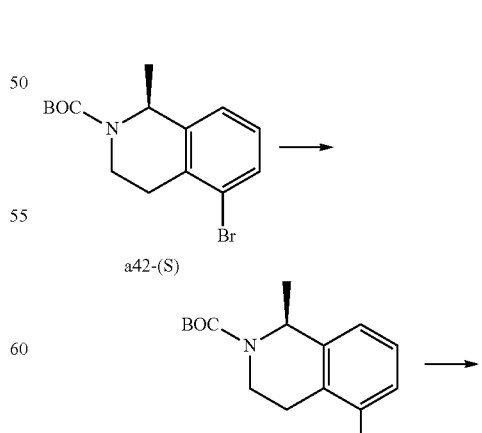

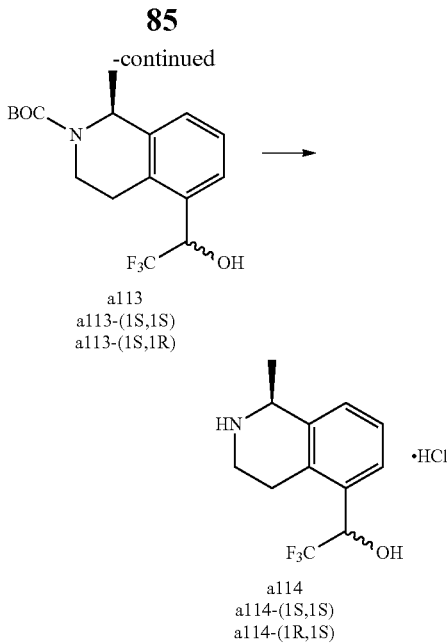

a113
a113-(1S,1S)
a113-(1S,1R)

a114
a114-(1S,1S)
a114-(1R,1S)

Synthesis of tert-butyl(1S)-5-formyl-1-methyl-3,4-dihydro-1H-isoquinoline-2-carboxylate a112

To a suspension of tert-butyl (1S)-5-bromo-1-methyl-3,4-dihydro-1H-isoquinoline-2-carboxylate a42-(S) (21.77 g, 66.65 mmol) in toluene (400 mL) in an autoclave were added N,N,N',N'-tetramethylethylenediamine (21.53 mL, 133.5 mmol), butyldi-1-adamantylphosphine (3.78 g, 10 mmol) and palladium(II)acetate (764 mg, 3.34 mmol). The reactor was flushed with nitrogen and placed under 5 bar of Syngas (CO/$H_2$ 1:1). The reaction mixture was heated at 120° C. for 16 h, then filtered through a path of Celite®. The organic layer was washed twice with water. The aqueous layer was extracted with toluene. The combined organic layers were dried over $MgSO_4$, filtered and concentrated under vacuum. The residue was purified by column chromatography using 20% heptane in DCM as eluent to yield 10.56 g of tert-butyl (1S)-5-formyl-1-methyl-3,4-dihydro-1H-isoquinoline-2-carboxylate a112.

Yield: 58%.

LCMS (ES): 176 (-Boc)/220 (-isoprene) $(M+H)^+$, 100% purity.

B.12.1. Synthesis of tert-butyl(1S)-1-methyl-5-(2,2,2-trifluoro-1-hydroxy-ethyl)-3,4-dihydro-1H-isoquinoline-2-carboxylate a113 and isomers a113-(1S,1S) and a113-(1S,1R)

To a solution of tert-butyl (1S)-5-formyl-1-methyl-3,4-dihydro-1H-isoquinoline-2-carboxylate a112 (5.19 g, 18.9 mmol) in DMF (50 mL) were added cesium fluoride (5.84 g, 37.7 mmol) and trifluoromethylsilane (6 mL, 40 mmol). The reaction mixture was heated at 60° C. overnight. The reaction mixture was poured in EtOAc (200 mL), then successively washed with water (100 mL), brine (2×100 mL) and water. The organic layer was dried over $MgSO_4$, filtered and concentrated under vacuum. The residue was purified by column chromatography using 2% MeOH in DCM as eluent to give 2.72 g of tert-butyl (1S)-1-methyl-5-(2,2,2-trifluoro-1-hydroxy-ethyl)-3,4-dihydro-1H-isoquinoline-2-carboxylate a113 (Yield: 41%, LCMS ($ES^+$): 290 (-isoprene) $(M+H)^+$, 100% purity). Chiral separation (LC, Chiralcel OD, 80*480, 200 mL/min, 220 nm, 30° C., eluent: EtOH/heptane 10/90) of 1.05 g of a113 afforded:

472 mg of tert-butyl (1S)-1-methyl-5-((1S)-2,2,2-trifluoro-1-hydroxy-ethyl)-3,4-dihydro-1H-isoquinoline-2-carboxylate a113-(1S,1S).

Yield: 7%.

LCMS ($ES^+$): 246 (-Boc)/290 (-isoprene) $(M+H)^+$, 100% purity.

Chiral analysis (LC, Chiralcel OD, 150*4.6 mm, 1.5 mL/min, 220 nm, 30° C., eluent: EtOH/heptane/DEA 10/90/0.1): RT 1.72 min, 100% ee.

514 mg of tert-butyl (1S)-1-methyl-5-((1R)-2,2,2-trifluoro-1-hydroxy-ethyl)-3,4-dihydro-1H-isoquinoline-2-carboxylate a113-(1S,1R).

Yield: 8%.

LCMS ($ES^+$): 246 (-Boc)/290 (-isoprene) $(M+H)^+$, 100% purity.

Chiral analysis (LC, Chiralcel OD, 150*4.6 mm, 1.5 mL/min, 220 nm, 30° C., eluent: EtOH/heptane/DEA 10/90/0.1): RT 4.12 min, 100% ee.

B.12.2. Synthesis of 2,2,2-trifluoro-1-[(1S)-1-methyl-1,2,3,4-tetrahydroisoquinolin-5-yl]ethanol hydrochloride a114

To a solution of tert-butyl (1S)-1-methyl-5-(2,2,2-trifluoro-1-hydroxy-ethyl)-3,4-dihydro-1H-isoquinoline-2-carboxylate a113 (1.67 g, 4.83 mmol) in EtOH (40 mL) at 0° C. was added a 4N solution of hydrochloric acid in dioxane (10 mL, 288 mmol). The reaction mixture was stirred overnight at rt. The solvent was removed under vacuum to give 1.3 g of 2,2,2-trifluoro-1-[(1S)-1-methyl-1,2,3,4-tetrahydroisoquinolin-5-yl]ethanol hydrochloride a114.

Yield: 96%.

LCMS ($ES^+$): 246 $(M+H)^+$.

Isomers a114-(1S,1S) and a114-(1R,1S) may be synthesized according to the same method using respectively tert-butyl (1S)-1-methyl-5-((1S)-2,2,2-trifluoro-1-hydroxy-ethyl)-3,4-dihydro-1H-isoquinoline-2-carboxylate a113-(1S,1S) and tert-butyl (1S)-1-methyl-5-((1R)-2,2,2-trifluoro-1-hydroxy-ethyl)-3,4-dihydro-1H-isoquinoline-2-carboxylate a113-(1S,1R) as starting material.

(1S)-2,2,2-trifluoro-1-[(1S)-1-methyl-1,2,3,4-tetrahydroisoquinolin-5-yl]ethanol hydrochloride a114-(1S,1S)

Yield: 96%.

LCMS ($ES^+$): 246 $(M+H)^+$, 100% purity.

(1R)-2,2,2-trifluoro-1-[(1S)-1-methyl-1,2,3,4-tetrahydroisoquinolin-5-yl]ethanol hydrochloride a114-(1R,1S)

Yield: 98%.

LCMS ($ES^+$): 246 $(M+H)^+$, 100% purity.

B.13. Synthesis of tert-butyl(1S)-5-(3-methoxy-3-oxo-propyl)-1-methyl-3,4-dihydro-1H-isoquinoline-2-carboxylate a116

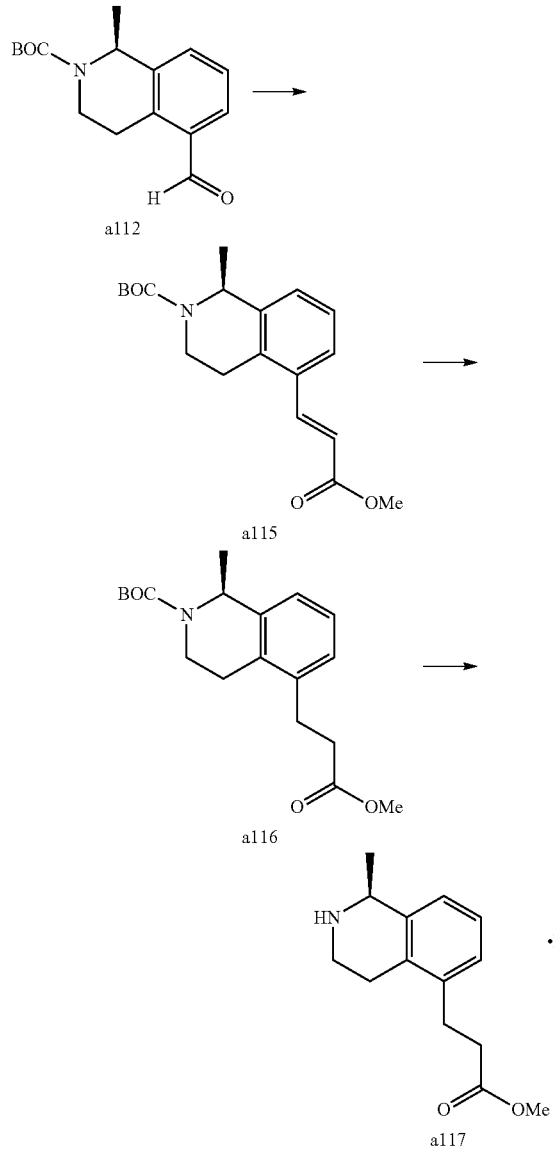

B.13.1. Synthesis of tert-butyl(1S)-5-[(E)-3-methoxy-3-oxo-prop-1-enyl]-1-methyl-3,4-dihydro-1H-isoquinoline-2-carboxylate a115

To a solution of tert-butyl (1S)-5-formyl-1-methyl-3,4-dihydro-1H-isoquinoline-2-carboxylate a112 (420 mg, 1.52 mmol) in THF (15 mL) was added methyl (triphenylphosphoranylidene)acetate (510 mg, 1.52 mmol). The reaction mixture was stirred overnight at 60° C., then concentrated under vacuum to afford 480 mg of tert-butyl (1S)-5-[(E)-3-methoxy-3-oxo-prop-1-enyl]-1-methyl-3,4-dihydro-1H-isoquinoline-2-carboxylate a115 which was used in the next step without any further purification.

Yield: 95% (crude).
LCMS (ES⁺): 232 (M+H)⁺.

B.13.2. Synthesis of tert-butyl(1S)-5-(3-methoxy-3-oxo-propyl)-1-methyl-3,4-dihydro-1H-isoquinoline-2-carboxylate a116

To a solution of crude tert-butyl (1S)-5-[(E)-3-methoxy-3-oxo-prop-1-enyl]-1-methyl-3,4-dihydro-1H-isoquinoline-2-carboxylate a115 (480 mg, 1.45 mmol) in EtOH (10 mL, 171.32 mmol) was added Pd/C. The reaction mixture was pressurized under 14 bars of hydrogen, stirred overnight at rt and filtered with a SPE Syringe. Solvent was removed under vacuum to give 820 mg of tert-butyl (1S)-5-(3-methoxy-3-oxo-propyl)-1-methyl-3,4-dihydro-1H-isoquinoline-2-carboxylate a116 which was used in the next step without any further purification.

Yield: 85% (crude).
LCMS (ES⁺): 234 (M+H)⁺.

B.13.3. Synthesis of methyl 3-[(1S)-1-methyl-1,2,3,4-tetrahydroisoquinolin-5-yl]propanoate hydrochloride a117

To a solution of crude tert-butyl (1S)-5-(3-methoxy-3-oxo-propyl)-1-methyl-3,4-dihydro-1H-isoquinoline-2-carboxylate a116 (820 mg, 1.23) in MeOH (10 mL) was added a 4N solution of hydrochloric acid in dioxane (5 mL, 20 mmol). The reaction mixture was stirred overnight at rt. The solvent was removed under vacuum to give 600 mg methyl 3-[(1S)-1-methyl-1,2,3,4-tetrahydroisoquinolin-5-yl]propanoate hydrochloride a117.

Yield: 90% (crude).

B.14. LCMS (ES⁺): 234 (M+H)⁺, 50% purity. Synthesis of 6-[(1S)-1-methyl-1,2,3,4-tetrahydroisoquinolin-5-yl]morpholin-3-one hydrochloride salts a123 and a124

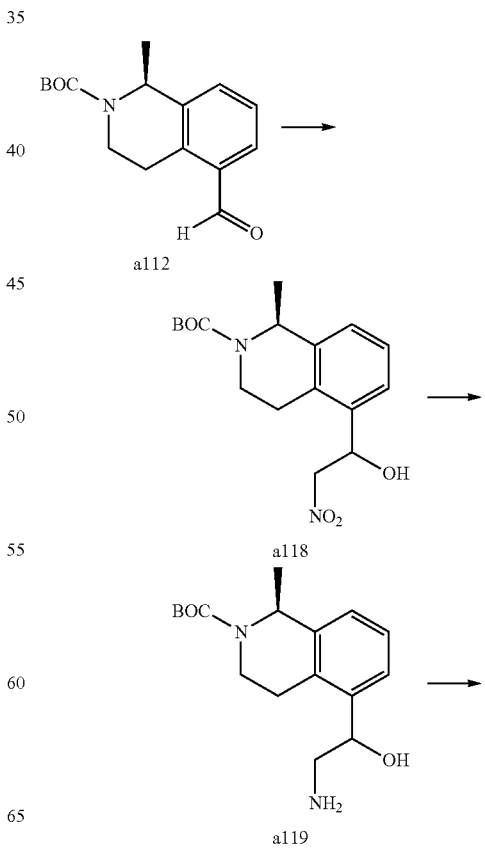

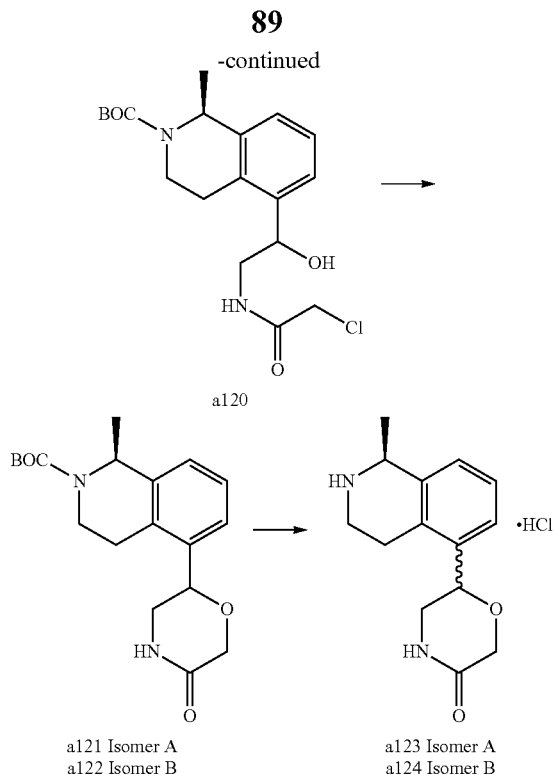

a120 a121 Isomer A
a122 Isomer B a123 Isomer A
a124 Isomer B

B.14.1. Synthesis of tert-butyl(1S)-5-(1-hydroxy-2-nitro-ethyl)-1-methyl-3,4-dihydro-1H-isoquinoline-2-carboxylate a118 tert-butyl (1S)-5-formyl-1-methyl-3,4-dihydro-1H-isoquinoline-2-carboxylate a112 (5 g, 18.16 mmol) was diluted in a mixture of nitromethane and EtOH (3:1, 20 mL). After addition of triethylamine (51 µL, 0.36 mmol), the reaction mixture was stirred at rt for 3 days. Volatiles were evaporated under vacuum, then the residue was purified by column chromatography using 0.45% MeOH in DCM (+0.05% NH₄OH) to yield 2.8 g of tert-butyl (1S)-5-(1-hydroxy-2-nitro-ethyl)-1-methyl-3,4-dihydro-1H-isoquinoline-2-carboxylate a118

Yield: 46%.
LCMS (ES⁺): 237 (-Boc) (M+H)⁺.

B.14.2. Synthesis of tert-butyl(1S)-5-(2-amino-1-hydroxy-ethyl)-1-methyl-3,4-dihydro-1H-isoquinoline-2-carboxylate a119

In an autoclave, tert-butyl (1S)-5-(1-hydroxy-2-nitroethyl)-1-methyl-3,4-dihydro-1H-isoquinoline-2-carboxylate a118 (2.8 g, 8.3 mmol) and Raney Nickel (100 mg) were mixed in dioxane (50 mL). The reaction mixture was pressurized under 20 bars of hydrogen and heated at 40° C. under a vigorous agitation for 48 h. The mixture was filtered trough Celite® and concentrated under vacuum to yield to 2.6 g of the crude tert-butyl (1S)-5-(2-amino-1-hydroxy-ethyl)-1-methyl-3,4-dihydro-1H-isoquinoline-2-carboxylate a119 which was used in the next step without any further purification.

Yield: 100% (crude).
LCMS (ES⁺): 307 (M+H)⁺.

B.14.3. Synthesis of tert-butyl(1S)-5-[2-[(2-chloroacetyl)amino]-1-hydroxy-ethyl]-1-methyl-3,4-dihydro-1H-isoquinoline-2-carboxylate a120

Triethylamine (3.6 mL, 25.5 mmol) was added dropwise at rt to a mixture of tert-butyl (1S)-5-(2-amino-1-hydroxy-ethyl)-1-methyl-3,4-dihydro-1H-isoquinoline-2-carboxylate a119 (2.6 g, 8.5 mmol) and chloroacetyl chloride (0.68 mL, 8.5 mmol) in DCM (50 mL). The reaction mixture was stirred at rt during 2 h, then diluted with DCM (150 mL) and successively washed with a 1N aqueous solution of hydrochloric acid (50 mL) and an aqueous saturated solution of sodium carbonate (50 mL). The organic layer was dried over MgSO₄, filtered and concentrated under vacuum to yield 3.2 g of tert-butyl (1S)-5-[2-[(2-chloroacetyl)amino]-1-hydroxy-ethyl]-1-methyl-3,4-dihydro-1H-isoquinoline-2-carboxylate a120 which was used in the next step without any further purification.

Yield: 100% (crude)
LCMS (ES⁺): 283/285 (-Boc) (M+H)⁺

B.14.4. Synthesis of tert-butyl(1S)-1-methyl-5-(5-oxomorpholin-2-yl)-3,4-dihydro-1H-isoquinoline-2-carboxylate isomers A a121 and B a122

Potassium tert-butoxide (665 mg, 5.75 mmol) was added to a solution of tert-butyl (1S)-5-[2-[(2-chloroacetyl)amino]-1-hydroxy-ethyl]-1-methyl-3,4-dihydro-1H-isoquinoline-2-carboxylate a120 (2.0 g, 5.2 mmol) in 2-propanol (50 mL). The reaction mixture was stirred at rt for 15 h, then concentrated under vacuum, the residue was diluted with EtOAc (150 mL), then successively washed with a 1N aqueous solution of hydrochloric acid (50 mL) and an aqueous saturated solution of sodium carbonate (50 mL). The organic layer was dried over MgSO₄, filtered and concentrated under vacuum. The residue was purified by reverse phase chromatography (basic mode, LCMS prep) to yield a mixture of the 2 diastereoisomers. The isomers were directly separated by chiral separation (SFC, Chiralpak AS, 50*265, 360 mL/min, 220 nm, 35° C., eluent: 15% MeOH) to afford:

180 mg of tert-butyl (1S)-1-methyl-5-[5-oxomorpholin-2-yl]-3,4-dihydro-1H-isoquinoline-2-carboxylate isomer A a121.
Yield: 10%.
LCMS (ES): 247 (-Boc)/291 (-isoprene) (M+H)⁺.
Chiral analysis (LC, Chiralpak AD, 150*4.6 mm, 1.5 mL/min, 220 nm, 30° C., eluent: EtOH/heptane/DEA 50/50/0.1): RT 2.37 min, 100% ee.

180 mg of tert-butyl (1S)-1-methyl-5-[5-oxomorpholin-2-yl]-3,4-dihydro-1H-isoquinoline-2-carboxylate isomer B a122.
Yield: 10%.
LCMS (ES⁺): 247 (-Boc)/291 (-isoprene) (M+H)⁺.
Chiral analysis (LC, Chiralpak AD, 150*4.6 mm, 1.5 mL/min, 220 nm, 30° C., eluent: EtOH/heptane/DEA 50/50/0.1): RT 1.82 min, 96.6% ee.

B.14.5. Synthesis of 6-[(1S)-1-methyl-1,2,3,4-tetrahydroisoquinolin-5-yl]morpholin-3-one hydrochloride isomers A a123 and a124

To a solution of tert-butyl (1S)-1-methyl-5-[5-oxomorpholin-2-yl]-3,4-dihydro-1H-isoquinoline-2-carboxylate isomer A a121 (150 mg, 0.43 mmol) in Et₂O (2 mL) was added a 4N solution of hydrochloric acid in dioxane (2 mL, 8 mmol). The reaction mixture was stirred at rt for 4 h. The solvent was removed under vacuum to give 123 mg of 6-[(1S)-1-methyl-1,2,3,4-tetrahydroisoquinolin-5-yl]morpholin-3-one hydrochloride isomers A a123.
Yield: 100% (crude).
LCMS (ES+): 245 (M+H)+.

Compound a124 may be synthetized according to the same method using tert-butyl (1S)-1-methyl-5-[5-oxomorpholin-2-yl]-3,4-dihydro-1H-isoquinoline-2-carboxylate isomer B a122 as starting material.

6-[(1S)-1-methyl-1,2,3,4-tetrahydroisoquinolin-5-yl]morpholin-3-one hydrochloride isomer B a124

Yield: 100% (crude).
LCMS (ES+): 245 (M+H)+.

EXAMPLES

C. Synthesis of Compounds of Formula I-A

C.1. Method A. Synthesis of 2-(2,6-dichlorophenyl)-1-(1-methyl-3,4-dihydroisoquinolin-2(1H)-yl) ethanone 1 and enantiomers

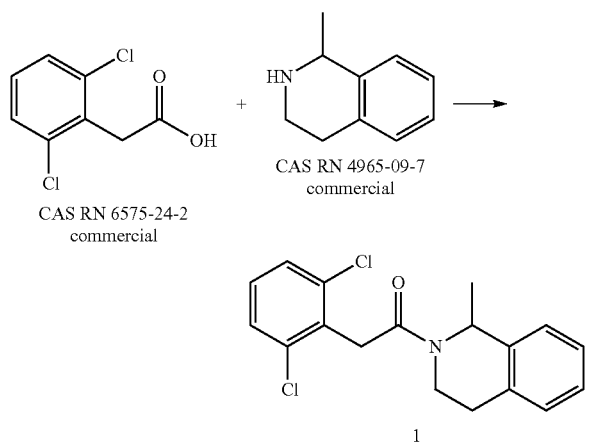

2,6-Dichlorophenylacetic acid (commercial, 535 mg, 2.61 mmol) was dissolved in DMF (4 mL). 1-Methyl-1,2,3,4-tetrahydroisoquinoline (commercial, 384 mg, 2.61 mmol) and TEA (1.1 mL, 7.80 mmol) were added at rt, then BOP (1.15 g, 2.61 mmol) was added. The mixture was stirred overnight at 60° C. The reaction mixture was diluted with EtOAc (100 mL), then successively washed with a 1N aqueous solution of HCl (100 mL), an aqueous saturated solution of NaHCO$_3$ and brine. The organic layer was dried over MgSO$_4$, filtered and concentrated under vacuum. The residue was first purified by silica gel column chromatography using 50% of DCM in hexanes, then by reverse phase chromatography (basic mode, standard LC) to yield 300 mg of racemate 2-(2,6-dichlorophenyl)-1-(1-methyl-3,4-dihydroisoquinolin-2(1H)-yl)ethanone 1 (Yield: 34%, LCMS (ES+): 334/336/338 (M+H)+, 99.1% purity).

Chiral separation (SFC, Chiralpak IA, 50*266 mm, 360 mL/min, 220 nm, 25° C., eluent: from 20 to 35% iPrOH) afforded:

125 mg of 2-(2,6-dichlorophenyl)-1-[(1S)-1-methyl-3,4-dihydroisoquinolin-2(1H)-yl]ethanone 2 as a solid.
Yield: 14%.
LCMS (ES+): 334/336/338 (M+H)+, 100% purity.
Chiral analysis (LC, Chiralpak AD, 250*4.6 mm, 1 mL/min, 220 nm, 30° C., eluent: iPrOH/n-heptane/DEA 50/50/0.1): RT 10.51 min, 100% ee.

128 mg of 2-(2,6-dichlorophenyl)-1-[(1R)-1-methyl-3,4-dihydroisoquinolin-2(1H)-yl]ethanone 3 as a solid.
Yield: 15%.
LCMS (ES+): 334/336/338 (M+H)+, 100% purity.
Chiral analysis (LC, Chiralpak AD, 250*4.6 mm, 1 mL/min, 220 nm, 30° C., eluent: iPrOH/n-heptane/DEA 50/50/0.1) RT 6.73 min, 100% ee.

The following compounds may be synthesized according a method analogous to Method A. When commercially available, starting material are identified by their CAS Register Numbers.

| No | Starting materials | Conditions | Reaction time | Purification conditions | Yield (%) |
|---|---|---|---|---|---|
| 4 | acid II: 227781-56-8 amine III: 111635-08-6 | DMF, TEA (5 eq), 60° C. | Overnight (PLS) | Basic RP (standard LC) | 12 |
| 5 & 6 | acid II: 6575-24-2 amine III: a44 | DMF, TEA (5 eq), 60° C. | Overnight (PLS) | Basic RP-LCMS | 13 & 13 |
| 7 | acid II: a6 amine III: 64982-61-2 | DCM, TEA (3 eq), rt | 4 h | NP (chromatoflash) from 0 to 4% MeOH in DCM | 97 |
| 8 | acid II: 6575-24-2 amine III: a55 | DCM, TEA (3 eq), rt | 1 h | Basic RP (standard LC) | 16 |
| 9 | 8 | chiral separation | | | 42 |
| 10 | acid II: 6575-24-2 amine III: 41565-98-4 | DMF, TEA (3 eq), 60° C. | Overnight (PLS) | Basic RP-LCMS | 14 |
| 11 | acid II: a2 amine III: 64982-61-2 | DCM, DIPEA (1.2 eq), rt | 1 h | Basic RP (standard LC) | 70 |
| 12 | acid II: 227781-56-8 amine III: a57 | DMF, DIPEA (3 eq), 50° C. | 2 h | Basic RP-LCMS | 37 |
| 13 | acid II: a32 amine III: 64982-61-2 | DMF, DIPEA (2.2 eq), 40° C. | Overnight (PLS) | Basic RP-LCMS | 56 |
| 14 | acid II: 521300-44-7 amine III: a51 | DMF, DIPEA (3 eq), 50° C. | Overnight (PLS) | Basic RP-LCMS | 32 |
| 15 | acid II: 1261522-11-5 amine III: a51 | DMF, DIPEA (3 eq), 50° C. | Overnight (PLS) | Basic RP-LCMS | 43 |

| No | Starting materials | Conditions | Reaction time | Purification conditions | Yield (%) |
|---|---|---|---|---|---|
| 16 | acid II: a16<br>amine III: 64982-61-2 | DCM, DIPEA<br>(2 eq), rt | 3 h 30 | Basic RP (standard LC) | 48 |
| 17 | acid II: a18<br>amine III: 64982-61-2 | DCM, DIPEA<br>(2 eq), rt | 4 h 30 | Basic RP (standard LC) | 82 |
| 18 | acid II: a22<br>amine III: 64982-61-2 | DCM, DIPEA<br>(2 eq), rt | 6 h | Basic RP (standard LC) | 71 |
| 19 | acid II: 1261522-11-5<br>amine III: a63-(S,R) | DCM, TEA (3 eq), rt | Overnight | Basic RP (standard LC) | 71 |
| 20 | acid II: 6575-24-2<br>amine III: a63-(S,R) | DCM, DIPEA<br>(2.2 eq), rt | Overnight (PLS) | Basic RP (standard LC) | 39 |
| 21 | acid II: 1261522-11-5<br>amine III: a63-(S,S) | DCM, DIPEA<br>(2 eq), rt | Overnight (PLS) | Basic RP (standard LC) | 39 |
| 22 | acid II: 6575-24-2<br>amine III: a63-(S,S) | DCM, TEA<br>(2.5 eq), rt | Overnight | Basic RP (standard LC) | 56 |
| 23 | acid II: 227781-56-8<br>amine III: a68 | DCM, DIPEA<br>(3.4 eq), rt | Overnight | Basic RP (standard LC) | 82 |
| 24 | acid II: 1261522-11-5<br>amine III: a68 | DCM, DIPEA<br>(3.4 eq), rt | Overnight | Basic RP (standard LC) | 92 |
| 25 | acid II: 227781-56-8<br>amine III: a63-(S,R) | DCM, DIPEA<br>(2.4 eq), rt | 48 h | Basic RP (standard LC) | 19 |
| 26 | acid II: a24<br>amine III: a63-(S,R) | DCM, DIPEA<br>(2.4 eq), rt | Overnight | Basic RP (standard LC) | 19 |
| a125 | acid II: 1261522-11-5<br>amine III: a41-(S) | DCM, DIPEA<br>(3 eq), rt | Overnight | NP (chromatoflash) from 30% heptane in DCM | 70 |
| 132 & 133 | acid II: 37777-76-7<br>amine III: a114 | DMF, DIPEA<br>(4 eq), rt | Overnight | Basic RP-LCMS | 30 & 30 |
| 134 | acid II: a111<br>amine III: a114-(1S,1S) | DMF, DIPEA<br>(7 eq), rt | Overnight | Basic RP-LCMS | 64 |

2-(3,5-dichloropyridin-4-yl)-1-[(1S)-1-methyl-3,4-dihydroisoquinolin-2(1H)-yl]ethanone 4

Chiral separation (SFC, Whelko-01 (R,R), 50*227 mm, 360 mL/min, 220 nm, 25° C., eluent: from 20 to 30% EtOH/MeOH) yielded 112 mg of 2-(3,5-dichloropyridin-4-yl)-1-[(1S)-1-methyl-3,4-dihydroisoquinolin-2(1H)-yl]ethanone 4 as a solid.
LCMS (ES$^+$): 335/337/339 (M+H)$^+$, 100% purity.
Chiral analysis (LC, Whelko-01 (R,R), 250*4.6 mm, 1 mL/min, 220 nm, 30° C., eluent: EtOH/n-heptane/DEA 50/50/0.1) RT 9.00 min (other enantiomer: RT 13.41 min), 100% ee.

N-{(1R)-2-[(2,6-dichlorophenyl)acetyl]-1-methyl-1,2,3,4-tetrahydroisoquinolin-5-yl}methanesulfonamide 5 and N-{(1S)-2-[(2,6-dichlorophenyl)acetyl]-1-methyl-1,2,3,4-tetrahydroisoquinolin-5-yl}methanesulfonamide 6

Chiral separation (SFC, Chiralpak AD, 50*216 mm, 360 mL/min, 220 nm, 25° C., eluent: 20% EtOH for 13 min, then 30% EtOH for 19 min, then 50% EtOH) yielded:
12 mg of N-{(1R)-2-[(2,6-dichlorophenyl)acetyl]-1-methyl-1,2,3,4-tetrahydroisoquinolin-5-yl}methanesulfonamide 5 as a yellow oil.
Yield: 13%.
LCMS (ES$^+$): 427/429/431 (M+H)$^+$, 98% purity.
Chiral analysis (LC, Chiralpak AD-H, 250*4.6 mm, 1 mL/min, 220 nm, 30° C., eluent: EtOH/n-heptane/DEA 50/50/0.1) RT 6.37 min, 98% ee.12 mg of N-{(1S)-2-[(2,6-dichlorophenyl)acetyl]-1-methyl-1,2,3,4-tetrahydroisoquinolin-5-yl}methanesulfonamide 6 as a yellow oil.
Yield: 13%.
LC-MS (ES$^+$): 427/439/431 (M+H)$^+$, 97.1% purity.
Chiral analysis (LC, Chiralpak AD-H, 250*4.6 mm, 1 mL/min, 220 nm, 30° C., eluent: EtOH/n-heptane/DEA 50/50/0.1) RT 9.93 min, 99.5% ee.

2,4-dichloro-3-{2-[(1S)-1-methyl-3,4-dihydroisoquinolin-2(1H)-yl]-2-oxoethyl}benzonitrile 7

LC-MS (ES$^+$): 359/361/363 (M+H)$^+$, 100% purity.
Appearance: white solid.

2-(2,6-dichlorophenyl)-1-(4,4-difluoro-1-methyl-3,4-dihydroisoquinolin-2(1H)-yl)ethanone 8

LCMS (ES$^+$): 370/372/374 (M+H)$^+$, 99.4% purity.
Appearance: beige solid.

2-(2,6-dichlorophenyl)-1-[4,4-difluoro-1-methyl-3,4-dihydroisoquinolin-2(1H)-yl]ethanone, isomer B9

Chiral separation (SFC, Chiralpak AD, 50*216 mm, 360 mL/min, 220 nm, 25° C., eluent: from 20% iPrOH) yielded 28 mg of 2-(2,6-dichlorophenyl)-1-[4,4-difluoro-1-methyl-3,4-dihydroisoquinolin-2(1H)-yl]ethanone isomer B 9 as a beige oil.
Yield: 41%.
LCMS (ES$^+$): 370/372/374 (M+H)$^+$, 95.2% purity.
Chiral analysis (LC, Chiralpak AD-H, 250*4.6 mm, 1 mL/min, 220 nm, 30° C., eluent: iPrOH/n-heptane/DEA 50/50/0.1) RT 5.29 min (other enantiomer: RT 4.72 min), 100% ee.

2-(2,6-dichlorophenyl)-1-(1,4,4-trimethyl-3,4-dihydroisoquinolin-2(1H)-yl)ethanone 10

LCMS (ES$^+$): 362/364/366 (M+H)$^+$, 99.7% purity.
Appearance: white solid.

2-(3-bromo-2,6-dichlorophenyl)-1-[(1S)-1-methyl-3,4-dihydroisoquinolin-2(1H)-yl]ethanone 11

LC-MS (ES+): 414/416/418 (M+H)+, 100% purity.
Appearance: off-white solid.

2-(3,5-dichloropyridin-4-yl)-1-[(1S)-5-(hydroxymethyl)-1-methyl-3,4-dihydroisoquinolin-2(1H)-yl]ethanone 12

LCMS (ES+): 365/367/369 (M+H)+, 100% purity.
Appearance: white solid.

2-(5-chloro-1H-pyrrolo[2,3-b]pyridin-4-yl)-1-[(1S)-1-methyl-3,4-dihydroisoquinolin-2(1H)-yl]ethanone 13

LCMS (ES+): 340/342 (M+H)+, 100% purity.
Appearance: off-white solid.

N-{(1S)-2-[(2-chloro-6-methylphenyl)acetyl]-1-methyl-1,2,3,4-tetrahydroisoquinolin-5-yl}methanesulfonamide 14

LCMS (ES+): 407/409 (M+H)+, 100% purity.
Appearance: sticky brown oil.

N-{(1S)-2-[(2-chloro-6-cyanophenyl)acetyl]-1-methyl-1,2,3,4-tetrahydroisoquinolin-5-yl}methanesulfonamide 15

LCMS (ES+): 418/420 (M+H)+, 95.2% purity.
Appearance: sticky brown oil.

2-(3,5-dichloro-2-methoxypyridin-4-yl)-1-[(1S)-1-methyl-3,4-dihydroisoquinolin-2(1H)-yl]ethanone 16

LCMS (ES+): 365/367/369 (M+H)+, 100% purity.
Appearance: off-white solid 2-(2-bromo-6-methoxyphenyl)-1-[(1S)-1-methyl-3,4-dihydroisoquinolin-2(1H)-yl]ethanone 17

LCMS (ES+): 374/376 (M+H)+, 97.3% purity.

2-(3-chloro-5-methylpyridin-4-yl)-1-[(1S)-1-methyl-3,4-dihydroisoquinolin-2(1H)-yl]ethanone 18

LCMS (ES+): 315/317 (M+H)+, 100% purity.

3-chloro-2-{2-[(1S,4R)-4-hydroxy-1-methyl-3,4-dihydroisoquinolin-2(1H)-yl]-2-oxoethyl}-benzonitrile 19

LCMS (ES+): 341/343 (M+H)+, 100% purity.
Chiral analysis (LC, Chiralpak AD-H, 250*4.6 mm, 1 mL/min, 220 nm, 30° C., eluent: EtOH/n-heptane/DEA 50/50/0.1) RT 5.78 min (other enantiomer: RT 11.88 min), 94.5% ee.
Appearance: white solid.

2-(2,6-dichlorophenyl)-1-[(1S,4R)-4-hydroxy-1-methyl-3,4-dihydroisoquinolin-2(1H)-yl]-ethanone 20

LCMS (ES+): 350/352/354 (M+H)+, 100% purity.
Chiral analysis (LC, Chiralpak AD-H, 250*4.6 mm, 1 mL/min, 220 nm, 30° C., eluent: EtOH/n-heptane/DEA 50/50/0.1) RT 4.37 min, 96.1% ee.
Appearance: beige solid.

3-chloro-2-{2-[(1S,4S)-4-hydroxy-1-methyl-3,4-dihydroisoquinolin-2(1H)-yl]-2-oxoethyl}-benzonitrile 21

LCMS (ES+): 341/343 (M+H)+, 99.3% purity.
Chiral analysis (LC, Chiralpak AD-H, 250*4.6 mm, 1 mL/min, 220 nm, 30° C., eluent: EtOH/n-heptane/DEA 50/50/0.1) RT 11.88 min (other enantiomer: RT 5.78 min), 96.2% ee.
Appearance: beige solid.

2-(2,6-dichlorophenyl)-1-[(1S,4S)-4-hydroxy-1-methyl-3,4-dihydroisoquinolin-2(1H)-yl]ethanone 22

LCMS (ES+): 350/352/354 (M+H)+, 100% purity.
Chiral analysis (LC, Chiralpak AD-H, 250*4.6 mm, 1 mL/min, 220 nm, 30° C., eluent: EtOH/n-heptane/DEA 50/50/0.1) RT6.03 min, 99.3% ee.
Appearance: white solid.

2-(3,5-dichloropyridin-4-yl)-1-[(1S)-1-methyl-5-(methylsulfonyl)-3,4-dihydroisoquinolin-2(1H)-yl]ethanone 23

LCMS (ES+): 413/415/417 (M+H)+, 100% purity.
Appearance: off-white oil.

3-chloro-2-{2-[(1S)-1-methyl-5-(methylsulfonyl)-3,4-dihydroisoquinolin-2(1H)-yl]-2-oxoethyl}benzonitrile 24

LCMS (ES+): 403/405 (M+H)+, 97.9% purity.
Appearance: off-white oil.

2-(3,5-dichloropyridin-4-yl)-1-[(1S,4R)-4-hydroxy-1-methyl-3,4-dihydroisoquinolin-2(1H)-yl]ethanone 25

LCMS (ES+): 351/353/355 (M+H)+, 100% purity.
Appearance: off-white solid.

2-(2,6-dichloro-4-fluorophenyl)-1-[(1S,4R)-4-hydroxy-1-methyl-3,4-dihydroisoquinolin-2(1H)-yl]ethanone 26

LCMS (ES+): 368/370/372 (M+H)+, 93.2% purity.
Appearance: off-white solid.

2-[2-[(1S)-5-bromo-1-methyl-3,4-dihydro-1H-isoquinolin-2-yl]-2-oxo-ethyl]-3-chloro-benzonitrile a125

LCMS (ES+): 403/405/407 (M+H)+, 100% purity.
Appearance: white solid.

2-(2-chloro-6-fluorophenyl)-1-[(1S)-1-methyl-5-[2,2,2-trifluoro-1-hydroxyethyl]-3,4-dihydroisoquinolin-2(1H)-yl]ethanone isomer A 132 and isomer B 133

Chiral separation (LC, Chiralcel OJ, 50*450 mm, 80 mL/min, 220 nm, 30° C., eluent: 100% MeOH) yielded:

18 mg of 2-(2-chloro-6-fluorophenyl)-1-[(1S)-1-methyl-5-[2,2,2-trifluoro-1-hydroxyethyl]-3,4-dihydroisoquinolin-2(1H)-yl]ethanone isomer A 132 as an oil.
Yield: 30%.
LCMS (ES$^+$): 416/418 (M+H)$^+$, 100% purity.
Chiral analysis (LC, Chiralpak OJ-H, 250*4.6 mm, 1 mL/min, 220 nm, 30° C., eluent: MeOH/DEA 100/0.1) RT 4.34 min, 100% ee.

18 mg of 2-(2-chloro-6-fluorophenyl)-1-[(1S)-1-methyl-5-[2,2,2-trifluoro-1-hydroxyethyl]-3,4-dihydroisoquinolin-2(1H)-yl]ethanone isomer B 133 as a solid.
Yield: 30%.
LCMS (ES$^+$): 416/418 (M+H)$^+$, 100% purity.
Chiral analysis (LC, Chiralpak OJ-H, 250*4.6 mm, 1 mL/min, 220 nm, 30° C., eluent: MeOH/DEA 100/0.1) RT 5.50 min, 99.6% ee.

2-(5-chloro-1H-indol-4-yl)-1-[(1S)-1-methyl-5-[(1S)-2,2,2-trifluoro-1-hydroxyethyl]-3,4-dihydroisoquinolin-2(1H)-yl]ethanone 134

LC-MS (ES$^+$): 427/439/441 (M+H)$^+$, 99% purity.
Appearance: yellow solid.

C.2. Synthesis of 2-(2-chloro-6-methoxyphenyl)-1-[(1S)-1-methyl-3,4-dihydroisoquinolin-2(1H)-yl]ethanone 27

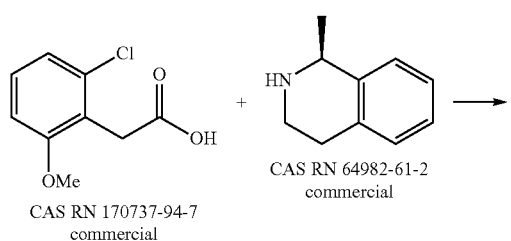

To a solution of (2-chloro-6-methoxyphenyl)acetic acid (commercial, 20 mg, 0.1 mmol) and (1S)-1-methyl-1,2,3,4-tetrahydroisoquinoline (commercial, 15 mg, 0.1 mmol) in DCM (1 mL) were added COMU (53.26 mg, 0.12 mmol) and DIPEA (40 µL, 0.23 mmol). The mixture was stirred at 35° C. overnight, then water (2 mL) was added. The reaction mixture was passed through an Isolute® separator phase cartridge, extracted twice with DCM (2 mL) and concentrated under vacuum. The residue was purified by reverse phase chromatography (Basic mode, LCMS prep) to yield 18 mg of 2-(2-chloro-6-methoxyphenyl)-1-[(1S)-1-methyl-3,4-dihydroisoquinolin-2(1H)-yl]ethanone 27.

Yield: 54%.
LCMS (ES$^+$): 330 (M+H)$^+$, 91.9% purity.

C.3. Synthesis of 2-[2-chloro-6-(trifluoromethyl)phenyl]-1-[(1S)-1-methyl-3,4-dihydroisoquinolin-2(1H)-yl]ethanone 28

To a solution of [2-chloro-6-(trifluoromethyl)phenyl]acetic acid (commercial, 24 mg, 0.1 mmol) and (1S)-1-methyl-1,2,3,4-tetrahydroisoquinoline (commercial, 15 mg, 0.1 mmol) in DCM (1 mL) were added COMU (53.26 mg, 0.12 mmol) and DIPEA (40 µL, 0.23 mmol).

The mixture was stirred at 35° C. overnight, then water (2 mL) was added. The reaction mixture was passed through an Isolute separator phase cartridge, extracted twice with DCM (2 mL) and concentrated under vacuum. The residue was purified by reverse phase chromatography (Basic mode, LCMS prep) to yield 18 mg of 2-[2-chloro-6-(trifluoromethyl)phenyl]-1-[(1S)-1-methyl-3,4-dihydroisoquinolin-2(1H)-yl]ethanone 28.
Yield: 48%.
LCMS (ES$^+$): 368 (M+H)$^+$, 93.6% purity.

C.4. Synthesis of 5-chloro-4-{2-[(1S)-1-methyl-3,4-dihydroisoquinolin-2(1H)-yl]-2-oxoethyl}pyridine-3-carbonitrile 29

(1S)-1-Methyl-1,2,3,4-tetrahydroisoquinoline (commercial, 34.95 mg, 0.24 mmol) was dissolved in DCM (4 mL).

At rt, trimethylaluminium (179.66 mg, 0.26 mL, 0.26 mmol) was added. The mixture was stirred for 45 min. Methyl (3-chloro-5-cyanopyridin-4-yl)acetate a38 (50 mg, 0.24 mmol) was then added. The mixture was stirred overnight. An additional amount of trimethylaluminium (179.66 mg, 0.26 mL, 0.26 mmol) was added and the mixture was stirred overnight. The reaction mixture was quenched with MeOH, water then sonicated, filtered, washed twice with MeOH. The solution was then passed through an acidic column, washed twice with MeOH and concentrated under vacuum. The residue was purified by reverse phase chromatography (basic mode, LCMS prep) to yield 50 mg of 5-chloro-4-{2-[(1S)-1-methyl-3,4-dihydroisoquinolin-2(1H)-yl]-2-oxoethyl}pyridine-3-carbonitrile 29 as an orange oil.

Yield: 64%.

LCMS (ES$^+$): 326/328/330 (M+H)$^+$, 100% purity.

C.5. Synthesis of N-({2-[(2,6-dichlorophenyl)acetyl]-1-methyl-1,2,3,4-tetrahydroisoquinolin-5-yl}methyl)methanesulfonamide 30

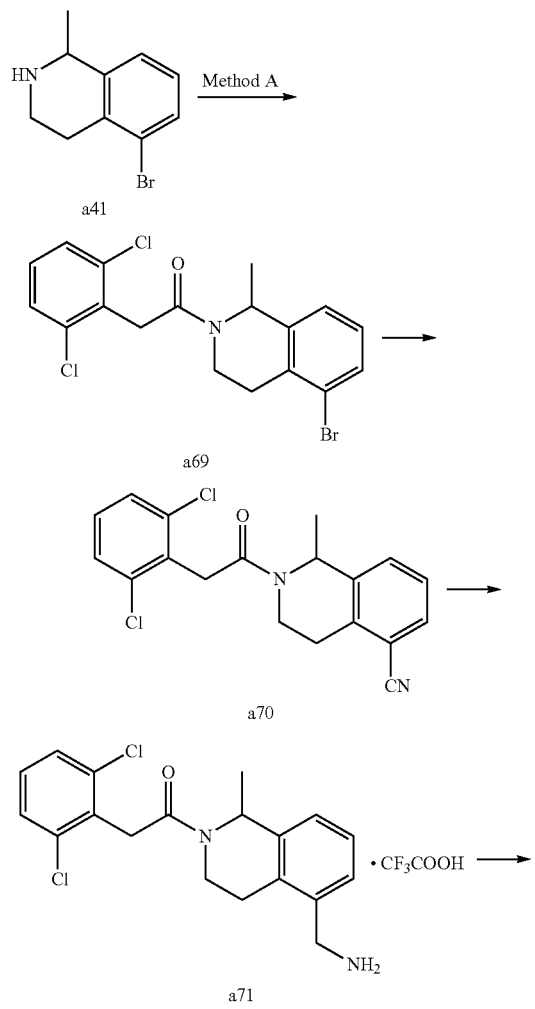

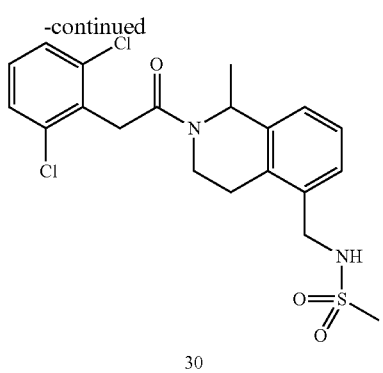

C.5.1. Synthesis of 1-(5-bromo-1-methyl-3,4-dihydroisoquinolin-2(1H)-yl)-2-(2,6-dichlorophenyl)ethanone a69

Compound a69 may be synthesized according to a method analogous to Method A using 5-bromo-1-methyl-1,2,3,4-tetrahydroisoquinoline a41 and (2,6-dichlorophenyl)acetic acid as starting materials. Conditions: DMF, DIPEA (4 eq), 60° C., 2 h.

Yield: 100% (crude).

C.5.2. LCMS (ES$^+$): 414/416/418 (M+H)$^+$, 70% purity. Synthesis of 2-[(2,6-dichlorophenyl)acetyl]-1-methyl-1,2,3,4-tetrahydroisoquinoline-5-carbonitrile a70

Under argon, 1-(5-bromo-1-methyl-3,4-dihydroisoquinolin-2(1H)-yl)-2-(2,6-dichlorophenyl) ethanone a69 (0.5 g, 0.85 mmol) was dissolved in DMF (2 mL). Tetrakis (triphenylphosphine)palladium(0) (99 mg, 85 μmol) and zinc cyanide (0.20 g, 1.69 mmol) were added. The tube was sealed and heated at 150° C. during 1 h under microwave irradiation. The reaction mixture was filtered, washed twice with EtOAc and concentrated under vacuum. The residue was diluted with EtOAc, washed twice with a saturated solution of NaHCO$_3$, once with brine then concentrated under vacuum to yield 580 mg of 2-[(2,6-dichlorophenyl)acetyl]-1-methyl-1,2,3,4-tetrahydroisoquinoline-5-carbonitrile a70 as a yellow oil which was used for the next step without any further purification.

LCMS (ES$^+$): 359/361/363 (M+H)$^+$.

C.5.3. Synthesis of 1-[5-(aminomethyl)-1-methyl-3,4-dihydroisoquinolin-2(1H)-yl]-2-(2,6-dichlorophenyl)ethanone trifluoroacetate a71

2-[(2,6-Dichlorophenyl)acetyl]-1-methyl-1,2,3,4-tetrahydroisoquinoline-5-carbonitrile a70 (0.07 g, 0.19 mmol) was dissolved in MeOH (3 mL). Nickel (II) chloride (2 mg, 10 μmol) was added and the mixture was cooled at 0° C. Sodium borohydride (21 mg, 0.57 mmol) was added by portions over 3 h. The reaction mixture was stirred overnight at rt, then a 5N aqueous solution of HCl was added until acidic pH. The mixture was stirred a few minutes then MeOH was added. The solution was passed through an acidic column, washed twice with MeOH. The product was eluted using a 2N methanolic solution of ammonia. The ammonia solution was concentrated under vacuum. The residue was purified twice by reverse phase chromatography (acidic mode, LCMS prep) to yield 30 mg of 1-[5-(aminomethyl)-1-methyl-3,4-dihydroisoquinolin-2(1H)-yl]-2-(2,6-dichlorophenyl)ethanone trifluoroacetate a71 as a yellow oil.

Yield: 42%.

LCMS (ES+): 363/365/367 (M+H)+, 978% purity.

C.5.4. N-({2-[(2,6-dichlorophenyl)acetyl]-1-methyl-1,2,3,4-tetrahydroisoquinolin-5-yl}methyl)methanesulfonamide 30

1-[5-(aminomethyl)-1-methyl-3,4-dihydroisoquinolin-2(1H)-yl]-2-(2,6-dichlorophenyl)ethanone trifluoroacetate a71 (20 mg, 42 µmol) was dissolved in DCM (3 mL). DIPEA (15 µL, 84 µmol) and methane sulfonylchloride (3 µL, 42 µmol) were added. The mixture was stirred at rt for 70h and concentrated under vacuum. Purification by reverse phase chromatography (basic mode, LCMS prep) afforded 10 mg of N-({2-[(2,6-dichlorophenyl)acetyl]-1-methyl-1,2,3,4-tetrahydroisoquinolin-5-yl}methyl)methanesulfonamide 30 as a white solid.

Yield: 54%.

LCMS (ES+): 441/443/445 (M+H)+, 98% purity.

C.6. Method C. Synthesis of 2-(2,6-dichlorophenyl)-1-[5-(3,5-dimethyl-1,2-oxazol-4-yl)-1-methyl-3,4-dihydroisoquinolin-2(1H)-yl]ethanone 31

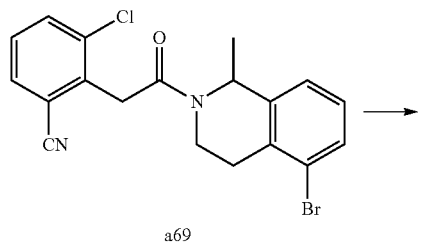

a69

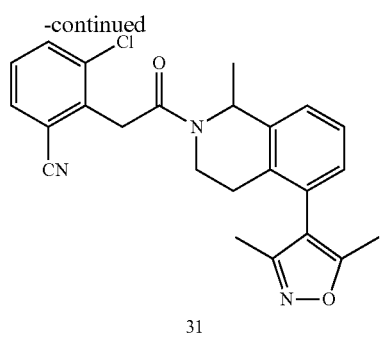

31

1-(5-Bromo-1-methyl-3,4-dihydroisoquinolin-2(1H)-yl)-2-(2,6-dichlorophenyl)ethanone a69 (50 mg, 0.12 mmol), 3,5-dimethylisoxazole-4-boronic acid (25 mg, 0.18 mmol) and $K_2CO_3$ (51 mg, 0.36 mmol) were dissolved in 1,4-dioxane (3 mL) in a tube under argon. Tetrakis(triphenylphosphine)palladium(0) (14 mg, 0.01 mmol) was added. The tube was sealed and heated at 130° C. during 1.5 h under microwave irradiation. The reaction mixture was concentrated under vacuum. The residue was diluted with EtOAc, sonicated, stirred, filtered, washed twice with EtOAc then concentrated under vacuum. The residue was purified by reverse phase chromatography (basic mode, LCMS prep) then triturated in $Et_2O$ to yield 14 mg of 2-(2,6-dichlorophenyl)-1-[5-(3,5-dimethyl-1,2-oxazol-4-yl)-1-methyl-3,4-dihydroisoquinolin-2(1H)-yl]ethanone 31 as a yellow solid.

Yield: 27%.

LCMS (ES+): 429/431/433 (M+H)+, 100% purity.

The following compounds may be synthesized according to a method analogous to Method C.6. When commercially available, starting material are identified by their CAS Register Numbers.

| No | Starting materials | Conditions | Reaction time | Purification conditions | Yield (%) |
|---|---|---|---|---|---|
| 135 | a125 and pyridine-3-boronic acid (RN 1692-25-7) | idem, 130° C. | 90 min | Basic RP (standard LC) | 38 |
| 136 | a125 and pyridine-4-boronic acid (RN 913835-65-1) | idem, 130° C. | 90 min | Basic RP (standard LC) | 76 |
| 137 | a125 and 2-amino-5-(4,4,5,5-tetramethyl-1,3,2-dioxaborolan-2-yl)pyridine (RN 827614-64-2) | idem, 130° C. | 90 min | Acidic RP (standard LC) | 59 |
| 138 | a125 and 3,5-dimethylisoxazole-4-boronic acid pinacol ester (RN 832114-00-8) | MW, 130° C. | 90 min | Acidic RP (standard LC) | 61 |
| 139 | a125 and 1-methyl-4-(4,4,5,5-tetramethyl-1,3,2-dioxaborolan-2-yl)-1H-pyrazole (RN 761446-44-0) | MW, 130° C. | 90 min | Basic RP-LCMS | 24 |
| 140 | a125 and 1-boc-pyrazole-4-boronic acid pinacol ester (RN 552846-17-0) | MW, 130° C. | 2*60 min | NP using 1% MeOH in DCM | 48 |
| 141 | a125 and 1-boc-3,5-dimethylpyrazole-4-boronic acid pinacol ester (RN 1073354-70-7) | MW, 130° C. | 2*60 min | Basic RP (standard LC) | 65 |

| No | Starting materials | Conditions | Reaction time | Purification conditions | Yield (%) |
|---|---|---|---|---|---|
| 142 | a102 and 1-boc-pyrazole-4-boronic acid pinacol ester (RN 552846-17-0) | MW, 130° C. | 60 min | Basic RP (standard LC) | 34 |
| 143 | a69-(S) and 2-methylpyridine-3-boronic acid (RN 899436-71-6) | 115° C. | 120 min | Basic RP (standard LC) | 69 |
| 144 | a69-(S) and 2-amino-5-(4,4,5,5-tetramethyl-1,3,2-dioxaborolan-2-yl)pyridine (RN 827614-64-2) | 115° C. | 120 min | SFC (column: 2-ethylpyridine) using 10% MeOH | 67 |
| 145 | a69-(S) and 1-boc-3,5-dimethylpyrazole-4-boronic acid pinacol ester (RN 1073354-70-7) | 115° C. | 120 min | SFC (column: 2-ethylpyridine) using 10% MeOH | 93 |

3-chloro-2-{2-[(1S)-1-methyl-5-(pyridin-3-yl)-3,4-dihydroisoquinolin-2(1H)-yl]-2-oxoethyl}benzonitrile 135

LCMS (ES$^+$): 402/404 (M+H)$^+$, 100% purity.

3-chloro-2-{2-[(1S)-1-methyl-5-(pyridin-4-yl)-3,4-dihydroisoquinolin-2(1H)-yl]-2-oxoethyl}benzonitrile 136

LCMS (ES$^+$): 402/404 (M+H)$^+$, 100% purity.

2-{2-[(1S)-5-(6-aminopyridin-3-yl)-1-methyl-3,4-dihydroisoquinolin-2(1H)-yl]-2-oxoethyl}-3-chlorobenzonitrile trifluoroacetate 137

LCMS (ES$^+$): 417/419 (M+H)$^+$, 98% purity.

3-chloro-2-{2-[(1S)-5-(3,5-dimethyl-1,2-oxazol-4-yl)-1-methyl-3,4-dihydroisoquinolin-2(1H)-yl]-2-oxoethyl}benzonitrile 138

LCMS (ES$^+$): 420/422 (M+H)$^+$, 98% purity.

3-chloro-2-{2-[(1S)-1-methyl-5-(1-methyl-1H-pyrazol-4-yl)-3,4-dihydroisoquinolin-2(1H)-yl]-2-oxoethyl}benzonitrile 139

LCMS (ES$^+$): 405/407 (M+H)$^+$, 96% purity.

3-chloro-2-{2-[(1S)-1-methyl-5-(1H-pyrazol-4-yl)-3,4-dihydroisoquinolin-2(1H)-yl]-2-oxoethyl}benzonitrile 140

LCMS (ES$^+$): 391/393 (M+H)$^+$, 100% purity.

3-chloro-2-{2-[(1S)-5-(3,5-dimethyl-1H-pyrazol-4-yl)-1-methyl-3,4-dihydroisoquinolin-2(1H)-yl]-2-oxoethyl}benzonitrile 141

LCMS (ES$^+$): 419/421 (M+H)$^+$, 100% purity.

2-(2,6-dichlorophenyl)-1-[(1S)-1-methyl-5-(1H-pyrazol-4-yl)-3,4-dihydroisoquinolin-2(1H)-yl]ethanone 142

LCMS (ES$^+$): 400/402/404 (M+H)$^+$, 91% purity.

2-(2,6-dichlorophenyl)-1-[(1S)-1-methyl-5-(2-methylpyridin-3-yl)-3,4-dihydroisoquinolin-2(1H)-yl]ethanone 143

LCMS (ES$^+$): 425/427/429 (M+H)$^+$, 91% purity.

1-[(1S)-5-(6-aminopyridin-3-yl)-1-methyl-3,4-dihydroisoquinolin-2(1H)-yl]-2-(2,6-dichlorophenyl)ethanone 144

LCMS (ES$^+$): 426/428/430 (M+H)$^+$, 97% purity.
Appearance: yellow solid.

2-(2,6-dichlorophenyl)-1-[(1S)-5-(3,5-dimethyl-1H-pyrazol-4-yl)-1-methyl-3,4-dihydroisoquinolin-2(1H)-yl]ethanone 145

LCMS (ES$^+$): 428/430/432 (M+H)$^+$, 96% purity.
Appearance: beige solid.

C.7. Synthesis of (1S)-2-[(2,6-dichlorophenyl)acetyl]-1-methyl-1,2,3,4-tetrahydroisoquinoline-5-carbonitrile 32

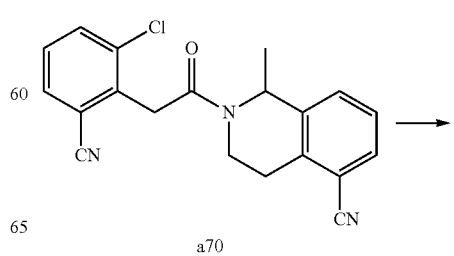

a70

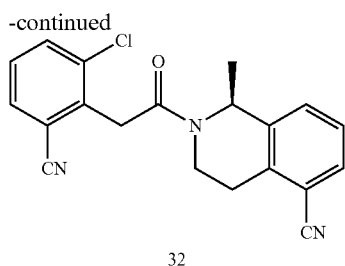

32

2-[2-(2,6-Dichlorophenyl)acetyl]-1-methyl-3,4-dihydro-1H-isoquinoline-5-carbonitrile a70 was purified by reverse phase chromatography (basic mode, standard LC), then by chiral separation (SFC, Whelko 01(R,R), 50*227 mm, 360 mL/min, 220 nm, 25° C., eluent: from 20 to 25% MeOH) to yield 20 mg of (1S)-2-[(2,6-dichlorophenyl)acetyl]-1-methyl-1,2,3,4-tetrahydroisoquinoline-5-carbonitrile 32 as an off-white solid.

Yield: 4%.

LCMS (ES$^+$): 359/361/363 (M+H)$^+$, 100% purity.

Chiral analysis (LC, Whelko-01 (R,R), 250*4.6 mm, 1 mL/min, 220 nm, 30° C., eluent: EtOH/n-heptane/DEA 50/50/0.1) RT 10.91 min (other enantiomer at 13.62 min), 100% ee.

C.8. Synthesis of N-{2-[(2,6-dichlorophenyl)acetyl]-1-methyl-1,2,3,4-tetrahydroisoquinolin-7-yl}methanesulfonamide 33

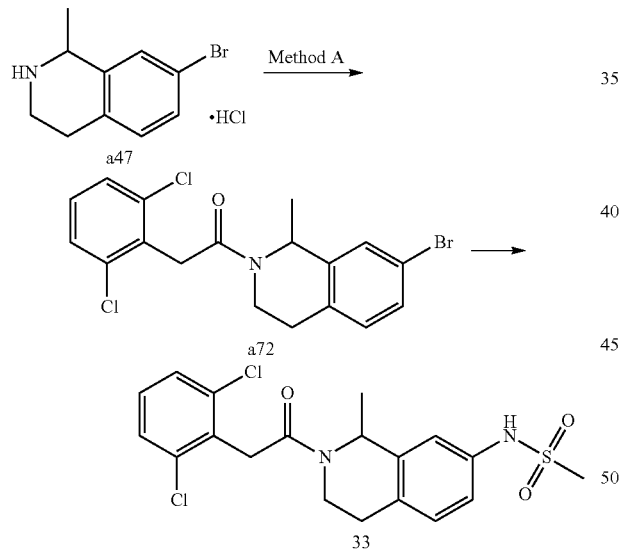

C.8.1. Synthesis of 1-(7-bromo-1-methyl-3,4-dihydroisoquinolin-2(1H)-yl)-2-(2,6-dichlorophenyl)ethanone a72

Compound a72 may be synthesized according to a method analogous to Method A using 7-bromo-1-methyl-1,2,3,4-tetrahydroisoquinoline hydrochloride a47 and (2,6-dichlorophenyl)acetic acid as starting materials. Conditions: DMF, DIPEA (4 eq), rt, overnight. Purification: reverse phase chromatography (basic mode, standard LC).

Yield: 26% (crude).

LCMS (ES$^+$): 412/414/416/418 (M+H)$^+$, 100% purity.

C.8.2. Synthesis of N-{2-[(2,6-dichlorophenyl)acetyl]-1-methyl-1,2,3,4-tetrahydroisoquinolin-7-yl}methanesulfonamide 33

1-(7-Bromo-1-methyl-3,4-dihydroisoquinolin-2(1H)-yl)-2-(2,6-dichlorophenyl)ethanone a72 (50 mg, 0.12 mmol), methanesulfonamide (23 mg, 0.24 mmol) and a solution of potassium phosphate tribasic (79 mg, 0.36 mmol) in water (0.5 mL) were dissolved in DMF (3 mL) under argon. (1R,2R)-(−)-1,2-Diaminocyclohexane (5.8 μL, 48 μmol) and CuI (4.6 mg, 24 μmol) were added. The mixture was stirred at 150° C. for 13 days. The reaction mixture was concentrated under vacuum. The residue was diluted with EtOAc, sonicated, stirred, filtered, washed twice with EtOAc then concentrated under vacuum. The residue was purified twice by reverse phase chromatography (basic mode, LCMS prep) to yield 12 mg of N-{2-[(2,6-dichlorophenyl)acetyl]-1-methyl-1,2,3,4-tetrahydroisoquinolin-7-yl}methanesulfonamide 33 as a white solid.

Yield: 23%.

LCMS (ES$^+$): 427/429/431 (M+H)$^+$, 100% purity.

C.9. Synthesis of N-({(1S)-2-[(2,6-dichlorophenyl)acetyl]-1-methyl-1,2,3,4-tetrahydroisoquinolin-5-yl}methyl)methanesulfonamide 34

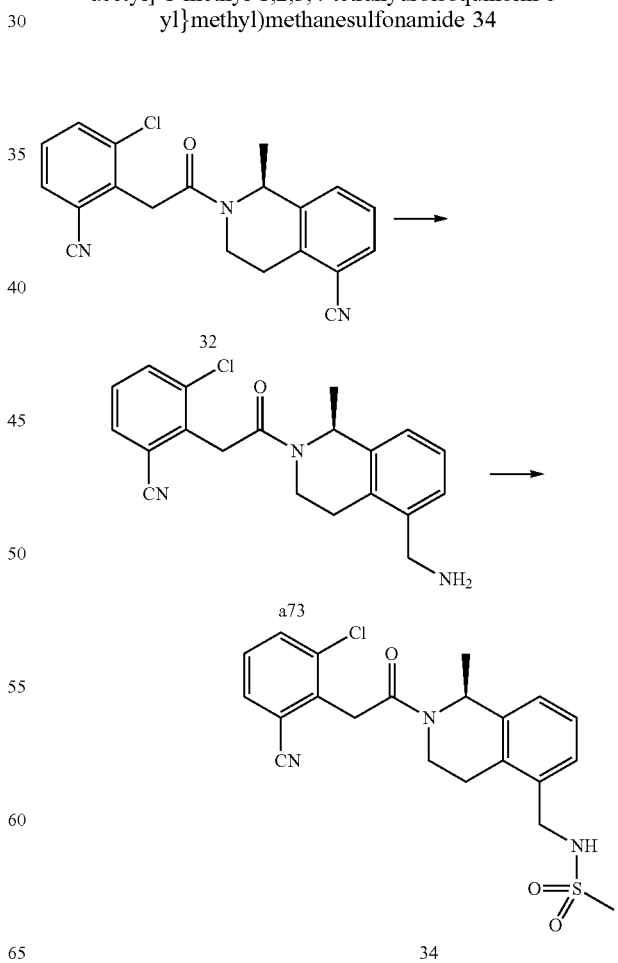

C.9.1. Synthesis of 1-[(1S)-5-(aminomethyl)-1-methyl-3,4-dihydroisoquinolin-2(1H)-yl]-2-(2,6-dichlorophenyl)ethanone a73

(1S)-2-[(2,6-dichlorophenyl)acetyl]-1-methyl-1,2,3,4-tetrahydroisoquinoline-5-carbonitrile 32 (435 g, 1.21 mmol) was dissolved in MeOH (10 mL). Nickel (II) chloride (14 mg, 60 μmol) was added and the mixture was cooled at 0° C. Sodium borohydride (92 mg, 2.42 mmol) was added and the reaction mixture was stirred overnight at rt. Nickel (II) chloride (14 mg, 60 μmol) and sodium borohydride (92 mg, 2.42 mmol) were added at 0° C. and the mixture was at rt. As the reaction was very slow and sodium borohydride (276 mg, 7.26 mmol) was added in 3 portions over 3 days. The reaction mixture was stirred at rt for 7 days in total, then cooled at 0° C. A 5N aqueous solution of HCl was added until acidic pH was reached, the mixture was stirred a few minutes then MeOH was added. The solution was passed through an acidic column, washed twice with MeOH. The product was eluted using a 2 N methanolic solution of ammonia. The ammonia solution was concentrated under vacuum. The residue was purified twice by reverse phase chromatography (acidic mode, LCMS prep) to yield 190 mg of 1-[(1S)-5-(aminomethyl)-1-methyl-3,4-dihydroisoquinolin-2(1H)-yl]-2-(2,6-dichlorophenyl)ethanone a73 as a yellow oil.

Yield: 43%.

LCMS (ES+): 363/365/367 (M+H)+.

C.9.2. Synthesis of N-({(1S)-2-[(2,6-dichlorophenyl)acetyl]-1-methyl-1,2,3,4-tetrahydroisoquinolin-5-yl}methyl)methanesulfonamide 34

1-[(1S)-5-(aminomethyl)-1-methyl-3,4-dihydroisoquinolin-2(1H)-yl]-2-(2,6-dichlorophenyl) ethanone a73 (20 mg, 55 μmol) was dissolved in DCM (850 μL). DIPEA (19 μL, 0.11 μmol) and methane sulfonylchloride (4 μL, 55 μmol) were added. The mixture was stirred at rt for 48 h then concentrated under vacuum. The residue was purified by reverse phase chromatography (basic mode, LCMS prep) to yield 4 mg of N-({(1S)-2-[(2,6-dichlorophenyl)acetyl]-1-methyl-1,2,3,4-tetrahydroisoquinolin-5-yl}methyl)methanesulfonamide 34 as a white solid.

Yield: 19%.

LCMS (ES+): 441/443/435 (M+H)+, 100% purity.

C.10. Synthesis of N-({(1S)-2-[(2,6-dichlorophenyl)acetyl]-1-methyl-1,2,3,4-tetrahydroisoquinolin-5-yl}methyl)acetamide 35

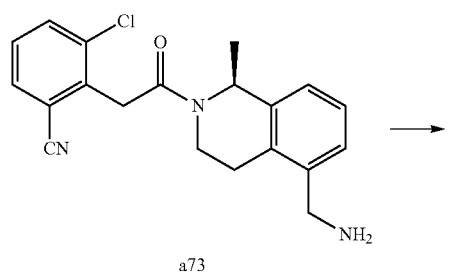

a73

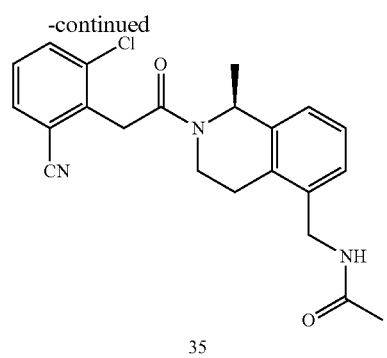

35

1-[(1S)-5-(aminomethyl)-1-methyl-3,4-dihydroisoquinolin-2(1H)-yl]-2-(2,6-dichlorophenyl) ethanone a73 (20 mg, 55 μmol) was dissolved in DCM (3 mL). N,N-Diisopropyl ethylamine (19 μL, 0.11 mmol) and acetyl chloride (4 μL, 55 μmol) were added. The mixture was stirred at rt overnight. The reaction mixture was concentrated under vacuum. The residue was purified by reverse phase chromatography (basic mode, LCMS prep) to yield 5 mg of N-({(1S)-2-[(2,6-dichlorophenyl)acetyl]-1-methyl-1,2,3,4-tetrahydroisoquinolin-5-yl}methyl)acetamide 35 as a white solid.

Yield: 25%.

LCMS (ES+): 405/407/409 (M+H)+, 100% purity.

C.11. Synthesis of 1-({(1S)-2-[(2,6-dichlorophenyl)acetyl]-1-methyl-1,2,3,4-tetrahydroisoquinolin-5-yl}methyl)-3-methylurea 36

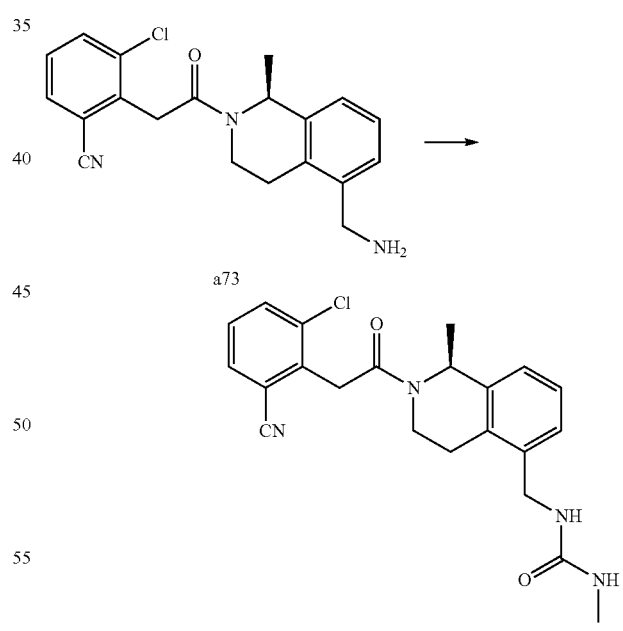

1-[(1S)-5-(aminomethyl)-1-methyl-3,4-dihydroisoquinolin-2(1H)-yl]-2-(2,6-dichlorophenyl) ethanone a73 (20 mg, 55 μmol) was dissolved in DCM (3 mL). (Methylimino)(oxo)methane (3 mg, 55 μmol) was added. The mixture was stirred at rt overnight. The reaction mixture was concentrated under vacuum. The residue was purified by reverse phase chromatography (basic mode, LCMS prep) to yield 5.7 mg of 1-({(1S)-2-[(2,6-dichlorophenyl)acetyl]-1-methyl-1,2,3,4-tetrahydroisoquinolin-5-yl}methyl)-3-methylurea 36 as a white solid.

Yield: 25%.

LCMS (ES$^+$): 420/422/424 (M+H)$^+$, 99.2% purity.

C.12. Synthesis of methyl({(1S)-2-[(2,6-dichlorophenyl)acetyl]-1-methyl-1,2,3,4-tetrahydroisoquinolin-5-yl}methyl)carbamate 37

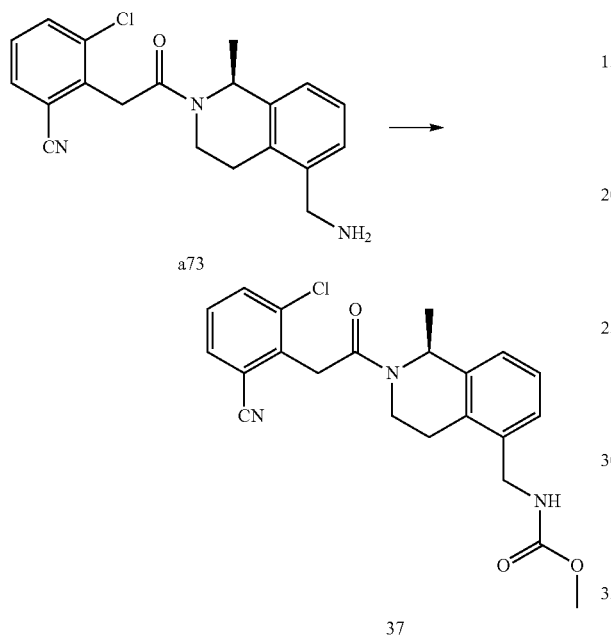

1-[(1S)-5-(aminomethyl)-1-methyl-3,4-dihydroisoquinolin-2(1H)-yl]-2-(2,6-dichlorophenyl) ethanone a73 (20 mg, 55 µmol) was dissolved in DCM (2 mL). N,N-Diisopropyl ethylamine (19 µL, 0.11 mmol) and methyl chloroformate (4 µL, 55 µmol) were added. The mixture was stirred at rt for 4 h and concentrated under vacuum. The residue was purified by reverse phase chromatography (basic mode, LCMS prep) to yield 9.5 mg of methyl ({(1S)-2-[(2,6-dichlorophenyl)acetyl]-1-methyl-1,2,3,4-tetrahydroisoquinolin-5-yl}methyl)carbamate 37 as a yellow gum.

Yield: 41%.

LCMS (ES$^+$): 421/423/425 (M+H)$^+$, 97.7% purity.

C.13. Synthesis of 2-(2,6-dichlorophenyl)-1-[(1S)-5-(hydroxymethyl)-1-methyl-3,4-dihydroisoquinolin-2(1H)-yl]ethanone 38

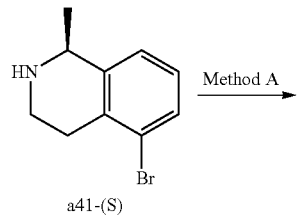

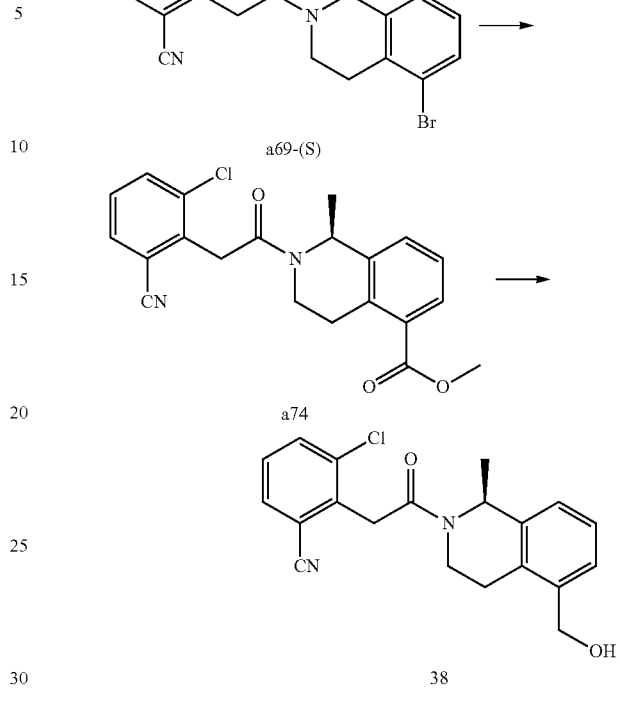

C.13.1. Synthesis of 1-[(1S)-5-bromo-1-methyl-3,4-dihydroisoquinolin-2(1H)-yl]-2-(2,6-dichlorophenyl)ethanone a69-(S)

Compound a69-(S) may be synthesized according to a method analogous to Method A using (1S)-5-bromo-1-methyl-1,2,3,4-tetrahydroisoquinoline hydrochloride a41-(S) and (2,6-dichlorophenyl)acetic acid as starting materials. Conditions: DCM, TEA (3 eq), rt, overnight. Purification conditions: column chromatography using 40% DCM in n-heptane as eluent.

Yield: 86%.

LCMS (ES$^+$): 412/414/416/418 (M+H)$^+$, 99% purity.

C.13.2. Synthesis of methyl(1S)-2-[(2,6-dichlorophenyl)acetyl]-1-methyl-1,2,3,4-tetrahydroisoquinoline-5-carboxylate a74

To a suspension of 1-[(1S)-5-bromo-1-methyl-3,4-dihydroisoquinolin-2(1H)-yl]-2-(2,6-dichlorophenyl)ethanone a69-(S) (2 g, 4.84 mmol) in MeOH (100 mL) were added dibromo[(S)-(−)-2,2'-bis(diphenylphosphino)-1,1'-binaphtyl]palladium (II) (420 mg, 0.47 mmol) and DIPEA (2.6 mL, 15 mmol). The mixture was stirred overnight at 120° C. in an autoclave under a pressure of carbon monoxide at 8 bars. The reaction mixture was concentrated under vacuum. The crude was poured in EtOAc (300 mL) and successively washed with an aqueous saturated solution of NaHCO$_3$ (100 mL), a 1N aqueous solution of HCl (100 mL) and water (250 mL). The organic layer was dried over MgSO$_4$, filtered and concentrated under vacuum. The residue was purified by reverse phase chromatography (basic mode, standard LC) to yield 1.17 g of methyl (1S)-2-[(2,6-dichlorophenyl)acetyl]-1-methyl-1,2,3,4-tetrahydroisoquinoline-5-carboxylate a74 as a white solid.

Yield: 61%.

LCMS (ES$^+$): 392/394/396 (M+H)$^+$, 99% purity.

C.13.3. Synthesis of 2-(2,6-dichlorophenyl)-1-[(1S)-5-(hydroxymethyl)-1-methyl-3,4-dihydroisoquinolin-2(1H)-yl]ethanone 38

To a solution of methyl (1S)-2-[(2,6-dichlorophenyl)acetyl]-1-methyl-1,2,3,4-tetrahydroisoquinoline-5-carboxylate a74 (660 mg, 1.68 mmol) in THF (10 mL) was added at rt lithium borohydride (380 mg, 16.57 mmol). The mixture is stirred overnight at rt, poured in EtOAc (100 mL) and washed with a 1N aqueous solution of HCl (50 mL). The organic layer was dried over MgSO$_4$, filtered and concentrated under vacuum. The residue was first purified by column chromatography using 2% MeOH in DCM. A second purification by reverse phase chromatography (basic mode, LCMS prep) was done on 90 mg of the crude compound to afford 49 mg of 2-(2,6-dichlorophenyl)-1-[(1S)-5-(hydroxymethyl)-1-methyl-3,4-dihydroisoquinolin-2(1H)-yl]ethanone 38 as a white solid.

Yield: 8%.

LCMS (ES$^+$): 364/366/368 (M+H)$^+$, 99% purity.

C.14. Synthesis of (1S)-2-[(2,6-dichlorophenyl)acetyl]-1-methyl-1,2,3,4-tetrahydroisoquinoline-5-carboxamide 39

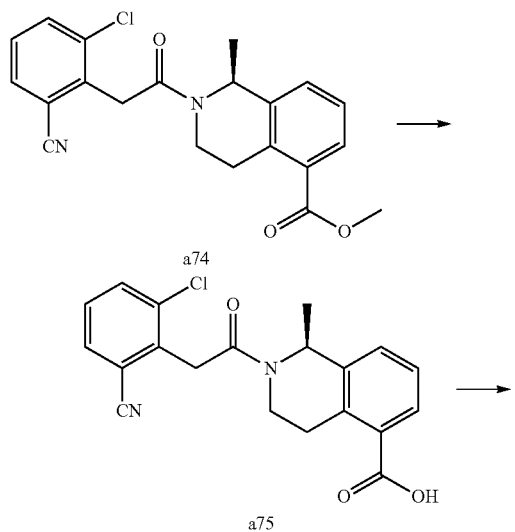

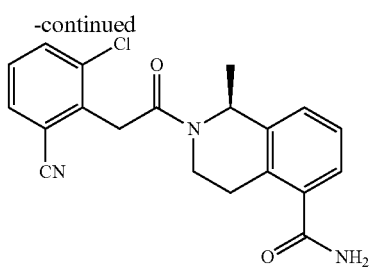

C.14.1. Synthesis of (1S)-2-[(2,6-dichlorophenyl)acetyl]-1-methyl-1,2,3,4-tetrahydroisoquinoline-5-carboxylic acid a75

Methyl (1S)-2-[(2,6-dichlorophenyl)acetyl]-1-methyl-1,2,3,4-tetrahydroisoquinoline-5-carboxylate a74 (650 mg, 1.66 mmol) was dissolved in 1,4-dioxane (10 mL). A 5N aqueous solution of NaOH (1.66 mL, 8.28 mmol) was added. The mixture was stirred at 80° C. overnight, then allowed to warm to rt. A 12N aqueous solution of HCl was added until acidic pH was reached. The reaction mixture was concentrated under vacuum. The residue was diluted with EtOAc. After sonication a precipitate was formed, filtered and washed twice with EtOAc. The filtrate was concentrated under vacuum to yield 550 mg of (1S)-2-[(2,6-dichlorophenyl)acetyl]-1-methyl-1,2,3,4-tetrahydroisoquinoline-5-carboxylic acid a75 as a yellow gum which was used in next step without any further purification.

Yield: 88% (crude).

LCMS (ES$^+$): 378/380/382 (M+H)$^+$.

C.14.2. Method B. Synthesis of (1S)-2-[(2,6-dichlorophenyl)acetyl]-1-methyl-1,2,3,4-tetrahydroisoquinoline-5-carboxamide 39

(1S)-2-[(2,6-dichlorophenyl)acetyl]-1-methyl-1,2,3,4-tetrahydroisoquinoline-5-carboxylic acid a75 (50 mg, 0.13 mmol) was dissolved in DMF (1 mL). DIPEA (117 µL, 0.66 mmol), BOP (70 mg, 0.16 mmol) and ammonia (7N in MeOH, 57 µL, 0.40 mmol) were added. The mixture was stirred at 70° C. overnight. The reaction mixture was concentrated under vacuum. The residue was diluted with EtOAc, then successively washed with a 1N aqueous solution of HCl and an aqueous saturated solution of NaHCO$_3$. The organic layer was dried over MgSO$_4$, filtered and concentrated under vacuum. The residue was purified by reverse phase chromatography (basic mode, LCMS prep) to yield 27 mg (1S)-2-[(2,6-dichlorophenyl)acetyl]-1-methyl-1,2,3,4-tetrahydroisoquinoline-5-carboxamide 39 as a yellow oil.

Yield: 54%.

LCMS (ES$^+$): 377/379/381 (M+H)$^+$, 98% purity.

The following compounds may be synthesized according to a method analogous to method B.

| No | Starting materials | Conditions | Reaction time | Purification conditions | Yield (%) |
|---|---|---|---|---|---|
| 40 | acid: a75<br>amine: methylamine hydrochloride (1 eq) | DMF, DIPEA (5 eq), 70° C. | Overnight (PLS) | Basic RP-LCMS | 46 |
| 41 | acid: a75<br>amine: dimethylamine (1 eq) | DMF, DIPEA (5 eq), 70° C. | Overnight (PLS) | Basic RP-LCMS | 43 |
| 42 | acid: a75<br>amine: isopropylamine (1 eq) | DCM, TEA (2 eq), rt | Overnight (PLS) | Phase separator Basic RP-LC-MS | 78 |
| 43 | acid: a75<br>amine: pyrrolidine (1 eq) | DCM, TEA (2 eq), rt | Overnight (PLS) | Phase separator Basic RP-LCMS | 16 |
| 44 | acid: a75<br>amine: methylpyrrolidine (1 eq) | DCM, TEA (3 eq), rt | Overnight | Phase separator Basic RP-LCMS | 23 |
| 45 | acid: a75<br>amine: trifluoroethylamine (1 eq) | DCM, TEA (2 eq), rt | Overnight (PLS) | Phase separator Basic RP-LCMS | 41 |
| 46 | acid: a75<br>amine: ethylamine (1 eq) | DCM, TEA (2 eq), rt | Overnight | Phase separator Basic RP-LCMS | 38 |
| 47 | acid: a75<br>amine: morpholine (1 eq) | DCM, TEA (3 eq), rt | Overnight (PLS) | Phase separator Basic RP-LCMS | 37 |
| 48 | acid: a75<br>amine: 4-(trifluoromethyl) piperidine (1 eq) | DCM, TEA (3 eq), rt | Overnight (PLS) | Phase separator Basic RP-LCMS | 42 |
| 49 | acid: a75<br>amine: 2,5-dimethylpyrrolidine (1 eq) | DCM, TEA (3 eq), rt | Overnight (PLS) | Phase separator Basic RP-LCMS | 29 |
| 50 | acid: a75<br>amine: 4H-1,2,4-triazol-3-amine (1 eq) | DCM, TEA (3 eq), rt | Overnight (PLS) | Phase separator Basic RP-LCMS | 25 |
| 51 | acid: a75<br>amine: 3-pyrrolidinol (1 eq) | DCM, TEA (3 eq), rt | Overnight (PLS) | Basic RP-standard LC | 73 |
| 52 | acid: a75<br>amine: 3,3-difluoropyrrolidine hydrochloride (1 eq) | DCM, TEA (3 eq), rt | Overnight (PLS) | Basic RP-standard LC | 68 |

(1S)-2-[(2,6-dichlorophenyl)acetyl]-N,1-dimethyl-1,2,3,4-tetrahydroisoquinoline-5-carboxamide 40

LCMS (ES+): 391/393/395 (M+H)+, 97.7% purity.
Appearance: off-white solid.

(1S)-2-[(2,6-dichlorophenyl)acetyl]-N,N,1-trimethyl-1,2,3,4-tetrahydroisoquinoline-5-carboxamide 41. LCMS (ES+): 405/407/409 (M+H)+, 96.8% purity.
Appearance: yellow oil.

(1S)-2-[(2,6-dichlorophenyl)acetyl]-1-methyl-N-(propan-2-yl)-1,2,3,4-tetrahydroisoquinoline-5-carboxamide 42

LCMS (ES+): 419/421/423 (M+H)+, 100% purity.
Appearance: white solid.

2-(2,6-dichlorophenyl)-1-[(1S)-1-methyl-5-(pyrrolidin-1-ylcarbonyl)-3,4-dihydroisoquinolin-2(1H)-yl]ethanone 43

LCMS (ES+): 459/461/463 (M+H)+, 100% purity.
Appearance: white solid.

2-(2,6-dichlorophenyl)-1-[(1S)-1-methyl-5-[(2-methylpyrrolidin-1-yl)carbonyl]-3,4-dihydroisoquinolin-2(1H)-yl]ethanone 44. LCMS (ES+): 445/447/449 (M+H)+, 100% purity.
Appearance: white solid.

(1S)-2-[(2,6-dichlorophenyl)acetyl]-1-methyl-N-(2,2,2-trifluoroethyl)-1,2,3,4-tetrahydroisoquinoline-5-carboxamide 45

LCMS (ES+): 431/433/435 (M+H)+, 100% purity.
Appearance: white solid.

(1S)-2-[(2,6-dichlorophenyl)acetyl]-N-ethyl-1-methyl-1,2,3,4-tetrahydroisoquinoline-5-carboxamide 46

LCMS (ES+): 405/407/409 (M+H)+, 95% purity.
Appearance: white solid.

2-(2,6-dichlorophenyl)-1-[(1S)-1-methyl-5-(morpholin-4-ylcarbonyl)-3,4-dihydroisoquinolin-2(1H)-yl]ethanone 47

LCMS (ES+): 447/449/451 (M+H)+, 100% purity.
Appearance: white solid.

2-(2,6-dichlorophenyl)-1-[(1S)-1-methyl-5-{[4-(trifluoromethyl)piperidin-1-yl]carbonyl}-3,4-dihydroisoquinolin-2(1H)-yl]ethanone 48

LCMS (ES+): 513/515/517 (M+H)+, 100% purity.
Appearance: yellow solid.

2-(2,6-dichlorophenyl)-1-[(1S)-5-[(2,5-dimethylpyrrolidin-1-yl)carbonyl]-1-methyl-3,4-dihydroisoquinolin-2(1H)-yl]ethanone 49

LCMS (ES+): 459/461/463 (M+H)+, 96% purity.
Appearance: white solid.

(1S)-2-[(2,6-dichlorophenyl)acetyl]-1-methyl-N-(4H-1,2,4-triazol-3-yl)-1,2,3,4-tetrahydroisoquinoline-5-carboxamide 50

LCMS (ES+): 444/446/448 (M+H)+, 93.7% purity.
Appearance: white solid.

2-(2,6-dichlorophenyl)-1-[(1S)-5-{[3-hydroxypyrrolidin-1-yl]carbonyl}-1-methyl-3,4-dihydroisoquinolin-2(1H)-yl]ethanone 51

LCMS (ES+): 447/449/451 (M+H)+, 100% purity.
Appearance: white solid.

2-(2,6-dichlorophenyl)-1-[(1S)-5-[(3,3-difluoropyrrolidin-1-yl)carbonyl]-1-methyl-3,4-dihydroisoquinolin-2(1H)-yl]ethanone 52

LCMS (ES+): 467/469/471 (M+H)+, 100% purity.
Appearance: light yellow oil.

C.15. Synthesis of (1S)-2-[(2,6-dichlorophenyl)acetyl]-1-methyl-N,N-di(propan-2-yl)-1,2,3,4-tetrahydroisoquinoline-5-carboxamide 53

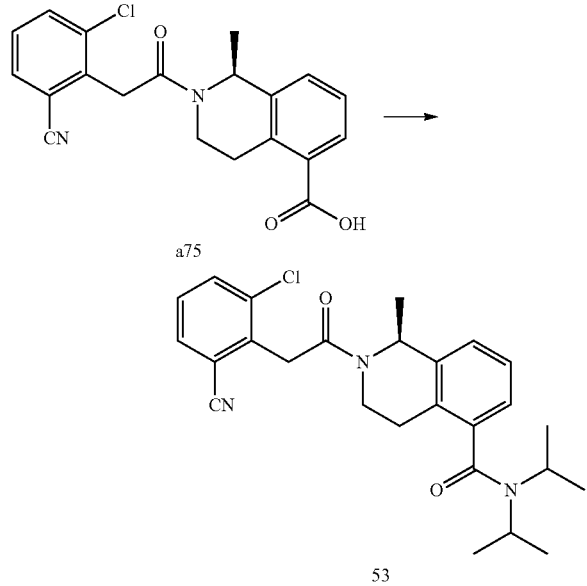

(1S)-2-[(2,6-dichlorophenyl)acetyl]-1-methyl-1,2,3,4-tetrahydroisoquinoline-5-carboxylic acid a75 (200 mg, 0.53 mmol) was dissolved in DCM (2 mL). Thionyl chloride (193 µL, 2.64 mmol) was added. The mixture was stirred at rt for 2 h. The reaction mixture was concentrated under vacuum. The residue was diluted with DCM (2 mL). The solution was cooled to 0° C. Diisopropylamine (347 µL, 2.64 mmol) was added. The mixture was stirred at rt for 1 h. The reaction mixture was concentrated under vacuum. The residue was diluted with EtOAc, then successively washed with a 0.5N aqueous solution of HCl and an aqueous saturated solution of NaHCO₃. The organic layer was dried over MgSO₄, filtered and concentrated under vacuum. The residue was purified by reverse phase chromatography (basic mode, standard LC) to yield 19 mg of (1S)-2-[(2,6-dichlorophenyl)acetyl]-1-methyl-N,N-di(propan-2-yl)-1,2,3,4-tetrahydroisoquinoline-5-carboxamide 53 as a yellow solid.

Yield: 8%.

LCMS (ES+): 461/463/465 (M+H)+, 100% purity.

C.16. Synthesis of (1S)-2-[(2,6-dichlorophenyl)acetyl]-1-methyl-N-(pyridin-2-yl)-1,2,3,4-tetrahydroisoquinoline-5-carboxamide 54

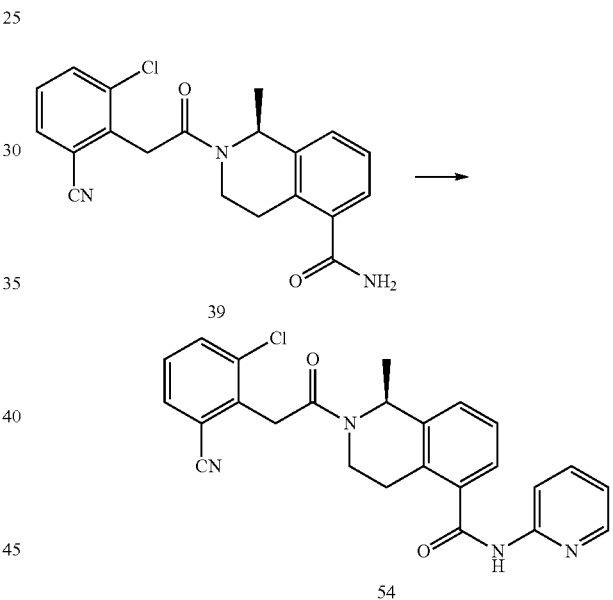

To a solution of (1S)-2-[(2,6-dichlorophenyl)acetyl]-1-methyl-1,2,3,4-tetrahydroisoquinoline-5-carboxamide 39 (85 mg, 0.22 mmol) in 1,4-dioxane (10 mL) were added 2-bromopyridine (53 mg, 0.34 mmol), potassium phosphate tribasic (98 mg, 0.45 mmol), (1R,2R)-(−)-1,2-diaminocyclohexane (27 µL, 0.225 mmol) and CuI (21 mg, 0.11 mmol) at rt. The mixture was stirred at 120° C. for 3 days. The reaction mixture was cooled to rt and quenched with a 1N aqueous solution of HCl, then extracted thrice with DCM. The organic layer was dried over MgSO₄, filtered and concentrated under vacuum. The residue was purified by reverse phase chromatography (basic mode, standard LC) to yield 26 mg of (1S)-2-[(2,6-dichlorophenyl)acetyl]-1-methyl-N-(pyridin-2-yl)-1,2,3,4-tetrahydroisoquinoline-5-carboxamide 54 as a yellow solid.

Yield: 25%.

LCMS (ES+): 454/456/458 (M+H)+, 99.4% purity.

C.17. Synthesis of 2-[2-chloro-6-(hydroxymethyl)phenyl]-1-[(1S)-1-methyl-3,4-dihydroisoquinolin-2(1H)-yl]ethanone 55

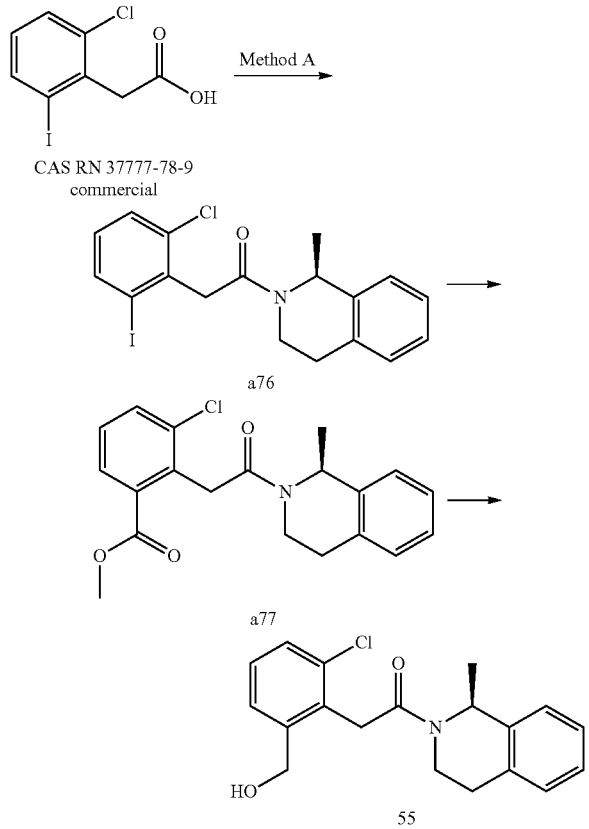

C.17.1. Synthesis of 2-(2-chloro-6-iodophenyl)-1-[(1S)-1-methyl-3,4-dihydroisoquinolin-2(1H)-yl]ethanone a76

Compound a76 may be synthesized according to a method analogous to Method A using (1S)-1-methyl-1,2,3,4-tetrahydroisoquinoline and (2-chloro-6-iodo)acetic acid as starting materials. Conditions: DCM, TEA (3 eq), rt, overnight.
Yield: 45% (crude).
LCMS (ES$^+$): 426/428 (M+H)$^+$.

C.17.2. Synthesis of methyl 3-chloro-2-{2-[(1S)-1-methyl-3,4-dihydroisoquinolin-2(1H)-yl]-2-oxoethyl}benzoate a77

2-(2-chloro-6-iodophenyl)-1-[(1S)-1-methyl-3,4-dihydroisoquinolin-2(1H)-yl]ethanone a76 (350 mg, 0.82 mmol) was dissolved in MeOH (15 mL) at rt. TEA (170 mg, 1.64 mmol) and ((S)-BINAP)PdBr$_2$ (73 mg, 0.08 mmol) were added. The mixture was placed under an atmosphere of CO at 60° C. for 5 h. The reaction mixture was filtered through Celite®, washed with MeOH and concentrated under vacuum. The residue was purified by silica gel column chromatography using up to 2% MeOH in DCM to yield 55 mg of methyl 3-chloro-2-{2-[(1S)-1-methyl-3,4-dihydroisoquinolin-2(1H)-yl]-2-oxoethyl}benzoate a77.
Yield: 19%.
LCMS (ES$^+$): 358/360/362 (M+H)$^+$.

C.17.3. Synthesis of 2-[2-chloro-6-(hydroxymethyl)phenyl]-1-[(1S)-1-methyl-3,4-dihydroisoquinolin-2(1H)-yl]ethanone 55

A solution of methyl 3-chloro-2-[2-[(1S)-1-methyl-3,4-dihydro-1H-isoquinolin-2-yl]-2-oxo-ethyl]benzoate a77 (15 mg, 0.04 mmol) was dissolved in THF (3 mL), cooled to 0° C. and lithium aluminium hydride (5 mg, 0.13 mmol) was added. The mixture was stirred at rt for 4 h, then quenched with a 1N aqueous solution of HCl (1 mL) and extracted with DCM. The organic layer was washed twice with an aqueous saturated solution of NaHCO$_3$, dried over MgSO$_4$, filtered and concentrated under vacuum. The residue was purified by reverse phase chromatography (basic mode, LCMS prep) to yield 3 mg of 2-[2-chloro-6-(hydroxymethyl)phenyl]-1-[(1S)-1-methyl-3,4-dihydroisoquinolin-2(1H)-yl]ethanone 55 as a beige solid.
Yield: 22%.
LCMS (ES$^+$): 330/332/334 (M+H)$^+$, 100% purity.

C.18. Synthesis of 3-chloro-N-methyl-2-{2-[(1S)-1-methyl-3,4-dihydroisoquinolin-2(1H)-yl]-2-oxoethyl}benzamide 56

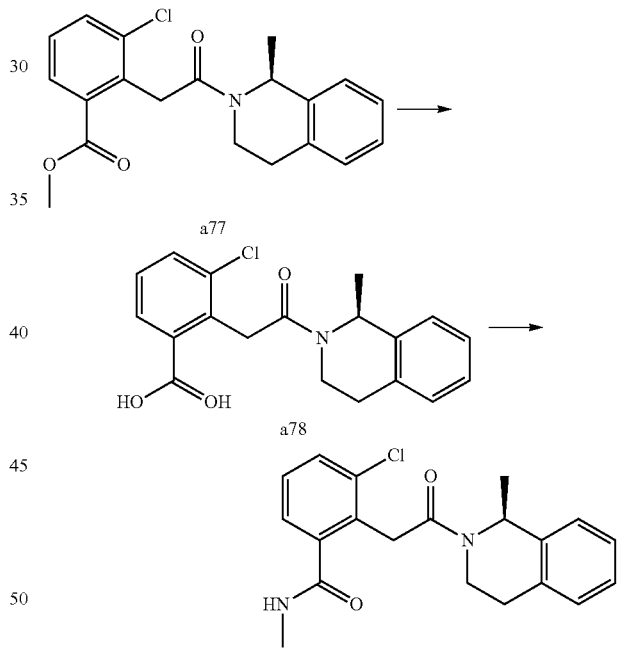

C.18.1. Synthesis of 3-chloro-2-[2-[(1S)-1-methyl-3,4-dihydro-1H-isoquinolin-2-yl]-2-oxo-ethyl]benzoic acid a78

Methyl 3-chloro-2-{2-[(1S)-1-methyl-3,4-dihydroisoquinolin-2(1H)-yl]-2-oxoethyl}benzoate a77 (40 mg, 0.11 mmol) was dissolved in a mixture THF/water (4:1, 5 mL) at rt. Lithium hydroxide (8 mg, 0.34 mmol) was added. The mixture was stirred at rt overnight. The reaction mixture was cooled to 0° C. and quenched with a 1N aqueous solution of HCl, then extracted thrice with DCM. The organic layer was dried over MgSO$_4$, filtered and concentrated under vacuum to yield 34 mg of 3-chloro-2-{2-[(1S)-1-methyl-3,4-dihydroisoquinolin-2(1H)-yl]-2-oxoethyl}benzoic acid a78 used in the next step without any further purification.

Yield: 88% (crude).

LCMS (ES$^+$): 344/346/348 (M+H)$^+$.

C.18.2. Synthesis of 3-chloro-N-methyl-2-{2-[(1S)-1-methyl-3,4-dihydroisoquinolin-2(1H)-yl]-2-oxoethyl}benzamide 56

3-Chloro-2-{2-[(1S)-1-methyl-3,4-dihydroisoquinolin-2(1H)-yl]-2-oxoethyl}benzoic acid a78 (16 mg, 0.05 mmol) and methylamine hydrochloride (3.2 mg, 0.05 mmol) were dissolved in DCM (3 mL) at rt. Then, TEA (14 mg, 0.14 mmol) and benzotriazol-1-yloxytris(dimethylamino)-phosphonium hexafluorophosphate (23 mg, 0.05 mmol) were added. The mixture was stirred at rt overnight. The reaction mixture was taken up with DCM (25 mL) and washed twice with an aqueous saturated solution of NaHCO$_3$. The organic layer was dried over MgSO$_4$, filtered and concentrated under vacuum. The residue was purified by reverse phase chromatography (basic mode, LCMS prep) to yield 4 mg of 3-chloro-N-methyl-2-{2-[(1S)-1-methyl-3,4-dihydroisoquinolin-2(1H)-yl]-2-oxoethyl}benzamide 56 as a white solid.

Yield: 24%.

LCMS (ES$^+$): 357/359/361 (M+H)$^+$, 100% purity.

C.19. Synthesis of 2-[2,6-dichloro-4-(hydroxymethyl)phenyl]-1-(1-methyl-3,4-dihydroisoquinolin-2(1H)-yl)ethanone 57

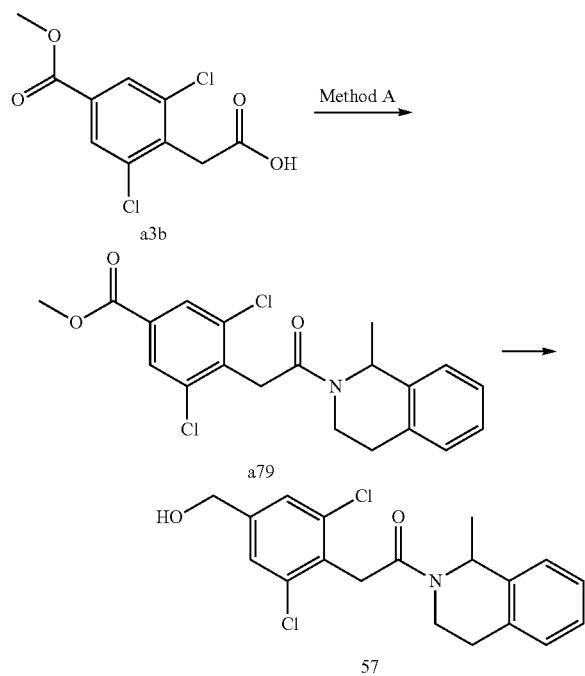

C.19.1. Synthesis of methyl 3,5-dichloro-4-[2-(1-methyl-3,4-dihydroisoquinolin-2(1H)-yl)-2-oxoethyl]benzoate a79

Compound a79 may be synthesized according to a method analogous to Method A using 1-methyl-1,2,3,4-tetrahydroisoquinoline and [2,6-dichloro-4-(methoxycarbonyl)phenyl]acetic acid a3b as starting material. Conditions: DCM, DIPEA (5 eq), rt, overnight. Yield: 140% (crude).

LCMS (ES$^+$): 392/394/396 (M+H)$^+$.

C.19.2. Synthesis of 2-[2,6-dichloro-4-(hydroxymethyl)phenyl]-1-(1-methyl-3,4-dihydroisoquinolin-2(1H)-yl)ethanone 57

Methyl 3,5-dichloro-4-[2-(1-methyl-3,4-dihydroisoquinolin-2(1H)-yl)-2-oxoethyl]benzoate a79 (100 mg, 0.18 mmol) was dissolved in THF (3 mL). Lithium borohydride (10 μL, 0.36 mmol) was added. The mixture was stirred at rt overnight. The reaction mixture was quenched by addition of a 1N aqueous solution of HCl, then concentrated under vacuum. The residue was dissolved in a 1N aqueous solution of HCl and extracted twice with DCM. The organic layer was dried over MgSO$_4$, filtered and concentrated under vacuum. The residue was triturated in Et$_2$O to yield 58 mg of 2-[2,6-dichloro-4-(hydroxymethyl)phenyl]-1-(1-methyl-3,4-dihydroisoquinolin-2(1H)-yl)ethanone 57 as a white solid.

Yield: 89%.

LCMS (ES$^+$): 364/366/368 (M+H)$^+$, 100% purity.

C.20. Synthesis of {(1S)-2-[(2,6-dichlorophenyl)acetyl]-1-methyl-1,2,3,4-tetrahydroisoquinolin-5-yl}methyl methyl carbonate 58

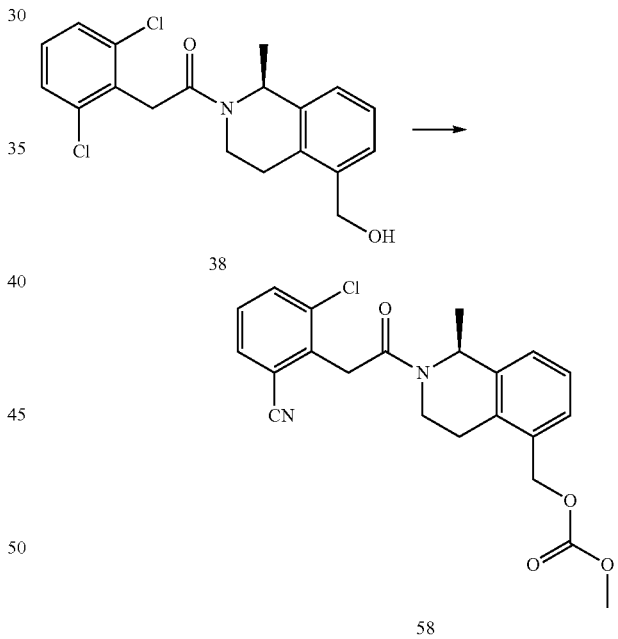

2-(2,6-dichlorophenyl)-1-[(1S)-5-(hydroxymethyl)-1-methyl-3,4-dihydroisoquinolin-2(1H)-yl]ethanone 38 (25 mg, 68 μmol) was dissolved in DCM (2 mL). DIPEA (24 μL, 0.14 mmol) and methyl chloroformate (5 μL, 68 μmol) were added. The mixture was stirred at rt. Methyl chloroformate (5 μL, 68 μmol) was added four times over a period of 30 days. The reaction mixture was concentrated under vacuum. The residue was purified by reverse phase chromatography (basic mode, LCMS prep) to yield 16 mg of {(1S)-2-[(2,6-dichlorophenyl)acetyl]-1-methyl-1,2,3,4-tetrahydroisoquinolin-5-yl}methyl methyl carbonate 58 as a yellow gum.

Yield: 55%.

LCMS (ES$^+$): 422/424/426 (M+H)$^+$, 100% purity.

C.21. Synthesis of 3-chloro-2-{2-[(1S)-1-methyl-3,4-dihydroisoquinolin-2(1H)-yl]-2-oxoethyl}benzonitrile 59

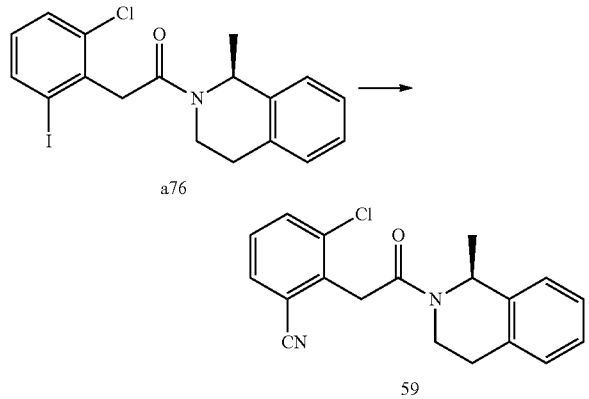

2-(2-Chloro-6-iodophenyl)-1-[(1S)-1-methyl-3,4-dihydroisoquinolin-2(1H)-yl]ethanone a76 (40 mg, 0.09 mmol) was dissolved in DMF (3 mL). Zinc cyanide (22 mg, 0.19 mmol) and tetrakis(triphenylphosphine)palladium(0) (10 mg, 0.05 mmol) were added. The mixture was placed under a microwaves irradiation at 150° C. for 1 h. The reaction mixture was taken up with DCM (25 mL) and washed twice with an aqueous saturated solution of NaHCO₃. The organic layer was dried over MgSO₄, filtered and concentrated under vacuum. The residue was purified by reverse phase chromatography (basic mode, LCMS prep) to yield 5 mg of 3-chloro-2-{2-[(1S)-1-methyl-3,4-dihydroisoquinolin-2(1H)-yl]-2-oxoethyl}benzonitrile 59 as a yellow oil.

Yield: 20%.

LCMS (ES⁺): 325/327/329 (M+H)⁺, 94% purity.

C.22. Synthesis of N-(2,4-dichloro-3-{2-[(1S)-1-methyl-3,4-dihydroisoquinolin-2(1H)-yl]-2-oxoethyl}phenyl)methanesulfonamide 60

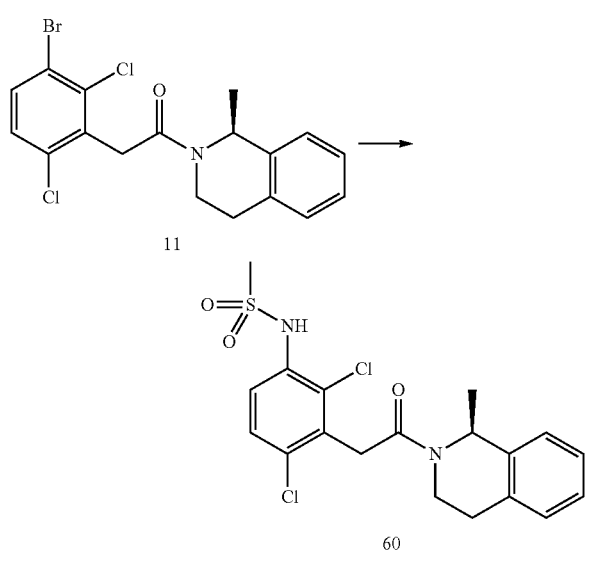 [SMILES: C[C@H]1c2ccccc2CCN1C(=O)Cc1c(Cl)ccc(Br)c1Cl ; CSc1ccc(Cl)c(CC(=O)N2CCc3ccccc3[C@@H]2C)c1Cl]

To a solution of 2-(3-bromo-2,6-dichlorophenyl)-1-[(1S)-1-methyl-3,4-dihydroisoquinolin-2(1H)-yl]ethanone 11 (100 mg, 0.24 mmol) in DMF (600 µL) were added methylsulfonamide (46 mg, 0.48 mmol), CuI (9 mg, 48 µmol), (1R,2R)-(−)-1,2-diaminocyclohexane (11 mg, 96 µmol) and potassium phosphate tribasic (159 mg, 0.72 mmol) at rt. The mixture was stirred at 150° C. for 3 days. The reaction mixture was cooled to rt, quenched with water, then extracted thrice with EtOAc. The organic layer was washed with brine, dried over Na₂SO₄, filtered and concentrated under vacuum. The residue was purified by reverse phase chromatography (basic mode, standard LC) to yield 33 mg of N-(2,4-dichloro-3-{2-[(1S)-1-methyl-3,4-dihydroisoquinolin-2(1H)-yl]-2-oxoethyl}phenyl)methanesulfonamide 60 as a brown solid foam.

Yield: 30%.

LCMS (ES⁺): 427/429/431 (M+H)⁺, 91.1% purity.

C.23. Synthesis of 2-[2,6-dichloro-3-(methylsulfanyl)phenyl]-1-[(1S)-1-methyl-3,4-dihydroisoquinolin-2(1H)-yl]ethanone 61

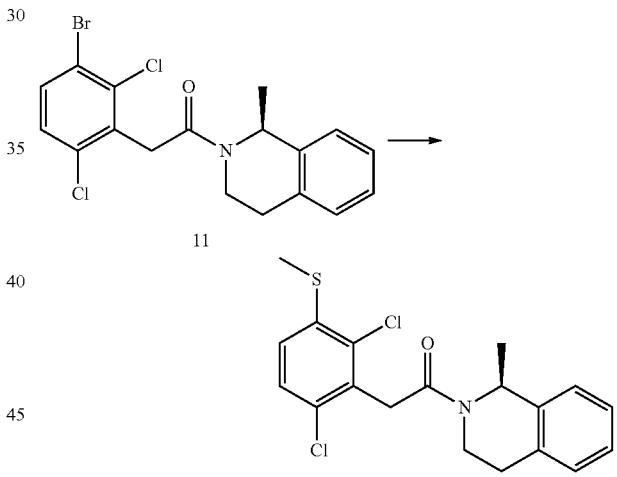

n-Butyllithium (2.5M solution in hexanes, 105 µL, 0.26 mmol) was added to a solution of 2-(3-bromo-2,6-dichlorophenyl)-1-[(1S)-1-methyl-3,4-dihydroisoquinolin-2(1H)-yl]ethanone 11 (100 mg, 0.24 mmol) in THF (1 mL) at −78° C. The mixture was stirred at −78° C. for 10 min., then dimethyl disulfide (45 mg, 0.48 mmol) was added. The reaction mixture was stirred at −78° C. for 1 h, then quenched with water and extracted thrice with EtOAc. The organic layer was washed with brine, dried over Na₂SO₄, filtered and concentrated under vacuum. The residue was purified by reverse phase chromatography (basic mode, standard LC) to yield 19 mg of 2-[2,6-dichloro-3-(methylsulfanyl)phenyl]-1-[(1S)-1-methyl-3,4-dihydroisoquinolin-2(1H)-yl]ethanone 61 as a brown oil.

Yield: 21%.

LCMS (ES⁺): 380/382/384 (M+H)⁺, 92.3% purity.

C.24. Synthesis of N-(3-chloro-2-{2-[(1S)-1-methyl-3,4-dihydroisoquinolin-2(1H)-yl]-2-oxoethyl}benzyl)methanesulfonamide 62

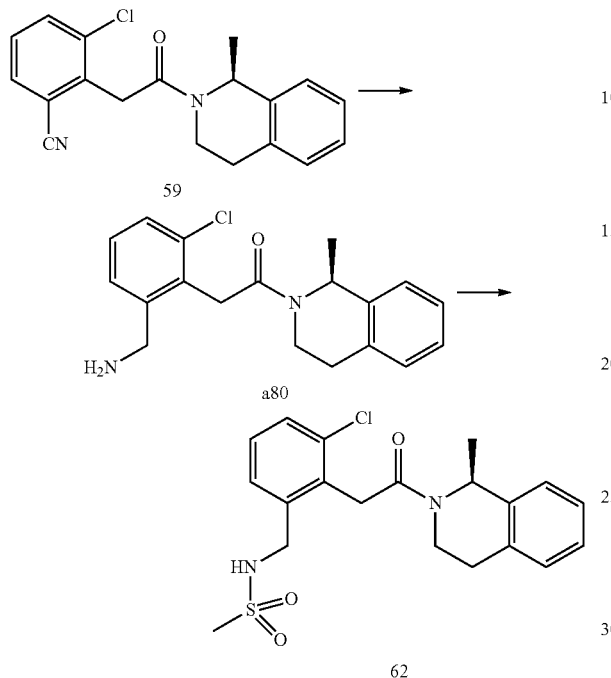

C.24.1. Synthesis of 2-[2-(aminomethyl)-6-chlorophenyl]-1-[(1S)-1-methyl-3,4-dihydroisoquinolin-2(1H)-yl]ethanone a80

3-chloro-2-{2-[(1S)-1-methyl-3,4-dihydroisoquinolin-2(1H)-yl]-2-oxoethyl}benzonitrile 59 was dissolved in MeOH (20 mL) at rt, then nickel(II) chloride (1 g, 4 mmol) was added. The mixture was cooled to 0° C. then sodium borohydride (162 mg, 4.29 mmol) was added. The mixture was stirred at rt for 5 days and at 50° C. for 2 days. The reaction mixture was cooled to 0° C., quenched with a 2N aqueous solution of HCl, filtered through an acidic column, which was then rinsed with a 2M solution of ammonia in MeOH. The ammonia solution was concentrated under vacuum. The residue was purified by reverse phase chromatography (basic mode, LCMS prep) to yield 50 mg of 2-[2-(aminomethyl)-6-chlorophenyl]-1-[(1S)-1-methyl-3,4-dihydro-1H-isoquinolin-2-yl]ethanone a80.
Yield: 14%.
LCMS (ES$^+$): 329/331 (M+H)$^+$.

C.24.2. Synthesis of N-(3-chloro-2-{2-[(1S)-1-methyl-3,4-dihydroisoquinolin-2(1H)-yl]-2-oxoethyl}benzyl)methanesulfonamide 62

DIPEA (26 µL, 0.15 mmol) was added to a solution of 2-[2-(aminomethyl)-6-chloro-phenyl]-1-[(1S)-1-methyl-3,4-dihydro-1H-isoquinolin-2-yl]ethanone a80 (25 mg, 76 µmol) in DCM (4 mL) at rt. The reaction mixture was cooled to 0° C. and methanesulfonyl chloride (9 mg, 76 µmol) was added. The mixture was stirred at rt overnight, then taken up with DCM (25 mL) and washed twice with an aqueous saturated solution of NaHCO$_3$. The organic layer was dried over MgSO$_4$, filtered and concentrated under vacuum. The residue was purified by reverse phase chromatography (basic mode, LCMS prep) to yield 10 mg of N-(3-chloro-2-{2-[(1S)-1-methyl-3,4-dihydroisoquinolin-2(1H)-yl]-2-oxoethyl}benzyl)methanesulfonamide 62 as a colorless oil.
Yield: 32%.
LCMS (ES$^+$): 407/409 (M+H)$^+$, 95% purity.

C.25. Synthesis of N-(3-chloro-2-{2-[(1S)-1-methyl-3,4-dihydroisoquinolin-2(1H)-yl]-2-oxoethyl}benzyl)acetamide 63

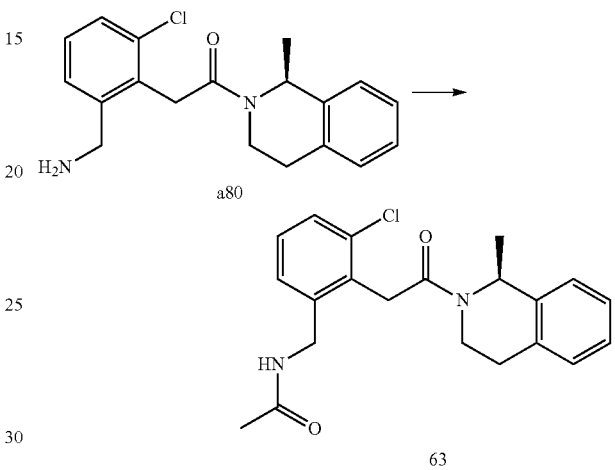

DIPEA (26 µL, 0.15 mmol) was added to a solution of 2-[2-(aminomethyl)-6-chlorophenyl]-1-[(1S)-1-methyl-3,4-dihydroisoquinolin-2(1H)-yl]ethanone a80 (25 mg, 0.07 mmol) in DCM (4 mL) at rt. The reaction mixture was cooled to 0° C. and acetyl chloride (6 mg, 76 µmol) was added. The mixture was stirred at rt overnight, then taken up with DCM (25 mL) and washed twice with an aqueous saturated solution of NaHCO$_3$. The organic layer was dried over MgSO$_4$, filtered and concentrated under vacuum. The residue was purified by reverse phase chromatography (basic mode, LCMS prep) to yield 6.5 mg N-(3-chloro-2-{2-[(1S)-1-methyl-3,4-dihydroisoquinolin-2(1H)-yl]-2-oxoethyl}benzyl)acetamide 63 as a colorless oil.
Yield: 23%.
LCMS (ES$^+$): 371/373 (M+H)$^+$, 94% purity.

C.26. Synthesis of 2-[2,6-dichloro-3-(methylsulfonyl)phenyl]-1-[(1S)-1-methyl-3,4-dihydroisoquinolin-2(1H)-yl]ethanone 64 & 2-[2,6-dichloro-3-(methylsulfinyl)phenyl]-1-[(1S)-1-methyl-3,4-dihydroisoquinolin-2(1H)-yl]ethanone 65

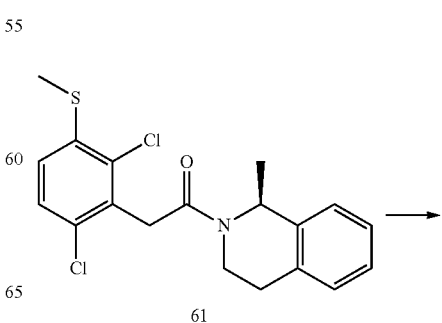

125

-continued

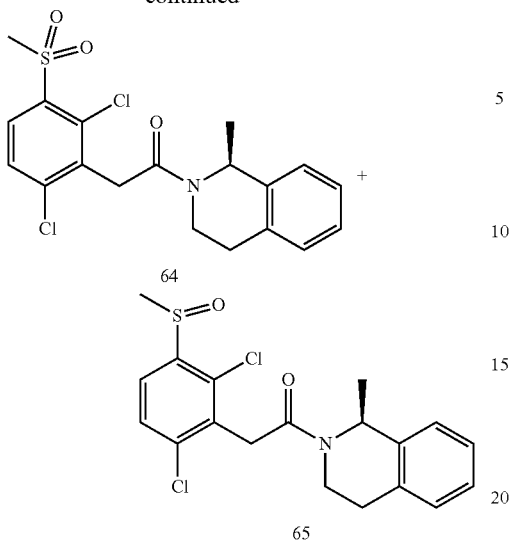

64

65

2-[2,6-Dichloro-3-(methylsulfanyl)phenyl]-1-[(1S)-1-methyl-3,4-dihydroisoquinolin-2(1H)-yl]ethanone 61 (120 mg, 0.31 mmol) was dissolved in DCM (5 mL) at rt and 3-chloroperoxybenzoic acid (94 mg, 0.41 mmol) was added. The mixture was stirred at rt for 3 h, then extracted thrice with an aqueous saturated solution of NaHCO$_3$. The organic layer was washed with brine, dried over Na$_2$SO$_4$, filtered and concentrated under vacuum. The residue was purified by reverse phase chromatography (basic mode, standard LC) to yield 2 fractions:

16 mg of 2-[2,6-dichloro-3-(methylsulfonyl)phenyl]-1-[(1S)-1-methyl-3,4-dihydroisoquinolin-2(1H)-yl]ethanone 64 as a brown oil.

Yield: 12%.

LCMS (ES$^+$): 412/414/416 (M+H)$^+$, 95% purity.

47 mg of 2-[2,6-dichloro-3-(methylsulfinyl)phenyl]-1-[(1S)-1-methyl-3,4-dihydroisoquinolin-2(1H)-yl]ethanone 65 as a white solid (after a second purification by column chromatography using 0 to 20% MeOH in DCM as eluent).

Yield: 37%.

LCMS (ES$^+$): 396/398/400 (M+H)$^+$, 96.9% purity.

C.27. Synthesis of 2-(2,6-dichlorophenyl)-1-[(1S)-1-methyl-5-[(methylsulfanyl)methyl]-3,4-dihydroisoquinolin-2(1H)-yl]ethanone 66

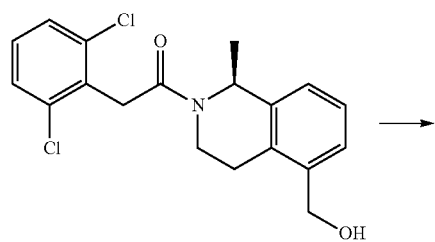

38

126

-continued

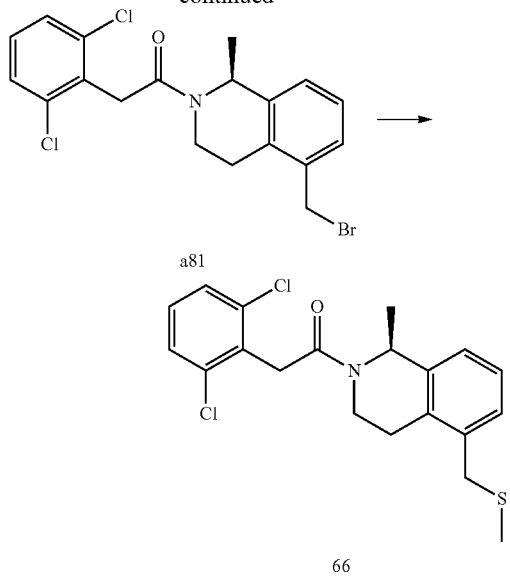

a81

66

C.27.1. Synthesis of 1-[(1S)-5-(bromomethyl)-1-methyl-3,4-dihydroisoquinolin-2(1H)-yl]-2-(2,6-dichlorophenyl)ethanone a81

To a solution of 2-(2,6-dichlorophenyl)-1-[(1S)-5-(hydroxymethyl)-1-methyl-3,4-dihydroisoquinolin-2(1H)-yl]ethanone 38 (202 mg, 0.55 mmol) in DCM (3 mL) was added dropwise phosphorus tribromide (100 µL, 1.0 mmol) at rt. The mixture was stirred overnight at rt, then diluted with DCM (100 mL) and washed with an aqueous saturated solution of NaHCO$_3$. The organic layer was dried over MgSO$_4$, filtered and concentrated under vacuum to yield 234 mg of 1-[(1S)-5-(bromomethyl)-1-methyl-3,4-dihydroisoquinolin-2(1H)-yl]-2-(2,6-dichlorophenyl)ethanone a81.

Yield: 94% (crude).

LCMS (ES$^+$): 428/430/432 (M+H)$^+$.

C.27.2. Synthesis of 2-(2,6-dichlorophenyl)-1-[(1S)-1-methyl-5-[(methylsulfanyl)methyl]-3,4-dihydroisoquinolin-2(1H)-yl]ethanone 66

To a solution of 1-[(1S)-5-(bromomethyl)-1-methyl-3,4-dihydroisoquinolin-2(1H)-yl]-2-(2,6-dichlorophenyl)ethanone a81 (23 mg, 54 µmol) in THF (1 mL) was added sodium methoxide (4 mg, 54 µmol) at rt. The mixture was stirred overnight at rt, then filtered and concentrated under vacuum. The residue was purified by reverse phase chromatography (basic mode, LCMS prep) to yield 8 mg of 2-(2,6-dichlorophenyl)-1-[(1S)-1-methyl-5-[(methylsulfanyl)methyl]-3,4-dihydroisoquinolin-2(1H)-yl]ethanone 66 as an oil.

Yield: 38%.

LCMS (ES$^+$): 394/396/398 (M+H)$^+$, 98% purity.

C.28. Synthesis of 2-(2,6-dichlorophenyl)-1-[(1S)-1-methyl-5-(methylsulfonyl)-3,4-dihydroisoquinolin-2(1H)-yl]ethanone 67

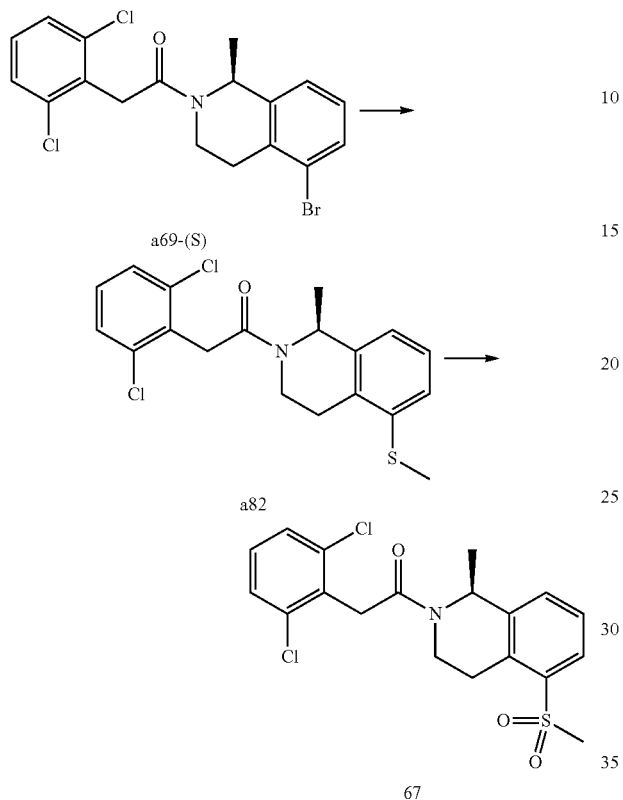

C.28.1. Synthesis of 2-(2,6-dichlorophenyl)-1-[(1S)-1-methyl-5-(methylsulfanyl)-3,4-dihydroisoquinolin-2(1H)-yl]ethanone a82

Sodium methoxide (360 mg, 4.84 mmol), 4,5-bis(diphenylphosphino)-9,9-dimethylxanthene (112 mg, 0.19 mmol), tris(dibenzylideneacetone) dipalladium(0) (90 mg, 97 µmol) and 1-[(1S)-5-bromo-1-methyl-3,4-dihydroisoquinolin-2(1H)-yl]-2-(2,6-dichlorophenyl)ethanone a69-(S) (400 mg, 0.97 mmol) were dissolved in toluene (8 mL) at rt. The mixture was stirred at 150° C. for 15 min under microwave irradiation. The reaction mixture was cooled to rt, filtered and concentrated under vacuum to yield 460 mg of 2-(2,6-dichlorophenyl)-1-[(1S)-1-methyl-5-(methylsulfanyl)-3,4-dihydro-1H-isoquinolin-2-yl]ethanone a82 which was used in the next step without any further purification.

Yield: 125% (crude).
LCMS (ES$^+$): 380/382/384 (M+H)$^+$.

C.28.2. Synthesis of 2-(2,6-dichlorophenyl)-1-[(1S)-1-methyl-5-(methylsulfonyl)-3,4-dihydroisoquinolin-2(1H)-yl]ethanone 67

2-(2,6-Dichlorophenyl)-1-[(1S)-1-methyl-5-(methylsulfanyl)-3,4-dihydro-1H-isoquinolin-2-yl]ethanone a82 (4.6 g, 12.10 mmol) was dissolved in DCM (640 mL) at rt and 3-chloroperoxybenzoic acid (7.6 g, 33.88 mmol) was added. The mixture was stirred at rt for 16 h, then extracted thrice with an aqueous saturated solution of NaHCO$_3$, dried over Na$_2$SO$_4$, filtered and concentrated under vacuum. The residue was purified by reverse phase chromatography (basic mode, standard LC) to yield 1.55 g of 2-(2,6-dichlorophenyl)-1-[(1S)-1-methyl-5-(methylsulfonyl)-3,4-dihydroisoquinolin-2(1H)-yl]ethanone 67 as a off-white solid.

Yield: 31%.
LCMS (ES$^+$): 412/414/416 (M+H)$^+$, 100% purity.

C.29. Synthesis of N-(3-chloro-2-{2-[(1S)-1-methyl-3,4-dihydroisoquinolin-2(1H)-yl]-2-oxoethyl}phenyl)methanesulfonamide 68

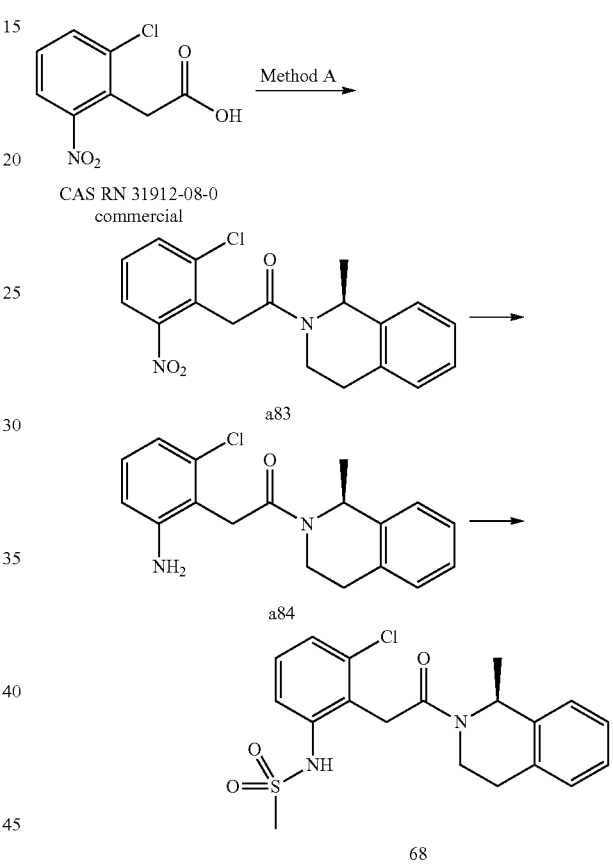

C.29.1. Synthesis of 2-(2-chloro-6-nitrophenyl)-1-[(1S)-1-methyl-3,4-dihydroisoquinolin-2(1H)-yl]ethanone a83

Compound a83 may be synthesized according to a method analogous to Method A using (1S)-1-methyl-1,2,3,4-tetrahydroisoquinoline and (2-chloro-6-nitrophenyl)acetic acid as starting materials. Conditions: DCM, DIPEA (1.2 eq), rt, overnight. Purification conditions: reverse phase chromatography (basic mode, LC standard).

Yield: 66%.
LCMS (ES$^+$): 345/347 (M+H)$^+$.

C.29.2. Synthesis 2-(2-amino-6-chlorophenyl)-1-[(1S)-1-methyl-3,4-dihydroisoquinolin-2(1H)-yl]ethanone a84

2-(2-Chloro-6-nitrophenyl)-1-[(1S)-1-methyl-3,4-dihydroisoquinolin-2(1H)-yl]ethanone a83 (500 mg, 1.45 mmol)

was dissolved in AcOH (20 mL) at rt and iron (405 mg, 7.25 mmol) was added. The mixture was stirred at rt for 16 h and concentrated under vacuum. The reaction mixture was neutralized with an aqueous saturated solution of NaHCO$_3$, then extracted thrice with EtOAc. The organic layer was dried over Na$_2$SO$_4$, filtered and concentrated under vacuum to yield 456 mg of 2-(2-amino-6-chlorophenyl)-1-[(1S)-1-methyl-3,4-dihydroisoquinolin-2(1H)-yl]ethanone a84 which was used in the next step without any further purification.

LCMS (ES$^+$): 315/317 (M+H)$^+$, 100% purity.

C.29.3. Synthesis of N-(3-chloro-2-{2-[(1S)-1-methyl-3,4-dihydroisoquinolin-2(1H)-yl]-2-oxoethyl}phenyl)methanesulfonamide 68

2-(2-Amino-6-chlorophenyl)-1-[(1S)-1-methyl-3,4-dihydroisoquinolin-2(1H)-yl]ethanone a84 (50 mg, 0.16 mmol) was dissolved in DCM (10 mL) at rt, then DIPEA (31 mg, 0.24 mmol) and methanesulfonyl chloride (19 mg, 0.17 mmol) were added. The mixture was stirred at rt for 2 h and concentrated under vacuum. The residue was purified by reverse phase chromatography (basic mode, LCMS prep) to yield 11 mg of N-(3-chloro-2-{2-[(1S)-1-methyl-3,4-dihydroisoquinolin-2(1H)-yl]-2-oxoethyl}phenyl)methanesulfonamide 68 as an off-white solid.

Yield: 18% (2 steps).
LCMS (ES$^+$): 393/395 (M+H)$^+$, 99.1% purity.

C.30. Synthesis of N-(3-chloro-2-{2-[(1S)-1-methyl-3,4-dihydroisoquinolin-2(1H)-yl]-2-oxoethyl}phenyl)acetamide 69

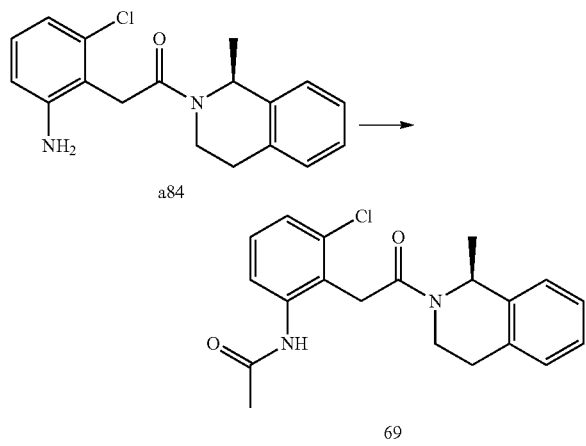

2-(2-Amino-6-chlorophenyl)-1-[(1S)-1-methyl-3,4-dihydroisoquinolin-2(1H)-yl]ethanone a84 (50 mg, 0.12 mmol) was dissolved in DCM (5 mL) at rt, then DIPEA (32 μL, 0.18 mmol) and acetyl chloride (10 mg, 0.20 mmol). The mixture was stirred at rt for 2 h and washed thrice times with an aqueous saturated solution of NaHCO$_3$. The organic layer was dried over Na$_2$SO$_4$, filtered and concentrated under vacuum. The residue was purified by reverse phase chromatography (basic mode, LCMS prep) to yield 12 mg of N-(3-chloro-2-{2-[(1S)-1-methyl-3,4-dihydroisoquinolin-2 (1H)-yl]-2-oxoethyl}phenyl)acetamide 69 as an off-white solid.

Yield: 28%.
LCMS (ES$^+$): 357/359 (M+H)$^+$, 100% purity.

C.31. Synthesis of 1-[(1S)-5-amino-1-methyl-3,4-dihydroisoquinolin-2(1H)-yl]-2-(2,6-dichlorophenyl)ethanone 70

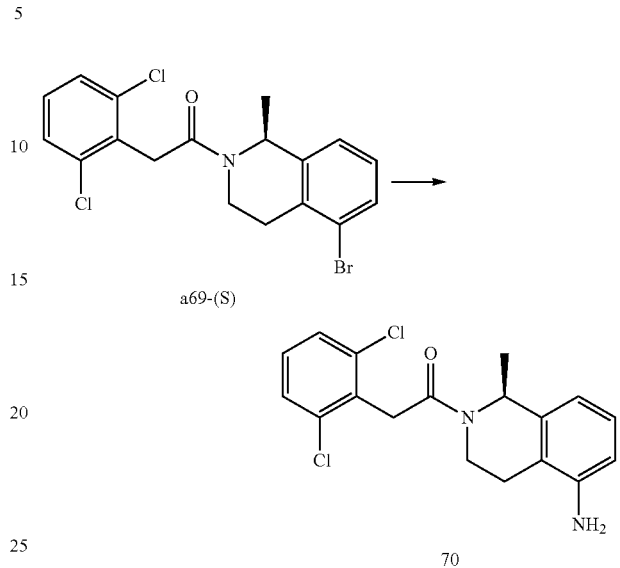

To a solution of 1-[(1S)-5-bromo-1-methyl-3,4-dihydroisoquinolin-2(1H)-yl]-2-(2,6-dichlorophenyl)ethanone a69-(S) (413 mg, 1.0 mmol) and sodium azide (975 mg, 15.0 mmol) in DMF (5 mL) were added potassium phosphate tribasic (657 mg, 3.0 mmol), cuprous iodide (40 mg, 0.21 mmol) and (1R,2R)-(−)-1,2-diaminocyclohexane (50 μL, 0.40 mmol). The mixture is stirred overnight at 120° C., then cooled to rt. The reaction mixture was diluted with EtOAc (100 mL) and washed twice with brine (250 mL). The organic layer was dried over MgSO$_4$, filtered and concentrated under vacuum. The residue was purified by reverse phase chromatography (basic mode, standard LC) to yield 245 mg of 1-[(1S)-5-amino-1-methyl-3,4-dihydroisoquinolin-2(1H)-yl]-2-(2,6-dichlorophenyl)ethanone 70 as a solid.

Yield: 70%.
LCMS (ES$^+$): 349/351/353 (M+H)$^+$, 100% purity.

C.32. Synthesis of 2-(2,6-dichlorophenyl)-1-[(1S)-5-[1-hydroxyethyl]-1-methyl-3,4-dihydroisoquinolin-2(1H)-yl]ethanone isomers A 71 & B 72

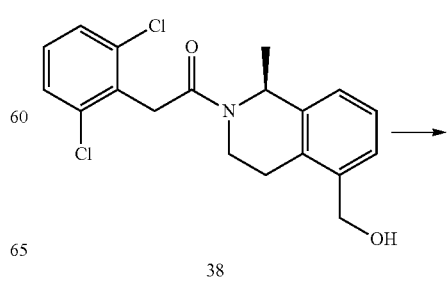

-continued

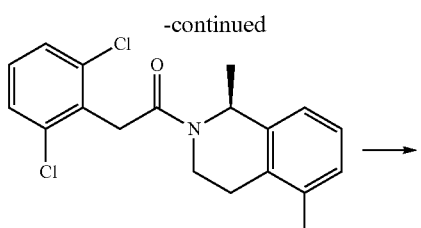
a85

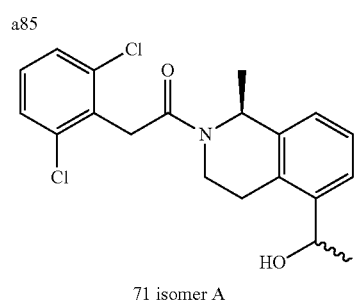
71 isomer A
72 isomer B

C.32.1. Synthesis of (1S)-2-[(2,6-dichlorophenyl)acetyl]-1-methyl-1,2,3,4-tetrahydroisoquinoline-5-carbaldehyde a85

To a solution of 2-(2,6-dichlorophenyl)-1-[(1S)-5-(hydroxymethyl)-1-methyl-3,4-dihydroisoquinolin-2(1H)-yl]ethanone 38 (370 mg, 1.01 mmol) in 1,4-dioxane (15 mL) was added manganese dioxide (1 g, 11.5 mmol) and the reaction mixture was overnight at rt. The reaction mixture is filtered on a SPE Syringe. The filtrate was concentrated under vacuum to yield 337 mg of (1S)-2-[(2,6-dichlorophenyl)acetyl]-1-methyl-1,2,3,4-tetrahydroisoquinoline-5-carbaldehyde a85 as a yellowish solid used in the next step without any further purification.

Yield: 87% (crude).
LCMS (ES+): 362/364/366 (M+H)+.

C.32.2. Synthesis of 2-(2,6-dichlorophenyl)-1-[(1S)-5-[1-hydroxyethyl]-1-methyl-3,4-dihydroisoquinolin-2(1H)-yl]ethanone isomers 71 & 72

To a solution of (1S)-2-[(2,6-dichlorophenyl)acetyl]-1-methyl-1,2,3,4-tetrahydroisoquinoline-5-carbaldehyde a85 (254 mg, 0.70 mmol) in THF (5 mL) was added dropwise methylmagnesium iodide (3M solution in Et$_2$O, 500 µL, 2 mmol) at −78° C. The mixture was stirred overnight at rt. The reaction mixture was diluted with DCM (100 mL) and washed with a 1N aqueous solution of HCl. The organic layer was dried over MgSO$_4$, filtered and concentrated under vacuum. The residue was purified by reverse phase chromatography (basic mode, standard LC) to yield 70 mg of racemate 2-(2,6-dichlorophenyl)-1-[(1S)-5-[1-hydroxyethyl]-1-methyl-3,4-dihydroisoquinolin-2(1H)-yl]ethanone (Yield: 26%). Chiral separation (SFC, Chiralcel OD, 50*266 mm, 360 mL/min, 220 nm, 40° C., eluent: from 20% MeOH) afforded:

24 mg of 2-(2,6-dichlorophenyl)-1-[(1S)-5-[1-hydroxyethyl]-1-methyl-3,4-dihydroisoquinolin-2(1H)-yl]ethanone isomer A 71 as a brown sticky oil.
Yield: 9%
LCMS (ES+): 378/380/382 (M+H)+, 97.2% purity.

Chiral analysis (LC, Chiralcel OD-H, 250*4.6 mm, 1 mL/min, 220 nm, 30° C., eluent: MeOH/DEA 100/0.1): RT 4.27 min, 100% ee.

33 mg of 2-(2,6-dichlorophenyl)-1-[(1S)-5-[1-hydroxyethyl]-1-methyl-3,4-dihydroisoquinolin-2(1H)-yl]ethanone isomer B 72 as brown sticky oil.
Yield: 12%
LCMS (ES+): 378/380/382 (M+H)+, 98% purity.
Chiral analysis (LC, Chiralcel OD-H, 250*4.6 mm, 1 mL/min, 220 nm, 30° C., eluent: MeOH/DEA 100/0.1): RT 5.44 min, 100% ee.

C.33. Synthesis of N-(2-{(1S)-2-[(2,6-dichlorophenyl)acetyl]-1-methyl-1,2,3,4-tetrahydroisoquinolin-5-yl}ethyl)methanesulfonamide 73

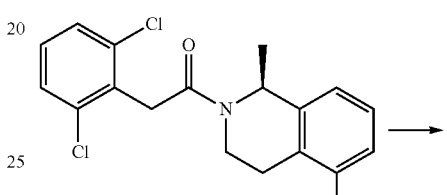
a81

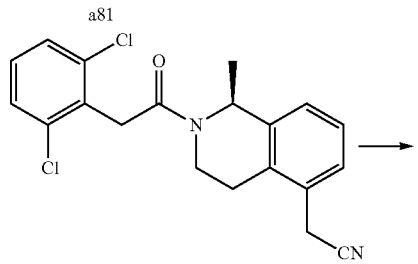
a86

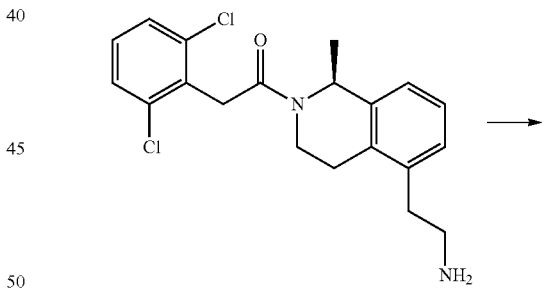
a87

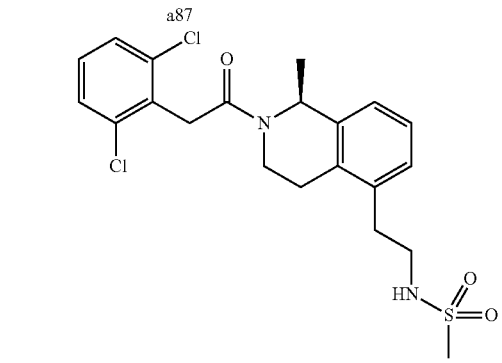
73

C.33.1. Synthesis of {(1S)-2-[(2,6-dichlorophenyl)acetyl]-1-methyl-1,2,3,4-tetrahydroisoquinolin-5-yl}acetonitrile a86

To a solution of 1-[(1S)-5-(bromomethyl)-1-methyl-3,4-dihydroisoquinolin-2(1H)-yl]-2-(2,6-dichlorophenyl)ethanone a81 (169 mg, 0.39 mmol) in DMF (3 mL, 38.94 mmol) was added sodium cyanide (21 mg, 0.43 mmol) at rt and the mixture was stirred overnight at 60° C. The reaction mixture was diluted with EtOAc (20 mL) and successively washed with an aqueous saturated solution of NaHCO$_3$ (100 mL), brine (100 mL) and water (100 mL). The organic layer was dried over MgSO$_4$, filtered and concentrated under vacuum to yield 120 mg of {(1S)-2-[(2,6-dichlorophenyl)acetyl]-1-methyl-1,2,3,4-tetrahydroisoquinolin-5-yl}acetonitrile a86 which was used in the next step without any further purification.

Yield: 82% (crude).

LCMS (ES$^+$): 373/375/377 (M+H)$^+$.

C.33.2. Synthesis of 1-[(1S)-5-(2-aminoethyl)-1-methyl-3,4-dihydroisoquinolin-2(1H)-yl]-2-(2,6-dichlorophenyl)ethanone a87

To a solution of {(1S)-2-[(2,6-dichlorophenyl)acetyl]-1-methyl-1,2,3,4-tetrahydroisoquinolin-5-yl}acetonitrile a86 (120 mg, 0.32 mmol) in THF (5 mL) was added dropwise borane dimethyl sulfide complex (2M solution in THF, 160 μL, 0.32 mmol) at rt and the mixture was stirred overnight at rt. An additional amount of borane dimethyl sulfide complex (2M solution in THF, 160 μL, 0.32 mmol) was then added and the reaction mixture was stirred overnight at rt. The reaction mixture was quenched with a 1N solution of HCl (2 mL) and stirred for 2 h at rt, then neutralized by addition of an ammonia solution in water. The mixture was then extracted twice with DCM (20 mL) The organic layer was dried over MgSO$_4$, filtered and concentrated under vacuum to yield 120 mg of 1-[(1S)-5-(2-aminoethyl)-1-methyl-3,4-dihydroisoquinolin-2(1H)-yl]-2-(2,6-dichlorophenyl)ethanone a87 which was used in the next step without any further purification.

Yield: 80% (crude).

LCMS (ES$^+$) 377/379/381 (M+H)$^+$.

C.33.3. Synthesis of N-(2-{(1S)-2-[(2,6-dichlorophenyl)acetyl]-1-methyl-1,2,3,4-tetrahydroisoquinolin-5-yl}ethyl)methanesulfonamide 73

To a solution of 1-[(1S)-5-(2-aminoethyl)-1-methyl-3,4-dihydroisoquinolin-2(1H)-yl]-2-(2,6-dichlorophenyl)ethanone a87 (120 mg, 0.25 mmol) in DCM (10 mL) was added TEA (150 μL, 1.1 mmol) and the mixture was stirred for 5 min. Methanesulfonyl chloride (20 μL, 0.30 mmol) was added. The reaction mixture was stirred overnight at rt, quenched with a 1N aqueous solution of HCl (3 mL). The organic layer was dried over MgSO$_4$, filtered and concentrated under vacuum. The residue was purified by reverse phase chromatography (basic mode, LCMS prep) to yield 31 mg of N-(2-{(1S)-2-[(2,6-dichlorophenyl)acetyl]-1-methyl-1,2,3,4-tetrahydroisoquinolin-5-yl}ethyl)methanesulfonamide 73 as a solid.

Yield: 26%.

LCMS (ES$^+$): 455/457/459 (M+H)$^+$, 99% purity.

C.34. Synthesis of 2-(2,6-dichlorophenyl)-1-[(1S)-1-methyl-5-[1-(methylsulfonyl)-4,5-dihydro-1H-imidazol-2-yl]-3,4-dihydroisoquinolin-2(1H)-yl]ethanone 74

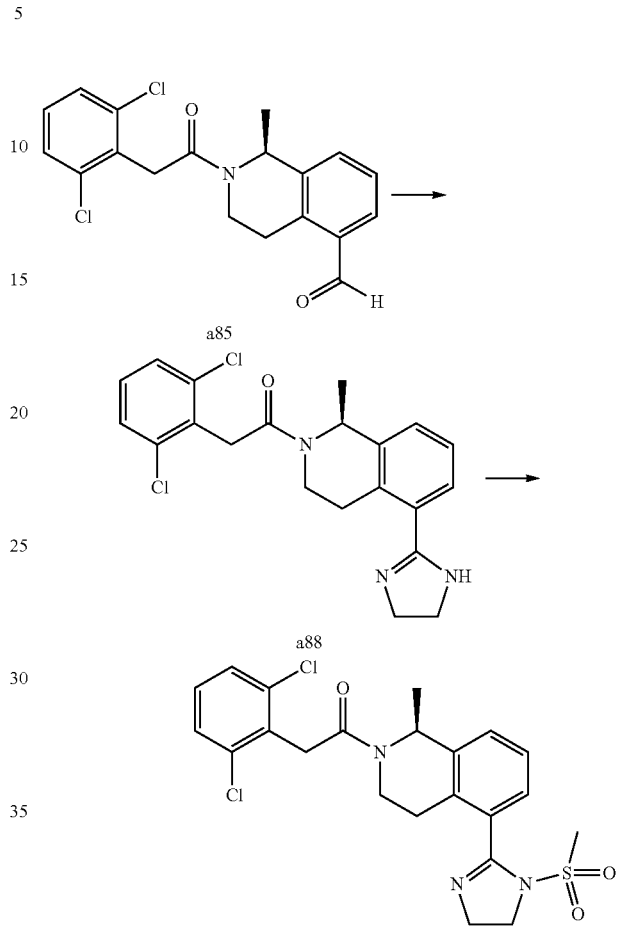

C.34.1. Synthesis of 2-(2,6-dichlorophenyl)-1-[(1S)-5-(4,5-dihydro-1H-imidazol-2-yl)-1-methyl-3,4-dihydroisoquinolin-2(1H)-yl]ethanone a88

(1S)-2-[(2,6-Dichlorophenyl)acetyl]-1-methyl-1,2,3,4-tetrahydroisoquinoline-5-carbaldehyde a85 (50 mg, 0.1380 mmol) was dissolved in DCM (1 mL) and ethylenediamine (10 μL, 0.14 mmol) was added at rt. The mixture was stirred at rt for 2 h, then cooled to 0° C. and N-bromosuccinimide (25 mg, 0.14 mmol) was added. The reaction mixture was stirred overnight at rt and concentrated under vacuum. The residue was taken up with MeOH and the resulting solution was passed through an acidic column. The product was eluted with a 2N methanolic solution of ammonia and concentrated under vacuum. Trituration in Et$_2$O yielded 40 mg of 2-(2,6-dichlorophenyl)-1-[(1S)-5-(4,5-dihydro-1H-imidazol-2-yl)-1-methyl-3,4-dihydroisoquinolin-2(1H)-yl]ethanone a88 as an off-white solid.

Yield: 72%.

LCMS (ES$^+$): 402/404/406 (M+H)$^+$, 81% purity.

C.34.2. Synthesis of 2-(2,6-dichlorophenyl)-1-[(1S)-1-methyl-5-[1-(methylsulfonyl)-4,5-dihydro-1H-imidazol-2-yl]-3,4-dihydroisoquinolin-2(1H)-yl]ethanone 74

To a solution of 2-(2,6-dichlorophenyl)-1-[(1S)-5-(4,5-dihydro-1H-imidazol-2-yl)-1-methyl-3,4-dihydroisoquinolin-2(1H)-yl]ethanone a88 (37 mg, 92 µmol) and TEA (25 µL, 0.18 mmol) in DCM (5 mL), was added methanesulfonyl chloride (9 µL, 0.11 mmol) at 0° C. After 45 min stirring at rt, the reaction mixture was quenched with a 1N aqueous solution of HCl (50 mL), then was washed with an aqueous saturated solution of NaHCO₃ (50 mL) and extracted thrice with DCM (20 mL). The organic layer was dried over MgSO₄, filtered and concentrated under vacuum. The residue was purified by reverse phase chromatography (basic mode, LC-MS prep) to yield 32 mg of 2-(2,6-dichlorophenyl)-1-[(1S)-1-methyl-5-[1-(methylsulfonyl)-4,5-dihydro-1H-imidazol-2-yl]-3,4-dihydroisoquinolin-2(1H)-yl]ethanone 74 as a white solid.

Yield: 72%.

LCMS (ES⁺): 480/482/484 (M+H)⁺, 92.5% purity.

C.35. Synthesis of 2-[2-chloro-6-(1H-pyrazol-4-yl)phenyl]-1-[(1S)-1-methyl-3,4-dihydroisoquinolin-2(1H)-yl]ethanone trifluoroacetate 75

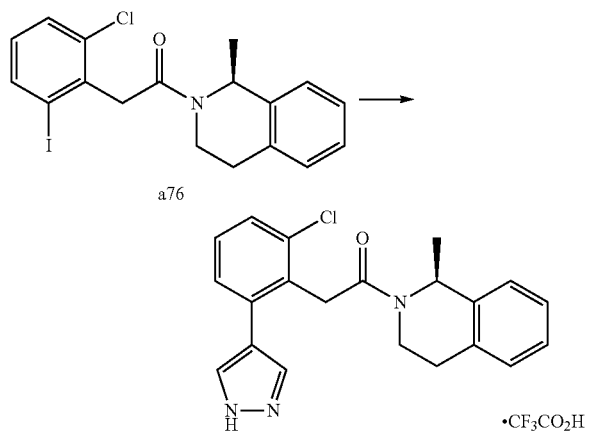

A mixture of 2-(2-chloro-6-iodophenyl)-1-[(1S)-1-methyl-3,4-dihydroisoquinolin-2(1H)-yl]ethanone a76 (20 mg, 47 µmol), tetrakis(triphenylphosphine)palladium(0) (5.5 mg, 5 µmol), 1H-pyrazole-4-boronic acid (11 mg, 94 µmol) and a 2N aqueous saturated solution of K₂CO₃ (500 µL) were stirred in 1,4-dioxane (1 mL) at rt, then at 130° C. for 50 min under microwave irradiation. The reaction mixture was cooled to rt, filtered and concentrated under vacuum. The residue was purified by reverse phase chromatography (acidic mode, LCMS prep) to yield 15 mg of 2-[2-chloro-6-(1H-pyrazol-4-yl)phenyl]-1-[(1S)-1-methyl-3,4-dihydroisoquinolin-2(1H)-yl]ethanone trifluoroacetate 75 as a colorless oil.

Yield: 65%.

LCMS (ES⁺): 366/368 (M+H)⁺, 97.1% purity.

C.36. Synthesis of (1S)-2-[(2,6-dichlorophenyl)acetyl]-1-methyl-2,3-dihydroisoquinolin-4(1H)-one 76

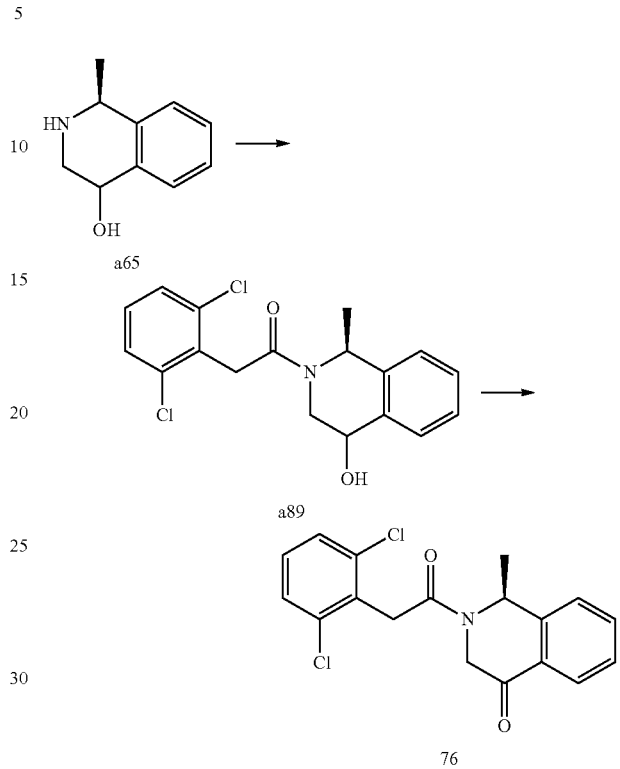

C.36.1. Synthesis of 2-(2,6-dichlorophenyl)-1-[(1S)-4-hydroxy-1-methyl-3,4-dihydroisoquinolin-2(1H)-yl]ethanone a89

Compound a89 may be synthesized according to a method analogous to Method A using (1S)-1-methyl-1,2,3,4-tetrahydroisoquinolin-4-ol a65 and (2,6-dichlorophenyl)acetic acid as starting materials. Conditions: DMF, DIPEA (2.5 eq), rt, overnight. Purification conditions: reverse phase chromatography (basic mode, LCMS prep).

Yield: 60%.

LCMS (ES⁺): 350/352/354 (M+H)⁺, 100% purity.

C.36.2. Synthesis of ((1S)-2-[(2,6-dichlorophenyl)acetyl]-1-methyl-2,3-dihydroisoquinolin-4(1H)-one 76

2-(2,6-Dichlorophenyl)-1-[(1S)-4-hydroxy-1-methyl-3,4-dihydroisoquinolin-2(1H)-yl]ethanone a89 (30 mg, 86 µmol) and Dess-Martin periodinane (102 mg, 0.24 mmol) were dissolved in DCM (7 mL) at rt. The mixture was stirred at rt for 40 h, then filtered and concentrated under vacuum. The residue was purified by reverse phase chromatography (basic mode, LCMS prep) to yield 8 mg of ((1S)-2-[(2,6-dichlorophenyl)acetyl]-1-methyl-2,3-dihydroisoquinolin-4(1H)-one 76 as an off-white solid glass.

Yield: 28%.

LCMS (ES⁺): 348/350/352 (M+H)⁺, 92% purity.

C.37. Synthesis of 2-{2,6-dichloro-4-[methylsulfinyl]phenyl}-1-[(1S)-1-methyl-3,4-dihydroisoquinolin-2(1H)-yl]ethanone isomer 77

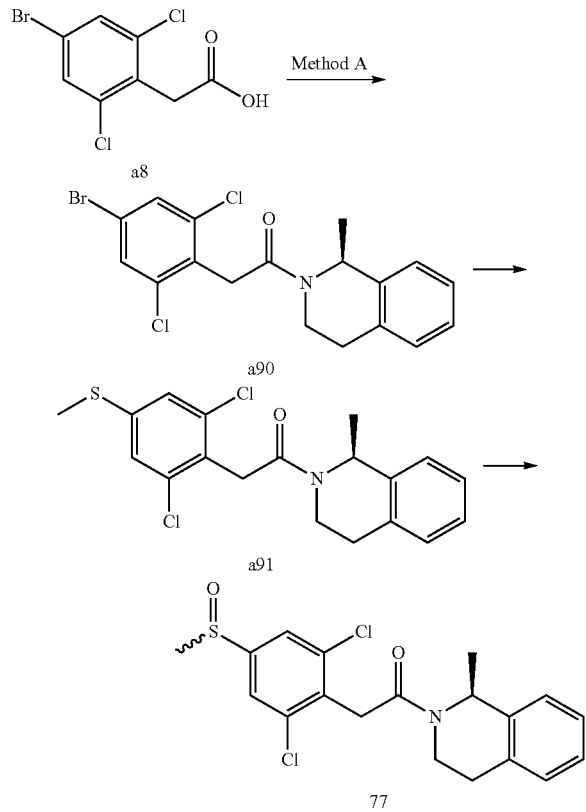

C.37.1. Synthesis of 2-(4-bromo-2,6-dichlorophenyl)-1-[(1S)-1-methyl-3,4-dihydroisoquinolin-2(1H)-yl]ethanone a90

Compound a90 may be synthesized according to a method analogous to Method A using (4-bromo-2,6-dichlorophenyl) acetic acid a8 and (1S)-1-methyl-1,2,3,4-tetrahydroisoquinoline. Conditions: DCM, TEA (3 eq), rt, overnight. Purification conditions: column chromatography using 0 to 4% MeOH in DCM.
Yield: 90%.
LCMS (ES$^+$): 412/414/416 (M+H)$^+$.

C.37.2. Synthesis of 2-[2,6-dichloro-4-(methylsulfanyl)phenyl]-1-[(1S)-1-methyl-3,4-dihydroisoquinolin-2(1H)-yl]ethanone a91

2-(4-Bromo-2,6-dichlorophenyl)-1-[(1S)-1-methyl-3,4-dihydroisoquinolin-2(1H)-yl]ethanone a90 (400 mg, 0.97 mmol) and methylsulfanylsodium (238 mg, 3.4 mmol) were dissolved in toluene (10 mL) at rt. DIPEA (250 mg, 1.94 mmol), 4,5-bis(diphenylphosphino)-9,9-dimethylxanthene (114 mg, 0.19 mmol) and tris(dibenzylideneacetone)dipalladium(0) (89 mg, 97 µmol) were added and the mixture was stirred under microwave irradiation at 150° C. for 80 min. The reaction mixture was taken up with DCM (25 mL), then washed twice with an aqueous saturated solution of NaHCO$_3$. The organic layer was dried over MgSO$_4$, filtered and concentrated under vacuum. The residue was purified by column chromatography using from 0 to 2% MeOH in DCM to yield 222 mg of 2-[2,6-dichloro-4-(methylsulfanyl)phenyl]-1-[(1S)-1-methyl-3,4-dihydroisoquinolin-2(1H)-yl]ethanone a91.
Yield: 60%.
LCMS (ES$^+$):380/382/384 (M+H)$^+$.

C.37.3. Synthesis of 2-{2,6-dichloro-4-[methylsulfinyl]phenyl}-1-[(1S)-1-methyl-3,4-dihydroisoquinolin-2(1H)-yl]ethanone isomer 77

2-[2,6-dichloro-4-(methylsulfanyl)phenyl]-1-[(1S)-1-methyl-3,4-dihydroisoquinolin-2(1H)-yl]ethanone a91 (180 mg, 0.47 mmol) was dissolved in DCM (10 mL). The mixture was cooled to 0° C. and 3-chloroperoxybenzoic acid (53 mg, 0.24 mmol) was added. The reaction mixture was stirred at 0° C. for 30 min, then taken up with DCM (25 mL) and washed twice with an aqueous saturated solution of NaHCO$_3$. The organic layer was dried over MgSO$_4$, filtered and concentrated under vacuum. The residue was purified by column chromatography (SiO$_2$), using from 0 to 4% MeOH in DCM to yield 95 mg of racemate 2-{2,6-dichloro-4-[methylsulfinyl]phenyl}-1-[(1S)-1-methyl-3,4-dihydroisoquinolin-2(1H)-yl]ethanone as a yellow gum (Yield: 51%). Chiral separation (SFC, Chiralpak AS, 50*265 mm, 360 mL/min, 220 nm, 40° C., eluent: 20% iPrOH for 18 min., then 30% iPrOH for 24 min., then 40% iPrOH for 27 min.), followed by reverse phase chromatography (basic mode, LCMS prep) yielded 7 mg of 2-{2,6-dichloro-4-[methylsulfinyl]phenyl}-1-[(1S)-1-methyl-3,4-dihydroisoquinolin-2(1H)-yl]ethanone isomer 77 as a white solid.
Yield: 15%.
LCMS (ES$^+$): 396/398/400 (M+H)$^+$, 100% purity.
Chiral analysis (LC, Chiralpak AS-H, 250*4.6 mm, 1 mL/min, 220 nm, 30° C., eluent: iPrOH/n-heptane/DEA 50/50/0.1) RT 13.9 min, (Other enantiomer at 9.98 min), 100% ee.

C.38. Synthesis of [2-(2,6-dichlorophenyl)-1-[(1S)-5-(N-cyano-S-methylsulfonimidoyl)-1-methyl-3,4-dihydroisoquinolin-2(1H)-yl]ethanone 78

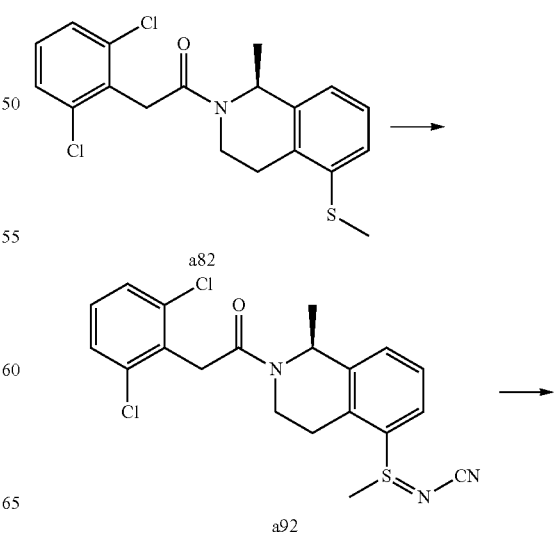

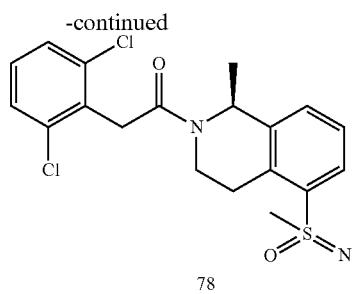

78

C.38.1. Synthesis of [{(1S)-2-[(2,6-dichlorophenyl)acetyl]-1-methyl-1,2,3,4-tetrahydroisoquinolin-5-yl}(methyl)-$\lambda^4$-sulfanylidene]cyanamide a92

2-(2,6-dichlorophenyl)-1-[(1S)-1-methyl-5-(methylsulfanyl)-3,4-dihydroisoquinolin-2(1H)-yl]ethanone a82 (900 mg, 2.34 mmol), cyanamide (130 mg, 3.10 mmol), N-bromosuccinimide (957 mg, 5.32 mmol) and potassium tert-butoxide (407 mg, 4.5 mmol) were mixed in MeOH (20 mL). The mixture was stirred at rt for 42 h, then diluted with DCM (200 mL) and successively washed with an aqueous saturated solution of sodium thiosulfate (50 mL) and brine (50 mL). The organic layer was dried over MgSO$_4$, filtered and concentrated under vacuum. The residue was purified by column chromatography using 0 to 5% MeOH in DCM as eluent. Trituration in Et$_2$O yielded 995 mg of [{(1S)-2-[(2,6-dichlorophenyl)acetyl]-1-methyl-1,2,3,4-tetrahydroisoquinolin-5-yl}(methyl)-$\lambda^4$-sulfanylidene]cyanamide a92 (mixture of diastereoisomers) as a white solid.

Yield: 100%.

LCMS (ES$^+$): 420/422/424 (M+H)$^+$.

C.38.2. Synthesis of [2-(2,6-dichlorophenyl)-1-[(1S)-5-(N-cyano-S-methylsulfonimidoyl)-1-methyl-3,4-dihydroisoquinolin-2(1H)-yl]ethanone 78

The mixture of diastereoisomers [{(1S)-2-[(2,6-dichlorophenyl)acetyl]-1-methyl-1,2,3,4-tetrahydroisoquinolin-5-yl}(methyl)-$\lambda^4$-sulfanylidene]cyanamide a92 (100 mg, 0.24 mmol), 3-chloroperoxybenzoic acid (80 mg, 0.36 mmol) and potassium carbonate (100 mg, 0.71 mmol) were mixed in EtOH (1 mL). The mixture was stirred at rt for 48 h, then diluted with DCM (150 mL) and successively washed with an aqueous saturated solution of sodium thiosulfate (50 mL) and brine (50 mL). The organic layer was dried over MgSO$_4$, filtered and concentrated under vacuum. The residue was purified by column chromatography using from 0 to 5% MeOH in DCM as eluent to yield 50 mg of [2-(2,6-dichlorophenyl)-1-[(1S)-5-(N-cyano-S-methylsulfonimidoyl)-1-methyl-3,4-dihydroisoquinolin-2(1H)-yl]ethanone 78 (mixture of diastereoisomers) as a white solid.

Yield: 48%.

LC-MS (ES$^+$): 436/438/440 (M+H)$^+$, 100% purity.

C.39. Synthesis of [2-(2,6-dichlorophenyl)-1-[(1S)-5-(N,S-dimethylsulfonimidoyl)-1-methyl-3,4-dihydroisoquinolin-2(1H)-yl]ethanone 79 and isomers 146 and 147

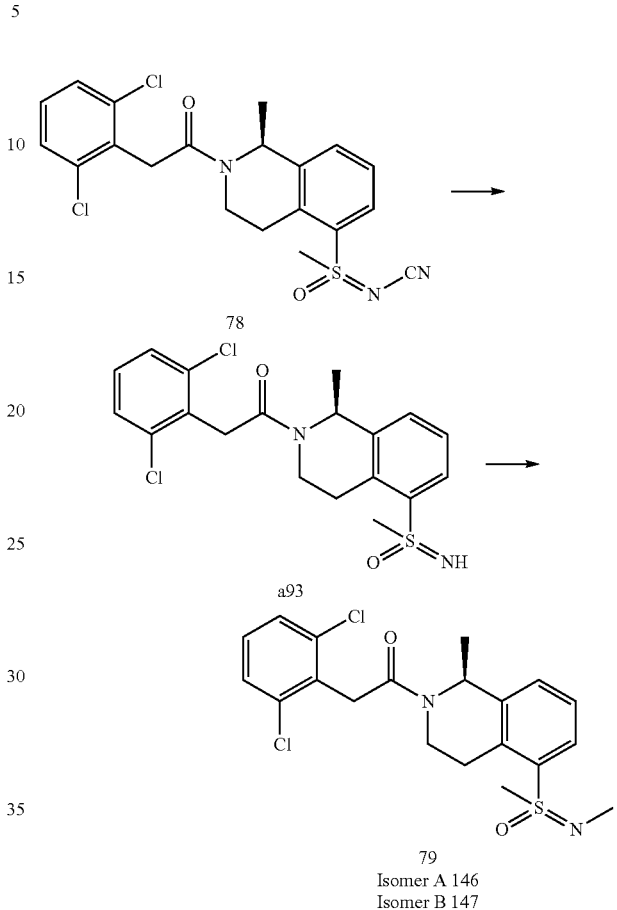

79
Isomer A 146
Isomer B 147

C.39.1. Synthesis of 2-(2,6-dichlorophenyl)-1-[(1S)-1-methyl-5-(S-methylsulfonimidoyl)-3,4-dihydroisoquinolin-2(1H)-yl]ethanone a93

The mixture of diastereoisomers [2-(2,6-dichlorophenyl)-1-[(1S)-5-(N-cyano-S-methylsulfonimidoyl)-1-methyl-3,4-dihydroisoquinolin-2(1H)-yl]ethanone 78 (436 mg, 1.00 mmol) was dissolved in a 50% aqueous solution of sulfuric acid (4 mL). The mixture was stirred at 100° C. for 4 h. The reaction mixture was cooled to rt, then diluted with EtOAc (50 mL) and washed thrice with a 1N aqueous solution of HCl (50 mL). The aqueous layer was basified with solid sodium bicarbonate and extracted thrice with DCM (50 mL). The organic layer was dried over MgSO$_4$, filtered and concentrated under vacuum. The residue was purified by reverse phase chromatography (basic mode, LCMS prep) to yield 120 mg of 2-(2,6-dichlorophenyl)-1-[(1S)-1-methyl-5-(S-methylsulfonimidoyl)-3,4-dihydroisoquinolin-2(1H)-yl]ethanone a93 (mixture of diastereoisomers) as a white solid.

Yield: 29%.

LCMS (ES$^+$): 411/413/415 (M+H)$^+$.

C.39.2. Synthesis of 2-(2,6-dichlorophenyl)-1-[(1S)-5-(N,S-dimethylsulfonimidoyl)-1-methyl-3,4-dihydroisoquinolin-2(1H)-yl]ethanone 79

The mixture of diastereoisomers 2-(2,6-dichlorophenyl)-1-[(1S)-1-methyl-5-(S-methyl-sulfonimidoyl)-3,4-dihydroisoquinolin-2(1H)-yl]ethanone a93 (55 mg, 0.13 mmol) was dissolved in a mixture of of an aqueous solution of formaldehyde (1.5 mL) and formic acid (0.5 mL). The mixture is stirred at 70° C. during 8 days, then diluted with water and basified with an aqueous saturated solution of sodium bicarbonate. The organic layer was extracted with DCM and eluted through a SPE cartridge, and the filtrate was concentrated under vacuum to provide 60 mg of 2-(2,6-dichlorophenyl)-1-[(1S)-5-(N,S-dimethylsulfonimidoyl)-1-methyl-3,4-dihydroisoquinolin-2(1H)-yl]ethanone 79 (Yield: 12%, LCMS (ES⁺): 425/427/429 (M+H)⁺).)

Chiral separation (SFC, Chiralpak IC, 78*380 mm, 200 mL/min, 220 nm, 30° C., eluent: from 100% EtOH), followed by reverse phase chromatography (basic mode, LCMS prep) afforded:

12 mg of 2-(2,6-dichlorophenyl)-1-[(1S)-5-(N,S-dimethylsulfonimidoyl)-1-methyl-3,4-dihydroisoquinolin-2(1H)-yl]ethanone isomer A 146 as a colorless oil.
Yield: 21%.
LCMS (ES⁺): 425/427/429 (M+H)⁺, 100% purity.
Chiral analysis (LC, Chiralpak IC, 250*4.6 mm, 1 mL/min, 220 nm, 30° C., eluent: EtOH/DEA 100/0.1): RT 9.88 min, 100% ee.

7 mg of 2-(2,6-dichlorophenyl)-1-[(1S)-5-(N,S-dimethylsulfonimidoyl)-1-methyl-3,4-dihydroisoquinolin-2(1H)-yl]ethanone isomer B 147 as a colorless oil.
Yield: 12%.
LCMS (ES⁺): 425/427/429 (M+H)⁺, 98% purity.
Chiral analysis (LC, Chiralpak IC, 250*4.6 mm, 1 mL/min, 220 nm, 30° C., eluent: EtOH/DEA 100/0.1) RT 13.42 min, 97.8% ee.

C.40. Synthesis of (1S)-2-[(2,6-dichlorophenyl)acetyl]-N,N,1-trimethyl-1,2,3,4-tetrahydroisoquinoline-5-sulfinamide 80

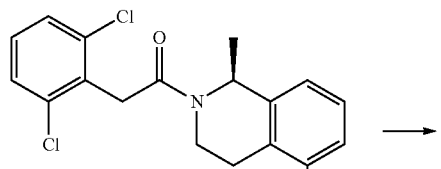

2-(2,6-Dichlorophenyl)-1-[(1S)-1-methyl-5-(S-methylsulfonimidoyl)-3,4-dihydroisoquinolin-2(1H)-yl]ethanone a93 (45 mg, 0.11 mmol) was dissolved in ACN (1 mL) at rt. Iodomethane (14 µl, 0.22 mmol) was added and the mixture was stirred at 50° C. for 4 h. The reaction mixture was cooled to rt, quenched with an aqueous saturated solution of sodium carbonate (50 mL) and extracted thrice with DCM (50 mL). The organic layer was dried over MgSO₄, filtered and concentrated under vacuum. The residue was purified by reverse phase chromatography (basic mode, LCMS prep) to yield 5 mg of (1S)-2-[(2,6-dichlorophenyl)acetyl]-N,N,1-trimethyl-1,2,3,4-tetrahydroisoquinoline-5-sulfinamide 80 as a white solid.
Yield: 10%.
LCMS (ES⁺): 425/427/429 (M+H)⁺, 90% purity.

C.41. Synthesis of 2-(2,6-dichlorophenyl)-1-[(1S)-1-methyl-5-[methylsulfinyl]-3,4-dihydroisoquinolin-2(1H)-yl]ethanone isomers 81 & 82

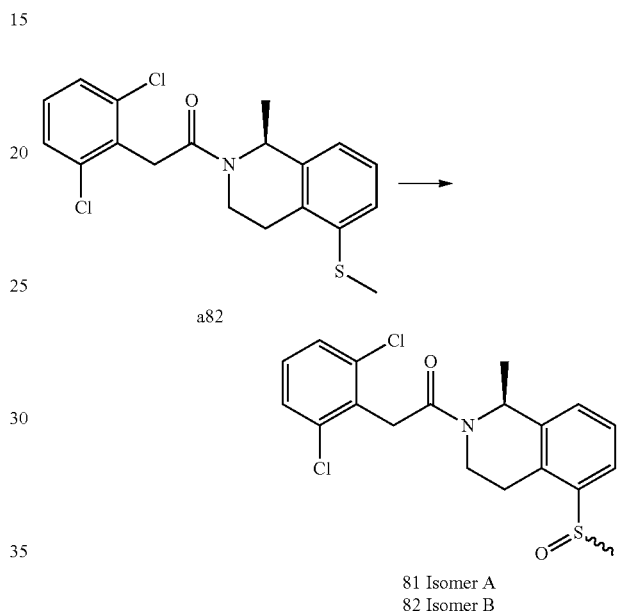

81 Isomer A
82 Isomer B 2-(2,6-Dichlorophenyl)-1-[(1S)-1-methyl-5-(methylsulfanyl)-3,4-dihydroisoquinolin-2(1H)-yl]ethanone a82 (90 mg, 0.24 mmol) was dissolved in a mixture of water and acetone (1:10, 22 mL). Oxone® (145 mg, 0.24 mmol) was added at 0° C. The mixture was stirred for 40 h, then cooled to rt. The reaction mixture was diluted with EtOAc (100 mL), then successively washed with a 10% aqueous solution of sodium thiosulfate, a 1N aqueous solution of HCl, an aqueous saturated solution of sodium carbonate and brine. The organic layer was dried over MgSO₄, filtered and concentrated under vacuum. The residue was purified by reverse phase chromatography (basic mode, LCMS prep) followed by chiral separation (SFC, Chiralcel OD, 50*266 mm, 360 mL/min, 220 nm, 40° C., eluent: 20% iPrOH) to yield:

8 mg of 2-(2,6-dichlorophenyl)-1-[(1S)-1-methyl-5-[methylsulfinyl]-3,4-dihydroisoquinolin-2(1H)-yl]ethanone isomer A 81 as a beige solid,
Yield: 8%.
LCMS (ES⁺): 396/398/400 (M+H)⁺, purity 99.4%.
Chiral analysis (LC, Chiralcel OD-H, 250*4.6 mm, 1 mL/min, 220 nm, 30° C., eluent: iPrOH/n-heptane/DEA 50/50/0.1) RT 7.71 min, 100% ee.

8 mg of 2-(2,6-dichlorophenyl)-1-[(1S)-1-methyl-5-[methylsulfinyl]-3,4-dihydroisoquinolin-2(1H)-yl]ethanone isomer B 82 as a beige solid.
Yield: 8%.
LCMS (ES⁺): 396/398/400 (M+H)⁺ purity 99.5%

Chiral analysis (LC, Chiralcel OD-H, 250*4.6 mm, 1 mL/min, 220 nm, 30° C., eluent: iPrOH/n-heptane/DEA 50/50/0.1) RT 9.45 min, 97% ee.

C.42. Synthesis of 2-(2,6-dichlorophenyl)-1-[(1S)-5-hydroxy-1-methyl-3,4-dihydroisoquinolin-2(1H)-yl]ethanone 83 & (1S)-2-[(2,6-dichlorophenyl)acetyl]-N,1-dimethyl-1,2,3,4-tetrahydroisoquinoline-5-sulfonamide 84

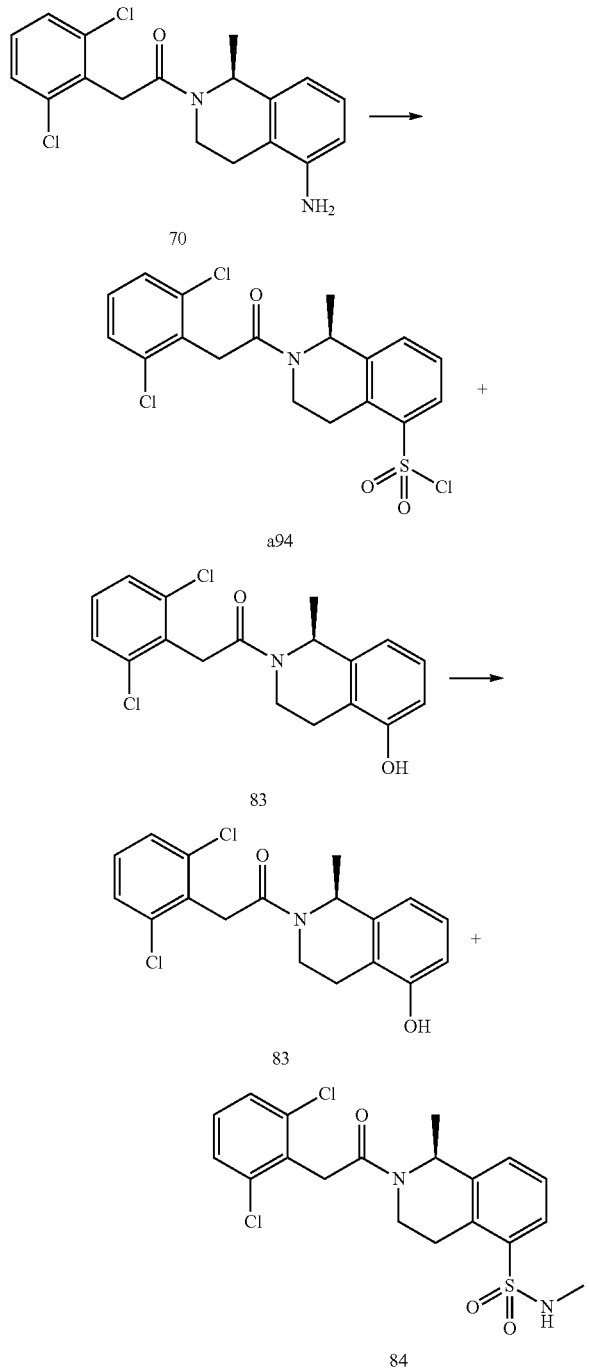 [SMILES: C[C@H]1c2cccc(N)c2CCN1C(=O)Cc1c(Cl)cccc1Cl ; C[C@H]1c2cccc(S(=O)(=O)Cl)c2CCN1C(=O)Cc1c(Cl)cccc1Cl ; C[C@H]1c2cccc(O)c2CCN1C(=O)Cc1c(Cl)cccc1Cl ; C[C@H]1c2cccc(O)c2CCN1C(=O)Cc1c(Cl)cccc1Cl ; CNS(=O)(=O)c1cccc2c1CCN(C(=O)Cc1c(Cl)cccc1Cl)[C@H]2C]

C.42.1. Synthesis of (1S)-2-[(2,6-dichlorophenyl)acetyl]-1-methyl-1,2,3,4-tetrahydroisoquinoline-5-sulfonyl chloride a94

Solution A was prepared as followed: thionyl chloride (122 μmL, 1.69 mmol) was added to water (2 mL) at 5° C. and the solution was stirring overnight at rt. Copper chloride (I) (30 mg, 0.31 mmol) was added and stirring at 5° C. was maintained.

To a solution of 1-[(1S)-5-amino-1-methyl-3,4-dihydroisoquinolin-2(1H)-yl]-2-(2,6-dichlorophenyl)ethanone 70 (107 mg, 0.31 mmol) in HCl 37% (2 mL) was added a solution of sodium nitrite (30 mg, 0.43 mmol) in water (10 mL) at 0° C. The reaction mixture was stirred at 0° C. for 15 min., then added dropwise at 5° C. to Solution A. The reaction mixture was stirred overnight at rt, then extracted thrice with DCM (20 mL). The organic layer was dried over $MgSO_4$, filtered and concentrated under vacuum to yield 170 mg of a mixture of (1S)-2-[(2,6-dichlorophenyl)acetyl]-1-methyl-1,2,3,4-tetrahydroisoquinoline-5-sulfonyl chloride a94 (LCMS: 432/434/436 (M+H$^+$)) and 2-(2,6-dichlorophenyl)-1-[(1S)-5-hydroxy-1-methyl-3,4-dihydroisoquinolin-2(1H)-yl]ethanone 83 ((LCMS: 350/352/354 (M+H$^+$)) in a 20:80 ratio. The crude mixture was used without further purification for the next step.

C.42.2. Synthesis of 2-(2,6-dichlorophenyl)-1-[(1S)-5-hydroxy-1-methyl-3,4-dihydroisoquinolin-2(1H)-yl]ethanone 83 and (1S)-2-[(2,6-dichlorophenyl)acetyl]-N,1-dimethyl-1,2,3,4-tetrahydroisoquinoline-5-sulfonamide 84

To a 20:80 mixture of a94 and 83 (170 mg) in DCM (5 mL) was added a solution of methylamine in EtOH (33%, 84 μL, 0.65 mmol) at rt. The mixture was stirred overnight at rt, then washed with brine and extracted thrice with DCM (10 mL). The organic layer was dried over $MgSO_4$, filtered and concentrated under vacuum. The residue was purified by reverse phase chromatography (acidic mode, LC-MS prep), followed by chiral separation (SFC, Chiralpak AS, 50*265 mm, 360 mL/min, 220 nm, 40° C., eluent: 20% MeOH) to yield:

6 mg of 2-(2,6-dichlorophenyl)-1-[(1S)-5-hydroxy-1-methyl-3,4-dihydroisoquinolin-2(1H)-yl]ethanone 83 as a red solid Yield: 5.6%.

LCMS (ES+): 350/352/354 (M+H)+, 99% purity.

Chiral analysis (LC, Chiralpak AS-H, 250*4.6 mm, 1 mL/min, 220 nm, 30° C., eluent: EtOH/DEA 100/0.1) RT 3.58 min, 97.9% ee.

4.5 mg of (1S)-2-[(2,6-dichlorophenyl)acetyl]-N,1-dimethyl-1,2,3,4-tetrahydroisoquinoline-5-sulfonamide 84 as a yellow oil Yield: 3%.

LCMS (ES$^+$): 427/429/431 (M+H)$^+$, 90% purity.

Chiral analysis (LC, Chiralpak AS-H, 250*4.6 mm, 1 mL/min, 220 nm, 30° C., eluent: EtOH/DEA 100/0.1) RT 4.84 min, 100% ee.

C.43. Synthesis of 2-[2-chloro-6-(methylsulfanyl)phenyl]-1-[(1S)-1-methyl-3,4-dihydroisoquinolin-2(1H)-yl]ethanone 85

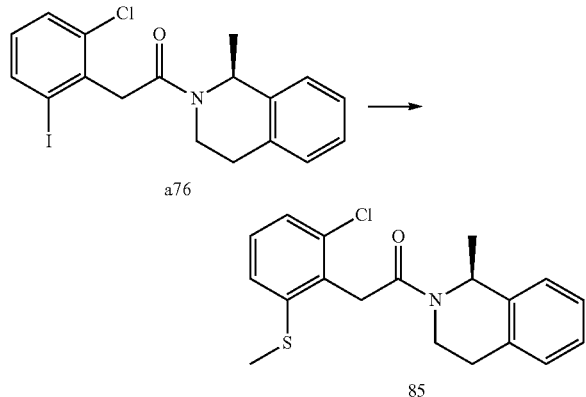

Sodium methoxide (89 mg, 5.87 mmol), 4,5-bis(diphenylphosphino)-9,9-dimethylxanthene (28 mg, 0.23 mmol), tris(dibenzylideneacetone) dipalladium(0) (22 mg, 0.12 mmol), DIPEA (409 µL, 2.35 mmol) and 2-(2-chloro-6-iodophenyl)-1-[(1S)-1-methyl-3,4-dihydroisoquinolin-2(1H)-yl]ethanone a76 (500 mg, 1.17 mmol) were dissolved in toluene (8 mL) at rt. The mixture was stirred at 150° C. for 15 min under microwave irradiation. The reaction mixture was cooled to rt, filtered and concentrated under vacuum to yield 630 mg of crude 2-[2-chloro-6-(methylsulfanyl)phenyl]-1-[(1S)-1-methyl-3,4-dihydroisoquinolin-2(1H)-yl]ethanone 85 used in the next step without any further purification.

Purification by reverse phase chromatography (basic mode, LCMS prep) of 20 mg of this crude afforded 15 mg of pure 2-[2-chloro-6-(methylsulfanyl)phenyl]-1-[(1S)-1-methyl-3,4-dihydroisoquinolin-2(1H)-yl]ethanone 85 as a beige oil.

LCMS (ES+): 346/348 (M+H)+, 97.6% purity.

C.44. Synthesis of 2-[2-chloro-6-(methylsulfinyl)phenyl]-1-[(1S)-1-methyl-3,4-dihydroisoquinolin-2(1H)-yl]ethanone 86 and 2-[2-chloro-6-(methylsulfonyl)phenyl]-1-[(1S)-1-methyl-3,4-dihydroisoquinolin-2(1H)-yl]ethanone 87

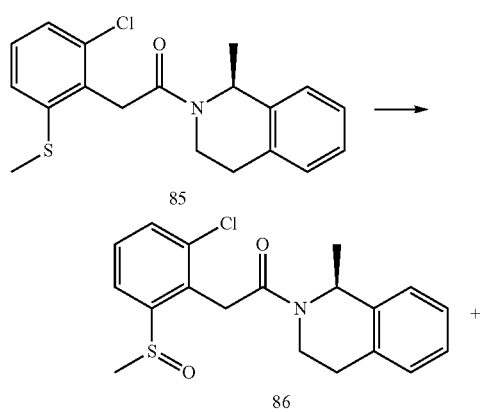

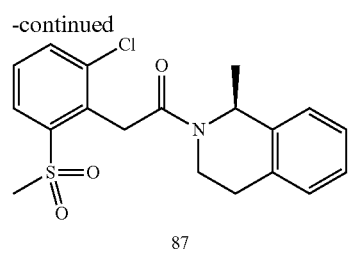

2-[2-chloro-6-(methylsulfanyl)phenyl]-1-[(1S)-1-methyl-3,4-dihydroisoquinolin-2(1H)-yl]ethanone 85 (200 mg, 0.58 mmol) was dissolved in DCM (10 mL) at rt. 3-Chloroperoxybenzoic acid (199 mg, 0.87 mmol) was added. The mixture was stirred at rt for 1 h, then quenched with an aqueous saturated solution of NaHCO$_3$ and extracted thrice with DCM. The organic layer was dried over Na$_2$SO$_4$, filtered and concentrated under vacuum. The residue was purified by reverse phase chromatography (basic mode, LCMS prep) to yield:

115 mg of 2-[2-chloro-6-(methylsulfinyl)phenyl]-1-[(1S)-1-methyl-3,4-dihydroisoquinolin-2(1H)-yl]ethanone 86 as an off-white solid.
Yield: 55%.
LCMS (ES+): 362/364 (M+H)+, 95.3% purity.

30 mg of 2-[2-chloro-6-(methylsulfonyl)phenyl]-1-[(1S)-1-methyl-3,4-dihydroisoquinolin-2(1H)-yl]ethanone 87 as an off-white solid.
Yield: 14%.
LCMS (ES+): 378/380 (M+H)+, 89% purity.

C.45. Synthesis of 2-[5-chloro-1-(methylsulfonyl)-1H-pyrrolo[2,3-b]pyridin-4-yl]-1-[(1S)-1-methyl-3,4-dihydroisoquinolin-2(1H)-yl]ethanone trifluoroacetate 88

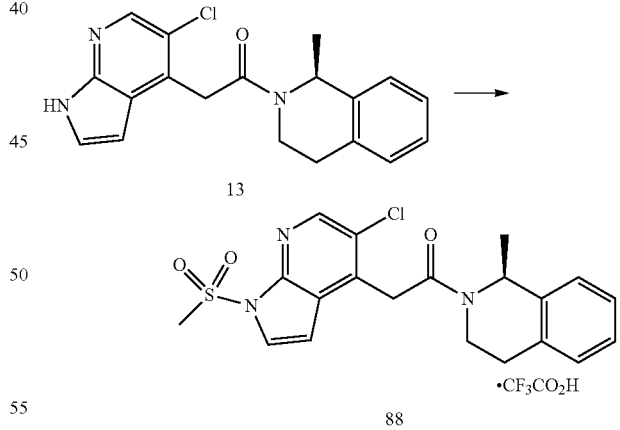

Methanesulfonyl chloride (3 µL, 38.95 µmol) was dissolved in DCM (1 mL) at rt, then DIPEA (10 µL, 57.51 µmol) and 2-(5-chloro-1H-pyrrolo[2,3-b]pyridin-4-yl)-1-[(1S)-1-methyl-3,4-dihydroisoquinolin-2(1H)-yl]ethanone 13 (13 mg, 38.26 mmol) were added. The mixture was stirred at rt for 280 h, then quenched with water and extracted twice with DCM. The organic layer was washed with an aqueous saturated solution of NaHCO$_3$, dried over Na$_2$SO$_4$, filtered and concentrated under vacuum. The residue was purified by reverse phase chromatographies (basic mode, followed by acidic mode, LC-MS prep) to yield 6 mg of 2-[5-chloro-1-(methylsulfonyl)-1H-pyrrolo[2,3-b]pyridin-4-yl]-1-[(1S)-1-methyl-3,4-dihydroisoquinolin-2(1H)-yl]ethanone trifluoroacetate 88 as a brown oil.

Yield: 31%.

LCMS (ES⁺): 418/420 (M+H)⁺, 88.6% purity.

C.46. Synthesis of 3,5-dichloro-4-{2-[(1S)-1-methyl-3,4-dihydroisoquinolin-2(1H)-yl]-2-oxoethyl}pyridin-2(1H)-one 89

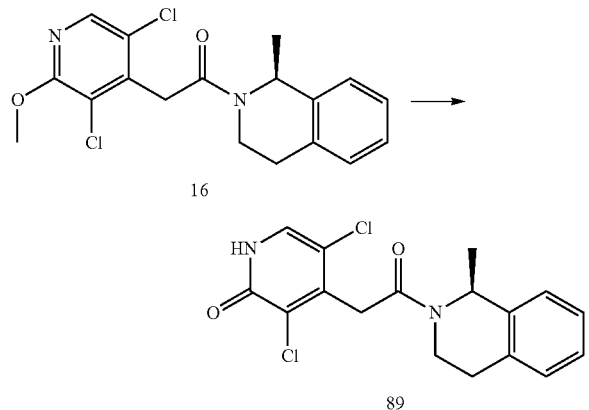 [SMILES: COc1ncc(Cl)c(CC(=O)N2CCc3ccccc3[C@@H]2C)c1Cl ; C[C@H]1c2ccccc2CCN1C(=O)Cc1c(Cl)c[nH]c(=O)c1Cl]

2-(3,5-dichloro-2-methoxypyridin-4-yl)-1-[(1S)-1-methyl-3,4-dihydroisoquinolin-2(1H)-yl]ethanone 16 (100 mg, 0.27 mmol) was dissolved in ACN (10 mL), then sodium iodide (41 mg, 0.27 mmol) and chlorotrimethylsilane (40 µL, 0.27 mmol) were added at rt. The mixture was stirred overnight at rt. Additional amounts of sodium iodide (41 mg, 0.27 mmol) and chlorotrimethylsilane (40 µL, 0.27 mmol) were added. The reaction mixture was stirred at rt for 2 days, then concentrated under vacuum. The residue was purified by reverse phase chromatography (basic mode, standard LC), then triturated in Et₂O to yield 83 mg of 3,5-dichloro-4-{2-[(1S)-1-methyl-3,4-dihydroisoquinolin-2(1H)-yl]-2-oxoethyl}pyridin-2(1H)-one 89 as a beige solid.

Yield: 85%.

LCMS (ES⁺): 351/353/355 (M+H)⁺, 100% purity.

C.47. Synthesis of 2-(2,6-dichlorophenyl)-1-[(1S)-1-methyl-5-(propan-2-ylsulfonyl)-3,4-dihydroisoquinolin-2(1H)-yl]ethanone 90

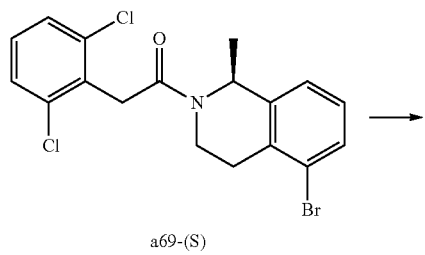

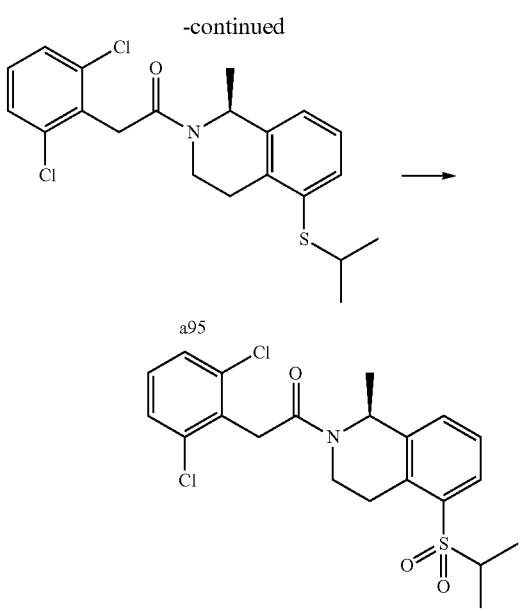

C.47.1. Synthesis of 2-(2,6-dichlorophenyl)-1-[(1S)-1-methyl-5-(propan-2-ylsulfanyl)-3,4-dihydroisoquinolin-2(1H)-yl]ethanone a95

1-[(1S)-5-bromo-1-methyl-3,4-dihydroisoquinolin-2(1H)-yl]-2-(2,6-dichlorophenyl)ethanone a69-(S) (200 mg, 0.48 mmol), tris(dibenzylideneacetone) dipalladium(0) (22 mg, 24 µmol), 4,5-bis(diphenylphosphino)-9,9-dimethylxanthene (28 mg, 50 µmol), DIPEA (169 µL, 0.97 mmol), sodium hydride (60% suspension in oil, 97 mg, 2.40 mmol) and 2-propanethiol (184 mg, 2.40 mmol) were mixed together in toluene (2 mL) at rt. The mixture was stirred at 150° C. for 2 h under microwave irradiation. The reaction mixture was cooled to rt, then diluted with EtOAc (250 mL) and successively washed with water (50 mL), a 1N aqueous solution of HCl, an aqueous saturated solution of sodium carbonate (50 mL) and brine (50 mL). The organic layer was dried over MgSO₄, filtered and concentrated under vacuum to yield 200 mg of crude 2-(2,6-dichlorophenyl)-1-[(1S)-1-methyl-5-(propan-2-ylsulfanyl)-3,4-dihydroisoquinolin-2(1H)-yl]ethanone a95 which was used in the next step without any further purification.

Yield: 100% (crude).

LCMS (ES⁺): 394/396/398 (M+H)⁺.

2-(2,6-dichlorophenyl)-1-[(1S)-5-(ethylsulfanyl)-1-methyl-3,4-dihydroisoquinolin-2(1H)-yl]ethanone a96 may be synthesized according to the method described above using a69-(S) and ethanethiol as starting materials.

Yield: 100% (crude).

LCMS (ES⁺): 394/396/398 (M+H)⁺.

C.47.2. Synthesis of 2-(2,6-dichlorophenyl)-1-[(1S)-1-methyl-5-(propan-2-ylsulfonyl)-3,4-dihydroisoquinolin-2(1H)-yl]ethanone 90

Crude 2-(2,6-dichlorophenyl)-1-[(1S)-1-methyl-5-(propan-2-ylsulfanyl)-3,4-dihydroisoquinolin-2(1H)-yl]ethanone a95 (200 mg, 0.40 mmol) and 3-chloroperoxybenzoic acid (300 mg, 1 mmol) were dissolved in chloroform (5 mL). The mixture was stirred at rt for 16 h, diluted with DCM (150 mL) and washed with an aqueous saturated solution of sodium carbonate (50 mL). The organic layer was dried over MgSO$_4$, filtered and concentrated under vacuum. The residue was purified by reverse phase chromatography (basic mode, LCMS prep) to yield 20 mg of 2-(2,6-dichlorophenyl)-1-[(1S)-1-methyl-5-(propan-2-ylsulfonyl)-3,4-dihydroisoquinolin-2(1H)-yl]ethanone 90 as a white solid.

Yield: 10%.

LCMS (ES$^+$): 440/442/444 (M+H)$^+$, 99.5% purity.

2-(2,6-Dichlorophenyl)-1-[(1S)-5-(ethylsulfonyl)-1-methyl-3,4-dihydroisoquinolin-2(1H)-yl]ethanone 91 may be synthesized according to the method described above using a96 as starting material. Purification by reverse phase chromatography (basic mode, LCMS prep) yielded 120 mg of 2-(2,6-dichlorophenyl)-1-[(1S)-5-(ethylsulfonyl)-1-methyl-3,4-dihydroisoquinolin-2(1H)-yl]ethanone 91 as an off-white solid.

Yield: 59%.

LCMS (ES$^+$): 426/428/430 (M+H)$^+$, 100% purity.

C.48. Synthesis of 3-methoxy-2-{2-[(1S)-1-methyl-3,4-dihydroisoquinolin-2(1H)-yl]-2-oxoethyl}benzonitrile 92

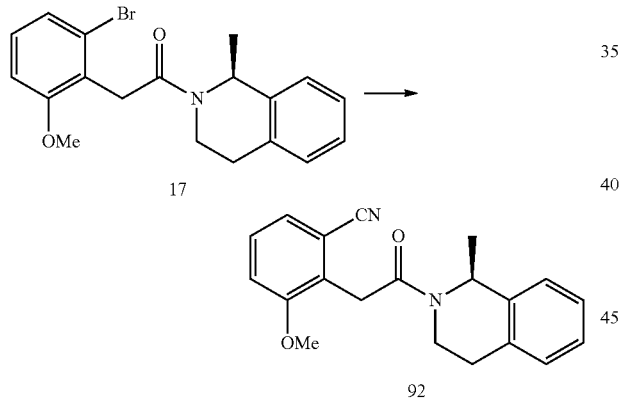

Under argon, 2-(2-bromo-6-methoxyphenyl)-1-[(1S)-1-methyl-3,4-dihydroisoquinolin-2(1H)-yl]ethanone 17 (100 mg, 0.27 mmol) was dissolved in DMF (5 mL). Tetrakis (triphenylphosphine)palladium(0) (31 mg, 27 µmol) and zinc cyanide (63 mg, 0.53 mmol) were added. The mixture was stirred at 150° C. for 1 h under microwave irradiation, then filtered. The filtrate was diluted with EtOAc, successively washed twice with an aqueous saturated solution of NaHCO$_3$ and brine. The organic layer was dried over MgSO$_4$, filtered and concentrated under vacuum. The residue was purified by reverse phase chromatography (basic mode, standard LC) to yield 28 mg of 3-methoxy-2-{2-[(1S)-1-methyl-3,4-dihydroisoquinolin-2(1H)-yl]-2-oxoethyl}benzonitrile 92 as a colorless oil.

Yield: 32%.

LCMS (ES$^+$): 321 (M+H)$^+$, 95% purity.

C.49. Synthesis of 2-{2-chloro-6-[(methylsulfonyl)methyl]phenyl}-1-[(1S)-1-methyl-3,4-dihydroisoquinolin-2(1H)-yl]ethanone 92b

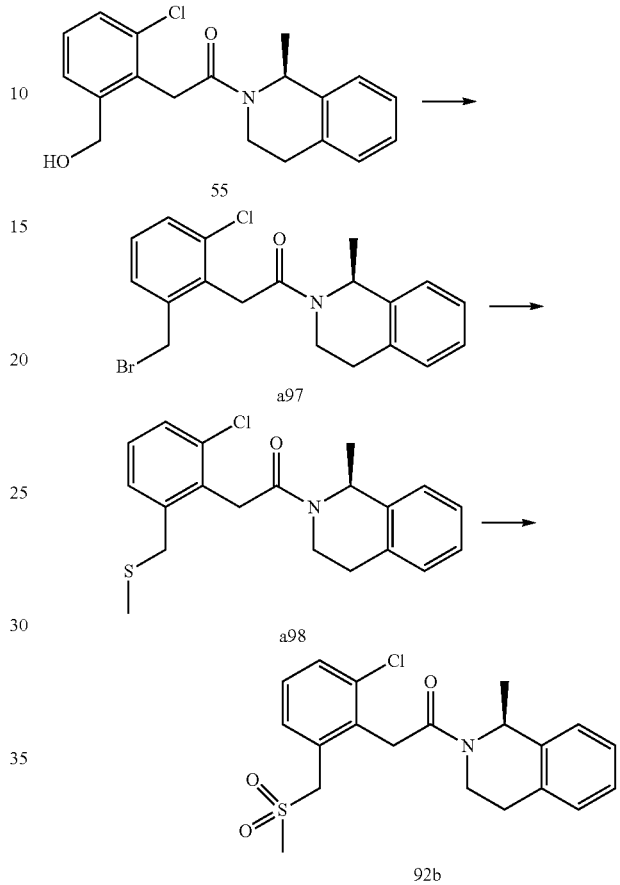

C.49.1. Synthesis of 2-[2-(bromomethyl)-6-chlorophenyl]-1-[(1S)-1-methyl-3,4-dihydro-1H-isoquinolin-2-yl]ethanone a97

2-[2-Chloro-6-(hydroxymethyl)phenyl]-1-[(1S)-1-methyl-3,4-dihydroisoquinolin-2(1H)-yl]ethanone 55 (340 mg, 1.03 mmol) was dissolved in DCM (20 mL) at rt. Phosphorus tribromide (307 mg, 1.13 mmol) was added dropwise at rt and the mixture was stirred overnight at rt. The reaction mixture was diluted with DCM (100 mL) and washed twice with an aqueous saturated solution of NaHCO$_3$. The organic layer was dried over MgSO$_4$, filtered and concentrated under vacuum to yield 390 mg of 2-[2-(bromomethyl)-6-chlorophenyl]-1-[(1S)-1-methyl-3,4-dihydroisoquinolin-2(1H)-yl]ethanone a97 which was used in the next step without any further purification.

Yield: 96% (crude).

LCMS (ES$^+$): 392/394/396 (M+H)$^+$.

C.49.2. Synthesis of 2-[2-chloro-6-(methylsulfanylmethyl)phenyl]-1-[(1S)-1-methyl-3,4-dihydro-1H-isoquinolin-2-yl]ethanone a98

2-[2-(bromomethyl)-6-chlorophenyl]-1-[(1S)-1-methyl-3,4-dihydroisoquinolin-2(1H)-yl]ethanone a97 (390 mg, 0.99 mmol) was dissolved in THF (15 mL) at rt. Sodium thiomethoxyde (73 mg, 0.99 mmol) was added. The mixture was stirred at rt overnight. The reaction mixture was taken up with DCM (100 mL) and washed twice with an aqueous saturated solution of NaHCO$_3$. The organic layer was dried over MgSO$_4$, filtered and concentrated under vacuum to yield 390 mg of 2-[2-chloro-6-(methylsulfanylmethyl)phenyl]-1-[(1S)-1-methyl-3,4-dihydro-1H-isoquinolin-2-yl]ethanone a98 which was used in the next step without any further purification.

Yield: 109% (crude).

LCMS (ES$^+$): 360/362 (M+H)$^+$.

C.49.3. Synthesis of 2-{2-chloro-6-[(methylsulfonyl)methyl]phenyl}-1-[(1S)-1-methyl-3,4-dihydroisoquinolin-2(1H)-yl]ethanone 92b 2-[2-chloro-6-(methylsulfanylmethyl)phenyl]-1-[(1S)-1-methyl-3,4-dihydro-1H-isoquinolin-2-yl]ethanone a98 (90 mg, 0.25 mmol) was dissolved in DCM (5 mL) and 3-chloroperoxybenzoic acid (140 mg, 0.62 mmol) was added. The mixture was stirred at rt for 2 h. The reaction mixture was taken up with DCM (25 mL) and washed with an aqueous saturated solution of NaHCO$_3$. The organic layer was dried over MgSO$_4$, filtered and concentrated under vacuum. The residue was purified by reverse phase chromatography (basic mode, LCMS prep) to yield 23 mg of 2-{2-chloro-6-[(methylsulfonyl)methyl]phenyl}-1-[(1S)-1-methyl-3,4-dihydroisoquinolin-2(1H)-yl]ethanone 92b as a white solid.

Yield: 24%.

LCMS (ES$^+$): 392/394 (M+H)$^+$, 96% purity.

C.50. Synthesis of 2-(2,6-dichlorophenyl)-1-[(1S)-1-methyl-5-[(methylsulfonyl)methyl]-3,4-dihydroisoquinolin-2(1H)-yl]ethanone 93

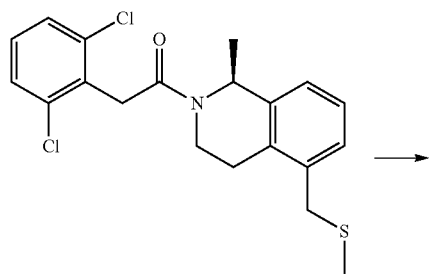

To a solution of 2-(2,6-dichlorophenyl)-1-[(1S)-1-methyl-5-[(methylsulfanyl)methyl]-3,4-dihydroisoquinolin-2(1H)-yl]ethanone 66 (165 mg, 0.42 mmol) in DCM (5 mL) and chloroperoxybenzoic acid (400 mg, 1.74 mmol). The mixture was stirred overnight at rt. The reaction mixture was taken up with DCM (100 mL) and successively washed with an aqueous saturated solution of NaHCO$_3$ (50 mL) and a 1N aqueous solution of HCl. The organic layer was dried over MgSO$_4$, filtered and concentrated under vacuum. The residue was purified by reverse phase chromatography (basic mode, LCMS prep) to yield 70 mg of 2-(2,6-dichlorophenyl)-1-[(1S)-1-methyl-5-[(methylsulfonyl)methyl]-3,4-dihydroisoquinolin-2(1H)-yl]ethanone 93 as a white solid.

Yield: 35%.

LCMS (ES$^+$): 426/428/430 (M+H)$^+$, 93% purity.

C.51. Synthesis of 2-(2,6-dichlorophenyl)-1-[(1S,4S)-4-methoxy-1-methyl-3,4-dihydroisoquinolin-2(1H)-yl]ethanone 94

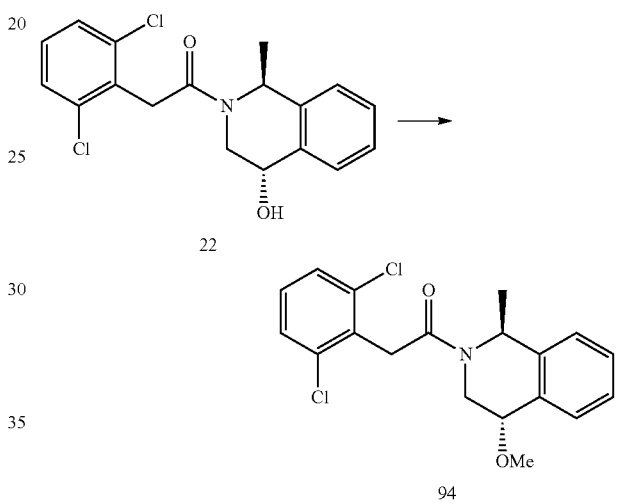

2-(2,6-dichlorophenyl)-1-[(1S,4S)-4-hydroxy-1-methyl-3,4-dihydroisoquinolin-2(1H)-yl]ethanone 22 (100 mg, 0.28 mmol) was dissolved in THF (5 mL) at rt, then sodium hydride (60% in mineral oil, 11 mg, 0.28 mmol) was added. The mixture was stirred at rt for 20 min and iodomethane (41 mg, 0.28 mmol) was added. The mixture was stirred at rt for 16 h. The reaction mixture was quenched with water and extracted twice with EtOAc. The organic layers was dried over Na$_2$SO$_4$, filtered and concentrated under vacuum. The residue was purified by reverse phase chromatography (basic mode, standard LC) to yield 69 mg of 2-(2,6-dichlorophenyl)-1-[(1S,4S)-4-methoxy-1-methyl-3,4-dihydroisoquinolin-2(1H)-yl]ethanone 94 as a beige oil.

Yield: 66%.

LCMS (ES$^+$): 364/366/368 (M+H)$^+$, 97.8% purity.

2-(2,6-Dichlorophenyl)-1-[(1S,4R)-4-methoxy-1-methyl-3,4-dihydroisoquinolin-2(1H)-yl]ethanone 95 may be synthesized according to the method described above using using 2-(2,6-dichlorophenyl)-1-[(1S,4R)-4-hydroxy-1-methyl-3,4-dihydroisoquinolin-2(1H)-yl]ethanone 20 as starting material. Purification by reverse phase chromatography (basic mode, standard LC) yielded 26 mg of 2-(2,6-dichlorophenyl)-1-[(1S,4R)-4-methoxy-1-methyl-3,4-dihydroisoquinolin-2(1H)-yl]ethanone 95 as a colorless oil.

Yield: 25%.

LCMS (ES$^+$): 364/366/368 (M+H)$^+$, 94% purity.

C.52. Synthesis of (1S,4S)-2-[(2,6-dichlorophenyl) acetyl]-1-methyl-1,2,3,4-tetrahydroisoquinolin-4-yl methylcarbamate 96

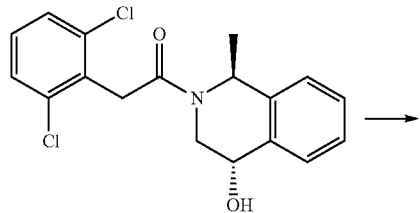

22

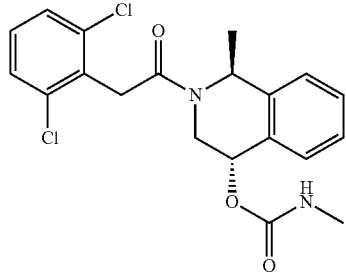

96

2-(2,6-Dichlorophenyl)-1-[(1S,4S)-4-hydroxy-1-methyl-3,4-dihydroisoquinolin-2(1H)-yl]ethanone 22 (100 mg, 0.28 mmol) was dissolved in THF (5 mL) at rt, then sodium hydride (60% in mineral oil, 11 mg, 0.28 mmol) was added. The mixture was stirred at rt for 20 min and (methylimino)(oxo)methane (18 mg, 0.31 mmol) was added. The mixture was stirred at rt for 64 h. The reaction mixture was quenched with water and extracted twice with EtOAc. The organic layer was dried over Na$_2$SO$_4$, filtered and concentrated under vacuum. The residue was purified by reverse phase chromatography (basic mode, standard LC) to yield 54 mg of (1S,4S)-2-[(2,6-dichlorophenyl)acetyl]-1-methyl-1,2,3,4-tetrahydroisoquinolin-4-yl methylcarbamate 96 as an off-white solid.

Yield: 47%.
LCMS (ES$^+$): 407/409/411 (M+H)$^+$, 95% purity.

C.53. Synthesis of (1S,4S)-2-[(2,6-dichlorophenyl) acetyl]-1-methyl-1,2,3,4-tetrahydroisoquinolin-4-yl methyl carbonate 97

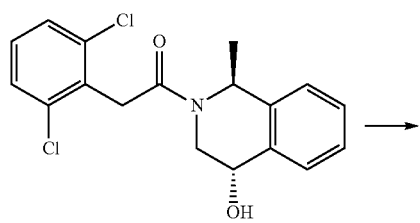

22

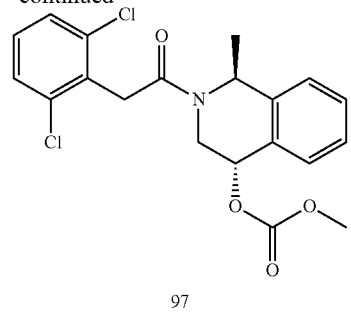

97

2-(2,6-Dichlorophenyl)-1-[(1S,4S)-4-hydroxy-1-methyl-3,4-dihydroisoquinolin-2(1H)-yl]ethanone 22 (100 mg, 0.28 mmol) was dissolved in DCM (5 mL) at rt, then DIPEA (61 μL, 0.60 mmol) and methyl chloroformate (23 μL, 0.91 mmol) were added. The mixture was stirred at rt for 10 days. The reaction mixture was quenched with water, washed with an aqueous saturated solution of NaHCO$_3$ and extracted thrice with DCM. The organic layer was dried over Na$_2$SO$_4$, filtered and concentrated under vacuum. The residue was purified by reverse phase chromatography (basic mode, standard LC) to yield 11 mg of (1S,4S)-2-[(2,6-dichlorophenyl)acetyl]-1-methyl-1,2,3,4-tetrahydroisoquinolin-4-yl methyl carbonate 97 as a colorless oil.

Yield: 9%.
LCMS (ES$^+$): 408/410/412 (M+H)$^+$, 96% purity.

C.54. Synthesis of (1S,4R)-2-[(2,6-dichlorophenyl) acetyl]-1-methyl-1,2,3,4-tetrahydroisoquinolin-4-yl methyl carbonate 98

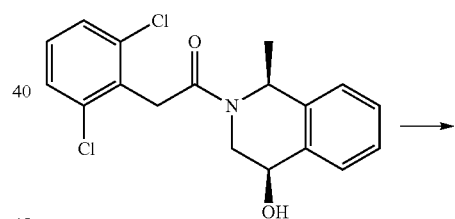

20

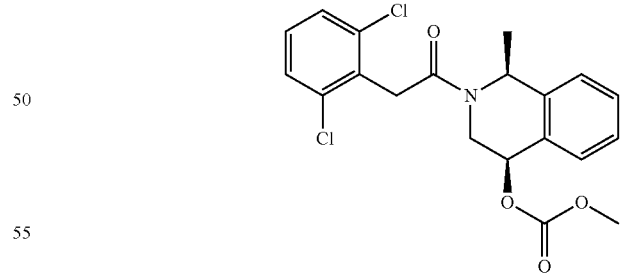

98

2-(2,6-Dichlorophenyl)-1-[(1S,4R)-4-hydroxy-1-methyl-3,4-dihydroisoquinolin-2(1H)-yl]ethanone 20 (100 mg, 0.28 mmol) was dissolved in THF (5 mL) at rt, then sodium hydride (60% in mineral oil, 25 mg, 0.63 mmol) was added. The mixture was stirred at rt for 20 min and methyl chloroformate (33 μL, 0.86 mmol) was added. The mixture was stirred at rt for 64 h. The reaction mixture was quenched with water and extracted thrice with EtOAc. The organic layer was dried over Na$_2$SO$_4$, filtered and concentrated under vacuum. The residue was purified by reverse phase chromatography (basic mode, standard LC) to yield 27 mg of (1S,4R)-2-[(2,6-dichlorophenyl)acetyl]-1-methyl-1,2,3,4-tetrahydroisoquinolin-4-yl methyl carbonate 98 as a colorless oil.

Yield: 23%.

LCMS (ES$^+$): 408/410/412 (M+H)$^+$, 93% purity.

C.55. Synthesis of 2-[2,6-dichloro-3-(hydroxymethyl)phenyl]-1-[(1S)-1-methyl-5-(methyl-sulfonyl)-3,4-dihydroisoquinolin-2(1H)-yl]ethanone 99

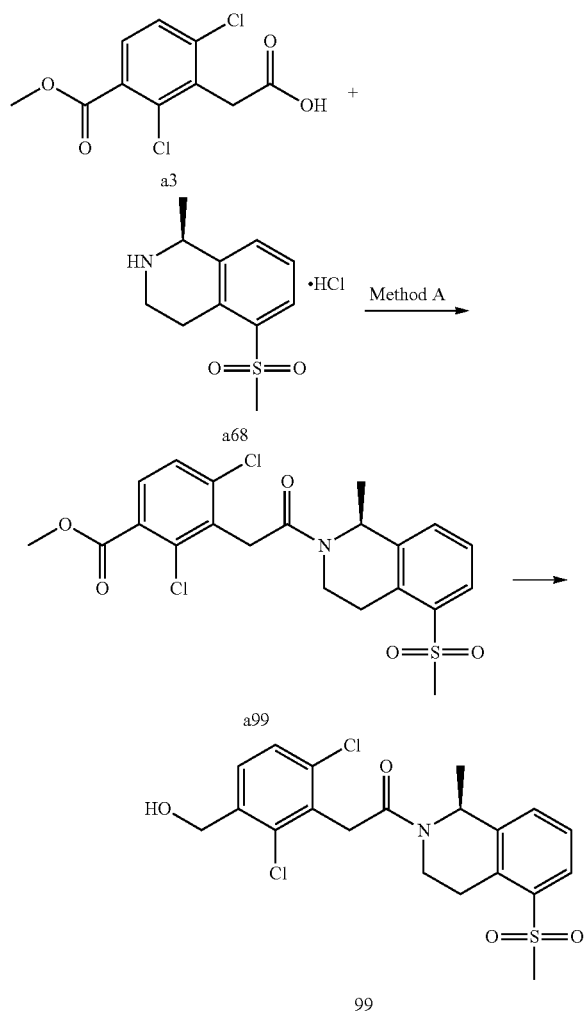

C.55.1. Synthesis of methyl 2,4-dichloro-3-{2-[(1S)-1-methyl-5-(methylsulfonyl)-3,4-dihydroisoquinolin-2(1H)-yl]-2-oxoethyl}benzoate a99

Compound a99 may be synthesized according to a method analogous to Method A using [2,6-dichloro-3-(methoxycarbonyl)phenyl]acetic acid a3 and (1S)-1-methyl-5-(methylsulfonyl)-1,2,3,4-tetrahydroisoquinoline hydrochloride a68. Conditions: DCM, DIPEA (2.5 eq), rt, overnight. Purification conditions: reverse phase chromatography (basic mode, LC standard).

Yield: 84%.

LCMS (ES$^+$): 470/472/474 (M+H)$^+$, 95.3% purity.

C.55.2. Synthesis of 2-[2,6-dichloro-3-(hydroxymethyl)phenyl]-1-[(1S)-1-methyl-5-(methyl-sulfonyl)-3,4-dihydroisoquinolin-2(1H)-yl]ethanone 99

Methyl 2,4-dichloro-3-{2-[(1S)-1-methyl-5-(methylsulfonyl)-3,4-dihydroisoquinolin-2(1H)-yl]-2-oxoethyl}benzoate a99 (200 mg, 0.42 mmol) was dissolved in THF (10 mL) at rt, then LiBH$_4$ (34 mg, 1.58 mmol) was added. The mixture was stirred at rt for 16 h. The reaction mixture was quenched with a 1N aqueous solution of HCl, then extracted twice with EtOAc. The organic layer was dried over Na$_2$SO$_4$, filtered and concentrated under vacuum. The residue was purified by reverse phase chromatography (basic mode, LC standard) to yield 163 mg of 2-[2,6-dichloro-3-(hydroxymethyl)phenyl]-1-[(1S)-1-methyl-5-(methylsulfonyl)-3,4-dihydroisoquinolin-2(1H)-yl]ethanone 99 as a colorless oil.

Yield: 86%.

LC-MS (ES$^+$): 442/444/446 (M+H)$^+$, 100% purity.

C.56. Synthesis of 2-(2,6-dichlorophenyl)-1-[(1S)-1-methyl-4-(methylsulfonyl)-3,4-dihydroisoquinolin-2(1H)-yl]ethanone 100

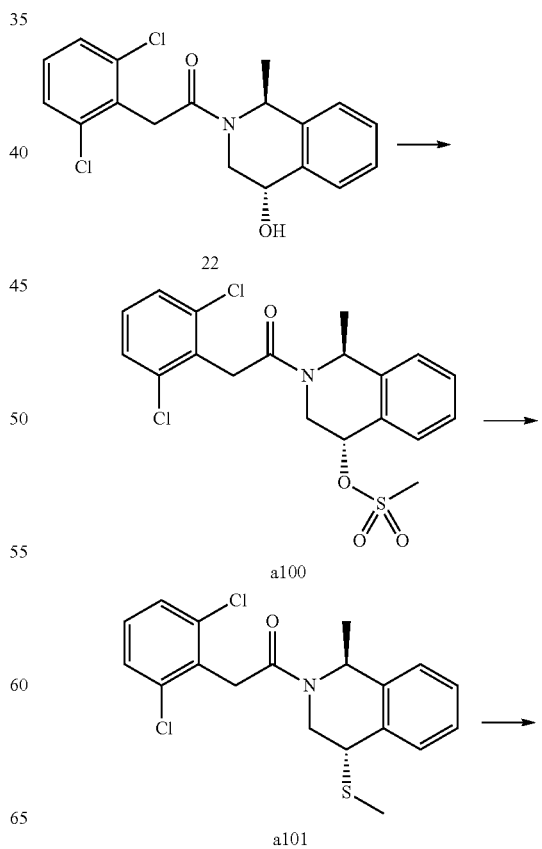

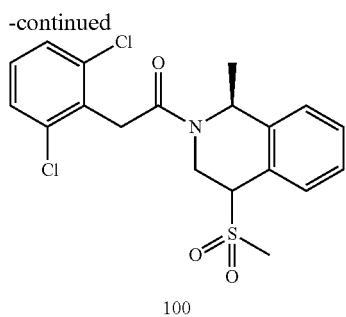

100

C.56.1. Synthesis of (1S,4S)-2-[(2,6-dichlorophenyl)acetyl]-1-methyl-1,2,3,4-tetrahydroisoquinolin-4-ylmethanesulfonate a100

2-(2,6-Dichlorophenyl)-1-[(1S,4S)-4-hydroxy-1-methyl-3,4-dihydroisoquinolin-2(1H)-yl]ethanone 22 (200 mg, 0.57 mmol) was dissolved in DCM (5 mL) at rt, then DIPEA (152 µL, 0.86 mmol) and methanesulfonyl chloride (47 µL, 0.60 mmol) were added. The mixture was stirred at rt for 16 h. The reaction mixture was washed with brine. The organic layer was dried over $Na_2SO_4$, filtered and concentrated under vacuum to yield 244 mg of (1S,4S)-2-[(2,6-dichlorophenyl)acetyl]-1-methyl-1,2,3,4-tetrahydroisoquinolin-4-yl methanesulfonate a100 which was used in the next step without any further purification.
Yield: 100% (crude).

C.56.2. Synthesis of 2-(2,6-dichlorophenyl)-1-[(1S)-1-methyl-4-(methylsulfanyl)-3,4-dihydroisoquinolin-2(1H)-yl]ethanone a101

(1S,4S)-2-[(2,6-dichlorophenyl)acetyl]-1-methyl-1,2,3,4-tetrahydroisoquinolin-4-yl methanesulfonate a100 (244 mg, 0.57 mmol) was dissolved in DMF (15 mL) at rt and sodium thiomethoxide (126 mg, 1.71 mmol) was added. The mixture was stirred at 65° C. for 96 h. The reaction mixture was cooled to rt, quenched with water (10 mL) and extracted thrice with EtOAc. The organic layer was washed with brine, dried over $Na_2SO_4$, filtered and concentrated under vacuum to yield 240 mg of 2-(2,6-dichlorophenyl)-1-[(1S)-1-methyl-4-(methylsulfanyl)-3,4-dihydroisoquinolin-2(1H)-yl]ethanone a101 which was used in the next step without any further purification.
Yield: 110% (crude).
LCMS (ES$^+$): 380/382/384 (M+H)$^+$.

C.56.3. Synthesis of 2-(2,6-dichlorophenyl)-1-[(1S)-1-methyl-4-(methylsulfonyl)-3,4-dihydroisoquinolin-2(1H)-yl]ethanone 100

2-(2,6-Dichlorophenyl)-1-[(1S)-1-methyl-4-(methylsulfanyl)-3,4-dihydroisoquinolin-2(1H)-yl]ethanone a101 (0.5706 mmol) was dissolved in DCM (30 mL) at rt and 3-chloroperoxybenzoic acid (256 mg, 1.14 mmol) was added. The mixture was stirred at rt for 16 h. The reaction mixture was quenched with a 2N aqueous solution of $Na_2S_2O_4$ and extracted thrice with DCM. The organic layer was washed with an aqueous saturated solution of $NaHCO_3$, dried over $Na_2SO_4$, filtered and concentrated under vacuum. The residue was purified by reverse phase chromatography (basic mode, standard LC), followed by a second reverse phase chromatography (acidic mode, LCMS prep) to yield 11 mg of 2-(2,6-dichlorophenyl)-1-[(1S)-1-methyl-4-(methylsulfonyl)-3,4-dihydroisoquinolin-2(1H)-yl]ethanone 100 as a beige oil.
Yield: 5% (3 steps).
LCMS (ES$^+$): 412/414/416 (M+H)$^+$, 91% purity.

C.57. Synthesis of 2-(2,6-dichlorophenyl)-1-[(1S)-1-methyl-5-(pyrrolidin-1-ylsulfonyl)-3,4-dihydroisoquinolin-2(1H)-yl]ethanone 101

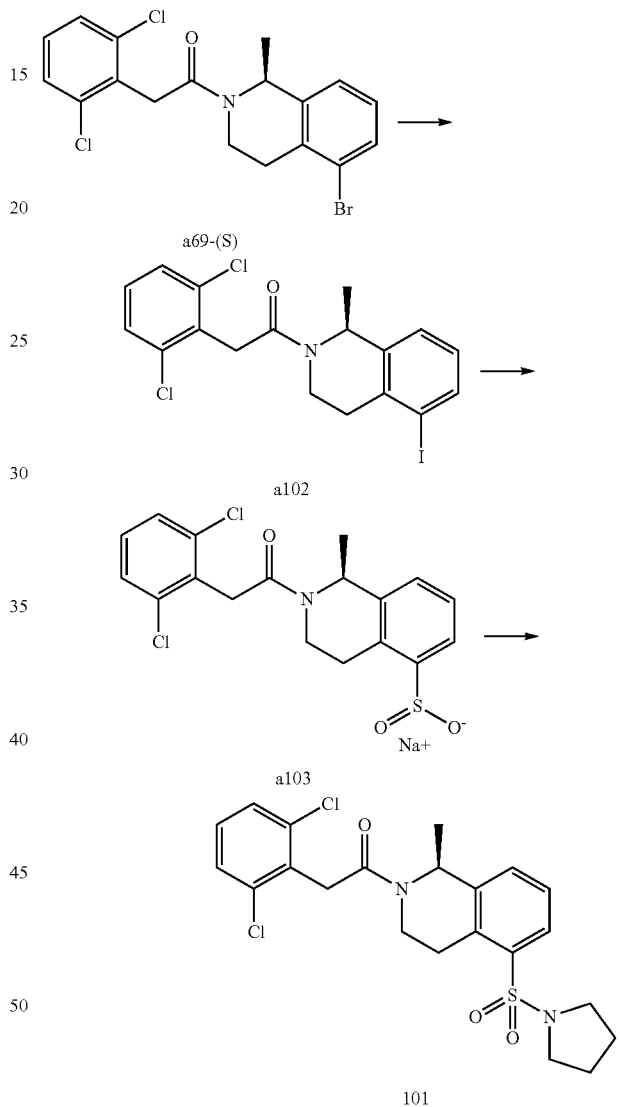

C.57.1. Synthesis of 2-(2,6-dichlorophenyl)-1-[(1S)-5-iodo-1-methyl-3,4-dihydro-1H-isoquinolin-2-yl]ethanone a102

Under inert atmosphere, 1-[(1S)-5-bromo-1-methyl-3,4-dihydroisoquinolin-2(1H)-yl]-2-(2,6-dichlorophenyl)ethanone a69-(S) (1.50 g, 3.63 mmol) was dissolved in 1,4-dioxane (15 mL), then sodium iodide (2.18 g, 14.5 mmol), cuprous iodide (138 mg, 0.72 mmol) and N,N'-dimethylenediamine (158 µL, 1.45 mmol) were added at rt. The mixture was stirred at 120° C. for 48 h. The reaction mixture was diluted with EtOAc (150 mL), then successively washed with a 1N aqueous solution of HCl (50 mL), an aqueous saturated solution of sodium carbonate (50 mL) and brine (50 mL). The organic layer was dried over $MgSO_4$, filtered and concentrated under vacuum to yield 1.3 g of 2-(2,6-dichlorophenyl)-1-[(1S)-5-iodo-1-methyl-3,4-dihydroisoquinolin-2(1H)-yl]ethanone a102 as an off-white solid.

Yield: 78%.

LCMS (ES$^+$): 460/462/464 (M+H)$^+$.

C.57.2. Synthesis of sodium (1S)-2-[(2,6-dichlorophenyl)acetyl]-1-methyl-1,2,3,4-tetrahydroisoquinoline-5-sulfinate a103

Under argon, 2-(2,6-dichlorophenyl)-1-[(1S)-5-iodo-1-methyl-3,4-dihydroisoquinolin-2(1H)-yl]ethanone a102 (200 mg, 0.43 mmol) was dissolved in dimethyl sulfoxide (3 mL). Sodium metabisulfite (169 mg, 0.87 mmol), sodium formate (66 mg, 0.95 mmol), tetrakis (triphenylphosphine) palladium(0) (101 mg, 87 µmol), 1,10-phenanthroline (24 mg, 0.13 mmol) were added. Oxygen was removed from the Schlenck tube by using a sequence vacuum/argon three times. The mixture was stirred at 70° C. for 2 h. The reaction mixture was cooled to rt to yield sodium (1S)-2-[(2,6-dichlorophenyl)acetyl]-1-methyl-1,2,3,4-tetrahydroisoquinoline-5-sulfinate a103 as a solution in dimethyl sulfoxide which was used in the next step without any further purification.

LCMS (ES$^+$): 398/400/402 (M+H)$^+$.

C.57.3. Method D. Synthesis of 2-(2,6-dichlorophenyl)-1-[(1S)-1-methyl-5-(pyrrolidin-1-ylsulfonyl)-3,4-dihydroisoquinolin-2(1H)-yl]ethanone 101

To a solution of sodium (1S)-2-[(2,6-dichlorophenyl)acetyl]-1-methyl-1,2,3,4-tetrahydroisoquinoline-5-sulfinate a103 (100 mg, 0.24 mmol) in dimethyl sulfoxide (1 mL) were added THF (3 mL) and pyrrolidine (40 µL, 0.48 mmol). The mixture was cooled at 0° C. N-bromosuccinimide (87 mg, 0.48 mmol) was added. The mixture was stirred at rt for 1 h. The reaction mixture was diluted with EtOAc, successively washed with a 1N aqueous solution of HCl, an aqueous saturated solution of $NaHCO_3$ and brine. The organic layer was dried over $MgSO_4$, filtered and concentrated under vacuum. The residue was purified by reverse phase chromatography (basic mode, LCMS prep) to yield 26 mg of 2-(2,6-dichlorophenyl)-1-[(1S)-1-methyl-5-(pyrrolidin-1-ylsulfonyl)-3,4-dihydroisoquinolin-2(1H)-yl]ethanone 102 as a yellow oil.

Yield: 23%.

LCMS (ES$^+$): 467/469/471 (M+H)$^+$, 100% purity.

Compounds 102, 103, 104, 105, 106, and 107 may be synthesized according to a method analogous to Method D.

(1S)-2-[(2,6-dichlorophenyl)acetyl]-N-ethyl-1-methyl-1,2,3,4-tetrahydroisoquinoline-5-sulfonamide 102

Purification by reverse phase chromatography (basic mode, LCMS prep) yielded 36 mg of compound 102 as a yellow oil.

Yield: 34%.

LCMS (ES$^+$): 441/443/445 (M+H)$^+$, 92.9% purity.

(1S)-2-[(2,6-dichlorophenyl)acetyl]-1-methyl-N-(propan-2-yl)-1,2,3,4-tetrahydroisoquinoline-5-sulfonamide 103

Purification by reverse phase chromatography (basic mode, LCMS prep) yielded 26 mg of compound 103 as a yellow oil.

Yield: 24%.

LCMS (ES$^+$): 455/457/459 (M+H)$^+$, 100% purity.

(1S)-2-[(2,6-dichlorophenyl)acetyl]-1-methyl-N-(2,2,2-trifluoroethyl)-1,2,3,4-tetrahydroisoquinoline-5-sulfonamide 104

Purification by reverse phase chromatography (basic mode, LCMS prep) yielded 25 mg of (1S)-2-[(2,6-dichlorophenyl)acetyl]-1-methyl-N-(2,2,2-trifluoroethyl)-1,2,3,4-tetrahydroisoquinoline-5-sulfonamide 104 as an orange oil.

Yield: 21%.

LCMS (ES$^+$): 495/497/499 (M+H)$^+$, 94.3% purity.

(1S)-2-[(2,6-dichlorophenyl)acetyl]-1-methyl-N-(4H-1,2,4-triazol-3-yl)-1,2,3,4-tetrahydroisoquinoline-5-sulfonamide 105

Purification by reverse phase chromatography (basic mode, LCMS prep) yielded 8 mg of (1S)-2-[(2,6-dichlorophenyl)acetyl]-1-methyl-N-(4H-1,2,4-triazol-3-yl)-1,2,3,4-tetrahydroisoquinoline-5-sulfonamide 105 as an orange oil.

Yield: 7%.

LCMS (ES$^+$): 480/482/484 (M+H)$^+$, 81.2% purity.

2-(2,6-dichlorophenyl)-1-[(1S)-5-[(3,3-difluoropyrrolidin-1-yl)sulfonyl]-1-methyl-3,4-dihydroisoquinolin-2(1H)-yl]ethanone 106

Purification by reverse phase chromatography (basic mode, LCMS prep) yielded 30 mg of 2-(2,6-dichlorophenyl)-1-[(1S)-5-[(3,3-difluoropyrrolidin-1-yl)sulfonyl]-1-methyl-3,4-dihydroisoquinolin-2(1H)-yl]ethanone 106 as an orange oil.

Yield: 41%.

LCMS (ES$^+$): 503/505/507 (M+H)$^+$, 86.7% purity.

(1S)—N-(cyanomethyl)-2-[(2,6-dichlorophenyl)acetyl]-1-methyl-1,2,3,4-tetrahydroisoquinoline-5-sulfonamide 107

Purification by reverse phase chromatography (basic mode, LCMS prep) yielded 8 mg of (1S)—N-(cyanomethyl)-2-[(2,6-dichlorophenyl)acetyl]-1-methyl-1,2,3,4-tetrahydroisoquinoline-5-sulfonamide 107 as an orange oil.

Yield: 12%.

LCMS (ES$^+$): 452/454/456 (M+H)$^+$, 98.9% purity.

C.58. Synthesis of (1S)-2-[(2,6-dichlorophenyl)acetyl]-1-methyl-1,2,3,4-tetrahydroisoquinoline-5-sulfonamide 108

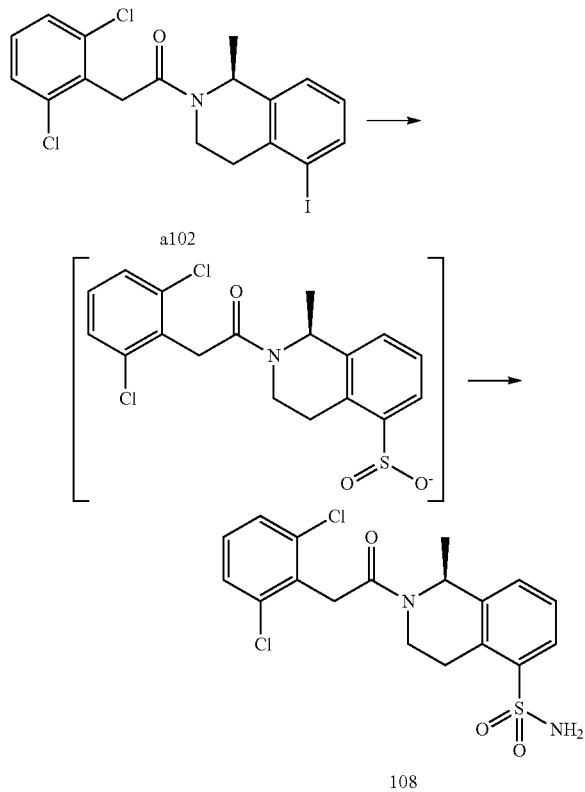

108

2-(2,6-dichlorophenyl)-1-[(1S)-5-iodo-1-methyl-3,4-dihydroisoquinolin-2(1H)-yl]ethanone a102 (500 mg, 1.08 mmol) was dissolved in dimethyl sulfoxide (5 mL). Sodium metabisulfite (421 mg, 2.18 mmol), sodium formate (166 mg, 2.40 mmol), palladium acetate (25 mg, 0.10 mmol) and 1,10-phenanthroline (59 mg, 0.32 mmol) were added. The mixture was stirred at 70° C. during 2 h. The reaction mixture was cooled to 0° C., diluted with THF (5 mL) and saturated with gas ammonia. N-bromosuccinimide (1.36 g, 7.55 mmol) in solution in THF (10 mL) was carefully added dropwise. The mixture was stirred at rt during 64 h. The reaction mixture was diluted with EtOAc (150 mL) and successively washed with a 1N aqueous solution of HCl (50 mL), an aqueous saturated solution of NaHCO₃ (50 mL) and brine (50 mL). The organic layer was dried over MgSO₄, filtered and concentrated under vacuum. The residue was purified by SFC column chromatography (column 2-ethylpyridine) using 20% MeOH to yield 350 mg of (1S)-2-[(2,6-dichlorophenyl)acetyl]-1-methyl-1,2,3,4-tetrahydroisoquinoline-5-sulfonamide 108 as a white solid.

Yield: 67%.
LCMS (ES⁺), 413/415/417 (M+H)⁺, 100% purity.

C.59. Method E. Synthesis of 2-(2,6-dichlorophenyl)-1-[(1S)-1-methyl-5-{[(5-methyl-1,2-oxazol-3-yl)methyl]sulfonyl}-3,4-dihydroisoquinolin-2(1H)-yl]ethanone 109

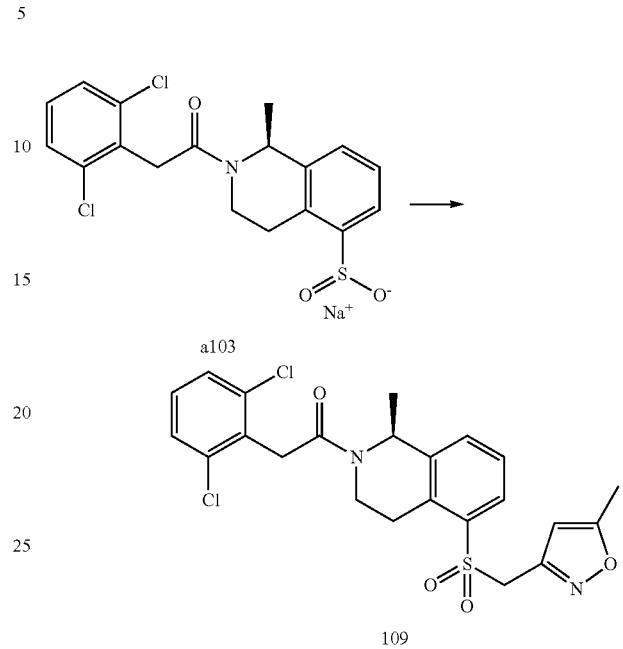

109

To a solution of sodium (1S)-2-[(2,6-dichlorophenyl)acetyl]-1-methyl-1,2,3,4-tetrahydroisoquinoline-5-sulfinate a103 (100 mg, 0.24 mmol) in dimethyl sulfoxide (1 mL) was added (bromomethyl)-5-methylisoxazole (84 mg, 0.48 mmol). The mixture was stirred at rt overnight. The reaction mixture was concentrated under vacuum. The residue was poured in EtOAc, sonicated and stirred. The precipitate was filtered off, rinsed twice with EtOAc then the filtrate was concentrated under vacuum. The residue was purified by reverse phase chromatography (acidic mode, LCMS prep, then in basic mode, LCMS prep) to yield 30 mg of 2-(2,6-dichlorophenyl)-1-[(1S)-1-methyl-5-{[(5-methyl-1,2-oxazol-3-yl)methyl]sulfonyl}-3,4-dihydroisoquinolin-2(1H)-yl]ethanone 109 as an orange oil.

Yield: 25%.
LCMS (ES⁺): 493/495/497 (M+H)⁺, 95.3% purity.

Compounds 110 and 111 may be synthesized according to a method analogous to Method E.

2-(2,6-dichlorophenyl)-1-[(1S)-1-methyl-5-[(pyridin-3-ylmethyl)sulfonyl]-3,4-dihydroisoquinolin-2(1H)-yl]ethanone 110

Purification by reverse phase chromatography (basic mode, LCMS prep) yielded 10 mg of compound 110 as an orange oil.

Yield: 8%.
LCMS (ES⁺): 389/391/393 (M+H)⁺, 90.8% purity.

2-(2,6-dichlorophenyl)-1-[(1S)-1-methyl-5-[(tetrahydro-2H-pyran-4-ylmethyl)sulfonyl]-3,4-dihydroisoquinolin-2(1H)-yl]ethanone 111

Purification by reverse phase chromatography (basic mode, LCMS prep) yielded 30 mg of 2-(2,6-dichlorophenyl)-1-[(1S)-1-methyl-5-[(tetrahydro-2H-pyran-4-ylmethyl)sulfonyl]-3,4-dihydroisoquinolin-2(1H)-yl]ethanone 111 as an orange oil.

Yield: 30%.
LCMS (ES+): 496/498/500 (M+H)+, 100% purity.

C.60. Synthesis of 2-(2,6-dichlorophenyl)-1-[(1S)-5-[(methoxymethyl)sulfonyl]-1-methyl-3,4-dihydroisoquinolin-2(1H)-yl]ethanone 112

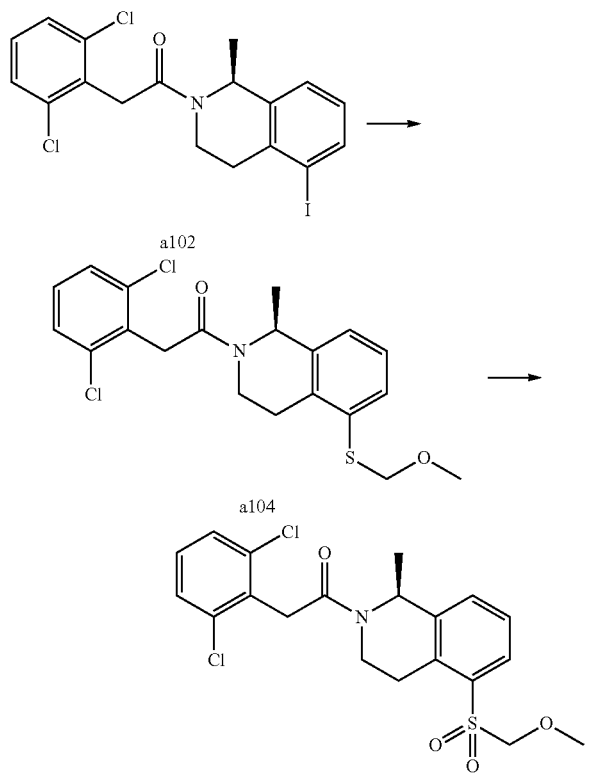

C.60.1. Synthesis of 2-(2,6-dichlorophenyl)-1-[(1S)-5-[(methoxymethyl)sulfanyl]-1-methyl-3,4-dihydroisoquinolin-2(1H)-yl]ethanone a104

2-(2,6-dichlorophenyl)-1-[(1S)-5-iodo-1-methyl-3,4-dihydroisoquinolin-2(1H)-yl]ethanone a102 (100 mg, 0.21 mmol) was dissolved in DMF (5 mL). Cuprous iodide (4 mg, 20 µmol), sulfur (21 mg, 0.65 mmol) and potassium carbonate (60 mg, 0.43 mmol) were added. The mixture was stirred at 90° C. for 64 h. The reaction mixture was cooled to rt, diluted with Et₂O (100 mL) and successively washed with a 1N aqueous solution of HCl (50 mL), a 1N aqueous solution of NaOH (50 mL) and brine (50 mL). The organic layer was dried over MgSO₄, filtered and concentrated under vacuum. The residue was dissolved in THF (10 mL) and sodium borohydride (50 mg, 1.31 mmol) was added. The mixture was stirred at 40° C. for 2 h. The reaction mixture was cooled to rt and 2-bromomethylmethylether (212 µL, 1.1 mmol) was added. The mixture was stirred at rt for 1 h. The reaction mixture was diluted with DCM (50 mL), then washed with water (50 mL). The organic layer was dried over MgSO₄, filtered and concentrated under vacuum to afford crude 2-(2,6-dichlorophenyl)-1-[(1S)-5-[(methoxymethyl)sulfanyl]-1-methyl-3,4-dihydroisoquinolin-2(1H)-yl] ethanone a104 used in the next step without any further purification.
LCMS (ES+): 424/426/428 (M+H)+.

C.60.2. Synthesis of 2-(2,6-dichlorophenyl)-1-[(1S)-5-[(methoxymethyl)sulfonyl]-1-methyl-3,4-dihydroisoquinolin-2(1H)-yl]ethanone 112

Crude 2-(2,6-dichlorophenyl)-1-[(1S)-5-[(methoxymethyl)sulfanyl]-1-methyl-3,4-dihydroisoquinolin-2(1H)-yl] ethanone a104 (100 mg, 0.25 mmol) was dissolved in DCM (5 mL) and 3-chloroperoxybenzoic acid (140 mg, 0.50 mmol) was added at rt. The mixture was stirred at rt for 2 h. The reaction mixture was then diluted with DCM (50 mL) and washed twice with an aqueous saturated solution of sodium carbonate (50 mL). The organic layer was dried over MgSO₄, filtered and concentrated under vacuum. The residue was purified by reverse phase chromatography (basic mode, LCMS prep) to yield 15 mg of 2-(2,6-dichlorophenyl)-1-[(1S)-5-[(methoxymethyl)sulfonyl]-1-methyl-3,4-dihydroisoquinolin-2(1H)-yl]ethanone 112 as a white solid.
Yield: 14% (2 steps).
LCMS (ES+): 442/444/446 (M+H)+, 96.5% purity.

C.61. Method F. Synthesis of 2-(2,6-dichlorophenyl)-1-[(1S)-1-methyl-5-[(1-oxidotetrahydro-1H-1λ⁴-thiophen-1-ylidene)amino]-3,4-dihydroisoquinolin-2(1H)-yl]ethanone 113

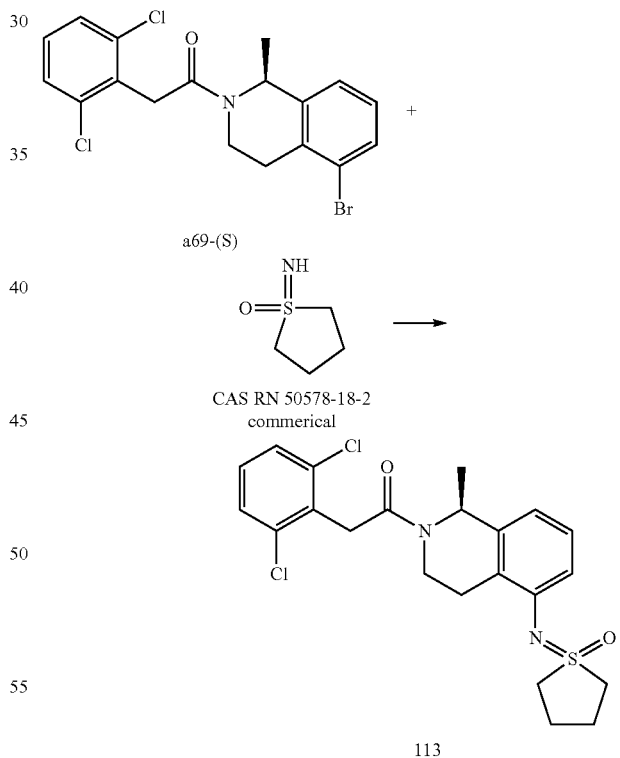

1-[(1S)-5-bromo-1-methyl-3,4-dihydroisoquinolin-2(1H)-yl]-2-(2,6-dichlorophenyl)ethanone a69-(S) (100 mg, 0.24 mmol), cesium carbonate (118 mg, 0.36 mmol), palladium(II) acetate (5.5 mg, 24 µmol), (+/−)-2,2′-bis(diphenylphosphino)-1,1′-binaphthyl (23 mg, 40 µmol), 1-iminothiolane 1-oxide (commercial, 36 mg, 0.30 mmol) were mixed in 1,4-dioxane (2 mL) in a sealed tube. The mixture was stirred at 110° C. for 64 h. The reaction mixture was diluted with EtOAc (50 mL) and successively washed with a 1N aqueous solution of HCl (20 mL) and an aqueous saturated solution of sodium carbonate (20 mL). The organic layer was dried over MgSO$_4$, filtered and concentrated under vacuum. The residue was purified by reverse phase chromatography (basic mode, LCMS prep) to yield 10 mg of 2-(2,6-dichlorophenyl)-1-[(1S)-1-methyl-5-[(1-oxidotetrahydro-1H-1λ$^4$-thiophen-1-ylidene)amino]-3,4-dihydroisoquinolin-2(1H)-yl]ethanone 113 as a yellow oil.

Yield: 9%.

LCMS (ES$^+$): 451/453/455 (M+H)$^+$, 100% purity.

The following compounds were synthesized according a method analogous to Method F. When commercially available, starting material are identified by their CAS Register Numbers.

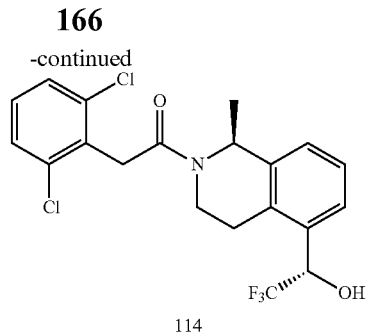
114

To a solution of (1S)-2-[(2,6-dichlorophenyl)acetyl]-1-methyl-1,2,3,4-tetrahydroisoquinoline-5-carbaldehyde a85

| No | Starting material | Catalyst/solvent, T ° C. | Reaction time | Purification conditions | Yield (%) |
|---|---|---|---|---|---|
| 148 | a69-(S) and (dimethanesulfinylidene)amine (RN 1520-31-6) | Pd$_2$(dba)$_3$, Toluene, 110° C. | Overnight | NP using 1.8% MeOH (+0.2% NH$_4$OH) in DCM | 88 |
| 149 | a102 and 1,4-oxathiane sulfoximine (RN 708257-15-2) | Pd(OAc)$_2$, Toluene, 110° C. | 48 h | Basic RP-LCMS | 49 |
| 150 | a125 and (dimethanesulfinylidene)amine (RN 1520-31-6) | Pd$_2$(dba)$_3$, Toluene, 110° C. | Overnight | Basic RP (standard LC) | 34 |

2-(2,6-dichlorophenyl)-1-[(1S)-5-{[dimethyl(oxido)-λ$^6$-sulfanylidene]amino}-1-methyl-3,4-dihydroisoquinolin-2(1H)-yl]ethanone 148

LC-MS (ES$^+$): 425/427/429 (M+H)$^+$, 100% purity.
Appearance: white solid.

2-(2,6-dichlorophenyl)-1-[(1S)-1-methyl-5-[(4-oxido-1,4λ$^4$-oxathian-4-ylidene)amino]-3,4-dihydroisoquinolin-2(1H)-yl]ethanone 149

LC-MS (ES$^+$): 467/469/471 (M+H)$^+$, 98.5% purity.
Appearance: white solid.

3-chloro-2-{2-[(1S)-5-{[dimethyl(oxido)-λ$^6$-sulfanylidene]amino}-1-methyl-3,4-dihydroisoquinolin-2(1H)-yl]-2-oxoethyl}benzonitrile 150

LC-MS (ES$^+$): 416/4181 (M+H)$^+$, 100% purity.
Appearance: beige solid.

C.62. Method G. Synthesis of 2-(2,6-dichlorophenyl)-1-[(1S)-1-methyl-5-((1S)-2,2,2-trifluoro-1-hydroxy-ethyl)-3,4-dihydroisoquinolin-2(1H)-yl]ethanone 114

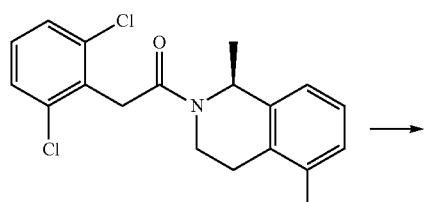
a85

(100 mg, 0.28 mmol) in DMF (3 mL) were added K$_2$CO$_3$ (10 mg, 72 μmol), cesium fluoride (100 mg, 0.64 mmol) and (trifluoromethyl)trimethylsilane (100 μL, 0.7 mmol). The mixture was stirred at 75° C., then cesium fluoride (100 mg, 0.64 mmol) and (trifluoromethyl)trimethylsilane (100 μL, 0.7 mmol) were added again. The reaction mixture was stirred overnight at 75° C., then diluted with EtOAc (100 mL) and successively washed with a 1N aqueous solution of HCl and water. The organic layer is dried over MgSO$_4$, filtered and concentrated under vacuum. The residue was purified by reverse phase chromatography (basic mode, standard LC) to afford 25 mg of 2-(2,6-dichlorophenyl)-1-[(1S)-1-methyl-5-((1S)-2,2,2-trifluoro-1-hydroxyethyl)-3,4-dihydroisoquinolin-2(1H)-yl]ethanone 114 as a solid.

Yield: 21%

LCMS (ES$^+$): 432/434/436 (M+H)$^+$, 94.8% purity.

Compounds 115, 116 and 117 could be synthesized according a method analogous to Method G.

2-(3,5-dichloropyridin-4-yl)-1-[(1S)-1-methyl-5-((1S)-2,2,2-trifluoro-1-hydroxyethyl)-3,4-dihydroisoquinolin-2(1H)-yl]ethanone 115

Chiral resolution (SFC, Chiralpak AD, 50*216 mm, 360 mL/min, 220 nm, 40° C., eluent: 20% MeOH) of racemate 2-(3,5-dichloropyridin-4-yl)-1-[(1S)-1-methyl-5-(2,2,2-trifluoro-1-hydroxyethyl)-3,4-dihydroisoquinolin-2(1H)-yl]ethanone afforded 14 mg of 2-(3,5-dichloropyridin-4-yl)-1-[(1S)-1-methyl-5-((1S)-2,2,2-trifluoro-1-hydroxyethyl)-3,4-dihydroisoquinolin-2(1H)-yl]ethanone 115 as a solid.

Yield: 33%.

LCMS (ES$^+$) 433/435/437 (M+H)$^+$, 98.8% purity.

Chiral analysis (LC, Chiralpak AD-H, 250*4.6 mm, 1 mL/min, 220 nm, 30° C., eluent: EtOH/n-heptane/DEA 50/50/0.1): RT 3.86 min (other enantiomer at 5.08 min), 99.8% ee.

3-chloro-2-{2-[(1S)-1-methyl-5-((1R)-2,2,2-trifluoro-1-hydroxyethyl)-3,4-dihydroisoquinolin-2(1H)-yl]-2-oxoethyl}benzonitrile 116 and 3-chloro-2-{2-[(1S)-1-methyl-5-((1S)-2,2,2-trifluoro-1-hydroxyethyl)-3,4-dihydroisoquinolin-2(1H)-yl]-2-oxoethyl}benzonitrile 117

Chiral resolution (SFC, Chiralcel OD, 50*266 mm, 360 mL/min, 220 nm, 40° C., eluent: 20% MeOH) of racemate 3-chloro-2-[2-[(1S)-1-methyl-5-[2,2,2-trifluoro-1-hydroxyethyl]-3,4-dihydro-1H-isoquinolin-2-yl]-2-oxo-ethyl]benzonitrile afforded:

23 mg of 3-chloro-2-{2-[(1S)-1-methyl-5-((1R)-2,2,2-trifluoro-1-hydroxyethyl)-3,4-dihydro-isoquinolin-2(1H)-yl]-2-oxoethyl}benzonitrile 116 as a sticky oil.
Yield: 50%.
LCMS (ES+): 423/425/427 (M+H)+, 98.8% purity.
Chiral analysis (LC, Chiralcel OD-H, 250*4.6 mm, 1 mL/min, 220 nm, 30° C., eluent: EtOH/n-heptane/DEA 50/50/0.1): RT 4.08 min, 100% ee.

23 mg of 3-chloro-2-{2-[(1S)-1-methyl-5-((1S)-2,2,2-trifluoro-1-hydroxyethyl)-3,4-dihydroiso-quinolin-2(1H)-yl]-2-oxoethyl}benzonitrile 117 as a solid.
Yield: 50%.
LCMS (ES+) 423/425/427 (M+H)+, 84.7% purity.
Chiral analysis (LC, Chiralcel OD-H, 250*4.6 mm, 1 mL/min, 220 nm, 30° C., eluent: EtOH/n-heptane/DEA 50/50/0.1): RT 5.84 min, 99.3% ee.

C.63. Synthesis of 2-(2,6-dichlorophenyl)-1-[(1S)-5-(N-ethyl-S-methylsulfonimidoyl)-1-methyl-3,4-dihydroisoquinolin-2(1H)-yl]ethanone 151

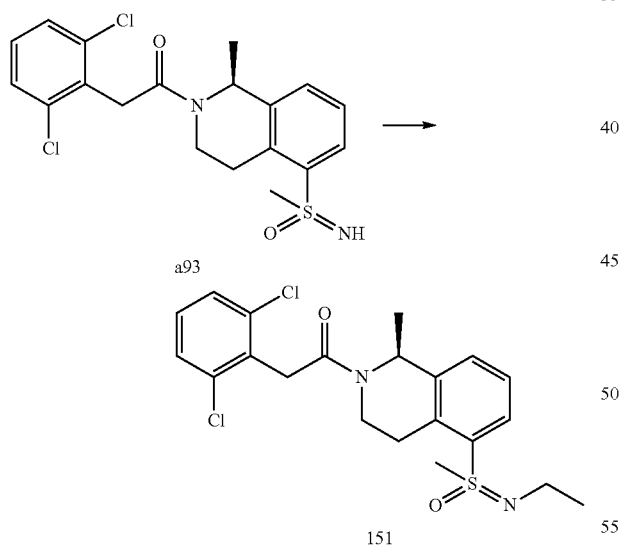

K$_2$CO$_3$ (51 mg, 0.36 mmol) and iodomethane (12 μL, 0.14 mmol) are added to a solution of 2-(2,6-dichlorophenyl)-1-[(1S)-1-methyl-5-(S-methylsulfonimidoyl)-3,4-dihydroiso-quinolin-2(1H)-yl]ethanone a93 (50 mg, 0.12 mmol) in ACN (2 mL) at rt. The mixture was stirred under microwave irradiation at 80° C. for 4 h. The reaction mixture was taken up with DCM (25 mL), then washed with an aqueous saturated solution of NaHCO$_3$. The organic layer was dried over MgSO$_4$, filtered and concentrated under vacuum. The residue was purified by reverse phase chromatography (basic mode, standard LC) to yield 17 mg of 2-(2,6-dichlorophenyl)-1-[(1S)-5-(N-ethyl-S-methylsulfonimidoyl)-1-methyl-3,4-dihydroisoquinolin-2(1H)-yl]ethanone 151.
Yield: 32%.
LCMS (ES+): 439/441/443 (M+H)+.

C.64. Synthesis of 2-(2,6-dichlorophenyl)-1-[(1S)-5-({[dimethyl(oxido)-sulfanylidene]amino}methyl)-1-methyl-3,4-dihydroisoquinolin-2(1H)-yl]ethanone 152

To a solution of 1-[(1S)-5-(bromomethyl)-1-methyl-3,4-dihydroisoquinolin-2(1H)-yl]-2-(2,6-dichlorophenyl)ethanone a81 (100 mg, 0.23) in DMF (2 mL) was added (dimethanesulfinylidene)amine (23 mg, 0.232 mmol) and the reaction mixture was stirred at 100° C. for 2 h. Purification by reverse phase chromatography (basic mode, LCMS prep) yielded 14 mg of 2-(2,6-dichlorophenyl)-1-[(1S)-5-({[dimethyl(oxido)-$\lambda^6$-sulfanylidene]amino}methyl)-1-methyl-3,4-dihydroisoquinolin-2(1H)-yl]ethanone 152 as a sticky oil.
Yield: 13%.
LCMS (ES+): 439/441/443 (M+H)+, 91% purity.

C.65. Synthesis of 2-(2,6-dichlorophenyl)-1-[(1S)-5-(1,1-difluoro-2-hydroxyethyl)-1-methyl-3,4-dihydroisoquinolin-2(1H)-yl]ethanone 153

-continued

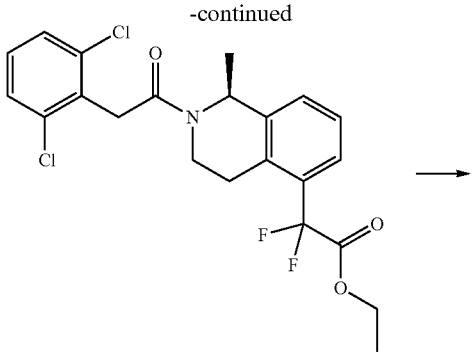
a126

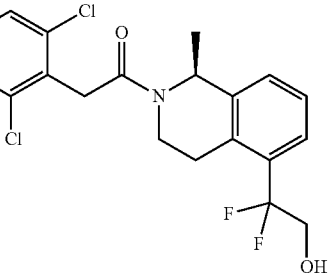
153

C.65.1. Synthesis of ethyl 2-[(1S)-2-[2-(2,6-dichlorophenyl)acetyl]-1-methyl-3,4-dihydro-1H-isoquinolin-5-yl]-2,2-difluoroacetate a126

2-(2,6-dichlorophenyl)-1-[(1S)-5-iodo-1-methyl-3,4-dihydro-1H-isoquinolin-2-yl]ethanone a102 (1.38 g, 3.00 mmol), ethyl bromodifluoroacetate (746 m g, 3.6 mmol), copper (381 mg, 6.00 mmol) were mixed in degased DMSO (6 mL). The reaction mixture was stirred at rt for 3 h, then diluted with EtOAc (150 mL) and washed with an aqueous saturated solution of NH$_4$Cl (50 mL). The organic layer was dried over MgSO$_4$, filtered and concentrated under vacuum to yield 1.37 g of crude ethyl 2-[(1S)-2-[2-(2,6-dichlorophenyl)acetyl]-1-methyl-3,4-dihydro-1H-isoquinolin-5-yl]-2,2-difluoroacetate a126

Yield: 100% (crude).

LCMS (ES$^+$) 456/458/460 (M+H)$^+$.

C.65.2. Synthesis of 2-(2,6-dichlorophenyl)-1-[(1S)-5-(1,1-difluoro-2-hydroxyethyl)-1-methyl-3,4-dihydroisoquinolin-2(1H)-yl]ethanone 153

2-[(1S)-2-[2-(2,6-dichlorophenyl)acetyl]-1-methyl-3,4-dihydro-1H-isoquinolin-5-yl]-2,2-difluoroacetate a126 (456 mg, 1.0 mmol) and sodium borohydride (76 mg, 2.0 mmol) are mixed in MeOH (8 mL). The reaction mixture was stirred at rt for 1 h, then diluted with DCM (50 mL) and washed with with an aqueous saturated solution of NH$_4$Cl (50 mL). The organic layer was dried over MgSO$_4$, filtered and concentrated under vacuum to yield 380 mg of 2-(2,6-dichlorophenyl)-1-[(1S)-5-(1,1-difluoro-2-hydroxy-ethyl)-1-methyl-3,4-dihydro-1H-isoquinolin-2-yl]ethanone 153 as a white solid.

Yield: 92%.

LCMS (ES$^+$) 414/416/418 (M+H)$^+$, 91.5% purity.

C.66. Synthesis of 1-[(1S)-5-(2-amino-1,1-difluoroethyl)-1-methyl-3,4-dihydroisoquinolin-2(1H)-yl]-2-(2,6-dichlorophenyl)ethanone 154 and N-(2-{(1S)-2-[(2,6-dichlorophenyl)acetyl]-1-methyl-1,2,3,4-tetrahydroisoquinolin-5-yl}-2,2-difluoroethyl) acetamide 155

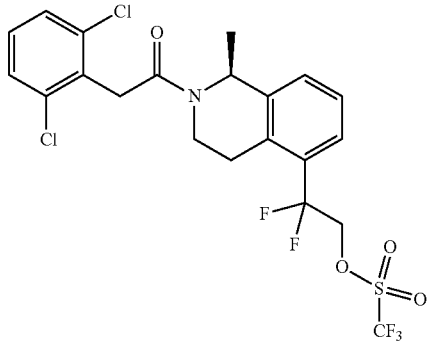
153 a127

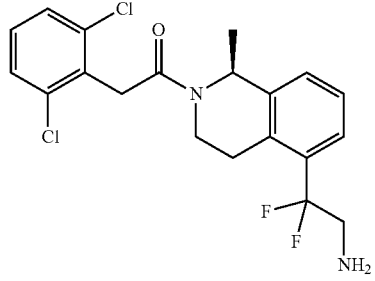
154

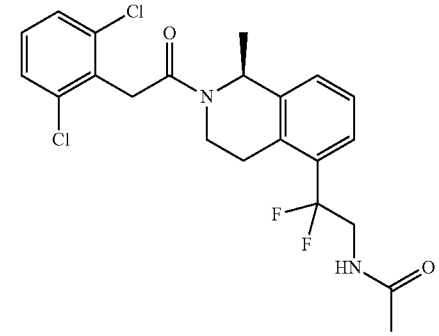
155

C.66.1. Synthesis of [2-[(1S)-2-[2-(2,6-dichlorophenyl)acetyl]-1-methyl-3,4-dihydro-1H-isoquinolin-5-yl]-2,2-difluoroethyl] trifluoromethanesulfonate a127

Under inert atmosphere, 2-(2,6-dichlorophenyl)-1-[(1S)-5-(1,1-difluoro-2-hydroxy-ethyl)-1-methyl-3,4-dihydro-1H-isoquinolin-2-yl]ethanone 153 (260 mg, 0.63 mmol), trifluoromethanesulfonic anhydride (110 µL, 0.69 mmol) and triethylamine (270 µL, 1.88 mmol) are mixed in DCM (10 mL). The reaction mixture was stirred at rt for 15 h, then diluted with DCM (50 mL) and washed with water (50 mL). The organic layer was dried over MgSO$_4$, filtered and concentrated under vacuum to yield 343 mg [2-[(1S)-2-[2-(2,6-dichlorophenyl)acetyl]-1-methyl-3,4-dihydro-1H-isoquinolin-5-yl]-2,2-difluoroethyl] trifluoromethanesulfonate a127.

Yield: 100% (crude).

LCMS (ES$^+$): 546/548/550 (M+H)$^+$.

C.66.2. Synthesis of 1-[(1S)-5-(2-amino-1,1-difluoroethyl)-1-methyl-3,4-dihydroisoquinolin-2(1H)-yl]-2-(2,6-dichlorophenyl)ethanone 154

A solution of [2-[(1S)-2-[2-(2,6-dichlorophenyl)acetyl]-1-methyl-3,4-dihydro-1H-isoquinolin-5-yl]-2,2-difluoroethyl] trifluoromethanesulfonate a127 (200 mg, 0.36 mmol) in DMF (3 mL) was saturated with ammonia. The reaction mixture was stirred at 80° C. for 3 h in a sealed tube. The reaction mixture was diluted with EtOAc (50 mL) and washed with water (20 mL). The organic layer was dried over MgSO$_4$, filtered and concentrated under vacuum. The residue was purified by reverse phase chromatography (acidic mode, LCMS prep) to yield 151 mg of 1-[(1S)-5-(2-amino-1,1-difluoroethyl)-1-methyl-3,4-dihydroisoquinolin-2(1H)-yl]-2-(2,6-dichlorophenyl)ethanone 154 as a yellow gum.

Yield: 100%.

LCMS (ES$^+$): 413/415/417 (M+H)$^+$, 98% purity.

C.66.3. Synthesis of N-(2-{(1S)-2-[(2,6-dichlorophenyl)acetyl]-1-methyl-1,2,3,4-tetrahydroisoquinolin-5-yl}-2,2-difluoroethyl)acetamide 155

1-[(1S)-5-(2-amino-1,1-difluoroethyl)-1-methyl-3,4-dihydroisoquinolin-2(1H)-yl]-2-(2,6-dichlorophenyl)ethanone 154 (100 mg, 0.24 mmol), triethylamine (100 µL, 0.7 mmol) and acetyl chloride (40 µL, 0.6 mmol) were mixed in DCM (2 mL). The reaction mixture was stirred at 80° C. for 3 h, then diluted with EtOAc (50 mL) and washed with water (20 mL). The organic layer was dried over MgSO$_4$, filtered and concentrated under vacuum. The residue was purified by reverse phase chromatography (acidic mode, LCMS prep) to yield 9 mg of N-(2-{(1S)-2-[(2,6-dichlorophenyl)acetyl]-1-methyl-1,2,3,4-tetrahydroisoquinolin-5-yl}-2,2-difluoroethyl)acetamide 155 as an off-white solid.

Yield: 8%.

LCMS (ES$^+$): 455/457/459 (M+H)$^+$, 92% purity.

C.67. Synthesis of 2-(2,6-dichlorophenyl)-1-[(1S)-5-[1,1-difluoro-2-(morpholin-4-yl)ethyl]-1-methyl-3,4-dihydroisoquinolin-2(1H)-yl]ethanone 156

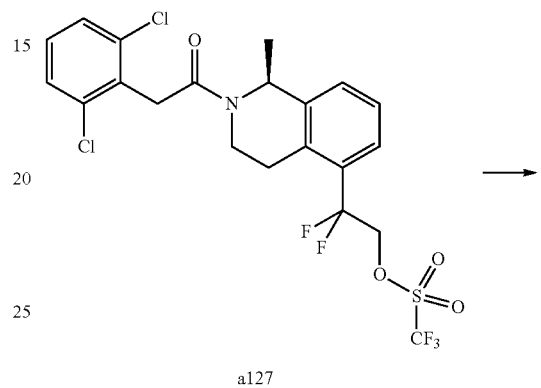

a127

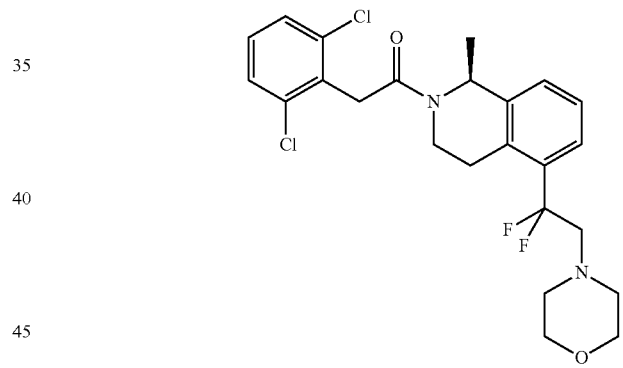

156

[2-[(1S)-2-[2-(2,6-dichlorophenyl)acetyl]-1-methyl-3,4-dihydro-1H-isoquinolin-5-yl]-2,2-difluoro-ethyl] trifluoromethanesulfonate a127 (25 mg, 0.05 mmol) was diluted with morpholine (500 µL). The reaction mixture was stirred at 80° C. for 3 h, then diluted with EtOAc (50 mL) and washed with water (20 mL). The organic layer was dried over MgSO$_4$, filtered and concentrated under vacuum. The residue was purified by reverse phase chromatography (basic mode, LCMS prep) to yield 10 mg of 2-(2,6-dichlorophenyl)-1-[(1S)-5-[1,1-difluoro-2-(morpholin-4-yl)ethyl]-1-methyl-3,4-dihydroisoquinolin-2(1H)-yl]ethanone 156 as an off-white solid.

Yield: 45%.

LCMS (ES$^+$): 483/485/487 (M+H)$^+$, 97% purity.

C.68. Synthesis of 2-(2,6-dichlorophenyl)-1-[(1S)-5-[1,1-difluoro-2-(methylamino)ethyl]-1-methyl-3,4-dihydroisoquinolin-2(1H)-yl]ethanone 157

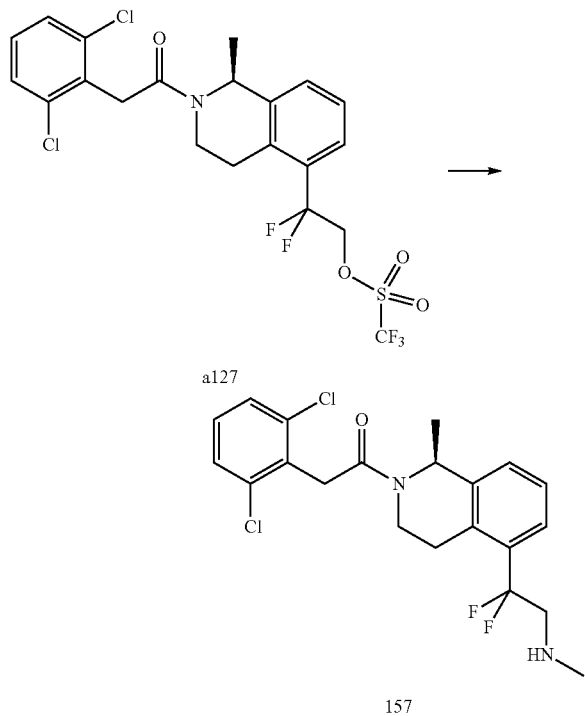

[2-[(1S)-2-[2-(2,6-dichlorophenyl)acetyl]-1-methyl-3,4-dihydro-1H-isoquinolin-5-yl]-2,2-difluoroethyl] trifluoromethanesulfonate a127 (55 mg, 0.10 mmol) was diluted with a solution of 33% wt. methylamine in EtOH (1 mL). The reaction mixture was stirred at rt for 15 h. The reaction mixture was diluted with EtOAc (50 mL) and washed with water (20 mL). The organic layer was dried over MgSO$_4$, filtered and concentrated under vacuum. The residue was purified by reverse phase chromatography (acidic mode, then basic mode, LCMS prep) to yield 7 mg of 2-(2,6-dichlorophenyl)-1-[(1S)-5-[1,1-difluoro-2-(methylamino)ethyl]-1-methyl-3,4-dihydroisoquinolin-2(1H)-yl]ethanone 157 as a colorless gum.

Yield: 17%.

LCMS (ES$^+$): 427/429/431 (M+H)$^+$, 99% purity.

C.69. Synthesis of 2-{(1S)-2-[(2,6-dichlorophenyl)acetyl]-1-methyl-1,2,3,4-tetrahydroisoquinolin-5-yl}-2,2-difluoroacetamide 158

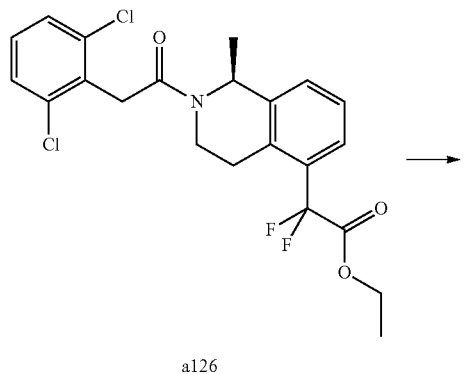

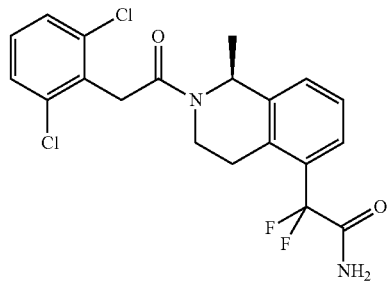

Ethyl 2-[(1S)-2-[2-(2,6-dichlorophenyl)acetyl]-1-methyl-3,4-dihydro-1H-isoquinolin-5-yl]-2,2-difluoroacetate a126 (600 mg, 1.32 mmol) was diluted with a saturated methanolic solution of ammonia (2 mL). The reaction mixture was stirred at 80° C. for 48 h in a sealed autoclave, then concentrated under reduced pressure to yield 562 mg of 2-{(1S)-2-[(2,6-dichlorophenyl)acetyl]-1-methyl-1,2,3,4-tetrahydroisoquinolin-5-yl}-2,2-difluoroacetamide 158 as a yellow solid.

Yield: 100%.

LCMS (ES$^+$): 427/429/431 (M+H)$^+$, 94% purity.

C.70. Synthesis of 2-{(1S)-2-[(2,6-dichlorophenyl)acetyl]-1-methyl-1,2,3,4-tetrahydroisoquinolin-5-yl}-2,2-difluoro-N-(1-methylcyclopropyl)acetamide 159

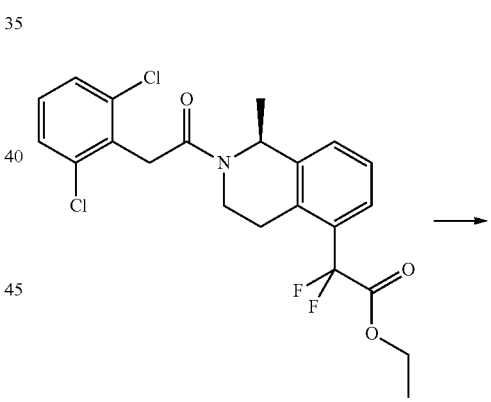

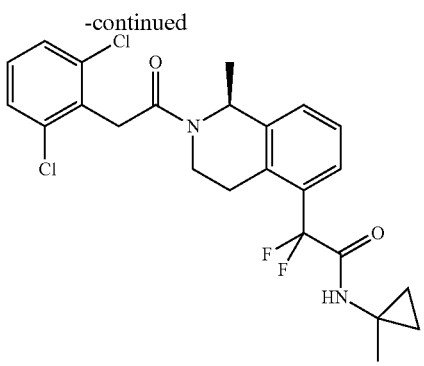

159

C.70.1. Synthesis of 2-[(1S)-2-[2-(2,6-dichlorophenyl)acetyl]-1-methyl-3,4-dihydro-1H-isoquinolin-5-yl]-2,2-difluoroacetic acid a128

To a solution of ethyl 2-[(1S)-2-[2-(2,6-dichlorophenyl)acetyl]-1-methyl-3,4-dihydro-1H-isoquinolin-5-yl]-2,2-difluoroacetate a126 (1.93 g, 4.23 mmol) in EtOH (20 mL) and water (5 mL) was added KOH (240 mg, 4.28 mmol) at rt. The reaction mixture was stirred overnight at rt, quenched with a 5N aqueous solution of HCl (5 mL), stirred at rt for 1 h. EtOH was removed under reduced pressure, then the aqueous layer was extracted thrice with DCM (100 mL). The organic layer was dried over MgSO$_4$, filtered and concentrated under vacuum. The residue was purified by reverse phase chromatography (basic mode, standard LC) to give 564 mg of 2-[(1S)-2-[2-(2,6-dichlorophenyl)acetyl]-1-methyl-3,4-dihydro-1H-isoquinolin-5-yl]-2,2-difluoroacetic acid a128.

Yield: 31%.
LCMS (ES$^+$): 428/430/432 (M+H)$^+$.

C.70.2. Synthesis of 2-{(1S)-2-[(2,6-dichlorophenyl)acetyl]-1-methyl-1,2,3,4-tetrahydroisoquinolin-5-yl}-2,2-difluoro-N-(1-methylcyclopropyl)acetamide 159

To a solution of 2-[(1S)-2-[2-(2,6-dichlorophenyl)acetyl]-1-methyl-3,4-dihydro-1H-isoquinolin-5-yl]-2,2-difluoroacetic acid a128 (280 mg, 0.65 mmol) and 1-methylcyclopropanamine hydrochloride (75 mg, 0.66 mmol) in DMF (4 mL) was added BOP (325 mg, 0.72 mmol) and the reaction mixture is stirred for 5 min. Then, DIPEA (0.5 mL, 3 mmol) was added and the reaction mixture was stirred overnight at 60° C. DIPEA (0.5 mL, 3 mmol) was added again to the reaction mixture which was stirred at 90° C. for 2 days. The reaction mixture was then diluted with EtOAc (50 mL) and successively washed with water (100 mL), 1N aqueous solution of HCl (100 mL), brine (100 mL) and water (100 mL). The organic layer was dried over MgSO$_4$, filtered and concentrated under vacuum. The residue was purified by reverse phase chromatography (basic mode, LCMS prep) to give 35 mg of 2-{(1S)-2-[(2,6-dichlorophenyl)acetyl]-1-methyl-1,2,3,4-tetrahydroisoquinolin-5-yl}-2,2-difluoro-N-(1-methylcyclopropyl)acetamide 159 as a solid.

Yield: 11%.
LCMS (ES$^+$): 481/483/485 (M+H)$^+$, 95% purity.

2-{(1S)-2-[(2,6-dichlorophenyl)acetyl]-1-methyl-1,2,3,4-tetrahydroisoquinolin-5-yl}-2,2-difluoro-N-(3-methyloxetan-3-yl)acetamide 160 may be synthesized according to a method analogous to the method described above using 2-[(1S)-2-[2-(2,6-dichlorophenyl)acetyl]-1-methyl-3,4-dihydro-1H-isoquinolin-5-yl]-2,2-difluoroacetic acid a128 and 3-methyloxetan-3-amine hydrochloride.

Yield: 10%.
LCMS (ES$^+$): 497/499/501 (M+H)$^+$, 80% purity.
Appearance: solid

C.71. Synthesis of 2-(2,6-dichlorophenyl)-1-[(1S)-1-methyl-5-(2H-1,2,3-triazol-4-yl)-3,4-dihydroisoquinolin-2(1H)-yl]ethanone 161

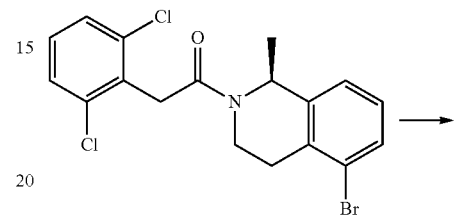

a69-(S)

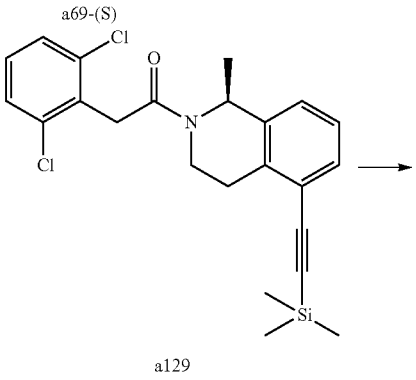

a129

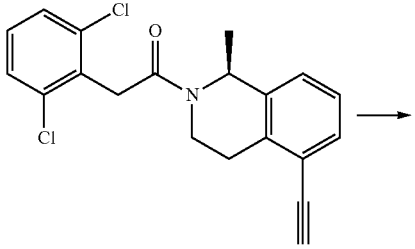

a130

161

C.71.1. Synthesis of 2-(2,6-dichlorophenyl)-1-[(1S)-1-methyl-5-(2-trimethylsilylethynyl)-3,4-dihydro-1H-isoquinolin-2-yl]ethanone a129

To 1-[(1S)-5-bromo-1-methyl-3,4-dihydroisoquinolin-2(1H)-yl]-2-(2,6-dichlorophenyl)ethanone a69-(S) (1 g, 2.42 mmol) in triethylamine (10 mL, 70.98 mmol) was added trimethylsilylacetylene (0.52 mL, 3.63 mmol), cuprous iodide (46 mg, 0.24 mmol), Pd(PPh$_3$)$_4$ (0.14 g, 0.12 mmol). The reaction mixture was stirred overnight at reflux, then quenched with water (50 mL). The residual mixture was extracted thrice with DCM (50 mL). The organic layer was washed with brine (50 mL), dried over MgSO$_4$, filtered and concentrated under vacuum. The residue was purified by reverse phase chromatography (basic mode, standard LC) to give 723 mg of 2-(2,6-dichlorophenyl)-1-[(1S)-1-methyl-5-(2-trimethylsilylethynyl)-3,4-dihydro-1H-isoquinolin-2-yl]ethanone a129 as an orange oil.

Yield: 69%.

LCMS (ES$^+$): 430/432/434 (M+H)$^+$.

C.71.2. Synthesis of 2-(2,6-dichlorophenyl)-1-[(1S)-5-ethynyl-1-methyl-3,4-dihydro-1H-isoquinolin-2-yl]ethanone a130

To a solution of 2-(2,6-dichlorophenyl)-1-[(1S)-1-methyl-5-(2-trimethylsilylethynyl)-3,4-dihydro-1H-isoquinolin-2-yl]ethanone a129 (723 mg, 1.68 mmol) in MeOH (15 mL) was added K$_2$CO$_3$ (0.46 g, 3.36 mmol). The reaction mixture was stirred overnight at rt, then quenched with a 1N aqueous solution of HCl (20 mL). The residual mixture was extracted thrice with DCM (50 mL). The organic layer was washed with brine (50 mL), dried over MgSO$_4$, filtered and concentrated under vacuum. The residue was purified filtered through a silica pad and eluted with DCM to give 478 mg of 2-(2,6-dichlorophenyl)-1-[(1S)-5-ethynyl-1-methyl-3,4-dihydro-1H-isoquinolin-2-yl]ethanone a130 as a beige solid.

Yield: 79%.

LCMS (ES$^+$): 358/360/362 (M+H)$^+$.

C.71.3. Synthesis of 2-(2,6-dichlorophenyl)-1-[(1S)-1-methyl-5-(2H-1,2,3-triazol-4-yl)-3,4-dihydroisoquinolin-2(1H)-yl]ethanone 161

To a solution of 2-(2,6-dichlorophenyl)-1-[(1S)-5-ethynyl-1-methyl-3,4-dihydro-1H-isoquinolin-2-yl]ethanone a130 (200 mg, 0.56 mmol) in DMF (2 mL) was added sodium azide (0.11 g, 1.69 mmol). The reaction mixture was stirred at 160° C. for 5 h under microwave irradiation, then quenched with water (20 mL). The residual mixture was extracted thrice with DCM (20 mL). The organic layer was washed with brine (20 mL), dried with over MgSO$_4$, filtered and concentrated under vacuum. The residue was purified by reverse phase chromatography (basic mode, standard LC) to give 25 mg of 2-(2,6-dichlorophenyl)-1-[(1S)-1-methyl-5-(2H-1,2,3-triazol-4-yl)-3,4-dihydroisoquinolin-2(1H)-yl]ethanone 161 as a white solid.

Yield: 11%.

LCMS (ES$^+$): 401/403/405 (M+H)$^+$, 99% purity.

C.72. Synthesis of 2-(2,6-dichlorophenyl)-1-[(1S)-5-(3-hydroxypropyl)-1-methyl-3,4-dihydroisoquinolin-2(1H)-yl]ethanone 162

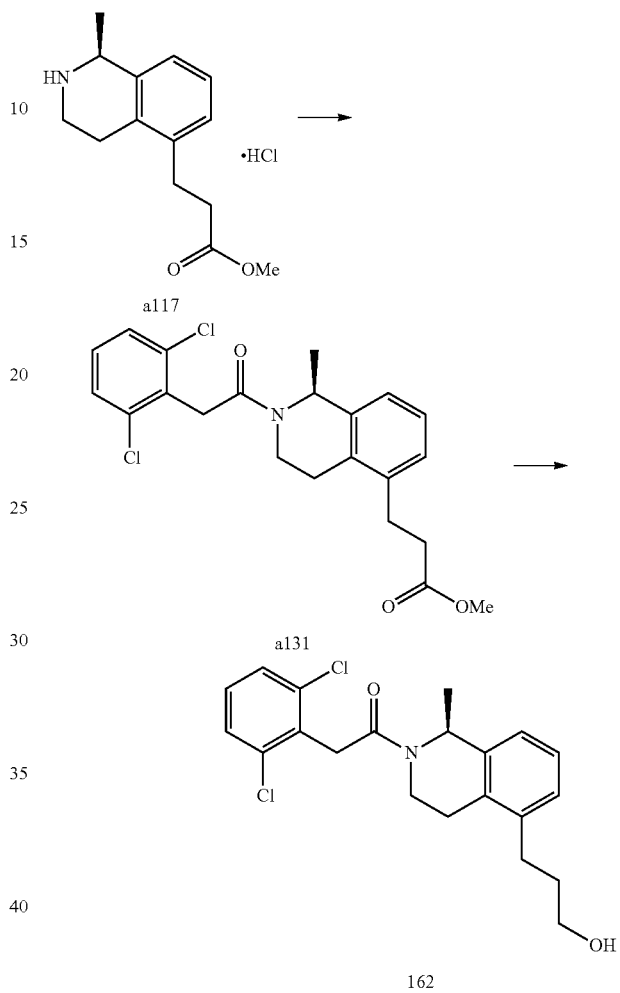

C.72.1. Synthesis of methyl 3-[(1S)-2-[2-(2,6-dichlorophenyl)acetyl]-1-methyl-3,4-dihydro-1H-isoquinolin-5-yl]propanoate a131

To a solution of methyl 3-[(1S)-1-methyl-1,2,3,4-tetrahydroisoquinolin-5-yl]propanoate hydrochloride a117 (820 mg, 1.82 mmol) and 2,6-dichlorophenylacetic acid (390 mg, 1.86 mmol) in ACN (10 mL) were added 1-(3-dimethylaminopropyl)-3-ethylcarbodiimide hydrochloride (420 mg, 2.19 mmol) and 1-hydroxybenzotriazole hydrate (115 mg, 0.75 mmol). The mixture was stirred for 15 min at rt, then 4-methylmorpholine (0.6 mL, 5 mmol) was added drop wise at 0° C. The reaction mixture was stirred overnight at rt, then concentrated under vacuum. The mixture was poured in water (100 mL) and extracted thrice with EtOAc (3*100 mL). The organic layer was washed twice with a 1N aqueous solution of HCl and with water (250 mL), then dried over MgSO$_4$, filtered and concentrated under vacuum. The residue was purified by reverse phase chromatography (basic mode, standard LC) to yield 195 mg of methyl 3-[(1S)-2-[2-(2,6-dichlorophenyl)acetyl]-1-methyl-3,4-dihydro-1H-isoquinolin-5-yl]propanoate a131.

Yield: 25%

LCMS (ES+): 420/422/424 (M+H)+.

C.72.2. Synthesis of 2-(2,6-dichlorophenyl)-1-[(1S)-5-(3-hydroxypropyl)-1-methyl-3,4-dihydroisoquinolin-2(1H)-yl]ethanone 162

To a solution of methyl 3-[(1S)-2-[2-(2,6-dichlorophenyl)acetyl]-1-methyl-3,4-dihydro-1H-isoquinolin-5-yl]propanoate a131 (33 mg, 78 µmol) in THF (2 mL) was added lithium borohydride (10 mg, 0.43 mmol) portion wise at rt. The reaction mixture was stirred overnight at rt, then quenched with water (1 mL) and stirred at rt for 1 h. DCM (10 mL) was added and, after 30 min of stirring, the mixture was passed through a SPE column. The filtrate was concentrated under vacuum and the residue was purified by reverse phase chromatography (basic mode, LCMS prep) to yield 1.2 mg of 2-(2,6-dichlorophenyl)-1-[(1S)-5-(3-hydroxypropyl)-1-methyl-3,4-dihydroisoquinolin-2(1H)-yl]ethanone 162 as a solid.

Yield: 4%

LCMS (ES+): 392/394/396 (M+H)+.

C.73. Synthesis of 6-[(1S)-2-[2-(2,6-dichlorophenyl)acetyl]-1-methyl-3,4-dihydro-1H-isoquinolin-5-yl]morpholin-3-one isomer A 163

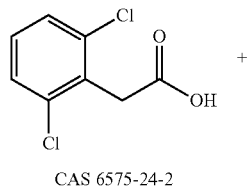

CAS 6575-24-2

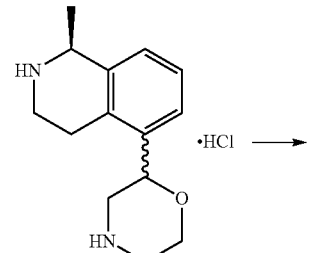

a123
Isomer A

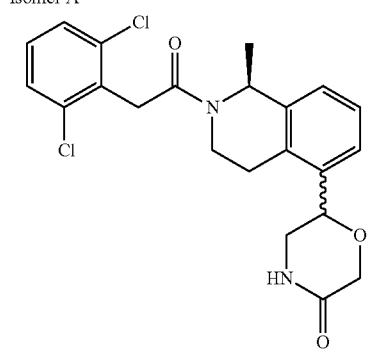

163
Isomer A 1-chloro-N,N,2-trimethylpropenylamine (111 mg, 0.8 mmol) was added to a solution of 2,6-dichlorophenylacetic acid (150 mg, 0.72 mmol) in DCM (2 mL). This solution was stirred at rt for 15 min, then was added to a solution of 6-[(1S)-1-methyl-1,2,3,4-tetrahydroisoquinolin-5-yl]morpholin-3-one hydrochloride isomer A a123 (150 mg, 0.53 mmol) and triethylamine (224 µL, 1.59 mmol) in DCM (2 mL) at rt. The reaction mixture was concentrated under vacuum and the residue was diluted with EtOAc (50 mL). The organic layer was successively washed with a 1N aqueous solution of HCl (2*20 mL) and an aqueous saturated solution of sodium bicarbonate (2*20 mL), then dried over MgSO4, filtered and concentrated under vacuum. The residue was purified by trituration in Et2O (5 mL) yielded 80 mg of 6-[(1S)-2-[2-(2,6-dichlorophenyl)acetyl]-1-methyl-3,4-dihydro-1H-isoquinolin-5-yl]morpholin-3-one isomer A 163 as a white solid.

Yield: 35%.

LCMS (ES+): 433/435/437 (M+H)+, 89% purity.

6-[(1S)-2-[2-(2,6-dichlorophenyl)acetyl]-1-methyl-3,4-dihydro-1H-isoquinolin-5-yl]morpholin-3-one isomer B 164 was synthesized according to the same procedure using 6-[(1S)-1-methyl-1,2,3,4-tetrahydroisoquinolin-5-yl]morpholin-3-one hydrochloride isomer B a124 and (2,6-dichlorophenyl)acetic acid as starting materials. Purification by trituration in Et2O (5 mL) yielded 125 mg of 6-[(1S)-2-[2-(2,6-dichlorophenyl)acetyl]-1-methyl-3,4-dihydro-1H-isoquinolin-5-yl]morpholin-3-one isomer B 164 as a white solid.

Yield: 54%.

LCMS (ES+): 433/435/437 (M+H)+, 93% purity.

C.74. Synthesis of 4-{(1S)-2-[(2-chloro-6-cyanophenyl)acetyl]-1-methyl-1,2,3,4-tetrahydroisoquinolin-5-yl}-1H-pyrazole-3-carbonitrile 165

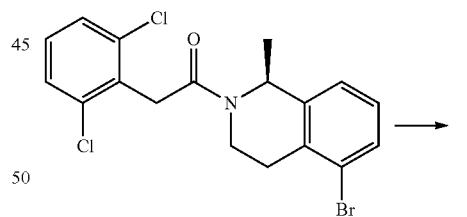

a125

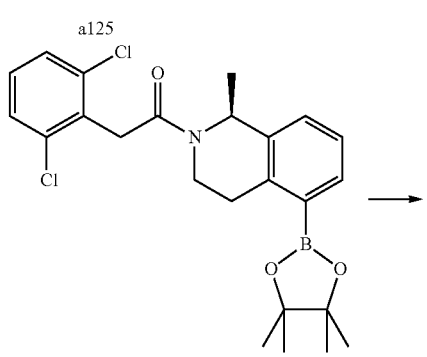

a132

-continued

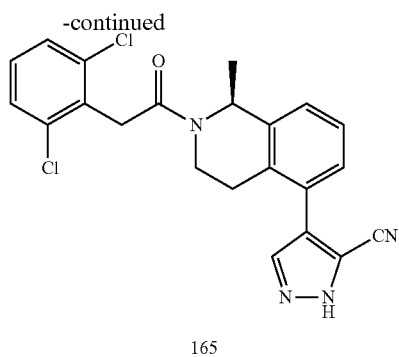

165

C.74.1. Synthesis of 3-chloro-2-[2-[(1S)-1-methyl-5-(4,4,5,5-tetramethyl-1,3,2-dioxaborolan-2-yl)-3,4-dihydro-1H-isoquinolin-2-yl]-2-oxo-ethyl]benzonitrile a132

Under argon, bis(pinacolato)diboron (2.57 g, 9.91 mmol), potassium acetate (0.61 mL, 14.86 mmol) and Pd(PPh$_3$)$_4$ (578 mg, 0.49 mmol) were added to a solution of 2-[2-[(1S)-5-bromo-1-methyl-3,4-dihydro-1H-isoquinolin-2-yl]-2-oxo-ethyl]-3-chloro-benzonitrile a125 (2 g, 4.95 mmol) in dioxane (50 mL). The reaction mixture was stirred overnight at 120° C., then concentrated under vacuum. The residue was diluted with EtOAc, filtered through Celite® and rinsed thrice with EtOAc. The filtrate was concentrated under vacuum, then the residue was purified by reverse phase chromatography (basic mode, standard LC) to yield 1.95 g of 3-chloro-2-[2-[(1S)-1-methyl-5-(4,4,5,5-tetramethyl-1,3,2-dioxaborolan-2-yl)-3,4-dihydro-1H-isoquinolin-2-yl]-2-oxo-ethyl]benzonitrile a132 as a white solid.

Yield: 87%.
LCMS (ES$^+$): 451/453 (M+H)$^+$.

C.74.2. Synthesis of 4-{(1S)-2-[(2-chloro-6-cyanophenyl)acetyl]-1-methyl-1,2,3,4-tetrahydroisoquinolin-5-yl}-1H-pyrazole-3-carbonitrile 165

Under argon, Pd(PPh$_3$)$_4$ (13 mg, 11 µmol) and water (300 µL, 20 mmol) were added to a suspension of 3-chloro-2-[2-[(1S)-1-methyl-5-(4,4,5,5-tetramethyl-1,3,2-dioxaborolan-2-yl)-3,4-dihydro-1H-isoquinolin-2-yl]-2-oxo-ethyl]benzonitrile a132 (50 mg, 0.11 mmol), 4-bromo-2H-pyrazole-3-carbonitrile (28 mg, 0.16 mmol) and potassium carbonate (19 µL, 0.33 mmol) in dioxane (3 mL). The reaction mixture was stirred at 130° C. for 60 min. 4-bromo-2H-pyrazole-3-carbonitrile (28 mg, 0.16 mmol) and Pd(PPh$_3$)$_4$ (13 mg, 11 µmol) were added after 90 min of additional reaction and once again after 60 min. The reaction mixture was then concentrated under vacuum. The residue was diluted with EtOAc, sonicated, filtered and rinsed with EtOAc. The filtrate was concentrated under vacuum. The residue was purified by SFC chromatography (column: 2-ethylpyridine, using 20% EtOH), then by reverse phase chromatography (basic mode, LCMS prep) to yield 3 mg of 4-{(1S)-2-[(2-chloro-6-cyanophenyl)acetyl]-1-methyl-1,2,3,4-tetrahydroisoquinolin-5-yl}-1H-pyrazole-3-carbonitrile 165 as a yellow oil.

Yield: 6.5%.
LCMS (ES$^+$): 416/418 (M+H)$^+$, 100% purity.

3-chloro-2-{2-[(1S)-1-methyl-5-[3-(trifluoromethyl)-1H-pyrazol-4-yl]-3,4-dihydroisoquinolin-2(1H)-yl]-2-oxoethyl}benzonitrile 166 may be synthesized according to a method analogous to the one described above using 3-chloro-2-[2-[(1S)-1-methyl-5-(4,4,5,5-tetramethyl-1,3,2-dioxaborolan-2-yl)-3,4-dihydro-1H-isoquinolin-2-yl]-2-oxo-ethyl]benzonitrile a132 and 3-(trifluoromethyl)-1H-pyrazole-4-boronic acid, pinacol ester as starting materials. Purification by SFC chromatography (phase: diol, using 7% EtOH), then by reverse phase chromatography (basic mode, LCMS prep) yielded 12 mg of 3-chloro-2-{2-[(1S)-1-methyl-5-[3-(trifluoromethyl)-1H-pyrazol-4-yl]-3,4-dihydroisoquinolin-2(1H)-yl]-2-oxoethyl}benzonitrile 166 as a white solid.

Yield: 21%.
LCMS (ES$^+$): 459/461 (M+H)$^+$, 100% purity.

2-{2-[(1S)-5-(2-aminopyridin-4-yl)-1-methyl-3,4-dihydroisoquinolin-2(1H)-yl]-2-oxoethyl}-3-chlorobenzonitrile trifluoroacetate 167 was synthesized according to the same procedure using 3-chloro-2-[2-[(1S)-1-methyl-5-(4,4,5,5-tetramethyl-1,3,2-dioxaborolan-2-yl)-3,4-dihydro-1H-isoquinolin-2-yl]-2-oxo-ethyl]benzonitrile a132 and 2-amino-4-bromopyridine as starting materials. Purification by reverse phase chromatography (acidic mode, LCMS prep) yielded 41 mg of 2-{2-[(1S)-5-(2-aminopyridin-4-yl)-1-methyl-3,4-dihydroisoquinolin-2(1H)-yl]-2-oxoethyl}-3-chlorobenzonitrile trifluoroacetate 167 as a white solid.

Yield: 69%.
LCMS (ES$^+$): 417/419 (M+H)$^+$, 99% purity.

C.75. Synthesis of 3-chloro-2-{2-[(1S)-1-methyl-5-(pyridin-2-yl)-3,4-dihydroisoquinolin-2(1H)-yl]-2-oxoethyl}benzonitrile 168

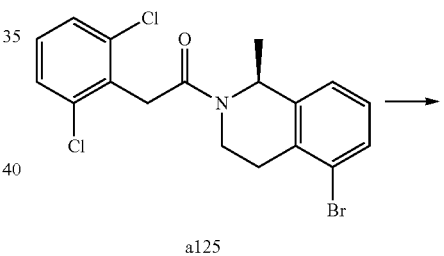

a125

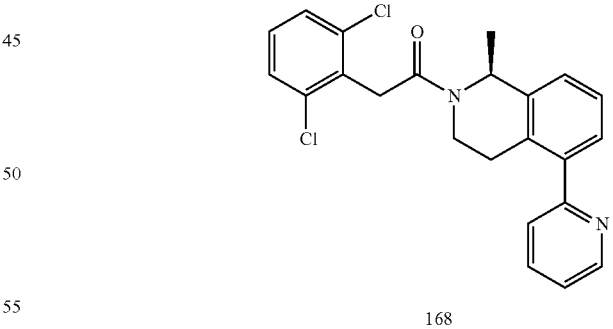

168

In a Schlenck tube, a mixture of 2-[2-[(1S)-5-bromo-1-methyl-3,4-dihydro-1H-isoquinolin-2-yl]-2-oxo-ethyl]-3-chloro-benzonitrile a125 (100 mg, 0.25 mmol), 2-pyridinylboronic acid MIDA ester (90.6 mg, 0.37 mmol), chloro(2-dicyclohexylphosphino-2',4',6'-tri-isopropyl-1,1'-biphenyl)[2-(2-aminoethyl)phenyl] palladium(II) methyl-tert-butyl ether adduct (10.4 mg, 12 µmol), copper(II) acetate (23 mL, 0.12 mmol), potassium phosphate tribasic (112 µL, 1.24 mmol) and diethanolamine (26 mg, 0.25 mmol) in DMF (1.5 mL) was stirred under argon at 100° C. for 24 h. The reaction mixture was diluted with EtOAc, then successively washed with a 1N aqueous solution of HCl, an aqueous saturated solution of NaHCO₃ and brine. The organic layer was dried over MgSO₄, filtered and concentrated under vacuum/The residue was purified by reverse phase chromatography (basic mode, standard LC) to yield 37 mg of 3-chloro-2-{2-[(1S)-1-methyl-5-(pyridin-2-yl)-3,4-dihydroisoquinolin-2 (1H)-yl]-2-oxoethyl}benzonitrile 168 as a yellow oil.

Yield: 37%.

LCMS (ES⁺): 402/404 (M+H)⁺, 99% purity.

Synthesis of Compounds of Formula I-B.

D.1. Synthesis of N-(2,6-dichlorophenyl)-1-methyl-3,4-dihydroisoquinoline-2(1H)-carboxamide 118 and enantiomers

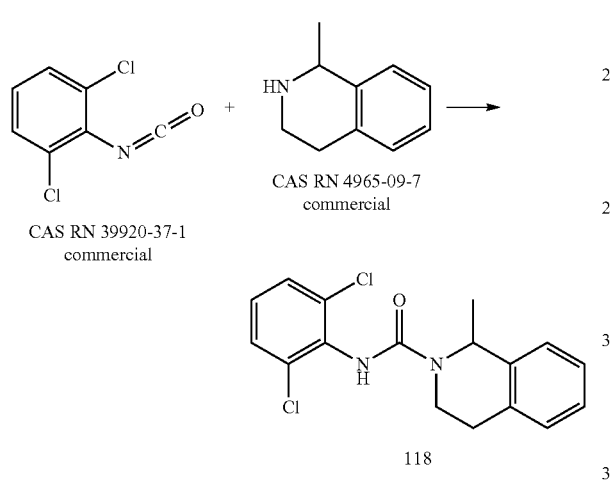

To a solution of 1-methyl-1,2,3,4-tetrahydroisoquinoline hydrochloride (commercial, 500 mg, 2.72 mmol) in THF (5 mL) were added TEA (1.2 mL, 8.5 mmol) and 1,3-dichloro-2-isocyanatobenzene (commercial, 522 mg, 2.72 mmol). The mixture was stirred overnight at 60° C., then concentrated under vacuum. The residue was taken up with DCM (100 mL), then the solution was successively washed with a 1N aqueous solution of NaOH (50 mL) and a 1N aqueous solution of HCl (50 mL). The organic layer was dried over MgSO₄, filtered and concentrated under vacuum. The residue was purified by reverse phase chromatography (basic mode, standard LC) to afford 273 mg of N-(2,6-dichlorophenyl)-1-methyl-3,4-dihydroisoquinoline-2(1H)-carboxamide 118 as a white solid.

Yield: 30%

LCMS (ES⁺): 335/337/339 (M+H)⁺, 98.8% purity.

Chiral separation of N-(2,6-dichlorophenyl)-1-methyl-3,4-dihydroisoquinoline-2(1H)-carboxamide 118 (SFC, Whelko-01 (R,R), 50*227 mm, 360 mL/min, 220 nm, 25° C., eluent: from 20 to 30% iPrOH) afforded:

115 mg of (1S)—N-(2,6-dichlorophenyl)-1-methyl-3,4-dihydroisoquinoline-2(1H)-carboxamide 119 as sticky solid.

Yield: 12%.

LCMS (ES⁺): 335/337/339 (M+H)+, 100% purity.

Chiral analysis (LC, Whelko-01 (R,R), 250*4.6 mm, 1 mL/min, 220 nm, 30° C., eluent: iPrOH/n-heptane/DEA 50/50/0.1): RT 7.26 min, 92% ee.

112 mg of (1R)—N-(2,6-dichlorophenyl)-1-methyl-3,4-dihydroisoquinoline-2(1H)-carboxamide 120 as a solid.

Yield: 12%.

LCMS (ES⁺): 335/337/339 (M+H)+, 97.8% purity.

Chiral analysis (LC, Whelko-01 (R,R), 250*4.6 mm, 1 mL/min, 220 nm, 30° C., eluent: iPrOH/n-heptane/DEA 50/50/0.1): RT 8.68 min, 99% ee.

D.2. Synthesis of (1S)—N-(2,6-dichlorophenyl)-1-methyl-5-[(methylsulfonyl)amino]-3,4-dihydroisoquinoline-2(1H)-carboxamide 121

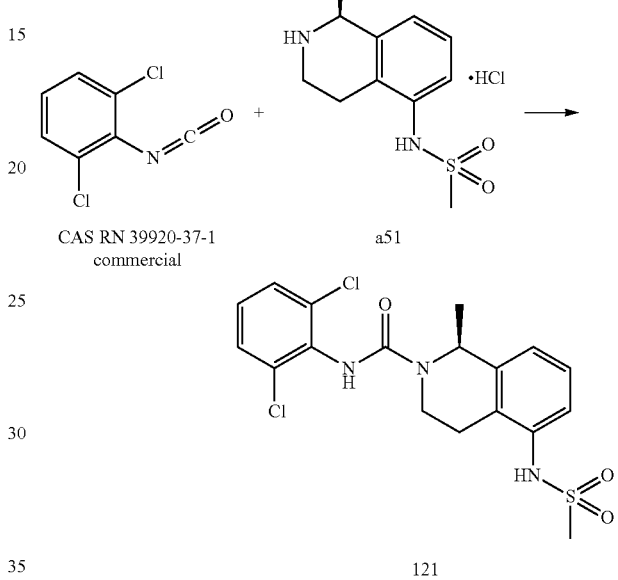

To a solution of N-[(1S)-1-methyl-1,2,3,4-tetrahydroisoquinolin-5-yl]methanesulfonamide hydrochloride a51 (100 mg, 0.36 mmol) in THF (2 mL) and DMF (1 mL) were added DIPEA (0.2 mL, 1.08 mmol) and 1,3-dichloro-2-isocyanatobenzene (commercial, 70 mg, 0.37 mmol). The mixture was stirred overnight at 50° C., then concentrated under vacuum. The residue was purified by reverse phase chromatography (basic mode, LCMS prep) to afford 40 mg of (1S)—N-(2,6-dichlorophenyl)-1-methyl-5-[(methylsulfonyl)amino]-3,4-dihydroisoquinoline-2(1H)-carboxamide 121 as a solid.

Yield: 26%.

LCMS (ES⁺): 428/430/432 (M+H)⁺, 94.2% purity.

D.3. Synthesis of (1S,4S)—N-(2,6-dichlorophenyl)-4-hydroxy-1-methyl-3,4-dihydroisoquinoline-2(1H)-carboxamide 122

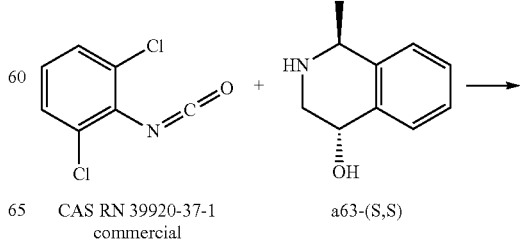

185

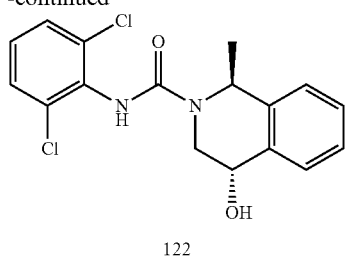

122

To a solution of (1S,4S)-1-methyl-1,2,3,4-tetrahydroisoquinolin-4-ol a63-(S,S) (35 mg, 0.21 mmol) in DCM (2 mL) was added 1,3-dichloro-2-isocyanatobenzene (commercial, 50 mg, 0.26 mmol). The mixture was stirred overnight at rt, then concentrated under vacuum. The residue was purified by reverse phase chromatography (basic mode, LCMS prep) to afford 32 mg of (1S,4S)—N-(2,6-dichlorophenyl)-4-hydroxy-1-methyl-3,4-dihydroisoquinoline-2(1H)-carboxamide 122 as an off-white solid.

Yield: 42%.

LCMS (ES$^+$): 351/353/355 (M+H)$^+$, 96% purity.

D.4. Synthesis of (1S,4R)—N-(2,6-dichlorophenyl)-4-hydroxy-1-methyl-3,4-dihydroisoquinoline-2(1H)-carboxamide 123

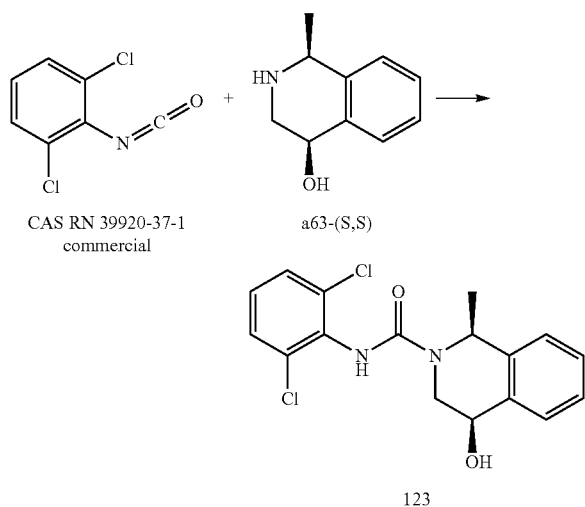

CAS RN 39920-37-1
commercial a63-(S,R)

123

To a solution of (1S,4R)-1-methyl-1,2,3,4-tetrahydroisoquinolin-4-ol a63-(S,R) (35 mg, 0.21 mmol) in DCM (2 mL) was added 1,3-dichloro-2-isocyanatobenzene (commercial, 50 mg, 0.26 mmol). The mixture was stirred overnight at rt, then concentrated under vacuum. The residue was purified by reverse phase chromatography (basic mode, LCMS prep) to afford mg of (1S,4R)—N-(2,6-dichlorophenyl)-4-hydroxy-1-methyl-3,4-dihydroisoquinoline-2(1H)-carboxamide 123 as an off-white solid.

Yield: 40%.

LCMS (ES$^+$): 351/353/355 (M+H)$^+$, 96% purity.

186

D.5. Synthesis of (1S)—N-(2,6-dichlorophenyl)-5-(hydroxymethyl)-1-methyl-3,4-dihydroisoquinoline-2(1H)-carboxamide 124

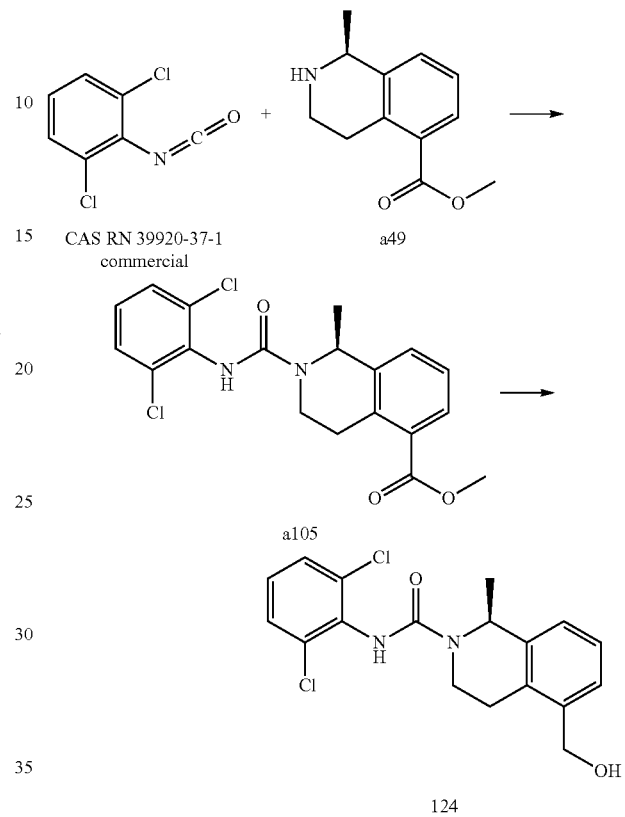

CAS RN 39920-37-1
commercial a49 a105

124

D.5.1. Synthesis of methyl(1S)-2-[(2,6-dichlorophenyl)carbamoyl]-1-methyl-1,2,3,4-tetrahydroisoquinoline-5-carboxylate a105

To a solution of methyl (1S)-1-methyl-1,2,3,4-tetrahydroisoquinoline-5-carboxylate a49 (230 mg, 1.12 mmol) in THF (3 mL) was added 1,3-dichloro-2-isocyanatobenzene (commercial, 215 mg, 1.14 mmol). The mixture was stirred overnight at rt, then concentrated under vacuum to afford 320 mg of methyl (1S)-2-[(2,6-dichlorophenyl)carbamoyl]-1-methyl-1,2,3,4-tetrahydroisoquinoline-5-carboxylate a105 which was used in next step without any further purification.

Yield: 62% (crude).

LCMS (ES$^+$): 393/395/397 (M+H)$^+$, 85% purity.

D.5.2. Synthesis of (1S)—N-(2,6-dichlorophenyl)-5-(hydroxymethyl)-1-methyl-3,4-dihydroisoquinoline-2(1H)-carboxamide 124

To a solution of methyl (1S)-2-[(2,6-dichlorophenyl)carbamoyl]-1-methyl-1,2,3,4-tetrahydroisoquinoline-5-carboxylate a105 (100 mg, 0.25 mmol) in THF (3 mL) was added in one portion lithium borohydride (35 mg, 1.53 mmol). The mixture was stirred overnight at rt, then lithium borohydride (35 mg, 1.53 mmol) was added again and the mixture was stirred overnight at rt. The reaction mixture was diluted with EtOAc (100 mL), then quenched with a 1N aqueous solution of HCl (50 mL). The organic layer was dried over MgSO$_4$, filtered and concentrated under vacuum.

The residue was purified by reverse phase chromatography (basic mode, LCMS prep) to yield 50 mg of (1S)—N-(2,6-dichlorophenyl)-5-(hydroxymethyl)-1-methyl-3,4-dihydroisoquinoline-2(1H)-carboxamide 124 as a white solid.
Yield: 54%.
LCMS (ES+): 365/367/369 (M+H)+, 100% purity.

D.6. Synthesis of (1S)—N-(2,6-dichlorophenyl)-1-methyl-5-(methylsulfonyl)-3,4-dihydroisoquinoline-2(1H)-carboxamide 125

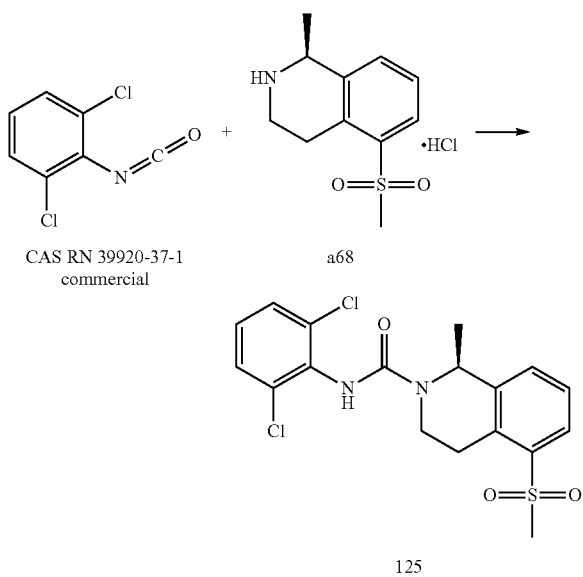

To a solution of (1S)-1-methyl-5-(methylsulfonyl)-1,2,3,4-tetrahydroisoquinoline hydrochloride a68 (70 mg, 0.27 mmol) in DCM (2 mL) were added DIPEA (57 µL, 0.32 mmol) and 1,3-dichloro-2-isocyanatobenzene (commercial, 56 mg, 0.29 mmol). The mixture was stirred overnight at rt, then quenched with water and washed with an aqueous saturated solution of NaHCO₃. The organic layer was dried over Na₂SO₄, filtered and concentrated under vacuum. The residue was purified by reverse phase chromatography (Basic mode, LCMS prep) to afford 72 mg of (1S)—N-(2,6-dichlorophenyl)-1-methyl-5-(methylsulfonyl)-3,4-dihydroisoquinoline-2(1H)-carboxamide 125 as a colorless glass solid.
Yield: 65%.
LCMS (ES+): 413/415/417 (M+H)+, 97.9% purity.

D.7. Synthesis of Compounds 126 to 131

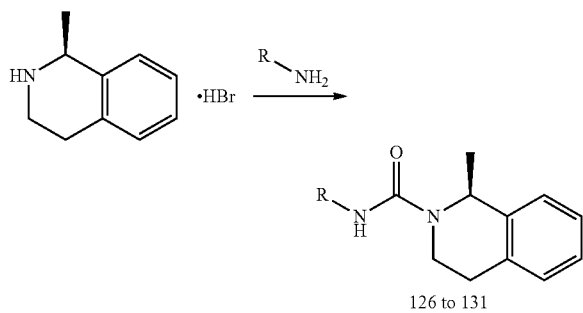

To a solution of anilines (0.12 mmol) in THF (800 µL) at 0° C., was added triphosgene (21 mg, 0.07 mmol). The mixture is stirred at rt for 1 h30, then TEA (70 µL, 0.50 mmol), (1S)-1-methyl-1,2,3,4-tetrahydroisoquinoline hydrobromide (commercial, 27 mg, 0.12 mmol). The mixture was stirred at rt for 1 h, then overnight at 60° C. The reaction mixture is diluted with EtOAc (2 mL), then washed with an aqueous saturated solution of NaHCO₃. The organic layer was dried over MgSO₄, filtered and concentrated under vacuum. The residue was purified by reverse phase chromatography (basic mode, LCMS prep).

compounds 126, 127, 128, 129, 130 and 131 were synthesized following this method.

(1S)—N-(2-bromo-6-fluorophenyl)-1-methyl-3,4-dihydroisoquinoline-2(1H)-carboxamide 126

Compound 126 was prepared using 2-bromo-6-fluoroaniline as starting material
Yield: 52%.
LCMS (ES+): 363 (M+H)+, 96.9% purity.

(1S)—N-(2-bromophenyl)-1-methyl-3,4-dihydroisoquinoline-2(1H)-carboxamide 127

Compound 127 was prepared using 2-bromo-aniline as starting material.
Yield: 65%.
LCMS (ES+): 345 (M+H)+, 95% purity.

(1S)—N-(2,6-dimethylphenyl)-1-methyl-3,4-dihydroisoquinoline-2(1H)-carboxamide 128

Compound 128 was prepared using 2,6-dimethylaniline as starting material
Yield: 48%.
LCMS (ES+): 294 (M+H)+, 96.9% purity.

(1S)—N-(5-bromo-2-chlorophenyl)-1-methyl-3,4-dihydroisoquinoline-2(1H)-carboxamide 129

Compound 129 was prepared using 5-bromo-2-chloroaniline as starting material
Yield: 39%.
LCMS (ES+): 380 (M+H)+, 97.1% purity.

(1S)—N-(2-chloro-6-methylphenyl)-1-methyl-3,4-dihydroisoquinoline-2(1H)-carboxamide 130

Compound 130 was prepared using 2-chloro-6-methylaniline as starting material
Yield: 41%.
LCMS (ES+): 315 (M+H)+, 73.2% purity.

(1S)—N-(2-bromo-6-methoxyphenyl)-1-methyl-3,4-dihydroisoquinoline-2(1H)-carboxamide 131

Compound 131 was prepared using 2-bromo-6-methoxyaniline as starting material
Yield: 48%.
LCMS (ES+): 315 (M+H)+, 97.4% purity.

E. cAMP HTRF Assay

Compounds according to the present invention do not directly activate the dopamine D1 receptor, but potentiate the effect of D1 agonists or the endogenous ligand on D1 receptors, dopamine, through an allosteric mechanism, and are therefore D1 positive allosteric modulators (D1 PAM).

Dopamine and other D1 agonists directly activate the dopamine D1 receptor by themselves.

The present assay allows to measure respectively the effects of compounds of the Examples in the absence of dopamine ("activation assay") and the effects of compounds of the Examples in the presence of dopamine ("potentiation assay").

The activation assay measures the stimulation of the production of cyclic adenosinemonophosphate (cAMP) in the HTRF assay, with the maximum increase in cAMP by increasing concentrations of the endogenous agonist, dopamine, defined as 100% activation. When tested compounds of the Examples lack significant direct agonist-like effects in that they produce less than 20% of activation (compared to dopamine maximal response) when present in a concentration of 10 µM.

The potentiation assay measures the ability of compounds to increase the levels of cAMP produced by a low-threshold concentration of dopamine. The concentration of dopamine used ($[EC_{20}]$) is designed to produce 20% stimulation compared to the maximal response (100%) seen with increasing the concentration of dopamine. To measure this potentiation we incubate increasing concentrations of the compound with the $[EC_20]$ of dopamine and measure the potentiation as increases in cAMP production. The $pEC_{50}$ of a compound is the −log 10 of the concentration of the compound which produces 50% of the potentiation of the cAMP levels and the Erel is the relative efficacy, defined as the maximal % potentiation produced by the compound compared to the maximal response produced by increasing concentrations of dopamine (Erel of 1=dopamine maximum response).

The particular conditions in which the compounds have been tested are described here below.

Methods D1 Cell Culture

Cells were cultured at 37° C. in a humidified atmosphere of 5% $CO_2$. Cells were grown in DMEM-F12+GlutaMAX™-I medium (GIBCO®, Invitrogen, Merelbeke, Belgium) containing 10% fetal bovine serum (BioWhittaker®, Lonza, Verviers, Belgium), 400 µg/mL Geneticin (GIBCO®), 100 IU/mL Penicillin and 100 IU/mL Streptomycin (Pen-Strep solution, BioWhittaker®). LMtk (Ltk−) mouse fibroblast cells expressing the dopamine D1 receptor (BioSignal Inc, Montreal, Canada, now Perkin Elmer) were used as they have been shown to couple efficiently and give robust functional responses (Watts et al, 1995).

cAMP Assay

The measurement of changes in intracellular cyclic adenosinemonophopshpate (cAMP) was determined using the HTRF cAMP dynamic assay kit from CisBio (Codolet, France). Using homogenous time-resolved fluoresence technology, the assay is based on competition between native cAMP produced by cells and cAMP labelled with the dye d2. The tracer binding is determined by an anti-cAMP antibody labeled with cryptate. The effects of the compound alone (agonism) was determined by performing the assay in the absence of dopamine, whilst the effect of the compound as a positive allosteric modulator (PAM) was determined in the presence of an $EC_{20}$ concentration of dopamine. Cells (20,000 per well) are incubated in 384 plates for 1 hour at room temperature in a final volume of 20 µL HBSS (Lonza, with calcium, magnesium and HEPES buffer 20 mM, pH 7.4) containing: isobutyl methylxanthine (Sigma, 0.1 mM final), varying concentrations of test compound (typically $10^{-9.5}$M to $10^{-4.5}$M) in the presence and absence of dopamine (1.1 nM final). The reaction is then terminated and the cells lysed by adding the d2 detection reagent in lysis buffer (10 microL) and the cryptate reagent in lysis buffer (10 microl) according to manufacturer's instructions. This is then incubated for a further 60 min at room temperature and changes in HTRF fluorescent emission ratio determined according to manufacturer's instructions using an Envision plate reader (Perkin Elmer, Zaventem, Belgium) with laser excitation. All incubations were performed in duplicate and results were compared to a concentration-effect curve to dopamine. ($10^{-11}$M to $10^{-6}$M).

Data Analysis

Data was analyzed using Excel and PRISM (GraphPad Software) to obtain $pEC_{50}$ and Erel using the 4-parameter logistic equation (DeLean et al, 1978) where Erel is the fitted maximal response of the test compound minus basal expressed as a percentage relative to that obtained with dopamine which was defined as 100%.

When tested in the cAMP HTRF assay, compounds of the Examples exhibit values of pEC50 greater than or equal to 5.5; ideally greater than or equal to 6.5; preferably greater than or equal to 7; more preferably greater than or equal to 8.

The invention claimed is:

1. A compound of formula (I), or a pharmaceutically acceptable salt thereof,

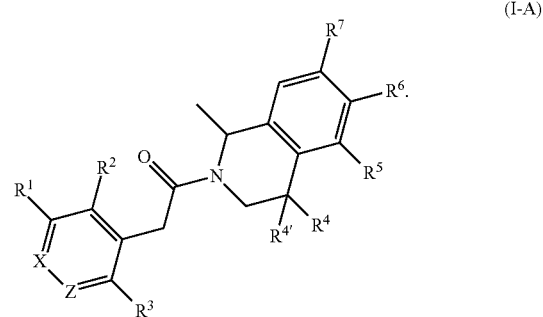

(I-A)

wherein
R¹ is hydrogen, halogen, cyano or hydroxy; $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl or ($C_{1-6}$-alkylsulfonyl)amino, any of which groups is optionally substituted by one or more substituents;

R² is hydrogen, cyano, or halogen; or $C_{1-6}$ alkyl, $C_{1-6}$ alkoxy, $C_{1-6}$ alkylsulfanyl, $C_{1-6}$ alkylsulfinyl, $C_{1-6}$ alkylsulfonyl, $C_{1-6}$ alkylsulfonylamino, ($C_{1-6}$ alkylsulfonyl)amino($C_{1-6}$ alkyl), $C_{1-6}$ alkylamido, ($C_{1-6}$ alkylacyl)amino, ($C_{1-6}$ alkylacyl)amino($C_{1-6}$ alkyl), or heteroaryl, any of which groups is optionally substituted by one or more substituents; or R¹ and R² are linked together to form with the adjacent aromatic group a heterocycle of formula (i):

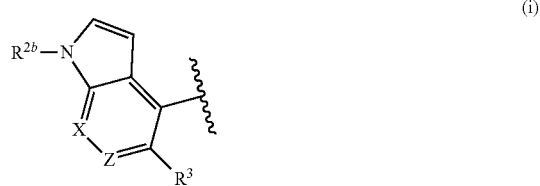

(i)

wherein $R^{2b}$ is hydrogen or $C_{1-6}$ alkylsulfonyl;

$R^3$ is halogen, $C_{1-6}$ alkyl, $C_{1-6}$ alkoxy or cyano;

$R^4$ is hydrogen, halogen, $C_{1-6}$ alkyl, hydroxy, $C_{1-6}$ alkoxy, $C_{1-6}$ alkylsulfonyl, $C_{1-6}$ alkoxycarbonyloxy or $C_{1-6}$ alkylaminocarbonyloxy;

$R^{4'}$ is hydrogen, halogen or $C_{1-6}$ alkyl; or $R^4$ and $R^{4'}$ together form an oxo group;

$R^5$ is hydrogen, cyano or hydroxy; or $C_{1-6}$ alkyl; $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino($C_{1-6}$ alkyl), $C_{1-6}$ alkylureido($C_{1-6}$ alkyl), $C_{1-6}$alkylcarbamate($C_{1-6}$ alkyl); amido; $C_{1-6}$alkoxycarbonyloxy($C_{1-6}$alkyl); amino group; N-cyano-S—($C_{1-6}$-alkyl)sulfonimidoyl, N,S-(di-$C_{1-6}$-alkyl)sulfonimidoyl, aminosulfinyl; $C_{1-6}$-alkylsulfinyl; aminosulfonyl; (di-$C_{1-6}$-alkyl)(oxido)-$\lambda^6$-sulfanylidene-amino, amino ($C_{1-6}$ alkyl), or amido($C_{1-6}$ alkyl); any of which groups is optionally substituted by one or more substituents;

$R^6$ is hydrogen;

$R^7$ is hydrogen or ($C_{1-6}$alkylsulfonyl)amino;

X is $CR^9$ or N; wherein $R^9$ is hydrogen, halogen or $C_{1-6}$-alkyl substituted by hydroxy;

Z is CH or N;

provided the compound is not (2-(2-fluorophenyl)-1-[(1R)-1-methyl-3,4-dihydro-2 (1H)-isoquinolinyl]-1-ethanone.

2. The compound according to claim 1 or a pharmaceutically acceptable salt thereof, wherein $R^1$ is hydrogen, halogen, hydroxy, $C_{1-6}$-alkyl hydroxy, $C_{1-6}$ alkoxy, $C_{1-6}$ alkylsulfanyl, $C_{1-6}$ alkylsulfinyl, $C_{1-6}$ alkylsulfonyl or ($C_{1-6}$-alkylsulfonyl)amino.

3. The compound according to claim 1 or a pharmaceutically acceptable salt thereof, wherein $R^2$ is hydrogen, halogen, $C_{1-6}$ alkyl unsubstituted or substituted by one or more halogens, $C_{1-6}$-alkyl hydroxy, $C_{1-6}$ alkoxy, $C_{1-6}$ alkylsulfanyl, $C_{1-6}$ alkylsulfinyl, $C_{1-6}$ alkylsulfonyl, cyano, $C_{1-6}$ alkylamido, pyrazolyl, or a group of formula —$CH_2R^{2a}$, —$NHR^{2a}$ or —$CH_2NHR^{2a}$ wherein $R^{2a}$ is selected from $C_{1-6}$ alkylacyl or $C_{1-6}$ alkylsulfonyl.

4. The compound according to claim 2 represented by formula (I-A-A) or a pharmaceutically acceptable salt thereof,

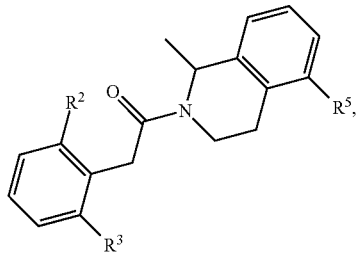

(I-A-A)

wherein
$R^2$ and $R^3$ are independently halogen or cyano, and
$R^5$ is hydrogen, cyano or hydroxy; or $C_{1-6}$ alkyl, $C_{1-6}$-alkylsulfonyl, $C_{1-6}$-alkylsulfonylamino; $C_{1-6}$-alkylsulfonylamino($C_{1-6}$ alkyl), heterocycle, $C_{1-6}$ alkylacylamino($C_{1-6}$ alkyl); $C_{1-6}$ alkylureido($C_{1-6}$ alkyl), $C_{1-6}$alkylcarbamate($C_{1-6}$ alkyl), amido, $C_{1-6}$alkoxycarbonyloxy($C_{1-6}$alkyl), amino; N-cyano-S—($C_{1-6}$-alkyl)sulfonimidoyl, N,S-(di-$C_{1-6}$-alkyl)sulfonimidoyl, aminosulfinyl, $C_{1-6}$-alkylsulfinyl; aminosulfonyl, alkyl)(oxido)-6-sulfanylidene-amino; amino($C_{1-6}$ alkyl) or amido($C_{1-6}$ alkyl), any of which groups may be optionally substituted by one or more substituents.

5. The compound according to claim 1 or a pharmaceutically acceptable salt thereof wherein $R^2$ is chloro or cyano.

6. The compound according to claim 1 or a pharmaceutically acceptable salt thereof wherein $R^3$ is chloro or cyano.

7. The compound according to claim 1 or a pharmaceutically acceptable salt thereof,
wherein $R^5$ is hydrogen, hydroxy, hydroxymethyl, (methylsulfanyl)methyl, 1-hydroxyethyl, 2,2,2-trifluoro-1-hydroxyethyl, 3,5-dimethyl-1,2-oxazol-4-yl, (methylsulfonyl)amino, [(methylsulfonyl)amino]methyl, 2-[(methylsulfonyl)amino]ethyl, (2,2,2-trifluoroethyl) carbamoyl, dipropan-2-ylcarbamoyl, 4H-1,2,4-triazol-3-ylcarbamoyl, (2,5-dimethylpyrrolidin-1-yl)carbonyl, [4-(trifluoromethyl)piperidin-1-yl]carbonyl, methylsulfonyl, (methoxymethyl)sulfonyl, ethylsulfonyl, propan-2-ylsulfonyl, (tetrahydro-2H-pyran-4-ylmethyl) sulfonyl, methylsulfamoyl, (cyanomethyl)sulfamoyl, ethylsulfamoyl, (2,2,2-trifluoroethyl)sulfamoyl, propan-2-ylsulfamoyl or (4H-1,2,4-triazol-3-yl)sulfamoyl.

8. The compound of formula (I) according to claim 1 selected from the group consisting of
2-(2,6-dichlorophenyl)-1-(1-methyl-3,4-dihydroisoquinolin-2(1H)-yl)ethanone;
2-(2,6-dichlorophenyl)-1-[(1S)-1-methyl-3,4-dihydroisoquinolin-2(1H)-yl]ethanone;
2-(2,6-dichlorophenyl)-1-[(1R)-1-methyl-3,4-dihydroisoquinolin-2(1H)-yl]ethanone;
2-(3,5-dichloropyridin-4-yl)-1-[(1S)-1-methyl-3,4-dihydroisoquinolin-2(1H)-yl]ethanone;
N-{(1R)-2-[(2,6-dichlorophenyl)acetyl]-1-methyl-1,2,3,4-tetrahydroisoquinolin-5-yl}methanesulfonamide;
N-{(1S)-2-[(2,6-dichlorophenyl)acetyl]-1-methyl-1,2,3,4-tetrahydroisoquinolin-5-yl}methanesulfonamide;
2,4-dichloro-3-{2-[(1S)-1-methyl-3,4-dihydroisoquinolin-2(1H)-yl]-2-oxoethyl}benzonitrile;
2-(2,6-dichlorophenyl)-1-(4,4-difluoro-1-methyl-3,4-dihydroisoquinolin-2(1H)-yl)ethanone;
2-(2,6-dichlorophenyl)-1-[4,4-difluoro-1-methyl-3,4-dihydroisoquinolin-2(1H)-yl]ethanone;
2-(2,6-dichlorophenyl)-1-(1,4,4-trimethyl-3,4-dihydroisoquinolin-2(1H)-yl)ethanone;
2-(3-bromo-2,6-dichlorophenyl)-1-[(1S)-1-methyl-3,4-dihydroisoquinolin-2(1H)-yl]ethanone;
2-(3,5-dichloropyridin-4-yl)-1-[(1S)-5-(hydroxymethyl)-1-methyl-3,4-dihydroisoquinolin-2(1H)-yl]ethanone;
2-(5-chloro-1H-pyrrolo[2,3-b]pyridin-4-yl)-1-[(1S)-1-methyl-3,4-dihydroisoquinolin-2(1H)-yl]ethanone;
N-{(1S)-2-[(2-chloro-6-methylphenyl)acetyl]-1-methyl-1,2,3,4-tetrahydroisoquinolin-5-yl}methanesulfonamide;
N-{(1S)-2-[(2-chloro-6-cyanophenyl)acetyl]-1-methyl-1,2,3,4-tetrahydroisoquinolin-5-yl}methanesulfonamide;
2-(3,5-dichloro-2-methoxypyridin-4-yl)-1-[(1S)-1-methyl-3,4-dihydroisoquinolin-2(1H)-yl]ethanone;
2-(2-bromo-6-methoxyphenyl)-1-[(1S)-1-methyl-3,4-dihydroisoquinolin-2(1H)-yl]ethanone;
2-(3-chloro-5-methylpyridin-4-yl)-1-[(1S)-1-methyl-3,4-dihydroisoquinolin-2(1H)-yl]ethanone;
3-chloro-2-{2-[(1 S,4R)-4-hydroxy-1-methyl-3,4-dihydroisoquinolin-2(1H)-yl]-2-oxoethyl}benzonitrile;
2-(2,6-dichlorophenyl)-1-[(1 S,4R)-4-hydroxy-1-methyl-3,4-dihydroisoquinolin-2(1H)-yl]ethanone;
3-chloro-2-{2-[(1 S,4S)-4-hydroxy-1-methyl-3,4-dihydroisoquinolin-2(1H)-yl]-2-oxoethyl}benzonitrile;

2-(2,6-dichlorophenyl)-1-[(1 S,4 S)-4-hydroxy-1-methyl-3,4-dihydroisoquinolin-2(1H)-yl]ethanone;
2-(3,5-dichloropyridin-4-yl)-1-[(1S)-1-methyl-5-(methylsulfonyl)-3,4-dihydroisoquinolin-2(1H)-yl]ethanone;
3-chloro-2-{2-[(1S)-1-methyl-5-(methylsulfonyl)-3,4-dihydroisoquinolin-2(1H)-yl]-2-oxoethyl}benzonitrile;
2-(3,5-dichloropyridin-4-yl)-1-[(1 S,4R)-4-hydroxy-1-methyl-3,4-dihydroisoquinolin-2(1H)-yl]ethanone;
2-(2,6-dichloro-4-fluorophenyl)-1-[(1 S,4 S)-4-hydroxy-1-methyl-3,4-dihydroisoquinolin-2(1H)-yl]ethanone;
2-(2-chloro-6-methoxyphenyl)-1-[(1S)-1-methyl-3,4-dihydroisoquinolin-2(1H)-yl]ethanone;
2-[2-chloro-6-(trifluoromethyl)phenyl]-1-[(1S)-1-methyl-3,4-dihydroisoquinolin-2(1H)-yl]ethanone;
5-chloro-4-{2-[(1S)-1-methyl-3,4-dihydroisoquinolin-2(1H)-yl]-2-oxoethyl}pyridine-3-carbonitrile;
N-({2-[(2,6-dichlorophenyl)acetyl]-1-methyl-1,2,3,4-tetrahydroisoquinolin-5-yl}methyl)methanesulfonamide;
2-(2,6-dichlorophenyl)-1-[5-(3,5-dimethyl-1,2-oxazol-4-yl)-1-methyl-3,4-dihydroisoquinolin-2(1H)-yl]ethanone;
(1S)-2-[(2,6-dichlorophenyl)acetyl]-1-methyl-1,2,3,4-tetrahydroisoquinoline-5-carbonitrile;
N-{2-[(2,6-dichlorophenyl)acetyl]-1-methyl-1,2,3,4-tetrahydroisoquinolin-7-yl}methanesulfonamide;
N-({(1S)-2-[(2,6-dichlorophenyl)acetyl]-1-methyl-1,2,3,4-tetrahydroisoquinolin-5-yl}methyl)methanesulfonamide;
N-({(1S)-2-[(2,6-dichlorophenyl)acetyl]-1-methyl-1,2,3,4-tetrahydroisoquinolin-5-yl}methyl)acetamide;
1-({(1S)-2-[(2,6-dichlorophenyl)acetyl]-1-methyl-1,2,3,4-tetrahydroisoquinolin-5-yl}methyl)-3-methylurea;
methyl ({(1S)-2-[(2,6-dichlorophenyl)acetyl]-1-methyl-1,2,3,4-tetrahydroisoquinolin-5-yl}methyl)carbamate;
2-(2,6-dichlorophenyl)-1-[(1S)-5-(hydroxymethyl)-1-methyl-3,4-dihydroisoquinolin-2(1H)-yl]ethanone;
2-(2,6-dichlorophenyl)-1-[(1S)-1-methyl-5-(pyrrolidin-1-ylcarbonyl)-3,4-dihydroisoquinolin-2(1H)-yl]ethanone;
2-(2,6-dichlorophenyl)-1-[(1S)-1-methyl-5-[(2-methylpyrrolidin-1-yl)carbonyl]-3,4-dihydroisoquinolin-2(1H)-yl]ethanone;
2-(2,6-dichlorophenyl)-1-[(1S)-1-methyl-5-(morpholin-4-ylcarbonyl)-3,4-dihydroisoquinolin-2(1H)-yl]ethanone;
2-(2,6-dichlorophenyl)-1-[(1S)-1-methyl-5-{[4-(trifluoromethyl)piperidin-1-yl]carbonyl}-3,4-dihydroisoquinolin-2(1H)-yl]ethanone;
2-(2,6-dichlorophenyl)-1-[(1S)-5-[(2,5-dimethylpyrrolidin-1-yl)carbonyl]-1-methyl-3,4-dihydroisoquinolin-2(1H)-yl]ethanone;
2-(2,6-dichlorophenyl)-1-[(1S)-5-{[(3 S)-3-hydroxypyrrolidin-1-yl]carbonyl}-1-methyl-3,4-dihydroisoquinolin-2(1H)-yl]ethanone;
2-(2,6-dichlorophenyl)-1-[(1S)-5-[(3,3-difluoropyrrolidin-1-yl)carbonyl]-1-methyl-3,4-dihydroisoquinolin-2(1H)-yl]ethanone;
2-[2-chloro-6-(hydroxymethyl)phenyl]-1-[(1S)-1-methyl-3,4-dihydroisoquinolin-2(1H)-yl]ethanone;
3-chloro-N-methyl-2-{2-[(1S)-1-methyl-3,4-dihydroisoquinolin-2(1H)-yl]-2-oxoethyl}benzamide;
2-[2,6-dichloro-4-(hydroxymethyl)phenyl]-1-(1-methyl-3,4-dihydroisoquinolin-2(1H)-yl)ethanone;
{(1S)-2-[(2,6-dichlorophenyl)acetyl]-1-methyl-1,2,3,4-tetrahydroisoquinolin-5-yl}methyl methyl carbonate;
3-chloro-2-{2-[(1S)-1-methyl-3,4-dihydroisoquinolin-2(1H)-yl]-2-oxoethyl}benzonitrile;
N-(2,4-dichloro-3-{2-[(1S)-1-methyl-3,4-dihydroisoquinolin-2(1H)-yl]-2-oxoethyl}phenyl)methanesulfonamide;
2-[2,6-dichloro-3-(methylsulfanyl)phenyl]-1-[(1S)-1-methyl-3,4-dihydroisoquinolin-2(1H)-yl]ethanone;
N-(3-chloro-2-{2-[(1S)-1-methyl-3,4-dihydroisoquinolin-2(1H)-yl]-2-oxoethyl}benzyl)methanesulfonamide;
N-(3-chloro-2-{2-[(1S)-1-methyl-3,4-dihydroisoquinolin-2(1H)-yl]-2-oxoethyl}benzyl)acetamide;
2-[2,6-dichloro-3-(methylsulfonyl)phenyl]-1-[(1S)-1-methyl-3,4-dihydroisoquinolin-2(1H)-yl]ethanone;
2-[2,6-dichloro-3-(methylsulfinyl)phenyl]-1-[(1S)-1-methyl-3,4-dihydroisoquinolin-2(1H)-yl]ethanone;
2-(2,6-dichlorophenyl)-1-[(1S)-1-methyl-5-[(methylsulfanyl)methyl]-3,4-dihydroisoquinolin-2(1H)-yl]ethanone;
2-(2,6-dichlorophenyl)-1-[(1S)-1-methyl-5-(methylsulfonyl)-3,4-dihydroisoquinolin-2(1H)-yl]ethanone;
N-(3-chloro-2-{2-[(1S)-1-methyl-3,4-dihydroisoquinolin-2(1H)-yl]-2-oxoethyl}phenyl)methanesulfonamide;
N-(3-chloro-2-{2-[(1S)-1-methyl-3,4-dihydroisoquinolin-2(1H)-yl]-2-oxoethyl}phenyl)acetamide;
1-[(1S)-5-amino-1-methyl-3,4-dihydroisoquinolin-2(1H)-yl]-2-(2,6-dichlorophenyl)ethanone;
2-(2,6-dichlorophenyl)-1-[(1S)-5-[1-hydroxyethyl]-1-methyl-3,4-dihydroisoquinolin-2(1H)-yl]ethanone;
N-(2-{(1S)-2-[(2,6-dichlorophenyl)acetyl]-1-methyl-1,2,3,4-tetrahydroisoquinolin-5-yl}ethyl)methanesulfonamide;
2-(2,6-dichlorophenyl)-1-[(1S)-1-methyl-5-[1-(methylsulfonyl)-4,5-dihydro-1H-imidazol-2-yl]-3,4-dihydroisoquinolin-2(1H)-yl]ethanone;
2-[2-chloro-6-(1H-pyrazol-4-yl)phenyl]-1-[(1S)-1-methyl-3,4-dihydroisoquinolin-2(1H)-yl]ethanone trifluoroacetate;
(1S)-2-[(2,6-dichlorophenyl)acetyl]-1-methyl-2,3-dihydroisoquinolin-4(1H)-one;
2-{2,6-dichloro-4-[methylsulfinyl]phenyl}-1-[(1S)-1-methyl-3,4-dihydroisoquinolin-2(1H)-yl]ethanone;
[2-(2,6-dichlorophenyl)-1-[(1S)-5-(N-cyano-S-methylsulfonimidoyl)-1-methyl-3,4-dihydroisoquinolin-2(1H)-yl]ethanone;
2-(2,6-dichlorophenyl)-1-[(1S)-5-(N, S-dimethylsulfonimidoyl)-1-methyl-3,4-dihydroisoquinolin-2(1H)-yl]ethanone;
(1S)-2-[(2,6-dichlorophenyl)acetyl]-N,N, 1-trimethyl-1,2,3,4-tetrahydroisoquinoline-5-sulfinamide;
2-(2,6-dichlorophenyl)-1-[(1S)-1-methyl-5-[(5)-methylsulfinyl]-3,4-dihydroisoquinolin-2(1H)-yl]ethanone;
2-(2,6-dichlorophenyl)-1-[(1S)-1-methyl-5-[methylsulfinyl]-3,4-dihydroisoquinolin-2(1H)-yl]ethanone;
(1S)-2-[(2,6-dichlorophenyl)acetyl]-N,1-dimethyl-1,2,3,4-tetrahydroisoquinoline-5-sulfonamide;
2-(2,6-dichlorophenyl)-1-[(1S)-5-hydroxy-1-methyl-3,4-dihydroisoquinolin-2(1H)-yl]ethanone;
2-[2-chloro-6-(methylsulfanyl)phenyl]-1-[(1S)-1-methyl-3,4-dihydroisoquinolin-2(1H)-yl]ethanone;
2-[2-chloro-6-(methylsulfinyl)phenyl]-1-[(1S)-1-methyl-3,4-dihydroisoquinolin-2(1H)-yl]ethanone;
2-[2-chloro-6-(methylsulfonyl)phenyl]-1-[(1S)-1-methyl-3,4-dihydroisoquinolin-2(1H)-yl]ethanone;
2-[5-chloro-1-(methylsulfonyl)-1H-pyrrolo[2,3-b]pyridin-4-yl]-1-[(1S)-1-methyl-3,4-dihydroisoquinolin-2(1H)-yl]ethanone trifluoroacetate;
3,5-dichloro-4-{2-[(1S)-1-methyl-3,4-dihydroisoquinolin-2(1H)-yl]-2-oxoethyl}pyridin-2(1H)-one;

2-(2,6-dichlorophenyl)-1-[(1S)-1-methyl-5-(propan-2-ylsulfonyl)-3,4-dihydroisoquinolin-2(1H)-yl]ethanone;

2-(2,6-dichlorophenyl)-1-[(1S)-5-(ethylsulfonyl)-1-methyl-3,4-dihydroisoquinolin-2(1H)-yl]ethanone;

3-methoxy-2-{2-[(1S)-1-methyl-3,4-dihydroisoquinolin-2(1H)-yl]-2-oxoethyl}benzonitrile;

2-{2-chloro-6-[(methylsulfonyl)methyl]phenyl}-1-[(1S)-1-methyl-3,4-dihydroisoquinolin-2(1H)-yl]ethanone;

2-(2,6-dichlorophenyl)-1-[(1S)-1-methyl-5-[(methylsulfonyl)methyl]-3,4-dihydroisoquinolin-2(1H)-yl]ethanone;

2-(2,6-dichlorophenyl)-1-[(1S,4S)-4-methoxy-1-methyl-3,4-dihydroisoquinolin-2(1H)-yl]ethanone;

2-(2,6-dichlorophenyl)-1-[(1S,4R)-4-methoxy-1-methyl-3,4-dihydroisoquinolin-2(1H)-yl]ethanone;

(1S,4S)-2-[(2,6-dichlorophenyl)acetyl]-1-methyl-1,2,3,4-tetrahydroisoquinolin-4-yl methylcarbamate;

(1S,4S)-2-[(2,6-dichlorophenyl)acetyl]-1-methyl-1,2,3,4-tetrahydroisoquinolin-4-yl methyl carbonate;

(1S,4R)-2-[(2,6-dichlorophenyl)acetyl]-1-methyl-1,2,3,4-tetrahydroisoquinolin-4-yl methyl carbonate;

2-[2,6-dichloro-3-(hydroxymethyl)phenyl]-1-[(1S)-1-methyl-5-(methylsulfonyl)-3,4-dihydroisoquinolin-2(1H)-yl]ethanone;

2-(2,6-dichlorophenyl)-1-[(1S)-1-methyl-4-(methylsulfonyl)-3,4-dihydroisoquinolin-2(1H)-yl]ethanone;

2-(2,6-dichlorophenyl)-1-[(1S)-1-methyl-5-(pyrrolidin-1-ylsulfonyl)-3,4-dihydroisoquinolin-2(1H)-yl]ethanone;

(1S)-2-[(2,6-dichlorophenyl)acetyl]-N-ethyl-1-methyl-1,2,3,4-tetrahydroisoquinoline-5-sulfonamide;

(1S)-2-[(2,6-dichlorophenyl)acetyl]-1-methyl-N-(propan-2-yl)-1,2,3,4-tetrahydroisoquinoline-5-sulfonamide;

(1S)-2-[(2,6-dichlorophenyl)acetyl]-1-methyl-N-(2,2,2-trifluoroethyl)-1,2,3,4-tetrahydroisoquinoline-5-sulfonamide;

(1S)-2-[(2,6-dichlorophenyl)acetyl]-1-methyl-N-(4H-1,2,4-triazol-3-yl)-1,2,3,4-tetrahydroisoquinoline-5-sulfonamide;

2-(2,6-dichlorophenyl)-1-[(1S)-5-[(3,3-difluoropyrrolidin-1-yl)sulfonyl]-1-methyl-3,4-dihydroisoquinolin-2(1H)-yl]ethanone;

(1S)—N-(cyanomethyl)-2-[(2,6-dichlorophenyl)acetyl]-1-methyl-1,2,3,4-tetrahydroisoquinoline-5-sulfonamide;

(1S)-2-[(2,6-dichlorophenyl)acetyl]-1-methyl-1,2,3,4-tetrahydroisoquinoline-5-sulfonamide;

2-(2,6-dichlorophenyl)-1-[(1S)-1-methyl-5-{[(5-methyl-1,2-oxazol-3-yl)methyl]sulfonyl}-3,4-dihydroisoquinolin-2(1H)-yl]ethanone;

2-(2,6-dichlorophenyl)-1-[(1S)-1-methyl-5-[(pyridin-3-ylmethyl)sulfonyl]-3,4-dihydroisoquinolin-2(1H)-yl]ethanone;

2-(2,6-dichlorophenyl)-1-[(1S)-1-methyl-5-[(tetrahydro-2H-pyran-4-ylmethyl)sulfonyl]-3,4-dihydroisoquinolin-2(1H)-yl]ethanone;

2-(2,6-dichlorophenyl)-1-[(1S)-5-[(methoxymethyl)sulfonyl]-1-methyl-3,4-dihydroisoquinolin-2(1H)-yl]ethanone;

2-(2,6-dichlorophenyl)-1-[(1S)-1-methyl-5-[(1-oxidotetrahydro-1H-1λ4-thiophen-1-ylidene)amino]-3,4-dihydroisoquinolin-2(1H)-yl]ethanone;

2-(2,6-dichlorophenyl)-1-[(1S)-1-methyl-5-((1S)-2,2,2-trifluoro-1-hydroxyethyl)-3,4-dihydroisoquinolin-2(1H)-yl]ethanone;

2-(3,5-dichloropyridin-4-yl)-1-[(1S)-1-methyl-5-((1S)-2,2,2-trifluoro-1-hydroxyethyl)-3,4-dihydroisoquinolin-2(1H)-yl]ethanone;

3-chloro-2-{2-[(1S)-1-methyl-5-((1R)-2,2,2-trifluoro-1-hydroxyethyl)-3,4-dihydroisoquinolin-2(1H)-yl]-2-oxoethyl}benzonitrile;

3-chloro-2-{2-[(1S)-1-methyl-5-((1S)-2,2,2-trifluoro-1-hydroxyethyl)-3,4-dihydroisoquinolin-2(1H)-yl]-2-oxoethyl}benzonitrile;

2-(2-chloro-6-fluorophenyl)-1-[(1S)-1-methyl-5-[2,2,2-trifluoro-1-hydroxyethyl]-3,4-dihydroisoquinolin-2(1H)-yl]ethanone;

2-(5-chloro-1H-indol-4-yl)-1-[(1S)-1-methyl-5-[(1S)-2,2,2-trifluoro-1-hydroxyethyl]-3,4-dihydroisoquinolin-2(1H)-yl]ethanone;

3-chloro-2-{2-[(1S)-1-methyl-5-(pyridin-3-yl)-3,4-dihydroisoquinolin-2(1H)-yl]-2-oxoethyl}benzonitrile;

3-chloro-2-{2-[(1S)-1-methyl-5-(pyridin-4-yl)-3,4-dihydroisoquinolin-2(1H)-yl]-2-oxoethyl}benzonitrile;

2-{2-[(1S)-5-(6-aminopyridin-3-yl)-1-methyl-3,4-dihydroisoquinolin-2(1H)-yl]-2-oxoethyl}-3-chlorobenzonitrile trifluoroacetate;

3-chloro-2-{2-[(1S)-5-(3,5-dimethyl-1,2-oxazol-4-yl)-1-methyl-3,4-dihydroisoquinolin-2(1H)-yl]-2-oxoethyl}benzonitrile;

3-chloro-2-{2-[(1S)-1-methyl-5-(1-methyl-1H-pyrazol-4-yl)-3,4-dihydroisoquinolin-2(1H)-yl]-2-oxoethyl}benzonitrile;

3-chloro-2-{2-[(1S)-1-methyl-5-(1H-pyrazol-4-yl)-3,4-dihydroisoquinolin-2(1H)-yl]-2-oxoethyl}benzonitrile;

3-chloro-2-{2-[(1S)-5-(3,5-dimethyl-1H-pyrazol-4-yl)-1-methyl-3,4-dihydroisoquinolin-2(1H)-yl]-2-oxoethyl}benzonitrile;

1-[(1S)-5-(6-aminopyridin-3-yl)-1-methyl-3,4-dihydroisoquinolin-2(1H)-yl]-2-(2,6-dichlorophenyl)ethanone;

2-(2,6-dichlorophenyl)-1-[(1S)-1-methyl-5-(2-methylpyridin-3-yl)-3,4-dihydroisoquinolin-2(1H)-yl]ethanone;

1-[(1S)-5-(6-aminopyridin-3-yl)-1-methyl-3,4-dihydroisoquinolin-2(1H)-yl]-2-(2,6-dichlorophenyl)ethanone;

2-(2,6-dichlorophenyl)-1-[(1S)-5-(3,5-dimethyl-1H-pyrazol-4-yl)-1-methyl-3,4-dihydroisoquinolin-2(1H)-yl]ethanone;

2-(2,6-dichlorophenyl)-1-[(1S)-5-{[dimethyl(oxido)-λ$^6$-sulfanylidene]amino}-1-methyl-3,4-dihydroisoquinolin-2(1H)-yl]ethanone;

2-(2,6-dichlorophenyl)-1-[(1S)-1-methyl-5-[(4-oxido-1,4-λ$^4$-oxathian-4-ylidene)amino]-3,4-dihydroisoquinolin-2(1H)-yl]ethanone;

3-chloro-2-{2-[(1S)-5-{[dimethyl(oxido)-λ$^6$-sulfanylidene]amino}-1-methyl-3,4-dihydroisoquinolin-2(1H)-yl]-2-oxoethyl}benzonitrile;

2-(2,6-dichlorophenyl)-1-[(1S)-5-(N-ethyl-5-methylsulfonimidoyl)-1-methyl-3,4-dihydroisoquinolin-2(1H)-yl]ethanone;

2-(2,6-dichlorophenyl)-1-[(1S)-5-({[dimethyl(oxido)-λ$^6$-sulfanylidene]amino}methyl)-1-methyl-3,4-dihydroisoquinolin-2(1H)-yl]ethanone;

2-(2,6-dichlorophenyl)-1-[(1S)-5-(1,1-difluoro-2-hydroxyethyl)-1-methyl-3,4-dihydroisoquinolin-2(1H)-yl]ethanone;

1-[(1S)-5-(2-amino-1,1-difluoroethyl)-1-methyl-3,4-dihydroisoquinolin-2(1H)-yl]-2-(2,6-dichlorophenyl)ethanone;

N-(2-{(1S)-2-[(2,6-dichlorophenyl)acetyl]-1-methyl-1,2,3,4-tetrahydroisoquinolin-5-yl}-2,2-difluoroethyl)acetamide;

2-(2,6-dichlorophenyl)-1-[(1S)-5-[1,1-difluoro-2-(morpholin-4-yl)ethyl]-1-methyl-3,4-dihydroisoquinolin-2(1H)-yl]ethanone;

2-(2,6-dichlorophenyl)-1-[(1S)-5-[1,1-difluoro-2-(methylamino)ethyl]-1-methyl-3,4-dihydroisoquinolin-2(1H)-yl]ethanone;

2-{(1S)-2-[(2,6-dichlorophenyl)acetyl]-1-methyl-1,2,3,4-tetrahydroisoquinolin-5-yl}-2,2-difluoroacetamide;

2-{(1S)-2-[(2,6-dichlorophenyl)acetyl]-1-methyl-1,2,3,4-tetrahydroisoquinolin-5-yl}-2,2-difluoro-N-(1-methylcyclopropyl)acetamide;

2-{(1S)-2-[(2,6-dichlorophenyl)acetyl]-1-methyl-1,2,3,4-tetrahydroisoquinolin-5-yl}-2,2-difluoro-N-(3-methyloxetan-3-yl)acetamide;

2-(2,6-dichlorophenyl)-1-[(1S)-1-methyl-5-(2H-1,2,3-triazol-4-yl)-3,4-dihydroisoquinolin-2(1H)-yl]ethanone;

2-(2,6-dichlorophenyl)-1-[(1S)-5-(3-hydroxypropyl)-1-methyl-3,4-dihydroisoquinolin-2(1H)-yl]ethanone;

6-[(1S)-2-[2-(2,6-dichlorophenyl)acetyl]-1-methyl-3,4-dihydro-1H-isoquinolin-5-yl]morpholin-3-one;

4-{(1S)-2-[(2-chloro-6-cyanophenyl)acetyl]-1-methyl-1,2,3,4-tetrahydroisoquinolin-5-yl}-1H-pyrazole-3-carbonitrile;

3-chloro-2-{2-[(1S)-1-methyl-5-[3-(trifluoromethyl)-1H-pyrazol-4-yl]-3,4-dihydroisoquinolin-2(1H)-yl]-2-oxoethyl}benzonitrile;

2-{2-[(1S)-5-(2-aminopyridin-4-yl)-1-methyl-3,4-dihydroisoquinolin-2(1H)-yl]-2-oxoethyl}-3-chlorobenzonitrile trifluoroacetate; or 3-chloro-2-{2-[(1S)-1-methyl-5-(pyridin-2-yl)-3,4-dihydroisoquinolin-2(1H)-yl]-2-oxoethyl}benzonitrile.

9. A pharmaceutical composition comprising a compound according to claim 1 or a pharmaceutically acceptable salt thereof, and a pharmaceutically acceptable carrier.

\* \* \* \* \*